US008222224B2

(12) United States Patent
Tucker

(10) Patent No.: US 8,222,224 B2

(45) **Date of Patent: *Jul. 17, 2012**

(54) CHIMERIC ADENOVIRAL VECTORS

(75) Inventor: Sean N. Tucker, San Francisco, CA (US)

(73) Assignee: Vaxart, Inc., San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/945,358

(22) Filed: Nov. 12, 2010

(65) Prior Publication Data

US 2011/0081375 A1 Apr. 7, 2011

Related U.S. Application Data

(62) Division of application No. 11/712,794, filed on Feb. 28, 2007, now Pat. No. 7,879,602.

(60) Provisional application No. 60/778,026, filed on Feb. 28, 2006, provisional application No. 60/801,645, filed on May 19, 2006, provisional application No. 60/802,992, filed on May 22, 2006, provisional application No. 60/821,492, filed on Aug. 4, 2006, provisional application No. 60/846,658, filed on Sep. 22, 2006, provisional application No. 60/848,195, filed on Sep. 28, 2006.

(51) Int. Cl.
*A61K 48/00* (2006.01)

(52) U.S. Cl. ..................................................... 514/44 R

(58) Field of Classification Search ................. 514/44 R
See application file for complete search history.

(56) References Cited

U.S. PATENT DOCUMENTS

| | | | | |
|---|---|---|---|---|
| 5,676,950 | A * | 10/1997 | Small et al. | 424/199.1 |
| 6,511,845 | B1 * | 1/2003 | Davis et al. | 435/320.1 |
| 7,879,602 | B2 * | 2/2011 | Tucker | 435/320.1 |
| 2002/0182223 | A1 | 12/2002 | LaCount et al. | |
| 2005/0239728 | A1 * | 10/2005 | Pachuk et al. | 514/44 |
| 2006/0287263 | A1 | 12/2006 | Davis et al. | |
| 2007/0219149 | A1 | 9/2007 | Hasegawa et al. | |

FOREIGN PATENT DOCUMENTS

| | | | |
|---|---|---|---|
| WO | WO 03/038057 | A2 | 5/2003 |
| WO | WO 2004/011624 | A2 | 2/2004 |
| WO | WO 2005/014038 | A1 | 2/2005 |
| WO | WO 2005/025614 | A2 | 3/2005 |

OTHER PUBLICATIONS

Ichinohe et al. (2005) J. Virol. vol. 79, No. 5, 2910-2919.*

Alexopoulou, L., et al., "Recognition of double-stranded RNA and activation of NF-κB by Toll-like receptor 3," *Nature* vol. 413, pp. 732-738 (Oct. 18, 2001).

Bell, J., et al., "The dsRNA binding site of human Toll-like receptor 3," *Proceedings of the National Academy of Sciences*, vol. 103(23), pp. 8792-8797 (Jun. 2006).

Calvert, J.G., et al., "Fowlpox Virus Recombinants Expressing the Envelope Glycoprotein of an Avian Reticuloendotheliosis Retrovirus Induce Neutralizing Antibodies and Reduce Viremia in Chickens," *Journal of Virology*, vol. 67, pp. 3069-3076 (1993).

Celma, M.L., et al., "Effect of Poliovirus Double-Stranded RNA on Viral and Host-Cell Protein Synthesis," *Proc. Natl. Acad. Sci. USA*, vol. 71, pp. 2440-2444 (1974).

De Benedetti, A. et al., "Inhibition of viral mRNA translation in interferon-treated L cells infected with reovirus," *Journal of Virology*, vol. 55, pp. 588-593 (1985).

Fenje, P., et al., "Protection of rabbits against experimental rabies of poly I-poly C," *Nature*, vol. 226, pp. 171-172 (1970).

Harms, X., et al., "Interferon-gamma inhibits transgene expression driven by SV40 or CMV promoters but augments expression driven by the mammalian MHC I promoter," *Human Gene Therapy*, vol. 6(10), pp. 1291-1297 (Oct. 1995).

He, F., et al., "WSSV ie1 promoter is more efficient than CMV promoter to express H5 hemagglutinin from influenza virus in baculovirus as a chicken vaccine," *BMC Microbiol.*, vol. 8, pp. 238 (Dec. 2008).

Ichinohe, T., et al., "Synthetic double-stranded RNA poly (I:C) Combined with mucosal vaccine protects against influenza virus infection," *Journal of Virology*, vol. 79(5), pp. 2910-2919 (Mar. 2005).

Kaempfer, R., et al. "Inhibition of cellular protein synthesis by double-stranded RNA: inactivation of an initiation factor," *Proc. Natl. Acad. Sci. USA*, vol. 70, pp. 1222-1226 (Apr. 1973) 70:1222-26.

Romero, R. et al., :"Cytokine inhibition of the hepatitis B virus core promoter," *Hepatology*, vol. 23, pp. 17-23 (1996).

Xiang, Z.Q., et al., "The effect of interferon-gamma on genetic immunization," *Vaccine*, vol. 15, pp. 896-898 (1997).

Office Action dated May 30, 2011 from Japanese Patent Application No. 2008-557403, together with English translation, 6 pages.

* cited by examiner

*Primary Examiner* — Anne Marie S Wehbe

(74) *Attorney, Agent, or Firm* — Kilpatrick Townsend & Stockton LLP

(57) ABSTRACT

The present invention provides chimeric adenoviral vectors and methods for using the vectors to elicit an immune response to an antigen of interest.

9 Claims, 10 Drawing Sheets

SEQUENCE LISTING

```
<160> NUMBER OF SEQ ID NOS: 17

<210> SEQ ID NO 1
<211> LENGTH: 11025
<212> TYPE: DNA
<213> ORGANISM: Artificial Sequence
<220> FEATURE:
```

<223> OTHER INFORMATION: chimeric adenoviral vector DS1

<400> SEQUENCE: 1

```
taacatcatc aataatatac cttattttgg attgaagcca atatgataat gaggggtgg     60
agtttgtgac gtggcgcggg gcgtgggaac ggggcgggtg acgtagtagt gtggcggaag   120
tgtgatgttg caagtgtggc ggaacacatg taagcgacgg atgtggcaaa agtgacgttt   180
ttggtgtgcg ccggtgtaca caggaagtga caattttcgc gcggttttag gcggatgttg   240
tagtaaattt gggcgtaacc gagtaagatt tggccatttt cgcgggaaaa ctgaataaga   300
ggaagtgaaa tctgaataat tttgtgttac tcatagcgcg taatactggt accgcggccg   360
cctcgagtct agagatctgg cgaaaggggg atgtgctgca aggcgattaa gttgggtaac   420
gccagggttt tcccagtcac gacgttgtaa aacgacggcc agtgaattgt aatacgactc   480
actatagggc gaattgggta ctggccacag agcttggccc attgcatacg ttgtatccat   540
atcataatat gtacatttat attggctcat gtccaacatt accgccatgt tgacattgat   600
tattgactag ttattaatag taatcaatta cggggtcatt agttcatagc ccatatatgg   660
agttccgcgt tacataactt acggtaaatg gcccgcctgg ctgaccgccc aacgaccccc   720
gcccattgac gtcaataatg acgtatgttc ccatagtaac gccaataggg actttccatt   780
gacgtcaatg ggtggagtat ttacggtaaa ctgcccactt ggcagtacat caagtgtatc   840
atatgccaag tacgccccct attgacgtca atgacggtaa atggcccgcc tggcattatg   900
cccagtacat gaccttatgg gactttccta cttggcagta catctacgta ttagtcatcg   960
ctattaccat ggtgatgcgg ttttggcagt acatcaatgg gcgtggatag cggtttgact  1020
cacggggatt tccaagtctc caccccattg acgtcaatgg gagtttgttt tggcaccaaa  1080
atcaacggga ctttccaaaa tgtcgtaaca actccgcccc attgacgcaa atgggcggta  1140
ggcgtgtacg gtgggaggtc tatataagca gagctcgttt agtgaaccgt cagatcgcct  1200
ggagacgcca tccacgctgt tttgacctcc atagaagaca ccgggaccga tccagcctga  1260
ctctagccta gctctgaagt tggtggtgag gccctgggca ggttggtatc aaggttacaa  1320
gacaggttta aggagaccaa tagaaactgg gcatgtggag acagagaaga ctcttgggtt  1380
tctgataggc actgactctc tctgcctatt ggtctatttt cccaccctta ggctgctggt  1440
ctgagcctag gagatctctc gaggtcgacg gtatagcttc tagagatccc tcgacctcga  1500
gatccattgt gctctaaagg agatacccgg ccagacaccc tcacctgcgg tgcccagctg  1560
cccaggctga ggcaagagaa ggccagaaac catgcccatg ggtctctgc aaccgctggc   1620
caccttgtac ctgctgggga tgctggtcgc ttccgtgcta gctgtggaga agctgtgggt  1680
gactgtatac tatggggtgc ctgtgtggaa ggaggccacc accaccctgt tctgtgcctc  1740
tgatgccaag gcctatgaca ctgaggtcca caatgtctgg gccacccatg cctgtgtgcc  1800
cactgacccc aaccctcagg aggtggtgct ggagaatgtg actgagcact tcaacatgtg  1860
gaagaacaac atggtggagc agatgcagga ggacatcatc agcctgtggg accagagcct  1920
gaagccctgt gtgaagctga ccccctgtg tgtgaccctg aactgcaagg atgtgaatgc   1980
caccaacacc accaatgact ctgagggcac tatggagagg ggtgagatca agaactgcag  2040
cttcaacatc accaccagca tcagggatga ggtgcagaag gagtatgccc tgttctacaa  2100
gctggatgtg gtgcccattg acaacaacaa caccagctac aggctgatca gctgtgacac  2160
ctctgtgatc acccaggcct gccccaagat cagctttgag cccatcccca tccactactg  2220
tgcccctgct ggctttgcca tcctgaagtg caatgacaag accttcaatg gcaaaggccc  2280
```

-continued

```
ttgcaagaat gtgagcactg tgcagtgcac tcatggcatc aggcctgtgg tgagcaccca   2340
gctgctgctg aatggcagcc tggctgagga ggaggtggtg atcaggtctg acaacttcac   2400
caacaatgcc aagaccatca ttgtgcagct gaaggagtct gtggagatca actgcaccag   2460
gcccaacaac aacaccagga agagcattca cattggccct ggcagggcct tctacaccac   2520
tggggagatc attggggaca tcaggcaggc ccactgcaac atcagcaggg ccaagtggaa   2580
tgacaccctg aagcagattg tgatcaagct gagggagcag tttgagaaca agaccattgt   2640
gttcaatcac agctctggtg gtgatcctga gattgtgatg cacagcttca actgtggtgg   2700
tgagttcttc tactgcaaca gcacccagct gttcaacagc acctggaaca acaacactga   2760
gggcagcaac aacactgagg gcaacaccat caccctgcct tgcaggatca agcagatcat   2820
caacatgtgg caggaggtgg gcaaggccat gtatgctcct cccatcaggg gccagatcag   2880
gtgcagcagc aacatcactg gcctgctgct gaccagggat ggtggcatca atgagaatgg   2940
cactgagatt ttcaggcctg gtggtgggga catgagggac aactggaggt ctgagctgta   3000
caagtacaag gtggtgaaga ttgagcccct tggtgtggct cccaccaagg ctaagcgcag   3060
ggtggtgcag agggagaagc gcgctgtggg ctgaggatcc cgagggtgag tgctcctgcc   3120
tggacgcatc ccggctatgc agccccagtc cagggcagca aggcaggccc cgtctgcctc   3180
ttcacccgga gcctctgccc gccccactca tgctcaggga gagggtcttc tggctttttc   3240
ccaggctctg ggcaggcaca ggctaggtgc ccctaaccca ggccctgcac acaaaggggc   3300
aggtgctggg ctcagacctg ccaagagcca tatccgggag gaccctgccc ctgacctaag   3360
cccaccccaa aggccaaact ctccactccc tcagctcgga caccttctct cctcccagat   3420
tccagtaact cccaatcttc tctctgcaga gcccaaatct tgtgacaaaa ctcacacatg   3480
cccaccgtgc ccaggtaagc cagcccaggc ctcgccctcc agctcaaggc gggacaggtg   3540
ccctagagta gcctgcatcc agggacaggc cccagccggg tgctgacacg tccacctcca   3600
tctcttcctc agcacctgaa ctcctggggg gaccgtcagt cttcctcttc cccccaaaac   3660
ccaaggacac cctcatgatc tcccggaccc ctgaggtcac atgcgtggtg gtggacgtga   3720
gccacgaaga ccctgaggtc aagttcaact ggtacgtgga cggcgtggag gtgcataatg   3780
ccaagacaaa gccgcgggag gagcagtaca acagcacgta ccgggtggtc agcgtcctca   3840
ccgtcctgca ccaggactgg ctgaatggca aggagtacaa gtgcaaggtc tccaacaaag   3900
ccctcccagc ccccatcgag aaaaccatct ccaaagccaa aggtgggacc cgtggggtgc   3960
gagggccaca tggacagagg ccggctcggc ccaccctctg ccctgagagt gaccgctgta   4020
ccaacctctg tcctacaggg cagccccgag aaccacaggt gtacaccctg cccccatccc   4080
gggatgagct gaccaagaac caggtcagcc tgacctgcct ggtcaaaggc ttctatccca   4140
gcgacatcgc cgtggagtgg gagagcaatg ggcagccgga gaacaactac aagaccacgc   4200
ctcccgtgct ggactccgac ggctccttct tcctctacag caagctcacc gtggacaaga   4260
gcaggtggca gcaggggaac gtcttctcat gctccgtgat gcatgaggct ctgcacaacc   4320
actacacgca gaagagcctc tccctgtctc cgggtaaatg agtgcgacgg ccgcaggtaa   4380
gccagcccag gcctcgccct ccagctcaag gcgggacagg tgccctagag tagcctgcat   4440
ccagggacag gccccagccg ggtgctgaca cgtccacctc catctcttcc tcaggtctgc   4500
ccgggtggca tccctgtgac ccctccccag tgcctctcct ggccctggaa gttgccactc   4560
cagtgcccac cagccttgtc ctaataaaat taagttgcat cattttgtct gactaggtgt   4620
ccttctataa tattatgggg tggagggggg tggtatggag caaggggccc aagttaactt   4680
```

-continued

```
gtttattgca gcttataatg gttacaaata aagcaatagc atcacaaatt tcacaaataa   4740
agcatttttt tcactgcatt ctagttgtgg tttgtccaaa ctcatcaatg tatcttatca   4800
tgtctggatc tgggcgtggt taagggtggg aaagaatata taaggtgggg gtcttatgta   4860
gttttgtatc tgttttgcag cagccgccgc cgccatgagc accaactcgt ttgatggaag   4920
cattgtgagc tcatatttga caacgcgcat gcccccatgg gccggggtgc gtcagaatgt   4980
gatgggctcc agcattgatg gtcgccccgt cctgcccgca aactctacta ccttgaccta   5040
cgagaccgtg tctggaacgc cgttggagac tgcagcctcc gccgccgctt cagccgctgc   5100
agccaccgcc cgcgggattg tgactgactt tgctttcctg agcccgcttg caagcagtgc   5160
agcttcccgt tcatccgccc gcgatgacaa gttgacggct cttttggcac aattggattc   5220
tttgacccgg gaacttaatg tcgtttctca gcagctgttg gatctgcgcc agcaggtttc   5280
tgccctgaag gcttcctccc ctcccaatgc ggtttaaaac ataaataaaa aaccagactc   5340
tgtttggatt tggatcaagc aagtgtcttg ctgtctttat ttaggggttt tgcgcgcgcg   5400
gtaggcccgg gaccagcggt ctcggtcgtt gagggtcctg tgtatttttt ccaggacgtg   5460
gtaaaggtga ctctggatgt tcagatacat gggcataagc ccgtctctgg ggtggaggta   5520
gcaccactgc agagcttcat gctgcggggt ggtgttgtag atgatccagt cgtagcagga   5580
gcgctgggcg tggtgcctaa aaatgtcttt cagtagcaag ctgattgcca ggggcaggcc   5640
cttggtgtaa gtgtttacaa agcggttaag ctgggatggg tgcatacgtg gggatatgag   5700
atgcatcttg gactgtattt ttaggttggc tatgttccca gccatatccc tccggggatt   5760
catgttgtgc agaaccacca gcacagtgta tccggtgcac ttgggaaatt tgtcatgtag   5820
cttagaagga aatgcgtgga agaacttgga gacgcccttg tgacctccaa gattttccat   5880
gcattcgtcc ataatgatgg caatgggccc acgggcggcg gcctgggcga agatatttct   5940
gggatcacta acgtcatagt tgtgttccag gatgagatcg tcataggcca tttttacaaa   6000
gcgcgggcgg agggtgccag actgcggtat aatggttcca tccggcccag gggcgtagtt   6060
accctcacag atttgcattt cccacgcttt gagttcagat gggggggatca tgtctacctg   6120
cggggcgatg aagaaaacgg tttccggggt aggggagatc agctgggaag aaagcaggtt   6180
cctgagcagc tgcgacttac cgcagccggt gggcccgtaa atcacaccta ttaccgggtg   6240
caactggtag ttaagagagc tgcagctgcc gtcatccctg agcagggggg ccacttcgtt   6300
aagcatgtcc ctgactcgca tgttttccct gaccaaatcc gccagaaggc gctcgccgcc   6360
cagcgatagc agttcttgca aggaagcaaa gtttttcaac ggtttgagac cgtccgccgt   6420
aggcatgctt ttgagcgttt gaccaagcag ttccaggcgg tcccacagct cggtcacctg   6480
ctctacggca tctcgatcca gcatatctcc tcgtttcgcg ggttggggcg gctttcgctg   6540
tacggcagta gtcggtgctc gtccagacgg gccagggtca tgtctttcca cgggcgcagg   6600
gtcctcgtca gcgtagtctg ggtcacggtg aaggggtgcg ctccgggctg cgcgctggcc   6660
agggtgcgct tgaggctggt cctgctggtg ctgaagcgct gccggtcttc gccctgcgcg   6720
tcggccaggt agcatttgac catggtgtca tagtccagcc cctccgcggc gtggcccttg   6780
gcgcgcagct tgcccttgga ggaggcgccg cacgaggggc agtgcagact tttgagggcg   6840
tagagcttgg gcgcgagaaa taccgattcc ggggagtagg catccgcgcc gcaggccccg   6900
cagacggtct cgcattccac gagccaggtg agctctggcc gttcggggtc aaaaaccagg   6960
tttcccccat gctttttgat gcgtttctta cctctggttt ccatgagccg gtgtccacgc   7020
tcggtgacga aaaggctgtc cgtgtccccg tatacagact tgagagggag tttaaacgaa   7080
```

```
ttcaatagct tgttgcatgg gcggcgatat aaaatgcaag gtgctgctca aaaaatcagg   7140
caaagcctcg cgcaaaaaag aaagcacatc gtagtcatgc tcatgcagat aaaggcaggt   7200
aagctccgga accaccacag aaaaagacac catttttctc tcaaacatgt ctgcgggttt   7260
ctgcataaac acaaaataaa ataacaaaaa aacatttaaa cattagaagc ctgtcttaca   7320
acaggaaaaa caacccttat aagcataaga cggactacgg ccatgccggc gtgaccgtaa   7380
aaaaactggt caccgtgatt aaaaagcacc accgacagct cctcggtcat gtccggagtc   7440
ataatgtaag actcggtaaa cacatcaggt tgattcatcg gtcagtgcta aaaagcgacc   7500
gaaatagccc gggggaatac atacccgcag gcgtagagac aacattacag cccccatagg   7560
aggtataaca aaattaatag gagagaaaaa cacataaaca cctgaaaaac cctcctgcct   7620
aggcaaaata gcaccctccc gctccagaac aacatacagc gcttcacagc ggcagcctaa   7680
cagtcagcct taccagtaaa aaagaaaacc tattaaaaaa acaccactcg acacggcacc   7740
agctcaatca gtcacagtgt aaaaaagggc caagtgcaga gcgagtatat ataggactaa   7800
aaaatgacgt aacggttaaa gtccacaaaa aacacccaga aaccgcacg cgaacctacg   7860
cccagaaacg aaagccaaaa aacccacaac ttcctcaaat cgtcacttcc gttttcccac   7920
gttacgtaac ttcccatttt aagaaaacta caattcccaa cacatacaag ttactccgcc   7980
ctaaaaccta cgtcacccgc cccgttccca cgccccgcgc cacgtcacaa actccacccc   8040
ctcattatca tattggcttc aatccaaaat aaggtatatt attgatgatg ttaattaaca   8100
tgcatggatc catatgcggt gtgaaatacc gcacagatgc gtaaggagaa aataccgcat   8160
caggcgctct tccgcttcct cgctcactga ctcgctgcgc tcggtcgttc ggctgcggcg   8220
agcggtatca gctcactcaa aggcggtaat acggttatcc acagaatcag gggataacgc   8280
aggaaagaac atgtgagcaa aaggccagca aaaggccagg aaccgtaaaa aggccgcgtt   8340
gctggcgttt ttccataggc tccgcccccc tgacgagcat cacaaaaatc gacgctcaag   8400
tcagaggtgg cgaaacccga caggactata aagataccag gcgtttcccc ctggaagctc   8460
cctcgtgcgc tctcctgttc cgaccctgcc gcttaccgga tacctgtccg cctttctccc   8520
ttcgggaagc gtggcgcttt ctcatagctc acgctgtagg tatctcagtt cggtgtaggt   8580
cgttcgctcc aagctgggct gtgtgcacga accccccgtt cagcccgacc gctgcgcctt   8640
atccggtaac tatcgtcttg agtccaaccc ggtaagacac gacttatcgc cactggcagc   8700
agccactggt aacaggatta gcagagcgag gtatgtaggc ggtgctacag agttcttgaa   8760
gtggtggcct aactacggct acactagaag gacagtattt ggtatctgcg ctctgctgaa   8820
gccagttacc ttcggaaaaa gagttggtag ctcttgatcc ggcaaacaaa ccaccgctgg   8880
tagcggtggt ttttttgttt gcaagcagca gattacgcgc agaaaaaaag gatctcaaga   8940
agatcctttg atcttttcta cggggtctga cgctcagtgg aacgaaaact cacgttaagg   9000
gattttggtc atgagattat caaaaaggat cttcacctag atccttttaa attaaaaatg   9060
aagttttaaa tcaatctaaa gtatatatga gtaaacttgg tctgacagtt accaatgctt   9120
aatcagtgag gcacctatct cagcgatctg tctatttcgt tcatccatag ttgcctgact   9180
ccccgtcgtg tagataacta cgatacggga gggcttacca tctggcccca gtgctgcaat   9240
gataccgcga gacccacgct caccggctcc agatttatca gcaataaacc agccagccgg   9300
aagggccgag cgcagaagtg gtcctgcaac tttatccgcc tccatccagt ctattaattg   9360
ttgccgggaa gctagagtaa gtagttcgcc agttaatagt ttgcgcaacg ttgttgccat   9420
tgctgcagcc atgagattat caaaaaggat cttcacctag atccttttca cgtagaaagc   9480
```

```
cagtccgcag aaacggtgct gaccccggat gaatgtcagc tactgggcta tctggacaag   9540

ggaaaacgca agcgcaaaga gaaagcaggt agcttgcagt gggcttacat ggcgatagct   9600

agactgggcg gttttatgga cagcaagcga accggaattg ccagctgggg cgccctctgg   9660

taaggttggg aagccctgca aagtaaactg gatggctttc tcgccgccaa ggatctgatg   9720

gcgcagggga tcaagctctg atcaagagac aggatgagga tcgtttcgca tgattgaaca   9780

agatggattg cacgcaggtt ctccggccgc ttgggtggag aggctattcg gctatgactg   9840

ggcacaacag acaatcggct gctctgatgc cgccgtgttc cggctgtcag cgcaggggcg   9900

cccggttctt tttgtcaaga ccgacctgtc cggtgccctg aatgaactgc aagacgaggc   9960

agcgcggcta tcgtggctgg ccacgacggg cgttccttgc gcagctgtgc tcgacgttgt  10020

cactgaagcg ggaagggact ggctgctatt gggcgaagtg ccggggcagg atctcctgtc  10080

atctcacctt gctcctgccg agaaagtatc catcatggct gatgcaatgc ggcggctgca  10140

tacgcttgat ccggctacct gcccattcga ccaccaagcg aaacatcgca tcgagcgagc  10200

acgtactcgg atggaagccg gtcttgtcga tcaggatgat ctggacgaag agcatcaggg  10260

gctcgcgcca gccgaactgt tcgccaggct caaggcgagc atgcccgacg gcgaggatct  10320

cgtcgtgacc catggcgatg cctgcttgcc gaatatcatg gtggaaaatg gccgcttttc  10380

tggattcatc gactgtggcc ggctgggtgt ggcggaccgc tatcaggaca tagcgttggc  10440

tacccgtgat attgctgaag agcttggcgg cgaatgggct gaccgcttcc tcgtgcttta  10500

cggtatcgcc gctcccgatt cgcagcgcat cgccttctat cgccttcttg acgagttctt  10560

ctgaattttg ttaaaatttt tgttaaatca gctcattttt taaccaatag gccgaaatcg  10620

gcaacatccc ttataaatca aaagaataga ccgcgatagg gttgagtgtt gttccagttt  10680

ggaacaagag tccactatta aagaacgtgg actccaacgt caaagggcga aaaaccgtct  10740

atcagggcga tggcccacta cgtgaaccat cacccaaatc aagttttttg cggtcgaggt  10800

gccgtaaagc tctaaatcgg aaccctaaag ggagcccccg atttagagct tgacggggaa  10860

agccggcgaa cgtggcgaga aaggaaggga agaaagcgaa aggagcgggc gctagggcgc  10920

tggcaagtgt agcggtcacg ctgcgcgtaa ccaccacacc cgcgcgctta atgcgccgct  10980

acagggcgcg tccattcgcc attcaggatc gaattaattc ttaat                 11025
```

<210> SEQ ID NO 2
<211> LENGTH: 11933
<212> TYPE: DNA
<213> ORGANISM: Artificial Sequence
<220> FEATURE:
<223> OTHER INFORMATION: chimeric adenoviral vector DS2

<400> SEQUENCE: 2

```
taacatcatc aataatatac cttattttgg attgaagcca atatgataat gaggggtgg     60

agtttgtgac gtggcgcggg gcgtgggaac ggggcgggtg acgtagtagt gtggcggaag    120

tgtgatgttg caagtgtggc ggaacacatg taagcgacgg atgtggcaaa agtgacgttt    180

ttggtgtgcg ccggtgtaca caggaagtga caattttcgc gcggttttag gcggatgttg    240

tagtaaattt gggcgtaacc gagtaagatt tggccatttt cgcgggaaaa ctgaataaga    300

ggaagtgaaa tctgaataat tttgtgttac tcatagcgcg taatactgct agagatctgg    360

cgaaaggggg atgtgctgca aggcgattaa gttgggtaac gccagggttt tcccagtcac    420

gacgttgtaa aacgacggcc agtgaattgt aatacgactc actatagggc gaattgggta    480

ctggccacag agcttggccc attgcatacg ttgtatccat atcataatat gtacatttat    540
```

```
attggctcat gtccaacatt accgccatgt tgacattgat tattgactag ttattaatag    600
taatcaatta cggggtcatt agttcatagc ccatatatgg agttccgcgt tacataactt    660
acggtaaatg gcccgcctgg ctgaccgccc aacgaccccc gcccattgac gtcaataatg    720
acgtatgttc ccatagtaac gccaataggg actttccatt gacgtcaatg ggtggagtat    780
ttacggtaaa ctgcccactt ggcagtacat caagtgtatc atatgccaag tacgccccct    840
attgacgtca atgacggtaa atggcccgcc tggcattatg cccagtacat gaccttatgg    900
gactttccta cttggcagta catctacgta ttagtcatcg ctattaccat ggtgatgcgg    960
ttttggcagt acatcaatgg gcgtggatag cggtttgact cacggggatt tccaagtctc   1020
caccccattg acgtcaatgg gagtttgttt tggcaccaaa atcaacggga ctttccaaaa   1080
tgtcgtaaca actccgcccc attgacgcaa atgggcggta ggcgtgtacg gtgggaggtc   1140
tatataagca gagctcgttt agtgaaccgt cagatcgcct ggagacgcca tccacgctgt   1200
tttgacctcc atagaagaca ccgggaccga tccagcctga ctctagccta gctctgaagt   1260
tggtggtgag gccctgggca ggttggtatc aaggttacaa gacaggttta aggagaccaa   1320
tagaaactgg gcatgtggag acagagaaga ctcttgggtt tctgataggc actgactctc   1380
tctgcctatt ggtctatttt cccaccctta ggctgctggt ctgagcctag gagatctctc   1440
gaggtcgacg gtatcgatgg gtacagcttc tagagatccc tcgacctcga gatccattgt   1500
gctctaaagg agatacccgg ccagacaccc tcacctgcgg tgcccagctg cccaggctga   1560
ggcaagagaa ggccagaaac catgcccatg ggtctctgc aaccgctggc caccttgtac    1620
ctgctgggga tgctggtcgc ttccgtgcta gctgtggaga agctgtgggt gactgtatac   1680
tatggggtgc ctgtgtggaa ggaggccacc accaccctgt tctgtgcctc tgatgccaag   1740
gcctatgaca ctgaggtcca caatgtctgg gccacccatg cctgtgtgcc cactgacccc   1800
aaccctcagg aggtggtgct ggagaatgtg actgagcact tcaacatgtg gaagaacaac   1860
atggtggagc agatgcagga ggacatcatc agcctgtggg accagagcct gaagccctgt   1920
gtgaagctga cccccctgtg tgtgaccctg aactgcaagg atgtgaatgc caccaacacc   1980
accaatgact ctgagggcac tatggagagg ggtgagatca agaactgcag cttcaacatc   2040
accaccagca tcagggatga ggtgcagaag gagtatgccc tgttctacaa gctggatgtg   2100
gtgcccattg acaacaacaa caccagctac aggctgatca gctgtgacac ctctgtgatc   2160
acccaggcct gccccaagat cagctttgag cccatcccca tccactactg tgcccctgct   2220
ggctttgcca tcctgaagtg caatgacaag accttcaatg gcaaaggccc ttgcaagaat   2280
gtgagcactg tgcagtgcac tcatggcatc aggcctgtgg tgagcaccca gctgctgctg   2340
aatggcagcc tggctgagga ggaggtggtg atcaggtctg acaacttcac caacaatgcc   2400
aagaccatca ttgtgcagct gaaggagtct gtggagatca actgcaccag gcccaacaac   2460
aacaccagga agagcattca cattggccct ggcagggcct tctacaccac tggggagatc   2520
attggggaca tcaggcaggc ccactgcaac atcagcaggg ccaagtggaa tgacaccctg   2580
aagcagattg tgatcaagct gagggagcag tttgagaaca agaccattgt gttcaatcac   2640
agctctggtg gtgatcctga gattgtgatg cacagcttca actgtggtgg tgagttcttc   2700
tactgcaaca gcacccagct gttcaacagc acctggaaca acaacactga gggcagcaac   2760
aacactgagg gcaacaccat caccctgcct tgcaggatca agcagatcat caacatgtgg   2820
caggaggtgg gcaaggccat gtatgctcct cccatcaggg gccagatcag gtgcagcagc   2880
aacatcactg gcctgctgct gaccagggat ggtggcatca atgagaatgg cactgagatt   2940
```

```
ttcaggcctg gtggtgggga catgagggac aactggaggt ctgagctgta caagtacaag   3000

gtggtgaaga ttgagcccct tggtgtggct cccaccaagg ctaagcgcag ggtggtgcag   3060

agggagaagc gcgctgtggg ctgaggatcc cgagggtgag tgctcctgcc tggacgcatc   3120

ccggctatgc agccccagtc cagggcagca aggcaggccc cgtctgcctc ttcacccgga   3180

gcctctgccc gccccactca tgctcaggga gagggtcttc tggctttttc ccaggctctg   3240

ggcaggcaca ggctaggtgc ccctaaccca ggccctgcac acaaaggggc aggtgctggg   3300

ctcagacctg ccaagagcca tatccgggag gaccctgccc ctgacctaag cccaccccaa   3360

aggccaaact ctccactccc tcagctcgga caccttctct cctcccagat tccagtaact   3420

cccaatcttc tctctgcaga gcccaaatct tgtgacaaaa ctcacacatg cccaccgtgc   3480

ccaggtaagc cagcccaggc ctcgccctcc agctcaaggc gggacaggtg ccctagagta   3540

gcctgcatcc agggacaggc cccagccggg tgctgacacg tccacctcca tctcttcctc   3600

agcacctgaa ctcctggggg gaccgtcagt cttcctcttc cccccaaaac ccaaggacac   3660

cctcatgatc tcccggaccc ctgaggtcac atgcgtggtg gtggacgtga gccacgaaga   3720

ccctgaggtc aagttcaact ggtacgtgga cggcgtggag gtgcataatg ccaagacaaa   3780

gccgcgggag gagcagtaca acagcacgta ccgggtggtc agcgtcctca ccgtcctgca   3840

ccaggactgg ctgaatggca aggagtacaa gtgcaaggtc tccaacaaag ccctcccagc   3900

ccccatcgag aaaaccatct ccaaagccaa aggtgggacc cgtggggtgc gagggccaca   3960

tggacagagg ccggctcggc ccaccctctg ccctgagagt gaccgctgta ccaacctctg   4020

tcctacaggg cagccccgag aaccacaggt gtacaccctg cccccatccc gggatgagct   4080

gaccaagaac caggtcagcc tgacctgcct ggtcaaaggc ttctatccca gcgacatcgc   4140

cgtggagtgg gagagcaatg ggcagccgga gaacaactac aagaccacgc ctcccgtgct   4200

ggactccgac ggctccttct tcctctacag caagctcacc gtggacaaga gcaggtggca   4260

gcaggggaac gtcttctcat gctccgtgat gcatgaggct ctgcacaacc actacacgca   4320

gaagagcctc tccctgtctc cgggtaaatg agtgcgacgg ccgcaggtaa gccagcccag   4380

gcctcgccct ccagctcaag gcgggacagg tgccctagag tagcctgcat ccagggacag   4440

gccccagccg ggtgctgaca cgtccacctc catctcttcc tcaggtctgc ccgggtggca   4500

tccctgtgac ccctccccag tgcctctcct ggccctggaa gttgccactc cagtgcccac   4560

cagccttgtc ctaataaaat taagttgcat cattttgtct gactaggtgt ccttctataa   4620

tattatgggg tggagggggg tggtatggag caaggggccc aagttaactt gtttattgca   4680

gcttataatg gttacaaata aagcaatagc atcacaaatt tcacaaataa agcatttttt   4740

tcactgcatt ctagttgtgg tttgtccaaa ctcatcaatg tatcttatca tgtctggatc   4800

tgggcgtggt taagggtggg aaagaatata taaggtgggg gtcttatgta gttttgtatc   4860

tgttttgcag cagccgccgc cgccatgagc accaactcgt ttgatggaag cattgtgagc   4920

tcatcggcgg ccgccctatt ctatagtgtc acctaaatgc tagagctcgc tgatcagcct   4980

cgactgtgcc ttctagttgc cagccatctg ttgtttgccc ctcccccgtg ccttccttga   5040

ccctggaagg tgccactccc actgtccttt cctaataaaa tgaggaaatt gcatcgcatt   5100

gtctgagtag gtgtcattct attctggggg gtggggtggg gcaggacagc aaggggagg    5160

attgggaaga caatagcagg catgctgggg atgcggtggg ctctatggct tctgaggcgg   5220

aaagaaccta tggcttctga ggcggaaaga accaaccacc gcggtggcgg ccgccacaca   5280

aaaaaccaac acacagatgt aatgaaaata aagatatttt atttctagag aaacgatatg   5340
```

```
ggctgaatac ggatccgtat tcagcccata tcgtttcctg caggaattcg ccctttagat   5400
atcatcgatg tctcggcggt ggtggcgcgt cgcgccgctg ggttttatag ggcgccgccg   5460
cggccgctcg agccataaaa ggcaactttc ggaacggcgc acgctgattg gccccgcgcc   5520
gctcactcac cggcttcgcc gcacagtgca gcattttttt accccctctc ccctcctttt   5580
gcgaaaaaaa aaaagagcga gagcgagatt gaggaagagg aggagggaga gttttggcgt   5640
tggccgcctt ggggtgctgg gcgtcgacga tatctaaggg cgaattcgat atcaagctag   5700
cttgtcgact cgaagatctg ggcgtggtta agggtgggaa agaatatata aggtgggggt   5760
cttatgtagt tttgtatctg ttttgcagca gccgccgccg ccatgagcac caactcgttt   5820
gatggaagca ttgtgagctc atatttgaca acgcgcatgc ccccatgggc cggggtgcgt   5880
cagaatgtga tgggctccag cattgatggt cgccccgtcc tgcccgcaaa ctctactacc   5940
ttgacctacg agaccgtgtc tggaacgccg ttggagactg cagcctccgc cgccgcttca   6000
gccgctgcag ccaccgcccg cgggattgtg actgactttg ctttcctgag cccgcttgca   6060
agcagtgcag cttcccgttc atccgcccgc gatgacaagt tgacggctct tttggcacaa   6120
ttggattctt tgacccggga acttaatgtc gtttctcagc agctgttgga tctgcgccag   6180
caggtttctg ccctgaaggc ttcctcccct cccaatgcgg tttaaaacat aaataaaaaa   6240
ccagactctg tttggatttg gatcaagcaa gtgtcttgct gtctttattt aggggttttg   6300
cgcgcgcggt aggcccggga ccagcggtct cggtcgttga gggtcctgtg tattttttcc   6360
aggacgtggt aaaggtgact ctggatgttc agatacatgg gcataagccc gtctctgggg   6420
tggaggtagc accactgcag agcttcatgc tgcggggtgg tgttgtagat gatccagtcg   6480
tagcaggagc gctgggcgtg gtgcctaaaa atgtctttca gtagcaagct gattgccagg   6540
ggcaggccct tggtgtaagt gtttacaaag cggttaagct gggatgggtg catacgtggg   6600
gatatgagat gcatcttgga ctgtattttt aggttggcta tgttcccagc catatccctc   6660
cggggattca tgttgtgcag aaccaccagc acagtgtatc cggtgcactt gggaaatttg   6720
tcatgtagct tagaaggaaa tgcgtggaag aacttggaga cgcccttgtg acctccaaga   6780
ttttccatgc attcgtccat aatgatggca atgggcccac gggcggcggc ctgggcgaag   6840
atatttctgg gatcactaac gtcatagttg tgttccagga tgagatcgtc ataggccatt   6900
tttacaaagc gcgggcggag ggtgccagac tgcggtataa tggttccatc cggcccaggg   6960
gcgtagttac cctcacagat ttgcatttcc cacgctttga gttcagatgg ggggatcatg   7020
tctacctgcg gggcgatgaa gaaaacggtt tccggggtag gggagatcag ctgggaagaa   7080
agcaggttcc tgagcagctg cgacttaccg cagccggtgg gcccgtaaat cacacctatt   7140
accgggtgca actggtagtt aagagagctg cagctgccgt catccctgag caggggggcc   7200
acttcgttaa gcatgtccct gactcgcatg ttttccctga ccaaatccgc cagaaggcgc   7260
tcgccgccca gcgatagcag ttcttgcaag gaagcaaagt ttttcaacgg tttgagaccg   7320
tccgccgtag gcatgctttt gagcgtttga ccaagcagtt ccaggcggtc ccacagctcg   7380
gtcacctgct ctacggcatc tcgatccagc atatctcctc gtttcgcggg ttggggcggc   7440
tttcgctgta cggcagtagt cggtgctcgt ccagacgggc cagggtcatg tctttccacg   7500
ggcgcagggt cctcgtcagc gtagtctggg tcacggtgaa ggggtgcgct ccgggctgcg   7560
cgctggccag ggtgcgcttg aggctggtcc tgctggtgct gaagcgctgc cggtcttcgc   7620
cctgcgcgtc ggccaggtag catttgacca tggtgtcata gtccagcccc tccgcggcgt   7680
ggcccttggc gcgcagcttg cccttggagg aggcgccgca cgaggggcag tgcagacttt   7740
```

```
tgagggcgta gagcttgggc gcgagaaata ccgattccgg ggagtaggca tccgcgccgc   7800

aggccccgca gacggtctcg cattccacga gccaggtgag ctctggccgt tcggggtcaa   7860

aaaccaggtt tcccccatgc tttttgatgc gtttcttacc tctggtttcc atgagccggt   7920

gtccacgctc ggtgacgaaa aggctgtccg tgtccccgta tacagacttg agagggagtt   7980

taaacgaatt caatagcttg ttgcatgggc ggcgatataa aatgcaaggt gctgctcaaa   8040

aaatcaggca aagcctcgcg caaaaaagaa agcacatcgt agtcatgctc atgcagataa   8100

aggcaggtaa gctccggaac caccacagaa aaagacacca tttttctctc aaacatgtct   8160

gcgggtttct gcataaacac aaaataaaat aacaaaaaaa catttaaaca ttagaagcct   8220

gtcttacaac aggaaaaaca acccttataa gcataagacg gactacggcc atgccggcgt   8280

gaccgtaaaa aaactggtca ccgtgattaa aaagcaccac cgacagctcc tcggtcatgt   8340

ccggagtcat aatgtaagac tcggtaaaca catcaggttg attcatcggt cagtgctaaa   8400

aagcgaccga aatagcccgg gggaatacat acccgcaggc gtagagacaa cattacagcc   8460

cccataggag gtataacaaa attaatagga gagaaaaaca cataaacacc tgaaaaaccc   8520

tcctgcctag gcaaaatagc accctcccgc tccagaacaa catacagcgc ttcacagcgg   8580

cagcctaaca gtcagcctta ccagtaaaaa agaaaaccta ttaaaaaaac accactcgac   8640

acggcaccag ctcaatcagt cacagtgtaa aaaagggcca agtgcagagc gagtatatat   8700

aggactaaaa aatgacgtaa cggttaaagt ccacaaaaaa cacccagaaa accgcacgcg   8760

aacctacgcc cagaaacgaa agccaaaaaa cccacaactt cctcaaatcg tcacttccgt   8820

tttcccacgt tacgtaactt cccattttaa gaaaactaca attcccaaca catacaagtt   8880

actccgccct aaaacctacg tcacccgccc cgttcccacg ccccgcgcca cgtcacaaac   8940

tccaccccct cattatcata ttggcttcaa tccaaaataa ggtatattat tgatgatgtt   9000

aattaacatg catggatcca tatgcggtgt gaaataccgc acagatgcgt aaggagaaaa   9060

taccgcatca ggcgctcttc cgcttcctcg ctcactgact cgctgcgctc ggtcgttcgg   9120

ctgcggcgag cggtatcagc tcactcaaag gcggtaatac ggttatccac agaatcaggg   9180

gataacgcag gaaagaacat gtgagcaaaa ggccagcaaa aggccaggaa ccgtaaaaag   9240

gccgcgttgc tggcgttttt ccataggctc cgcccccctg acgagcatca caaaaatcga   9300

cgctcaagtc agaggtggcg aaacccgaca ggactataaa gataccaggc gtttccccct   9360

ggaagctccc tcgtgcgctc tcctgttccg accctgccgc ttaccggata cctgtccgcc   9420

tttctccctt cgggaagcgt ggcgctttct catagctcac gctgtaggta tctcagttcg   9480

gtgtaggtcg ttcgctccaa gctgggctgt gtgcacgaac cccccgttca gcccgaccgc   9540

tgcgccttat ccggtaacta tcgtcttgag tccaacccgg taagacacga cttatcgcca   9600

ctggcagcag ccactggtaa caggattagc agagcgaggt atgtaggcgg tgctacagag   9660

ttcttgaagt ggtggcctaa ctacggctac actagaagga cagtatttgg tatctgcgct   9720

ctgctgaagc cagttacctt cggaaaaaga gttggtagct cttgatccgg caaacaaacc   9780

accgctggta gcggtggttt ttttgtttgc aagcagcaga ttacgcgcag aaaaaaagga   9840

tctcaagaag atcctttgat cttttctacg gggtctgacg ctcagtggaa cgaaaactca   9900

cgttaaggga ttttggtcat gagattatca aaaaggatct tcacctagat ccttttaaat   9960

taaaaatgaa gttttaaatc aatctaaagt atatatgagt aaacttggtc tgacagttac  10020

caatgcttaa tcagtgaggc acctatctca gcgatctgtc tatttcgttc atccatagtt  10080

gcctgactcc ccgtcgtgta gataactacg atacgggagg gcttaccatc tggccccagt  10140
```

```
gctgcaatga taccgcgaga cccacgctca ccggctccag atttatcagc aataaaccag  10200

ccagccggaa gggccgagcg cagaagtggt cctgcaactt tatccgcctc catccagtct  10260

attaattgtt gccgggaagc tagagtaagt agttcgccag ttaatagttt gcgcaacgtt  10320

gttgccattg ctgcagccat gagattatca aaaaggatct tcacctagat ccttttcacg  10380

tagaaagcca gtccgcagaa acggtgctga ccccggatga atgtcagcta ctgggctatc  10440

tggacaaggg aaaacgcaag cgcaaagaga aagcaggtag cttgcagtgg gcttacatgg  10500

cgatagctag actgggcggt tttatggaca gcaagcgaac cggaattgcc agctggggcg  10560

ccctctggta aggttgggaa gccctgcaaa gtaaactgga tggctttctc gccgccaagg  10620

atctgatggc gcaggggatc aagctctgat caagagacag gatgaggatc gtttcgcatg  10680

attgaacaag atggattgca cgcaggttct ccggccgctt gggtggagag gctattcggc  10740

tatgactggg cacaacagac aatcggctgc tctgatgccg ccgtgttccg gctgtcagcg  10800

caggggcgcc cggttctttt tgtcaagacc gacctgtccg gtgccctgaa tgaactgcaa  10860

gacgaggcag cgcggctatc gtggctggcc acgacgggcg ttccttgcgc agctgtgctc  10920

gacgttgtca ctgaagcggg aagggactgg ctgctattgg gcgaagtgcc ggggcaggat  10980

ctcctgtcat ctcaccttgc tcctgccgag aaagtatcca tcatggctga tgcaatgcgg  11040

cggctgcata cgcttgatcc ggctacctgc ccattcgacc accaagcgaa acatcgcatc  11100

gagcgagcac gtactcggat ggaagccggt cttgtcgatc aggatgatct ggacgaagag  11160

catcaggggc tcgcgccagc cgaactgttc gccaggctca aggcgagcat gcccgacggc  11220

gaggatctcg tcgtgaccca tggcgatgcc tgcttgccga atatcatggt ggaaaatggc  11280

cgcttttctg gattcatcga ctgtggccgg ctgggtgtgg cggaccgcta tcaggacata  11340

gcgttggcta cccgtgatat tgctgaagag cttggcggcg aatgggctga ccgcttcctc  11400

gtgctttacg gtatcgccgc tcccgattcg cagcgcatcg ccttctatcg ccttcttgac  11460

gagttcttct gaattttgtt aaaatttttg ttaaatcagc tcatttttta accaataggc  11520

cgaaatcggc aacatccctt ataaatcaaa agaatagacc gcgatagggt tgagtgttgt  11580

tccagtttgg aacaagagtc cactattaaa gaacgtggac tccaacgtca aagggcgaaa  11640

aaccgtctat cagggcgatg gcccactacg tgaaccatca cccaaatcaa gtttttgcg  11700

gtcgaggtgc cgtaaagctc taaatcggaa ccctaaaggg agcccccgat ttagagcttg  11760

acggggaaag ccggcgaacg tggcgagaaa ggaagggaag aaagcgaaag gagcgggcgc  11820

tagggcgctg gcaagtgtag cggtcacgct gcgcgtaacc accacacccg cgcgcttaat  11880

gcgccgctac agggcgcgtc cattcgccat tcaggatcga attaattctt aat         11933
```

<210> SEQ ID NO 3
<211> LENGTH: 46
<212> TYPE: DNA
<213> ORGANISM: Artificial Sequence
<220> FEATURE:
<223> OTHER INFORMATION: toll-like receptor 3 (TLR-3) agonist

<400> SEQUENCE: 3

```
gaaacgatat gggctgaata cttaagtatt cagcccatat cgtttc                46
```

<210> SEQ ID NO 4
<211> LENGTH: 1190
<212> TYPE: DNA
<213> ORGANISM: Artificial Sequence
<220> FEATURE:
<223> OTHER INFORMATION: toll-like receptor 3 (TLR-3) agonist

<400> SEQUENCE: 4

```
cgggcccccc ctcgaggtcg acggtatcga taagcttgat atcgaattcg cccttagata     60
tcgtcgacgc ccagcacccc aaggcggcca acgccaaaac tctccctcct cctcttcctc    120
aatctcgctc tcgctctttt tttttttcgc aaaaggaggg gagagggggt aaaaaaatgc    180
tgcactgtgc ggcgaagccg gtgagtgagc ggcgcggggc caatcagcgt gcgccgttcc    240
gaaagttgcc ttttatggct cgagcggccg cggcggcgcc ctataaaacc cagcggcgcg    300
acgcgccacc accgccgaga catcgatgat atctaaaggg cgaattcctg cagcccgggg    360
gatccactag tctagatgca tgctcgagcg gccgccagtg tgatggatat ctgcagaatt    420
cgcccttcag ctgcggatcc attcgccatt caggctgcgc aactgttggg aagggcgatc    480
ggtgcgggcc tcttcgctat tacgccagct ggcgaaaggg ggatgtgctg caaggcgatt    540
aagttgggta acgccagggt tttcccagtc acgacgttgt aaaacgacgg ccagtgaatt    600
gtaatacgac tcactatagg gcgaattggg taccgggccc cccctcgagg tcgacggtat    660
cgataagctt gatatcgaat tcctgcagcc cgggggatcc actagtttct agaaataaaa    720
tatctttatt ttcattacat ctgtgtgttg gttttttgtg tggcggccgc caccgcggtg    780
gagctatcga attcaagctt gtcgactcga agatcctaga ctagtggatc ccccgggctg    840
caggaattcg ccctttagat atcatcgatg tctcggcggt ggtggcgcgt cgcgccgctg    900
ggttttatag ggcgccgccg cggccgctcg agccataaaa ggcaactttc ggaacggcgc    960
acgctgattg gccccgcgcc gctcactcac cggcttcgcc gcacagtgca gcattttttt   1020
accccctctc ccctcctttt gcgaaaaaaa aaaagagcga gagcgagatt gaggaagagg   1080
aggagggaga gttttggcgt tggccgcctt ggggtgctgg gcgtcgacga tatctaaggg   1140
cgaattcgat atcaagctta tcgataccgt cgacctcgag ggggggcccg              1190
```

<210> SEQ ID NO 5
<211> LENGTH: 1757
<212> TYPE: DNA
<213> ORGANISM: Artificial Sequence
<220> FEATURE:
<223> OTHER INFORMATION: toll-like receptor 3 (TLR-3) agonist

<400> SEQUENCE: 5

```
cgggcccccc ctcgaggtcg acggtatcga taagcttgat atcgaattcg cccttagata     60
tcgtcgacgc ccagcacccc aaggcggcca acgccaaaac tctccctcct cctcttcctc    120
aatctcgctc tcgctctttt tttttttcgc aaaaggaggg gagagggggt aaaaaaatgc    180
tgcactgtgc ggcgaagccg gtgagtgagc ggcgcggggc caatcagcgt gcgccgttcc    240
gaaagttgcc ttttatggct cgagcggccg cggcggcgcc ctataaaacc cagcggcgcg    300
acgcgccacc accgccgaga catcgatgat atctaaaggg cgaattcctg cagcccgggg    360
gatccactag tctagatgca tgctcgagcg gccgccagtg tgatggatat ctgcagaatt    420
cgcccttcag ctgcggatcc attcgccatt caggctgcgc aactgttggg aagggcgatc    480
ggtgcgggcc tcttcgctat tacgccagct ggcgaaaggg ggatgtgctg caaggcgatt    540
aagttgggta acgccagggt tttcccagtc acgacgttgt aaaacgacgg ccagtgaatt    600
gtaatacgac tcactatagg gcgaattggg taccgggccc cccctcgagg tcgacggtat    660
cgataagctt gatatcgaat tcctgcagcc cgggggatcc actagtttct agaaataaaa    720
tatctttatt ttcattacat ctgtgtgttg gttttttgtg tggcggccgc caccgcggtg    780
gagctatcga attcaagctt gtcgactcga agatcgtaca caggaagtga caattttcgc    840
```

```
gcggttttag gcggatgttg tagtaaattt gggcgtaacc gagtaagatt tggccatttt    900

cgcgggaaaa ctgaataaga ggaagtgaaa tctgaataat tttgtgttac tcatagcgcg    960

taatactggt accgggcccc ccctcgaggt cgacggtatc gataagcttg atatcgaatt   1020

cgcccttaga tatcgtcgac gcccagcacc ccaaggcggc caacgccaaa actctccctc   1080

ctcctcttcc tcaatctcgc tctcgctctt tttttttttc gcaaaaggag gggagagggg   1140

gtaaaaaaat gctgcactgt gcggcgaagc cggtgagtga gcggcgcggg gccaatcagc   1200

gtgcgccgtt ccgaaagttg ccttttatgg ctcgagcggc cgcggcggcg ccctataaaa   1260

cccagcggcg cgacgcgcca ccaccgccga gacatcgatg atatctaaag ggcgaattcc   1320

tgcagcccgg gggatccact agtctagaac tagtggatcc cccgggctgc aggaattcga   1380

tatcaagctt atcgataccg tcgacctcga ggggggggcc ggtacccaat tcgccctata   1440

gtgagtcgta ttacaattca ctggccgtcg ttttacaacg tcgtgactgg gaaaaccctg   1500

gcgttaccca acttaatcgc cttgcagcac atcccccttt cgccagctgg cgtaatagcg   1560

aagaggcccg caccgatcgc ccttcccaac agttgcgcag cctgaatggc gaatggatcc   1620

gcagctgaag ggcgaattct gcagatatcc atcacactgg cggccgctcg agcatgcatc   1680

tagaaataaa atatctttat tttcattaca tctgtgtgtt ggtttttttgt gtggcggccg   1740

ccaccgcggt ggagcta                                                  1757
```

```
<210> SEQ ID NO 6
<211> LENGTH: 10153
<212> TYPE: DNA
<213> ORGANISM: Artificial Sequence
<220> FEATURE:
<223> OTHER INFORMATION: chimeric adenoviral vector encoding influenza
      hemagglutinin (HA) and TLR-3 agonist luc in same
      orientation

<400> SEQUENCE: 6

taacatcatc aataatatac cttattttgg attgaagcca atatgataat gagggggtgg     60

agtttgtgac gtggcgcggg gcgtgggaac ggggcgggtg acgtagtagt gtggcggaag    120

tgtgatgttg caagtgtggc ggaacacatg taagcgacgg atgtggcaaa agtgacgttt    180

ttggtgtgcg ccggtgtaca caggaagtga caattttcgc gcggttttag gcggatgttg    240

tagtaaattt gggcgtaacc gagtaagatt tggccatttt cgcgggaaaa ctgaataaga    300

ggaagtgaaa tctgaataat tttgtgttac tcatagcgcg taatactgct agagatctgg    360

cgaaaggggg atgtgctgca aggcgattaa gttgggtaac gccagggttt tcccagtcac    420

gacgttgtaa aacgacggcc agtgaattgt aatacgactc actatagggc gaattgggta    480

ctggccacag agcttggccc attgcatacg ttgtatccat atcataatat gtacatttat    540

attggctcat gtccaacatt accgccatgt tgacattgat tattgactag ttattaatag    600

taatcaatta cggggtcatt agttcatagc ccatatatgg agttccgcgt tacataactt    660

acggtaaatg gcccgcctgg ctgaccgccc aacgaccccc gcccattgac gtcaataatg    720

acgtatgttc ccatagtaac gccaataggg actttccatt gacgtcaatg ggtggagtat    780

ttacggtaaa ctgcccactt ggcagtacat caagtgtatc atatgccaag tacgccccct    840

attgacgtca atgacggtaa atggcccgcc tggcattatg cccagtacat gaccttatgg    900

gactttccta cttggcagta catctacgta ttagtcatcg ctattaccat ggtgatgcgg    960

ttttggcagt acatcaatgg gcgtggatag cggtttgact cacggggatt tccaagtctc   1020

caccccattg acgtcaatgg gagtttgttt tggcaccaaa atcaacggga ctttccaaaa   1080
```

```
tgtcgtaaca actccgcccc attgacgcaa atgggcggta ggcgtgtacg gtgggaggtc   1140
tatataagca gagctcgttt agtgaaccgt cagatcgcct ggagacgcca tccacgctgt   1200
tttgacctcc atagaagaca ccgggaccga tccagcctga ctctagccta gctctgaagt   1260
tggtggtgag gccctgggca ggttggtatc aaggttacaa gacaggttta aggagaccaa   1320
tagaaactgg gcatgtggag acagagaaga ctcttgggtt tctgataggc actgactctc   1380
tctgcctatt ggtctatttt cccaccctta ggctgctggt ctgagcctag gagatctctc   1440
gaggtcgacg gtatcgatgc caccatggag aaaatcgtcc tgttgctcgc tattgtgtct   1500
ctagtgaaga gcgatcaaat ttgtatcggc taccatgcca ataactcaac agagcaggtc   1560
gatactatca tggagaaaaa cgtaacagtt actcatgccc aagacatctt ggaaaagacc   1620
cacaacggca aactttgcga cctggatgga gtgaagcccc tgatcctccg ggactgttca   1680
gtcgctggtt ggctgctcgg gaaccctatg tgtgatgagt ttatcaacgt gcctgaatgg   1740
tcttacattg tggagaaggc taaccctacc aatgacctct gctatcctgg gtcatttaac   1800
gattacgagg aactgaaaca cctgttgtct agaattaacc actttgaaaa gatacagatt   1860
atacccaagt ctagttggag tgatcacgaa gcctcctcag gcgttagctc agcgtgtccc   1920
tatctgggct ctccatcctt ctttagaaat gtggtctggt taatcaaaaa gaacagtacc   1980
tacccaacca tcaaaaagtc ttataacaat accaatcagg aggacctgct cgtgttgtgg   2040
ggtatccatc acccgaacga cgccgctgaa cagactaggc tgtatcagaa ccccactaca   2100
tacatcagta ttggcacgag tactctgaac cagcgattag tgccaaagat tgcaacacgg   2160
agcaaagtaa atgggcaatc tggcaggatg gagttttttct ggacaatctt aaaacccaac   2220
gatgcgataa atttcgagtc caatggcaat ttcatcgccc ctgaatacgc ctataagatc   2280
gtgaaaaagg gggactctgc aattatgaag tccgaattag agtatggcaa ttgcaacacg   2340
aagtgccaga caccaatggg agccattaat agctcaatgc ccttccataa tattcatcca   2400
ttgaccattg gggagtgccc aaagtacgtg aagtccaacc gcctggtcct cgcaaccggt   2460
ctaagaaata gcccgcagag agaatcgcgg aggaagaaac gtggcctgtt tggcgcgatt   2520
gccggattca tcgagggagg ctggcagggt atggtcgatg gttggtacgg ataccaccat   2580
agcaacgaac aggggtccgg ctatgcagca gataaggaga gcactcagaa agctattgac   2640
ggagttacaa acaaggttaa tagtattata gataaaatga acacgcaatt cgaggccgtt   2700
gggagggagt ttaacaatct ggaacgccgg atcgaaaatc tgaataagaa aatggaagac   2760
ggcttccttg acgtgtggac ttataatgca gagctgcttg tactcatgga gaacgagagg   2820
accctggatt tccacgatag caacgtgaag aacctttacg acaaggtgag acttcagctc   2880
cgagacaacg ccaaggagct ggggaatgga tgcttcgagt ttaccacaa atgtgacaat   2940
gagtgcatgg aaagtatacg caacgggacc tacaattacc ctcagtatag cgaagaggct   3000
cggctcaaac gcgaagagat aagcggggtg aaattggaat caatcggaac atatcaaatc   3060
ctgtccatct attccaccgt cgcctcttcg ctggccctcg ctatcatgat ggctggtctg   3120
tccctatgga tgtgttccaa tggaagcctt cagtgccgta tttgtatatg agcggccgcc   3180
ctattctata gtgtcaccta aatgctagag ctcgctgatc agcctcgact gtgccttcta   3240
gttgccagcc atctgttgtt tgcccctccc ccgtgccttc cttgaccctg gaaggtgcca   3300
ctcccactgt cctttcctaa taaaatgagg aaattgcatc gcattgtctg agtaggtgtc   3360
attctattct ggggggtggg gtggggcagg acagcaaggg ggaggattgg gaagacaata   3420
gcaggcatgc tggggatgcg gtgggctcta tggcttctga ggcggaaaga accaaccacc   3480
```

```
gcggtggcgg ccgccacaca aaaaaccaac acacagatgt aatgaaaata aagatatttt   3540
atttctagag aaacgatatg ggctgaatac ggatccgtat tcagcccata tcgtttcctg   3600
caggaattcg ccctttagat atcatcgatg tctcggcggt ggtggcgcgt cgcgccgctg   3660
ggttttatag ggcgccgccg cggccgctcg agccataaaa ggcaactttc ggaacggcgc   3720
acgctgattg gccccgcgcc gctcactcac cggcttcgcc gcacagtgca gcattttttt   3780
accccctctc ccctcctttt gcgaaaaaaa aaaagagcga gagcgagatt gaggaagagg   3840
aggagggaga gttttggcgt tggccgcctt ggggtgctgg gcgtcgacga tatctaaggg   3900
cgaattcgat atcaagctag cttgtcgact cgaagatctg ggcgtggtta agggtgggaa   3960
agaatatata aggtgggggt cttatgtagt tttgtatctg ttttgcagca gccgccgccg   4020
ccatgagcac caactcgttt gatggaagca ttgtgagctc atatttgaca acgcgcatgc   4080
ccccatgggc cggggtgcgt cagaatgtga tgggctccag cattgatggt cgccccgtcc   4140
tgcccgcaaa ctctactacc ttgacctacg agaccgtgtc tggaacgccg ttggagactg   4200
cagcctccgc cgccgcttca gccgctgcag ccaccgcccg cgggattgtg actgactttg   4260
ctttcctgag cccgcttgca agcagtgcag cttcccgttc atccgcccgc gatgacaagt   4320
tgacggctct tttggcacaa ttggattctt tgacccggga acttaatgtc gtttctcagc   4380
agctgttgga tctgcgccag caggtttctg ccctgaaggc ttcctcccct cccaatgcgg   4440
tttaaaacat aaataaaaaa ccagactctg tttggatttg gatcaagcaa gtgtcttgct   4500
gtctttattt aggggttttg cgcgcgcggt aggcccggga ccagcggtct cggtcgttga   4560
gggtcctgtg tatttttttcc aggacgtggt aaaggtgact ctggatgttc agatacatgg   4620
gcataagccc gtctctgggg tggaggtagc accactgcag agcttcatgc tgcggggtgg   4680
tgttgtagat gatccagtcg tagcaggagc gctgggcgtg gtgcctaaaa atgtctttca   4740
gtagcaagct gattgccagg ggcaggccct tggtgtaagt gtttacaaag cggttaagct   4800
gggatgggtg catacgtggg gatatgagat gcatcttgga ctgtattttt aggttggcta   4860
tgttcccagc catatccctc cggggattca tgttgtgcag aaccaccagc acagtgtatc   4920
cggtgcactt gggaaatttg tcatgtagct tagaaggaaa tgcgtggaag aacttggaga   4980
cgcccttgtg acctccaaga ttttccatgc attcgtccat aatgatggca atgggcccac   5040
gggcggcggc ctgggcgaag atatttctgg gatcactaac gtcatagttg tgttccagga   5100
tgagatcgtc ataggccatt tttacaaagc gcgggcggag ggtgccagac tgcggtataa   5160
tggttccatc cggcccaggg gcgtagttac cctcacagat ttgcatttcc cacgctttga   5220
gttcagatgg ggggatcatg tctacctgcg gggcgatgaa gaaaacggtt tccggggtag   5280
gggagatcag ctgggaagaa agcaggttcc tgagcagctg cgacttaccg cagccggtgg   5340
gcccgtaaat cacacctatt accgggtgca actggtagtt aagagagctg cagctgccgt   5400
catccctgag caggggggcc acttcgttaa gcatgtccct gactcgcatg ttttccctga   5460
ccaaatccgc cagaaggcgc tcgccgccca gcgatagcag ttcttgcaag gaagcaaagt   5520
ttttcaacgg tttgagaccg tccgccgtag gcatgctttt gagcgtttga ccaagcagtt   5580
ccaggcggtc ccacagctcg gtcacctgct ctacggcatc tcgatccagc atatctcctc   5640
gtttcgcggg ttggggcggc tttcgctgta cggcagtagt cggtgctcgt ccagacgggc   5700
cagggtcatg tctttccacg ggcgcagggt cctcgtcagc gtagtctggg tcacggtgaa   5760
ggggtgcgct ccgggctgcg cgctggccag ggtgcgcttg aggctggtcc tgctggtgct   5820
gaagcgctgc cggtcttcgc cctgcgcgtc ggccaggtag catttgacca tggtgtcata   5880
```

```
gtccagcccc tccgcggcgt ggcccttggc gcgcagcttg cccttggagg aggcgccgca   5940
cgaggggcag tgcagacttt tgagggcgta gagcttgggc gcgagaaata ccgattccgg   6000
ggagtaggca tccgcgccgc aggccccgca gacggtctcg cattccacga gccaggtgag   6060
ctctggccgt tcggggtcaa aaaccaggtt tcccccatgc tttttgatgc gtttcttacc   6120
tctggtttcc atgagccggt gtccacgctc ggtgacgaaa aggctgtccg tgtccccgta   6180
tacagacttg agagggagtt taaacgaatt caatagcttg ttgcatgggc ggcgatataa   6240
aatgcaaggt gctgctcaaa aaatcaggca aagcctcgcg caaaaaagaa agcacatcgt   6300
agtcatgctc atgcagataa aggcaggtaa gctccggaac caccacagaa aaagacacca   6360
tttttctctc aaacatgtct gcgggtttct gcataaacac aaaataaaat aacaaaaaaa   6420
catttaaaca ttagaagcct gtcttacaac aggaaaaaca acccttataa gcataagacg   6480
gactacggcc atgccggcgt gaccgtaaaa aaactggtca ccgtgattaa aaagcaccac   6540
cgacagctcc tcggtcatgt ccggagtcat aatgtaagac tcggtaaaca catcaggttg   6600
attcatcggt cagtgctaaa aagcgaccga aatagcccgg gggaatacat acccgcaggc   6660
gtagagacaa cattacagcc cccataggag gtataacaaa attaatagga gagaaaaaca   6720
cataaacacc tgaaaaaccc tcctgcctag gcaaaatagc accctcccgc tccagaacaa   6780
catacagcgc ttcacagcgg cagcctaaca gtcagcctta ccagtaaaaa agaaaaccta   6840
ttaaaaaaac accactcgac acggcaccag ctcaatcagt cacagtgtaa aaaagggcca   6900
agtgcagagc gagtatatat aggactaaaa aatgacgtaa cggttaaagt ccacaaaaaa   6960
cacccagaaa accgcacgcg aacctacgcc cagaaacgaa agccaaaaaa cccacaactt   7020
cctcaaatcg tcacttccgt ttcccacgt tacgtaactt cccattttaa gaaaactaca   7080
attcccaaca catacaagtt actccgccct aaaacctacg tcacccgccc cgttcccacg   7140
ccccgcgcca cgtcacaaac tccacccct cattatcata ttggcttcaa tccaaaataa   7200
ggtatattat tgatgatgtt aattaacatg catggatcca tatgcggtgt gaaataccgc   7260
acagatgcgt aaggagaaaa taccgcatca ggcgctcttc cgcttcctcg ctcactgact   7320
cgctgcgctc ggtcgttcgg ctgcggcgag cggtatcagc tcactcaaag gcggtaatac   7380
ggttatccac agaatcaggg gataacgcag gaaagaacat gtgagcaaaa ggccagcaaa   7440
aggccaggaa ccgtaaaaag gccgcgttgc tggcgttttt ccataggctc cgcccccctg   7500
acgagcatca caaaaatcga cgctcaagtc agaggtggcg aaacccgaca ggactataaa   7560
gataccaggc gtttccccct ggaagctccc tcgtgcgctc tcctgttccg accctgccgc   7620
ttaccggata cctgtccgcc tttctccctt cgggaagcgt ggcgctttct catagctcac   7680
gctgtaggta tctcagttcg gtgtaggtcg ttcgctccaa gctgggctgt gtgcacgaac   7740
cccccgttca gcccgaccgc tgcgccttat ccggtaacta tcgtcttgag tccaacccgg   7800
taagacacga cttatcgcca ctggcagcag ccactggtaa caggattagc agagcgaggt   7860
atgtaggcgg tgctacagag ttcttgaagt ggtggcctaa ctacggctac actagaagga   7920
cagtatttgg tatctgcgct ctgctgaagc cagttacctt cggaaaaaga gttggtagct   7980
cttgatccgg caaacaaacc accgctggta gcggtggttt ttttgtttgc aagcagcaga   8040
ttacgcgcag aaaaaaagga tctcaagaag atcctttgat cttttctacg gggtctgacg   8100
ctcagtggaa cgaaaactca cgttaaggga ttttggtcat gagattatca aaaaggatct   8160
tcacctagat ccttttaaat taaaaatgaa gttttaaatc aatctaaagt atatatgagt   8220
aaacttggtc tgacagttac caatgcttaa tcagtgaggc acctatctca gcgatctgtc   8280
```

tatttcgttc atccatagtt gcctgactcc ccgtcgtgta gataactacg atacgggagg 8340
gcttaccatc tggccccagt gctgcaatga taccgcgaga cccacgctca ccggctccag 8400
atttatcagc aataaaccag ccagccggaa gggccgagcg cagaagtggt cctgcaactt 8460
tatccgcctc catccagtct attaattgtt gccgggaagc tagagtaagt agttcgccag 8520
ttaatagttt gcgcaacgtt gttgccattg ctgcagccat gagattatca aaaaggatct 8580
tcacctagat ccttttcacg tagaaagcca gtccgcagaa acggtgctga ccccggatga 8640
atgtcagcta ctgggctatc tggacaaggg aaaacgcaag cgcaaagaga aagcaggtag 8700
cttgcagtgg gcttacatgg cgatagctag actgggcggt tttatggaca gcaagcgaac 8760
cggaattgcc agctggggcg ccctctggta aggttgggaa gccctgcaaa gtaaactgga 8820
tggctttctc gccgccaagg atctgatggc gcaggggatc aagctctgat caagagacag 8880
gatgaggatc gtttcgcatg attgaacaag atggattgca cgcaggttct ccggccgctt 8940
gggtggagag gctattcggc tatgactggg cacaacagac aatcggctgc tctgatgccg 9000
ccgtgttccg gctgtcagcg caggggcgcc cggttctttt tgtcaagacc gacctgtccg 9060
gtgccctgaa tgaactgcaa gacgaggcag cgcggctatc gtggctggcc acgacgggcg 9120
ttccttgcgc agctgtgctc gacgttgtca ctgaagcggg aagggactgg ctgctattgg 9180
gcgaagtgcc ggggcaggat ctcctgtcat ctcaccttgc tcctgccgag aaagtatcca 9240
tcatggctga tgcaatgcgg cggctgcata cgcttgatcc ggctacctgc ccattcgacc 9300
accaagcgaa acatcgcatc gagcgagcac gtactcggat ggaagccggt cttgtcgatc 9360
aggatgatct ggacgaagag catcaggggc tcgcgccagc cgaactgttc gccaggctca 9420
aggcgagcat gcccgacggc gaggatctcg tcgtgaccca tggcgatgcc tgcttgccga 9480
atatcatggt ggaaaatggc cgcttttctg gattcatcga ctgtggccgg ctgggtgtgg 9540
cggaccgcta tcaggacata gcgttggcta cccgtgatat tgctgaagag cttggcggcg 9600
aatgggctga ccgcttcctc gtgctttacg gtatcgccgc tcccgattcg cagcgcatcg 9660
ccttctatcg ccttcttgac gagttcttct gaattttgtt aaaatttttg ttaaatcagc 9720
tcatttttta accaataggc cgaaatcggc aacatccctt ataaatcaaa agaatagacc 9780
gcgatagggt tgagtgttgt tccagtttgg aacaagagtc cactattaaa gaacgtggac 9840
tccaacgtca aagggcgaaa aaccgtctat cagggcgatg gcccactacg tgaaccatca 9900
cccaaatcaa gttttttgcg gtcgaggtgc cgtaaagctc taaatcggaa ccctaaaggg 9960
agcccccgat ttagagcttg acggggaaag ccggcgaacg tggcgagaaa ggaagggaag 10020
aaagcgaaag gagcgggcgc tagggcgctg gcaagtgtag cggtcacgct gcgcgtaacc 10080
accacacccg cgcgcttaat gcgccgctac agggcgcgtc cattcgccat tcaggatcga 10140
attaattctt aat 10153

<210> SEQ ID NO 7
<211> LENGTH: 10153
<212> TYPE: DNA
<213> ORGANISM: Artificial Sequence
<220> FEATURE:
<223> OTHER INFORMATION: chimeric adenoviral vector encoding influenza hemagglutinin (HA) and TLR-3 agonist luc in opposite orientation (DS2b-for)

<400> SEQUENCE: 7
taacatcatc aataatatac cttattttgg attgaagcca atatgataat gagggggtgg 60
agtttgtgac gtggcgcggg gcgtgggaac ggggcgggtg acgtagtagt gtggcggaag 120

```
tgtgatgttg caagtgtggc ggaacacatg taagcgacgg atgtggcaaa agtgacgttt    180
ttggtgtgcg ccggtgtaca caggaagtga caattttcgc gcggttttag gcggatgttg    240
tagtaaattt gggcgtaacc gagtaagatt tggccatttt cgcgggaaaa ctgaataaga    300
ggaagtgaaa tctgaataat tttgtgttac tcatagcgcg taatactgct agagatctgg    360
cgaaaggggg atgtgctgca aggcgattaa gttgggtaac gccagggttt tcccagtcac    420
gacgttgtaa aacgacggcc agtgaattgt aatacgactc actatagggc gaattgggta    480
ctggccacag agcttggccc attgcatacg ttgtatccat atcataatat gtacatttat    540
attggctcat gtccaacatt accgccatgt tgacattgat tattgactag ttattaatag    600
taatcaatta cggggtcatt agttcatagc ccatatatgg agttccgcgt tacataactt    660
acggtaaatg gcccgcctgg ctgaccgccc aacgaccccc gcccattgac gtcaataatg    720
acgtatgttc ccatagtaac gccaataggg actttccatt gacgtcaatg ggtggagtat    780
ttacggtaaa ctgcccactt ggcagtacat caagtgtatc atatgccaag tacgccccct    840
attgacgtca atgacggtaa atggcccgcc tggcattatg cccagtacat gaccttatgg    900
gactttccta cttggcagta catctacgta ttagtcatcg ctattaccat ggtgatgcgg    960
ttttggcagt acatcaatgg gcgtggatag cggtttgact cacggggatt tccaagtctc   1020
caccccattg acgtcaatgg gagtttgttt tggcaccaaa atcaacggga ctttccaaaa   1080
tgtcgtaaca actccgcccc attgacgcaa atgggcggta ggcgtgtacg gtgggaggtc   1140
tatataagca gagctcgttt agtgaaccgt cagatcgcct ggagacgcca tccacgctgt   1200
tttgacctcc atagaagaca ccgggaccga tccagcctga ctctagccta gctctgaagt   1260
tggtggtgag gccctgggca ggttggtatc aaggttacaa gacaggttta aggagaccaa   1320
tagaaactgg gcatgtggag acagagaaga ctcttgggtt tctgataggc actgactctc   1380
tctgcctatt ggtctatttt cccaccctta ggctgctggt ctgagcctag gagatctctc   1440
gaggtcgacg gtatcgatgc caccatggag aaaatcgtcc tgttgctcgc tattgtgtct   1500
ctagtgaaga gcgatcaaat ttgtatcggc taccatgcca ataactcaac agagcaggtc   1560
gatactatca tggagaaaaa cgtaacagtt actcatgccc aagacatctt ggaaaagacc   1620
cacaacggca aactttgcga cctggatgga gtgaagcccc tgatcctccg ggactgttca   1680
gtcgctggtt ggctgctcgg gaaccctatg tgtgatgagt ttatcaacgt gcctgaatgg   1740
tcttacattg tggagaaggc taaccctacc aatgacctct gctatcctgg gtcatttaac   1800
gattacgagg aactgaaaca cctgttgtct agaattaacc actttgaaaa gatacagatt   1860
atacccaagt ctagttggag tgatcacgaa gcctcctcag gcgttagctc agcgtgtccc   1920
tatctgggct ctccatcctt ctttagaaat gtggtctggt taatcaaaaa gaacagtacc   1980
tacccaacca tcaaaaagtc ttataacaat accaatcagg aggacctgct cgtgttgtgg   2040
ggtatccatc acccgaacga cgccgctgaa cagactaggc tgtatcagaa ccccactaca   2100
tacatcagta ttggcacgag tactctgaac cagcgattag tgccaaagat tgcaacacgg   2160
agcaaagtaa atgggcaatc tggcaggatg gagttttttct ggacaatctt aaaacccaac   2220
gatgcgataa atttcgagtc caatggcaat ttcatcgccc ctgaatacgc ctataagatc   2280
gtgaaaaagg gggactctgc aattatgaag tccgaattag agtatggcaa ttgcaacacg   2340
aagtgccaga caccaatggg agccattaat agctcaatgc ccttccataa tattcatcca   2400
ttgaccattg ggagtgccc aaagtacgtg aagtccaacc gcctggtcct cgcaaccggt   2460
ctaagaaata gcccgcagag agaatcgcgg aggaagaaac gtggcctgtt tggcgcgatt   2520
```

-continued

```
gccggattca tcgagggagg ctggcagggt atggtcgatg gttggtacgg ataccaccat   2580
agcaacgaac aggggtccgg ctatgcagca gataaggaga gcactcagaa agctattgac   2640
ggagttacaa acaaggttaa tagtattata gataaaatga acacgcaatt cgaggccgtt   2700
gggagggagt ttaacaatct ggaacgccgg atcgaaaatc tgaataagaa aatggaagac   2760
ggcttccttg acgtgtggac ttataatgca gagctgcttg tactcatgga gaacgagagg   2820
accctggatt tccacgatag caacgtgaag aacctttacg acaaggtgag acttcagctc   2880
cgagacaacg ccaaggagct ggggaatgga tgcttcgagt tttaccacaa atgtgacaat   2940
gagtgcatgg aaagtatacg caacgggacc tacaattacc ctcagtatag cgaagaggct   3000
cggctcaaac gcgaagagat aagcggggtg aaattggaat caatcggaac atatcaaatc   3060
ctgtccatct attccaccgt cgcctcttcg ctggccctcg ctatcatgat ggctggtctg   3120
tccctatgga tgtgttccaa tggaagcctt cagtgccgta tttgtatatg agcggccgcc   3180
ctattctata gtgtcaccta aatgctagag ctcgctgatc agcctcgact gtgccttcta   3240
gttgccagcc atctgttgtt tgcccctccc ccgtgccttc cttgaccctg gaaggtgcca   3300
ctcccactgt cctttcctaa taaaatgagg aaattgcatc gcattgtctg agtaggtgtc   3360
attctattct ggggggtggg gtggggcagg acagcaaggg ggaggattgg gaagacaata   3420
gcaggcatgc tggggatgcg gtgggctcta tggcttctga ggcggaaaga accaaccacc   3480
gcggtggcgg ccgccacaca aaaaaccaac acacagatgt aatgaaaata aagatatttt   3540
atttctagag aaacgatatg ggctgaatac ggatccgtat tcagcccata tcgtttcctg   3600
caggaattcg ccctttagat atcatcgatg tctcggcggt ggtggcgcgt cgcgccgctg   3660
ggttttatag ggcgccgccg cggccgctcg agccataaaa ggcaactttc ggaacggcgc   3720
acgctgattg gccccgcgcc gctcactcac cggcttcgcc gcacagtgca gcattttttt   3780
acccctctc ccctcctttt gcgaaaaaaa aaaagagcga gagcgagatt gaggaagagg   3840
aggagggaga gttttggcgt tggccgcctt ggggtgctgg gcgtcgacga tatctaaggg   3900
cgaattcgat atcaagctag cttgtcgact cgaagatctg ggcgtggtta agggtgggaa   3960
agaatatata aggtgggggt cttatgtagt tttgtatctg ttttgcagca gccgccgccg   4020
ccatgagcac caactcgttt gatggaagca ttgtgagctc atatttgaca acgcgcatgc   4080
ccccatgggc cggggtgcgt cagaatgtga tgggctccag cattgatggt cgccccgtcc   4140
tgcccgcaaa ctctactacc ttgacctacg agaccgtgtc tggaacgccg ttggagactg   4200
cagcctccgc cgccgcttca gccgctgcag ccaccgcccg cgggattgtg actgactttg   4260
ctttcctgag cccgcttgca agcagtgcag cttcccgttc atccgcccgc gatgacaagt   4320
tgacggctct tttggcacaa ttggattctt tgacccggga acttaatgtc gtttctcagc   4380
agctgttgga tctgcgccag caggtttctg ccctgaaggc ttcctcccct cccaatgcgg   4440
tttaaaacat aaataaaaaa ccagactctg tttggatttg gatcaagcaa gtgtcttgct   4500
gtctttattt aggggttttg cgcgcgcggt aggcccggga ccagcggtct cggtcgttga   4560
gggtcctgtg tatttttcc aggacgtggt aaaggtgact ctggatgttc agatacatgg   4620
gcataagccc gtctctgggg tggaggtagc accactgcag agcttcatgc tgcggggtgg   4680
tgttgtagat gatccagtcg tagcaggagc gctgggcgtg gtgcctaaaa atgtctttca   4740
gtagcaagct gattgccagg ggcaggccct tggtgtaagt gtttacaaag cggttaagct   4800
gggatgggtg catacgtggg gatatgagat gcatcttgga ctgtattttt aggttggcta   4860
tgttcccagc catatccctc cggggattca tgttgtgcag aaccaccagc acagtgtatc   4920
```

-continued

```
cggtgcactt gggaaatttg tcatgtagct tagaaggaaa tgcgtggaag aacttggaga   4980
cgcccttgtg acctccaaga ttttccatgc attcgtccat aatgatggca atgggcccac   5040
gggcggcggc ctgggcgaag atatttctgg gatcactaac gtcatagttg tgttccagga   5100
tgagatcgtc ataggccatt tttacaaagc gcgggcggag ggtgccagac tgcggtataa   5160
tggttccatc cggcccaggg gcgtagttac cctcacagat ttgcatttcc cacgctttga   5220
gttcagatgg ggggatcatg tctacctgcg gggcgatgaa gaaaacggtt tccggggtag   5280
gggagatcag ctgggaagaa agcaggttcc tgagcagctg cgacttaccg cagccggtgg   5340
gcccgtaaat cacacctatt accgggtgca actggtagtt aagagagctg cagctgccgt   5400
catccctgag caggggggcc acttcgttaa gcatgtccct gactcgcatg ttttccctga   5460
ccaaatccgc cagaaggcgc tcgccgccca gcgatagcag ttcttgcaag gaagcaaagt   5520
ttttcaacgg tttgagaccg tccgccgtag gcatgctttt gagcgtttga ccaagcagtt   5580
ccaggcggtc ccacagctcg gtcacctgct ctacggcatc tcgatccagc atatctcctc   5640
gtttcgcggg ttggggcggc tttcgctgta cggcagtagt cggtgctcgt ccagacgggc   5700
cagggtcatg tctttccacg ggcgcagggt cctcgtcagc gtagtctggg tcacggtgaa   5760
ggggtgcgct ccgggctgcg cgctggccag ggtgcgcttg aggctggtcc tgctggtgct   5820
gaagcgctgc cggtcttcgc cctgcgcgtc ggccaggtag catttgacca tggtgtcata   5880
gtccagcccc tccgcggcgt ggcccttggc gcgcagcttg cccttggagg aggcgccgca   5940
cgaggggcag tgcagacttt tgagggcgta gagcttgggc gcgagaaata ccgattccgg   6000
ggagtaggca tccgcgccgc aggccccgca gacggtctcg cattccacga gccaggtgag   6060
ctctggccgt tcggggtcaa aaaccaggtt tcccccatgc tttttgatgc gtttcttacc   6120
tctggtttcc atgagccggt gtccacgctc ggtgacgaaa aggctgtccg tgtccccgta   6180
tacagacttg agagggagtt taaacgaatt caatagcttg ttgcatgggc ggcgatataa   6240
aatgcaaggt gctgctcaaa aaatcaggca aagcctcgcg caaaaaagaa agcacatcgt   6300
agtcatgctc atgcagataa aggcaggtaa gctccggaac caccacagaa aaagacacca   6360
tttttctctc aaacatgtct gcgggtttct gcataaacac aaaataaaat aacaaaaaaa   6420
catttaaaca ttagaagcct gtcttacaac aggaaaaaca accottataa gcataagacg   6480
gactacggcc atgccggcgt gaccgtaaaa aaactggtca ccgtgattaa aaagcaccac   6540
cgacagctcc tcggtcatgt ccggagtcat aatgtaagac tcggtaaaca catcaggttg   6600
attcatcggt cagtgctaaa aagcgaccga aatagcccgg gggaatacat acccgcaggc   6660
gtagagacaa cattacagcc cccataggag gtataacaaa attaatagga gagaaaaaca   6720
cataaacacc tgaaaaaccc tcctgcctag gcaaaatagc accctcccgc tccagaacaa   6780
catacagcgc ttcacagcgg cagcctaaca gtcagcctta ccagtaaaaa agaaaaccta   6840
ttaaaaaaac accactcgac acggcaccag ctcaatcagt cacagtgtaa aaaagggcca   6900
agtgcagagc gagtatatat aggactaaaa aatgacgtaa cggttaaagt ccacaaaaaa   6960
cacccagaaa accgcacgcg aacctacgcc cagaaacgaa agccaaaaaa cccacaactt   7020
cctcaaatcg tcacttccgt ttcccacgt tacgtaactt cccattttaa gaaaactaca   7080
attcccaaca catacaagtt actccgccct aaaacctacg tcacccgccc cgttcccacg   7140
ccccgcgcca cgtcacaaac tccacccccct cattatcata ttggcttcaa tccaaaataa   7200
ggtatattat tgatgatgtt aattaacatg catggatcca tatgcggtgt gaaataccgc   7260
acagatgcgt aaggagaaaa taccgcatca ggcgctcttc cgcttcctcg ctcactgact   7320
```

```
cgctgcgctc ggtcgttcgg ctgcggcgag cggtatcagc tcactcaaag gcggtaatac   7380
ggttatccac agaatcaggg gataacgcag gaaagaacat gtgagcaaaa ggccagcaaa   7440
aggccaggaa ccgtaaaaag gccgcgttgc tggcgttttt ccataggctc cgcccccctg   7500
acgagcatca caaaaatcga cgctcaagtc agaggtggcg aaacccgaca ggactataaa   7560
gataccaggc gtttccccct ggaagctccc tcgtgcgctc tcctgttccg accctgccgc   7620
ttaccggata cctgtccgcc tttctccctt cgggaagcgt ggcgctttct catagctcac   7680
gctgtaggta tctcagttcg gtgtaggtcg ttcgctccaa gctgggctgt gtgcacgaac   7740
cccccgttca gcccgaccgc tgcgccttat ccggtaacta tcgtcttgag tccaacccgg   7800
taagacacga cttatcgcca ctggcagcag ccactggtaa caggattagc agagcgaggt   7860
atgtaggcgg tgctacagag ttcttgaagt ggtggcctaa ctacggctac actagaagga   7920
cagtatttgg tatctgcgct ctgctgaagc cagttacctt cggaaaaaga gttggtagct   7980
cttgatccgg caaacaaacc accgctggta gcggtggttt ttttgtttgc aagcagcaga   8040
ttacgcgcag aaaaaaagga tctcaagaag atcctttgat cttttctacg gggtctgacg   8100
ctcagtggaa cgaaaactca cgttaaggga ttttggtcat gagattatca aaaaggatct   8160
tcacctagat ccttttaaat taaaaatgaa gttttaaatc aatctaaagt atatatgagt   8220
aaacttggtc tgacagttac caatgcttaa tcagtgaggc acctatctca gcgatctgtc   8280
tatttcgttc atccatagtt gcctgactcc ccgtcgtgta gataactacg atacgggagg   8340
gcttaccatc tggccccagt gctgcaatga taccgcgaga cccacgctca ccggctccag   8400
atttatcagc aataaaccag ccagccggaa gggccgagcg cagaagtggt cctgcaactt   8460
tatccgcctc catccagtct attaattgtt gccgggaagc tagagtaagt agttcgccag   8520
ttaatagttt gcgcaacgtt gttgccattg ctgcagccat gagattatca aaaaggatct   8580
tcacctagat ccttttcacg tagaaagcca gtccgcagaa acggtgctga ccccggatga   8640
atgtcagcta ctgggctatc tggacaaggg aaaacgcaag cgcaaagaga aagcaggtag   8700
cttgcagtgg gcttacatgg cgatagctag actgggcggt tttatggaca gcaagcgaac   8760
cggaattgcc agctggggcg ccctctggta aggttgggaa gccctgcaaa gtaaactgga   8820
tggctttctc gccgccaagg atctgatggc gcaggggatc aagctctgat caagagacag   8880
gatgaggatc gtttcgcatg attgaacaag atggattgca cgcaggttct ccggccgctt   8940
gggtggagag gctattcggc tatgactggg cacaacagac aatcggctgc tctgatgccg   9000
ccgtgttccg gctgtcagcg caggggcgcc cggttctttt tgtcaagacc gacctgtccg   9060
gtgccctgaa tgaactgcaa gacgaggcag cgcggctatc gtggctggcc acgacgggcg   9120
ttccttgcgc agctgtgctc gacgttgtca ctgaagcggg aagggactgg ctgctattgg   9180
gcgaagtgcc ggggcaggat ctcctgtcat ctcaccttgc tcctgccgag aaagtatcca   9240
tcatggctga tgcaatgcgg cggctgcata cgcttgatcc ggctacctgc ccattcgacc   9300
accaagcgaa acatcgcatc gagcgagcac gtactcggat ggaagccggt cttgtcgatc   9360
aggatgatct ggacgaagag catcaggggc tcgcgccagc cgaactgttc gccaggctca   9420
aggcgagcat gcccgacggc gaggatctcg tcgtgaccca tggcgatgcc tgcttgccga   9480
atatcatggt ggaaaatggc cgcttttctg gattcatcga ctgtggccgg ctgggtgtgg   9540
cggaccgcta tcaggacata gcgttggcta cccgtgatat tgctgaagag cttggcggcg   9600
aatgggctga ccgcttcctc gtgctttacg gtatcgccgc tcccgattcg cagcgcatcg   9660
ccttctatcg ccttcttgac gagttcttct gaattttgtt aaaatttttg ttaaatcagc   9720
```

```
tcatttttta accaataggc cgaaatcggc aacatccctt ataaatcaaa agaatagacc   9780

gcgatagggt tgagtgttgt tccagtttgg aacaagagtc cactattaaa gaacgtggac   9840

tccaacgtca aagggcgaaa aaccgtctat cagggcgatg gcccactacg tgaaccatca   9900

cccaaatcaa gttttttgcg gtcgaggtgc cgtaaagctc taaatcggaa ccctaaaggg   9960

agcccccgat ttagagcttg acggggaaag ccggcgaacg tggcgagaaa ggaagggaag  10020

aaagcgaaag gagcgggcgc tagggcgctg gcaagtgtag cggtcacgct gcgcgtaacc  10080

accacacccg cgcgcttaat gcgccgctac agggcgcgtc cattcgccat tcaggatcga  10140

attaattctt aat                                                     10153


<210> SEQ ID NO 8
<211> LENGTH: 46
<212> TYPE: DNA
<213> ORGANISM: Artificial Sequence
<220> FEATURE:
<223> OTHER INFORMATION: short hairpin RNA TLR-3 agonist

<400> SEQUENCE: 8

gatggtgctt caagctagta cttaagtact agcttgaagc accatc                    46


<210> SEQ ID NO 9
<211> LENGTH: 48
<212> TYPE: DNA
<213> ORGANISM: Artificial Sequence
<220> FEATURE:
<223> OTHER INFORMATION: short hairpin RNA TLR-3 agonist (g1)

<400> SEQUENCE: 9

gatggtgctt caagctagta cggatccgta ctagcttgaa gcaccatc                  48


<210> SEQ ID NO 10
<211> LENGTH: 48
<212> TYPE: DNA
<213> ORGANISM: Artificial Sequence
<220> FEATURE:
<223> OTHER INFORMATION: short hairpin RNA TLR-3 agonist (luc), luc1
      segment of DNA designed to make hairpin of
      double-stranded RNA

<400> SEQUENCE: 10

gaaacgatat gggctgaata cggatccgta ttcagcccat atcgtttc                  48


<210> SEQ ID NO 11
<211> LENGTH: 46
<212> TYPE: DNA
<213> ORGANISM: Artificial Sequence
<220> FEATURE:
<223> OTHER INFORMATION: short hairpin RNA TLR-3 agonist (m1), dsRNA
      hairpin

<400> SEQUENCE: 11

cctaataatt atcaaaatgt ggatccacat tttgataatt attagg                    46


<210> SEQ ID NO 12
<211> LENGTH: 44
<212> TYPE: DNA
<213> ORGANISM: Artificial Sequence
<220> FEATURE:
<223> OTHER INFORMATION: short hairpin RNA TLR-3 agonist

<400> SEQUENCE: 12

cctaataatt atcaaaatgt aattacattt tgataattat tagg                      44
```

<210> SEQ ID NO 13
<211> LENGTH: 9387
<212> TYPE: DNA
<213> ORGANISM: Artificial Sequence
<220> FEATURE:
<223> OTHER INFORMATION: chimeric adenoviral vector DS1c encoding hemagglutinin (HA) from influenza A/PR/8/34 in pShuttle-CMV vector (Ad-CMV-HA plus TLR-3 agonist)

<400> SEQUENCE: 13

```
taacatcatc aataatatac cttattttgg attgaagcca atatgataat gaggggtgg      60

agtttgtgac gtggcgcggg gcgtgggaac ggggcgggtg acgtagtagt gtggcggaag    120

tgtgatgttg caagtgtggc ggaacacatg taagcgacgg atgtggcaaa agtgacgttt    180

ttggtgtgcg ccggtgtaca caggaagtga caattttcgc gcggttttag gcggatgttg    240

tagtaaattt gggcgtaacc gagtaagatt tggccatttt cgcgggaaaa ctgaataaga    300

ggaagtgaaa tctgaataat tttgtgttac tcatagcgcg taatactgta atagtaatca    360

attacggggt cattagttca tagcccatat atggagttcc gcgttacata acttacggta    420

aatggcccgc ctggctgacc gcccaacgac ccccgcccat tgacgtcaat aatgacgtat    480

gttcccatag taacgccaat agggactttc cattgacgtc aatgggtgga gtatttacgg    540

taaactgccc acttggcagt acatcaagtg tatcatatgc caagtacgcc ccctattgac    600

gtcaatgacg gtaaatggcc cgcctggcat tatgcccagt acatgacctt atgggacttt    660

cctacttggc agtacatcta cgtattagtc atcgctatta ccatggtgat gcggttttgg    720

cagtacatca atgggcgtgg atagcggttt gactcacggg gatttccaag tctccacccc    780

attgacgtca atgggagttt gttttggcac caaaatcaac gggactttcc aaaatgtcgt    840

aacaactccg ccccattgac gcaaatgggc ggtaggcgtg tacggtggga ggtctatata    900

agcagagctg gtttagtgaa ccgtcagatc cgctagagat ctggtaccga gctcggatcc    960

gccaccatgg aggcaaacct actggtcctg ttatgtgcac ttgcagctgc agatgcagac   1020

acaatatgta taggctacca tgcgaacaat tcaaccgaca ctggtgacac agtactcgag   1080

aagaatgtga cagtgacaca ctctgttaac ctgctcgaag acagccacaa cggaaaacta   1140

tgtagattaa aaggaatagc cccactacaa ttggggaaat gtaacatcgc cggatggctc   1200

ttgggaaacc cagaatgcga cccactgctt ccagtgagat catggtccta cattgtagaa   1260

acaccaaact ctgagaatgg aatatgttat ccaggagatt tcatcgacta tgaggagctg   1320

agggagcaat tgagctcagt gtcatcattc gaaagattcg aaatatttcc caaagaaagc   1380

tcatggccca accacaacac aaccaaagga gtaacggcag catgctccca tgcggggaaa   1440

agcagttttt acagaaattt gctatggctg acggagaagg agggctcata cccaaagctg   1500

aaaaattctt atgtgaacaa gaaagggaaa gaagtccttg tactgtgggg tattcatcac   1560

ccgtctaaca gtaaggatca acagaatatc tatcagaatg aaaatgctta tgtctctgta   1620

gtgacttcaa attataacag gagatttacc ccggaaatag cagaaagacc caaagtaaga   1680

gatcaagctg ggaggatgaa ctattactgg accttgctaa aacccggaga cacaataata   1740

tttgaggcaa atggaaatct aatagcacca aggtatgctt tcgcactgag tagaggcttt   1800

gggtccggca tcatcacctc aaacgcatca atgcatgagt gtaacacgaa gtgtcaaaca   1860

cccctgggag ctataaacag cagtctccct ttccagaata tacacccagt cacaatagga   1920

gagtgcccaa aatacgtcag gagtgccaaa ttgaggatgg ttacaggact aaggaacatt   1980

ccgtccattc aatccagagg tctatttgga gccattgccg gttttattga gggggatgg    2040

actggaatga tagatggatg gtacggttat catcatcaga atgaacaggg atcaggctat   2100
```

```
gcagcggatc aaaaaagcac acaaaatgcc attaacggga ttacaaacaa ggtgaactct   2160

gttatcgaga aaatgaacat tcaattcaca gctgtgggta aagaattcaa caaattagaa   2220

aaaaggatgg aaaatttaaa taaaaaagtt gatgatggat ttctggacat ttggacatat   2280

aatgcagaat tgttagttct actggaaaat gaaaggactc tggatttcca tgactcaaat   2340

gtgaagaatc tgtatgagaa agtaaaaagc caattaaaga ataatgccaa agaaatcgga   2400

aatggatgtt ttgagttcta ccacaagtgt gacaatgaat gcatggaaag tgtaagaaat   2460

gggacttatg attatcccaa atattcagaa gagtcaaagt tgaacaggga aaaggtagat   2520

ggagtgaaat tggaatcaat ggggatctat cagattctgg cgatctactc aactgtcgcc   2580

agttcactgg tgcttttggt ctccctgggg gcaatcagtt tctggatgtg ttctaatgga   2640

tctttgcagt gcagaatatg catctgagat tagaatttca gagatatgag gaaaaacacc   2700

cttgtttcta ctcccaagct ttaatgcggt agtttatcac agttaaattg ctaacgcagt   2760

caggcaccgt gtatgaaatc taacaatgcg ctcatcgtca tcctcggcac cgtcaccctg   2820

gatgctgtag gcataggctt ggttatgccg gtactgccgg gcctcttgcg ggatgggcgg   2880

ccgctcgagc ctaagcttct agataagata tccgatccac cggatctaga taactgatca   2940

taatcagcca taccacattt gtagaggttt tacttgcttt aaaaaacctc ccacacctcc   3000

ccctgaacct gaaacataaa atgaatgcaa ttgttgttgt taacttgttt attgcagctt   3060

ataatggtta caaataaagc aatagcatca caaatttcac aaataaagca tttttttcac   3120

tgcattctag ttgtggtttg tccaaactca tcaatgtatc ttaacgcgga tctgggcgtg   3180

gttaagggtg ggaaagaata tataaggtgg gggtcttatg tagttttgta tctgttttgc   3240

agcagccgcc gccgccatga gcaccaactc gtttgatgga agcattgtga gctcatattt   3300

gacaacgcgc atgcccccat gggccggggt gcgtcagaat gtgatgggct ccagcattga   3360

tggtcgcccc gtcctgcccg caaactctac taccttgacc tacgagaccg tgtctggaac   3420

gccgttggag actgcagcct ccgccgccgc ttcagccgct gcagccaccg cccgcgggat   3480

tgtgactgac tttgctttcc tgagcccgct tgcaagcagt gcagcttccc gttcatccgc   3540

ccgcgatgac aagttgacgg ctcttttggc acaattggat tctttgaccc gggaacttaa   3600

tgtcgtttct cagcagctgt tggatctgcg ccagcaggtt tctgccctga aggcttcctc   3660

ccctcccaat gcggtttaaa acataaataa aaaaccagac tctgtttgga tttggatcaa   3720

gcaagtgtct tgctgtcttt atttaggggt tttgcgcgcg cggtaggccc gggaccagcg   3780

gtctcggtcg ttgagggtcc tgtgtatttt ttccaggacg tggtaaaggt gactctggat   3840

gttcagatac atgggcataa gcccgtctct ggggtggagg tagcaccact gcagagcttc   3900

atgctgcggg gtggtgttgt agatgatcca gtcgtagcag gagcgctggg cgtggtgcct   3960

aaaaatgtct ttcagtagca agctgattgc caggggcagg cccttggtgt aagtgtttac   4020

aaagcggtta agctgggatg ggtgcatacg tggggatatg agatgcatct tggactgtat   4080

ttttaggttg gctatgttcc cagccatatc cctccgggga ttcatgttgt gcagaaccac   4140

cagcacagtg tatccggtgc acttgggaaa tttgtcatgt agcttagaag gaaatgcgtg   4200

gaagaacttg gagacgccct tgtgacctcc aagattttcc atgcattcgt ccataatgat   4260

ggcaatgggc ccacgggcgg cggcctgggc gaagatattt ctgggatcac taacgtcata   4320

gttgtgttcc aggatgagat cgtcataggc catttttaca aagcgcgggc ggagggtgcc   4380

agactgcggt ataatggttc catccggccc aggggcgtag ttaccctcac agatttgcat   4440

ttcccacgct ttgagttcag atggggggat catgtctacc tgcggggcga tgaagaaaac   4500
```

ggtttccggg gtaggggaga tcagctggga agaaagcagg ttcctgagca gctgcgactt 4560
accgcagccg gtgggcccgt aaatcacacc tattaccggg tgcaactggt agttaagaga 4620
gctgcagctg ccgtcatccc tgagcagggg ggccacttcg ttaagcatgt ccctgactcg 4680
catgttttcc ctgaccaaat ccgccagaag gcgctcgccg cccagcgata gcagttcttg 4740
caaggaagca aagtttttca acggtttgag accgtccgcc gtaggcatgc ttttgagcgt 4800
ttgaccaagc agttccaggc ggtcccacag ctcggtcacc tgctctacgg catctcgatc 4860
cagcatatct cctcgtttcg cgggttgggg cggctttcgc tgtacggcag tagtcggtgc 4920
tcgtccagac gggccagggt catgtctttc cacgggcgca gggtcctcgt cagcgtagtc 4980
tgggtcacgg tgaaggggtg cgctccgggc tgcgcgctgg ccagggtgcg cttgaggctg 5040
gtcctgctgg tgctgaagcg ctgccggtct tcgccctgcg cgtcggccag gtagcatttg 5100
accatggtgt catagtccag cccctccgcg gcgtggccct tggcgcgcag cttgcccttg 5160
gaggaggcgc cgcacgaggg gcagtgcaga cttttgaggg cgtagagctt gggcgcgaga 5220
aataccgatt ccggggagta ggcatccgcg ccgcaggccc cgcagacggt ctcgcattcc 5280
acgagccagg tgagctctgg ccgttcgggg tcaaaaacca ggtttccccc atgctttttg 5340
atgcgtttct tacctctggt ttccatgagc cggtgtccac gctcggtgac gaaaaggctg 5400
tccgtgtccc cgtatacaga cttgagaggg agtttaaacg aattcaatag cttgttgcat 5460
gggcggcgat ataaaatgca aggtgctgct caaaaaatca ggcaaagcct cgcgcaaaaa 5520
agaaagcaca tcgtagtcat gctcatgcag ataaaggcag gtaagctccg gaaccaccac 5580
agaaaaagac accatttttc tctcaaacat gtctgcgggt ttctgcataa acacaaaata 5640
aaataacaaa aaaacattta aacattagaa gcctgtctta caacaggaaa aacaaccctt 5700
ataagcataa gacggactac ggccatgccg gcgtgaccgt aaaaaaactg gtcaccgtga 5760
ttaaaaagca ccaccgacag ctcctcggtc atgtccggag tcataatgta agactcggta 5820
aacacatcag gttgattcat cggtcagtgc taaaaagcga ccgaaatagc ccgggggaat 5880
acatacccgc aggcgtagag acaacattac agcccccata ggaggtataa caaaattaat 5940
aggagagaaa aacacataaa cacctgaaaa accctcctgc ctaggcaaaa tagcaccctc 6000
ccgctccaga acaacataca gcgcttcaca gcggcagcct aacagtcagc cttaccagta 6060
aaaaagaaaa cctattaaaa aaacaccact cgacacggca ccagctcaat cagtcacagt 6120
gtaaaaaagg gccaagtgca gagcgagtat atataggact aaaaaatgac gtaacggtta 6180
aagtccacaa aaaacaccca gaaaaccgca cgcgaaccta cgcccagaaa cgaaagccaa 6240
aaaacccaca acttcctcaa atcgtcactt ccgttttccc acgttacgta acttcccatt 6300
ttaagaaaac tacaattccc aacacataca agttactccg ccctaaaacc tacgtcaccc 6360
gccccgttcc cacgccccgc gccacgtcac aaactccacc ccctcattat catattggct 6420
tcaatccaaa ataaggtata ttattgatga tgttaattaa catgcatgga tccatatgcg 6480
gtgtgaaata ccgcacagat gcgtaaggag aaaataccgc atcaggcgct cttccgcttc 6540
ctcgctcact gactcgctgc gctcggtcgt tcggctgcgg cgagcggtat cagctcactc 6600
aaaggcggta atacggttat ccacagaatc aggggataac gcaggaaaga acatgtgagc 6660
aaaaggccag caaaaggcca ggaaccgtaa aaaggccgcg ttgctggcgt ttttccatag 6720
gctccgcccc cctgacgagc atcacaaaaa tcgacgctca agtcagaggt ggcgaaaccc 6780
gacaggacta taaagatacc aggcgtttcc ccctggaagc tccctcgtgc gctctcctgt 6840
tccgaccctg ccgcttaccg gatacctgtc cgcctttctc ccttcgggaa gcgtggcgct 6900
ttctcatagc tcacgctgta ggtatctcag ttcggtgtag gtcgttcgct ccaagctggg 6960
ctgtgtgcac gaaccccccg ttcagcccga ccgctgcgcc ttatccggta actatcgtct 7020
tgagtccaac ccggtaagac acgacttatc gccactggca gcagccactg gtaacaggat 7080
tagcagagcg aggtatgtag gcggtgctac agagttcttg aagtggtggc ctaactacgg 7140
ctacactaga aggacagtat ttggtatctg cgctctgctg aagccagtta ccttcggaaa 7200
aagagttggt agctcttgat ccggcaaaca aaccaccgct ggtagcggtg gtttttttgt 7260
ttgcaagcag cagattacgc gcagaaaaaa aggatctcaa gaagatcctt tgatcttttc 7320
tacggggtct gacgctcagt ggaacgaaaa ctcacgttaa gggattttgg tcatgagatt 7380
atcaaaaagg atcttcacct agatcctttt aaattaaaaa tgaagtttta aatcaatcta 7440
aagtatatat gagtaaactt ggtctgacag ttaccaatgc ttaatcagtg aggcacctat 7500
ctcagcgatc tgtctatttc gttcatccat agttgcctga ctccccgtcg tgtagataac 7560
tacgatacgg gagggcttac catctggccc cagtgctgca atgataccgc gagacccacg 7620
ctcaccggct ccagatttat cagcaataaa ccagccagcc ggaagggccg agcgcagaag 7680
tggtcctgca actttatccg cctccatcca gtctattaat tgttgccggg aagctagagt 7740
aagtagttcg ccagttaata gtttgcgcaa cgttgttgcc attgctgcag ccatgagatt 7800
atcaaaaagg atcttcacct agatcctttt cacgtagaaa gccagtccgc agaaacggtg 7860
ctgaccccgg atgaatgtca gctactgggc tatctggaca agggaaaacg caagcgcaaa 7920
gagaaagcag gtagcttgca gtgggcttac atggcgatag ctagactggg cggttttatg 7980
gacagcaagc gaaccggaat tgccagctgg ggcgccctct ggtaaggttg ggaagccctg 8040
caaagtaaac tggatggctt tctcgccgcc aaggatctga tggcgcaggg gatcaagctc 8100
tgatcaagag acaggatgag gatcgtttcg catgattgaa caagatggat tgcacgcagg 8160
ttctccggcc gcttgggtgg agaggctatt cggctatgac tgggcacaac agacaatcgg 8220
ctgctctgat gccgccgtgt tccggctgtc agcgcagggg cgcccggttc tttttgtcaa 8280
gaccgacctg tccggtgccc tgaatgaact gcaagacgag gcagcgcggc tatcgtggct 8340
ggccacgacg ggcgttcctt gcgcagctgt gctcgacgtt gtcactgaag cgggaaggga 8400
ctggctgcta ttgggcgaag tgccggggca ggatctcctg tcatctcacc ttgctcctgc 8460
cgagaaagta tccatcatgg ctgatgcaat gcggcggctg catacgcttg atccggctac 8520
ctgcccattc gaccaccaag cgaaacatcg catcgagcga gcacgtactc ggatggaagc 8580
cggtcttgtc gatcaggatg atctggacga agagcatcag gggctcgcgc cagccgaact 8640
gttcgccagg ctcaaggcga gcatgcccga cggcgaggat ctcgtcgtga cccatggcga 8700
tgcctgcttg ccgaatatca tggtggaaaa tggccgcttt tctggattca tcgactgtgg 8760
ccggctgggt gtggcggacc gctatcagga catagcgttg gctacccgtg atattgctga 8820
agagcttggc ggcgaatggg ctgaccgctt cctcgtgctt tacggtatcg ccgctcccga 8880
ttcgcagcgc atcgccttct atcgccttct tgacgagttc ttctgaattt tgttaaaatt 8940
tttgttaaat cagctcattt tttaaccaat aggccgaaat cggcaacatc ccttataaat 9000
caaaagaata gaccgcgata gggttgagtg ttgttccagt ttggaacaag agtccactat 9060
taaagaacgt ggactccaac gtcaaagggc gaaaaaccgt ctatcagggc gatggcccac 9120
tacgtgaacc atcacccaaa tcaagttttt tgcggtcgag gtgccgtaaa gctctaaatc 9180
ggaaccctaa agggagcccc cgatttagag cttgacgggg aaagccggcg aacgtggcga 9240
gaaaggaagg gaagaaagcg aaaggagcgg gcgctagggc gctggcaagt gtagcggtca 9300

```
cgctgcgcgt aaccaccaca cccgcgcgct taatgcgccg ctacagggcg cgtccattcg   9360

ccattcagga tcgaattaat tcttaat                                       9387


<210> SEQ ID NO 14
<211> LENGTH: 8473
<212> TYPE: DNA
<213> ORGANISM: Artificial Sequence
<220> FEATURE:
<223> OTHER INFORMATION: chimeric adenoviral vector DS2beta-luc encoding
      TLR-3 agonist luc and human beta actin promotor,
      generic shuttle vector, rapid cloning vector

<400> SEQUENCE: 14

taacatcatc aataatatac cttattttgg attgaagcca atatgataat gagggggtgg     60

agtttgtgac gtggcgcggg gcgtgggaac ggggcgggtg acgtagtagt gtggcggaag    120

tgtgatgttg caagtgtggc ggaacacatg taagcgacgg atgtggcaaa agtgacgttt    180

ttggtgtgcg ccggtgtaca caggaagtga caattttcgc gcggttttag gcggatgttg    240

tagtaaattt gggcgtaacc gagtaagatt tggccatttt cgcgggaaaa ctgaataaga    300

ggaagtgaaa tctgaataat tttgtgttac tcatagcgcg taatactgct agagatctgg    360

cgaaaggggg atgtgctgca aggcgattaa gttgggtaac gccagggttt tcccagtcac    420

gacgttgtaa aacgacggcc agtgaattgt aatacgactc actatagggc gaattgggta    480

ctggccacag agcttggccc attgcatacg ttgtatccat atcataatat gtacatttat    540

attggctcat gtccaacatt accgccatgt tgacattgat tattgactag ttattaatag    600

taatcaatta cggggtcatt agttcatagc ccatatatgg agttccgcgt tacataactt    660

acggtaaatg gcccgcctgg ctgaccgccc aacgaccccc gcccattgac gtcaataatg    720

acgtatgttc ccatagtaac gccaataggg actttccatt gacgtcaatg ggtggagtat    780

ttacggtaaa ctgcccactt ggcagtacat caagtgtatc atatgccaag tacgccccct    840

attgacgtca atgacggtaa atggcccgcc tggcattatg cccagtacat gaccttatgg    900

gactttccta cttggcagta catctacgta ttagtcatcg ctattaccat ggtgatgcgg    960

ttttggcagt acatcaatgg gcgtggatag cggtttgact cacggggatt tccaagtctc   1020

caccccattg acgtcaatgg gagtttgttt tggcaccaaa atcaacggga ctttccaaaa   1080

tgtcgtaaca actccgcccc attgacgcaa atgggcggta ggcgtgtacg gtgggaggtc   1140

tatataagca gagctcgttt agtgaaccgt cagatcgcct ggagacgcca tccacgctgt   1200

tttgacctcc atagaagaca ccgggaccga tccagcctga ctctagccta gctctgaagt   1260

tggtggtgag gccctgggca ggttggtatc aaggttacaa gacaggttta aggagaccaa   1320

tagaaactgg gcatgtggag acagagaaga ctcttgggtt tctgataggc actgactctc   1380

tctgcctatt ggtctatttt cccaccctta ggctgctggt ctgagcctag gagatctctc   1440

gaggtcgacg gtatcgatgg gtaccggcgg ccgccctatt ctatagtgtc acctaaatgc   1500

tagagctcgc tgatcagcct cgactgtgcc ttctagttgc cagccatctg ttgtttgccc   1560

ctcccccgtg ccttccttga ccctggaagg tgccactccc actgtccttt cctaataaaa   1620

tgaggaaatt gcatcgcatt gtctgagtag gtgtcattct attctggggg gtggggtggg   1680

gcaggacagc aagggggagg attgggaaga caatagcagg catgctgggg atgcggtggg   1740

ctctatggct tctgaggcgg aaagaaccta tggcttctga ggcggaaaga accaaccacc   1800

gcggtggcgg ccgccacaca aaaaaccaac acacagatgt aatgaaaata aagatatttt   1860

atttctagag aaacgatatg ggctgaatac ggatccgtat tcagcccata tcgtttcctg   1920
```

```
caggaattcg ccctttagat atcatcgatg tctcggcggt ggtggcgcgt cgcgccgctg   1980
ggttttatag ggcgccgccg cggccgctcg agccataaaa ggcaactttc ggaacggcgc   2040
acgctgattg gccccgcgcc gctcactcac cggcttcgcc gcacagtgca gcattttttt   2100
accccctctc cctccttttt gcgaaaaaaa aaaagagcga gagcgagatt gaggaagagg   2160
aggagggaga gttttggcgt tggccgcctt ggggtgctgg gcgtcgacga tatctaaggg   2220
cgaattcgat atcaagctag cttgtcgact cgaagatctg ggcgtggtta agggtgggaa   2280
agaatatata aggtgggggt cttatgtagt tttgtatctg ttttgcagca gccgccgccg   2340
ccatgagcac caactcgttt gatggaagca ttgtgagctc atatttgaca acgcgcatgc   2400
ccccatgggc cggggtgcgt cagaatgtga tgggctccag cattgatggt cgccccgtcc   2460
tgcccgcaaa ctctactacc ttgacctacg agaccgtgtc tggaacgccg ttggagactg   2520
cagcctccgc cgccgcttca gccgctgcag ccaccgcccg cgggattgtg actgactttg   2580
ctttcctgag cccgcttgca agcagtgcag cttcccgttc atccgcccgc gatgacaagt   2640
tgacggctct tttggcacaa ttggattctt tgacccggga acttaatgtc gtttctcagc   2700
agctgttgga tctgcgccag caggtttctg ccctgaaggc ttcctcccct cccaatgcgg   2760
tttaaaacat aaataaaaaa ccagactctg tttggatttg gatcaagcaa gtgtcttgct   2820
gtctttattt aggggttttg cgcgcgcggt aggcccggga ccagcggtct cggtcgttga   2880
gggtcctgtg tatttttttcc aggacgtggt aaaggtgact ctggatgttc agatacatgg   2940
gcataagccc gtctctgggg tggaggtagc accactgcag agcttcatgc tgcggggtgg   3000
tgttgtagat gatccagtcg tagcaggagc gctgggcgtg gtgcctaaaa atgtctttca   3060
gtagcaagct gattgccagg ggcaggccct tggtgtaagt gtttacaaag cggttaagct   3120
gggatgggtg catacgtggg gatatgagat gcatcttgga ctgtattttt aggttggcta   3180
tgttcccagc catatccctc cggggattca tgttgtgcag aaccaccagc acagtgtatc   3240
cggtgcactt gggaaatttg tcatgtagct tagaaggaaa tgcgtggaag aacttggaga   3300
cgcccttgtg acctccaaga ttttccatgc attcgtccat aatgatggca atgggcccac   3360
gggcggcggc ctgggcgaag atatttctgg gatcactaac gtcatagttg tgttccagga   3420
tgagatcgtc ataggccatt tttacaaagc gcgggcggag ggtgccagac tgcggtataa   3480
tggttccatc cggcccaggg gcgtagttac cctcacagat ttgcatttcc cacgctttga   3540
gttcagatgg ggggatcatg tctacctgcg gggcgatgaa gaaaacggtt tccggggtag   3600
gggagatcag ctgggaagaa agcaggttcc tgagcagctg cgacttaccg cagccggtgg   3660
gcccgtaaat cacacctatt accgggtgca actggtagtt aagagagctg cagctgccgt   3720
catccctgag caggggggcc acttcgttaa gcatgtccct gactcgcatg ttttccctga   3780
ccaaatccgc cagaaggcgc tcgccgccca gcgatagcag ttcttgcaag gaagcaaagt   3840
ttttcaacgg tttgagaccg tccgccgtag gcatgctttt gagcgtttga ccaagcagtt   3900
ccaggcggtc ccacagctcg gtcacctgct ctacggcatc tcgatccagc atatctcctc   3960
gtttcgcggg ttggggcggc tttcgctgta cggcagtagt cggtgctcgt ccagacgggc   4020
cagggtcatg tctttccacg ggcgcagggt cctcgtcagc gtagtctggg tcacggtgaa   4080
ggggtgcgct ccgggctgcg cgctggccag ggtgcgcttg aggctggtcc tgctggtgct   4140
gaagcgctgc cggtcttcgc cctgcgcgtc ggccaggtag catttgacca tggtgtcata   4200
gtccagcccc tccgcggcgt ggcccttggc gcgcagcttg cccttggagg aggcgccgca   4260
cgaggggcag tgcagacttt tgagggcgta gagcttgggc gcgagaaata ccgattccgg   4320
```

```
ggagtaggca tccgcgccgc aggccccgca gacggtctcg cattccacga gccaggtgag   4380
ctctggccgt tcggggtcaa aaaccaggtt tcccccatgc tttttgatgc gtttcttacc   4440
tctggtttcc atgagccggt gtccacgctc ggtgacgaaa aggctgtccg tgtccccgta   4500
tacagacttg agagggagtt taaacgaatt caatagcttg ttgcatgggc ggcgatataa   4560
aatgcaaggt gctgctcaaa aaatcaggca aagcctcgcg caaaaaagaa agcacatcgt   4620
agtcatgctc atgcagataa aggcaggtaa gctccggaac caccacagaa aaagacacca   4680
tttttctctc aaacatgtct gcgggtttct gcataaacac aaaataaaat aacaaaaaaa   4740
catttaaaca ttagaagcct gtcttacaac aggaaaaaca acccttataa gcataagacg   4800
gactacggcc atgccggcgt gaccgtaaaa aaactggtca ccgtgattaa aaagcaccac   4860
cgacagctcc tcggtcatgt ccggagtcat aatgtaagac tcggtaaaca catcaggttg   4920
attcatcggt cagtgctaaa aagcgaccga aatagcccgg gggaatacat acccgcaggc   4980
gtagagacaa cattacagcc cccataggag gtataacaaa attaatagga gagaaaaaca   5040
cataaacacc tgaaaaaccc tcctgcctag gcaaaatagc accctcccgc tccagaacaa   5100
catacagcgc ttcacagcgg cagcctaaca gtcagcctta ccagtaaaaa agaaaaccta   5160
ttaaaaaaac accactcgac acggcaccag ctcaatcagt cacagtgtaa aaaagggcca   5220
agtgcagagc gagtatatat aggactaaaa aatgacgtaa cggttaaagt ccacaaaaaa   5280
cacccagaaa accgcacgcg aacctacgcc cagaaacgaa agccaaaaaa cccacaactt   5340
cctcaaatcg tcacttccgt tttcccacgt tacgtaactt cccattttaa gaaaactaca   5400
attcccaaca catacaagtt actccgccct aaaacctacg tcacccgccc cgttcccacg   5460
ccccgcgcca cgtcacaaac tccacccccct cattatcata ttggcttcaa tccaaaataa   5520
ggtatattat tgatgatgtt aattaacatg catggatcca tatgcggtgt gaaataccgc   5580
acagatgcgt aaggagaaaa taccgcatca ggcgctcttc cgcttcctcg ctcactgact   5640
cgctgcgctc ggtcgttcgg ctgcggcgag cggtatcagc tcactcaaag gcggtaatac   5700
ggttatccac agaatcaggg gataacgcag gaaagaacat gtgagcaaaa ggccagcaaa   5760
aggccaggaa ccgtaaaaag gccgcgttgc tggcgttttt ccataggctc cgcccccctg   5820
acgagcatca caaaaatcga cgctcaagtc agaggtggcg aaacccgaca ggactataaa   5880
gataccaggc gtttccccct ggaagctccc tcgtgcgctc tcctgttccg accctgccgc   5940
ttaccggata cctgtccgcc tttctccctt cgggaagcgt ggcgctttct catagctcac   6000
gctgtaggta tctcagttcg gtgtaggtcg ttcgctccaa gctgggctgt gtgcacgaac   6060
cccccgttca gcccgaccgc tgcgccttat ccggtaacta tcgtcttgag tccaacccgg   6120
taagacacga cttatcgcca ctggcagcag ccactggtaa caggattagc agagcgaggt   6180
atgtaggcgg tgctacagag ttcttgaagt ggtggcctaa ctacggctac actagaagga   6240
cagtatttgg tatctgcgct ctgctgaagc cagttacctt cggaaaaaga gttggtagct   6300
cttgatccgg caaacaaacc accgctggta gcggtggttt ttttgtttgc aagcagcaga   6360
ttacgcgcag aaaaaaagga tctcaagaag atcctttgat cttttctacg gggtctgacg   6420
ctcagtggaa cgaaaactca cgttaaggga ttttggtcat gagattatca aaaaggatct   6480
tcacctagat ccttttaaat taaaaatgaa gttttaaatc aatctaaagt atatatgagt   6540
aaacttggtc tgacagttac caatgcttaa tcagtgaggc acctatctca gcgatctgtc   6600
tatttcgttc atccatagtt gcctgactcc ccgtcgtgta gataactacg atacgggagg   6660
gcttaccatc tggccccagt gctgcaatga taccgcgaga cccacgctca ccggctccag   6720
```

```
atttatcagc aataaaccag ccagccggaa gggccgagcg cagaagtggt cctgcaactt   6780

tatccgcctc catccagtct attaattgtt gccgggaagc tagagtaagt agttcgccag   6840

ttaatagttt gcgcaacgtt gttgccattg ctgcagccat gagattatca aaaaggatct   6900

tcacctagat ccttttcacg tagaaagcca gtccgcagaa acggtgctga ccccggatga   6960

atgtcagcta ctgggctatc tggacaaggg aaaacgcaag cgcaaagaga aagcaggtag   7020

cttgcagtgg gcttacatgg cgatagctag actgggcggt tttatggaca gcaagcgaac   7080

cggaattgcc agctggggcg ccctctggta aggttgggaa gccctgcaaa gtaaactgga   7140

tggctttctc gccgccaagg atctgatggc gcaggggatc aagctctgat caagagacag   7200

gatgaggatc gtttcgcatg attgaacaag atggattgca cgcaggttct ccggccgctt   7260

gggtggagag gctattcggc tatgactggg cacaacagac aatcggctgc tctgatgccg   7320

ccgtgttccg gctgtcagcg caggggcgcc cggttctttt tgtcaagacc gacctgtccg   7380

gtgccctgaa tgaactgcaa gacgaggcag cgcggctatc gtggctggcc acgacgggcg   7440

ttccttgcgc agctgtgctc gacgttgtca ctgaagcggg aagggactgg ctgctattgg   7500

gcgaagtgcc ggggcaggat ctcctgtcat ctcaccttgc tcctgccgag aaagtatcca   7560

tcatggctga tgcaatgcgg cggctgcata cgcttgatcc ggctacctgc ccattcgacc   7620

accaagcgaa acatcgcatc gagcgagcac gtactcggat ggaagccggt cttgtcgatc   7680

aggatgatct ggacgaagag catcaggggc tcgcgccagc cgaactgttc gccaggctca   7740

aggcgagcat gcccgacggc gaggatctcg tcgtgaccca tggcgatgcc tgcttgccga   7800

atatcatggt ggaaaatggc cgcttttctg gattcatcga ctgtggccgg ctgggtgtgg   7860

cggaccgcta tcaggacata gcgttggcta cccgtgatat tgctgaagag cttggcggcg   7920

aatgggctga ccgcttcctc gtgctttacg gtatcgccgc tcccgattcg cagcgcatcg   7980

ccttctatcg ccttcttgac gagttcttct gaattttgtt aaaatttttg ttaaatcagc   8040

tcatttttta accaataggc cgaaatcggc aacatccctt ataaatcaaa agaatagacc   8100

gcgatagggt tgagtgttgt tccagtttgg aacaagagtc cactattaaa gaacgtggac   8160

tccaacgtca aagggcgaaa aaccgtctat cagggcgatg gcccactacg tgaaccatca   8220

cccaaatcaa gttttttgcg gtcgaggtgc cgtaaagctc taaatcggaa ccctaaaggg   8280

agcccccgat ttagagcttg acggggaaag ccggcgaacg tggcgagaaa ggaagggaag   8340

aaagcgaaag gagcgggcgc tagggcgctg gcaagtgtag cggtcacgct gcgcgtaacc   8400

accacacccg cgcgcttaat gcgccgctac agggcgcgtc cattcgccat tcaggatcga   8460

attaattctt aat                                                      8473
```

```
<210> SEQ ID NO 15
<211> LENGTH: 9073
<212> TYPE: DNA
<213> ORGANISM: Artificial Sequence
<220> FEATURE:
<223> OTHER INFORMATION: chimeric adenoviral vector DS2C-luc encoding
      TLR-3 agonist luc and cytomegalovirus (CMV) promotor,
      generic shuttle vector, rapid cloning vector

<400> SEQUENCE: 15

taacatcatc aataatatac cttattttgg attgaagcca atatgataat gagggggtgg     60

agtttgtgac gtggcgcggg gcgtgggaac ggggcgggtg acgtagtagt gtggcggaag    120

tgtgatgttg caagtgtggc ggaacacatg taagcgacgg atgtggcaaa agtgacgttt    180

ttggtgtgcg ccggtgtaca caggaagtga caattttcgc gcggttttag gcggatgttg    240
```

```
tagtaaattt gggcgtaacc gagtaagatt tggccatttt cgcgggaaaa ctgaataaga    300
ggaagtgaaa tctgaataat tttgtgttac tcatagcgcg taatactgct agagatctgg    360
cgaaaggggg atgtgctgca aggcgattaa gttgggtaac gccagggttt tcccagtcac    420
gacgttgtaa aacgacggcc agtgaattgt aatacgactc actatagggc gaattgggta    480
ctggccacag agcttggccc attgcatacg ttgtatccat atcataatat gtacatttat    540
attggctcat gtccaacatt accgccatgt tgacattgat tattgactag ttattaatag    600
taatcaatta cggggtcatt agttcatagc ccatatatgg agttccgcgt tacataactt    660
acggtaaatg gcccgcctgg ctgaccgccc aacgaccccc gcccattgac gtcaataatg    720
acgtatgttc ccatagtaac gccaataggg actttccatt gacgtcaatg ggtggagtat    780
ttacggtaaa ctgcccactt ggcagtacat caagtgtatc atatgccaag tacgccccct    840
attgacgtca atgacggtaa atggcccgcc tggcattatg cccagtacat gaccttatgg    900
gactttccta cttggcagta catctacgta ttagtcatcg ctattaccat ggtgatgcgg    960
ttttggcagt acatcaatgg gcgtggatag cggtttgact cacggggatt tccaagtctc   1020
caccccattg acgtcaatgg gagtttgttt tggcaccaaa atcaacggga ctttccaaaa   1080
tgtcgtaaca actccgcccc attgacgcaa atgggcggta ggcgtgtacg gtgggaggtc   1140
tatataagca gagctcgttt agtgaaccgt cagatcgcct ggagacgcca tccacgctgt   1200
tttgacctcc atagaagaca ccgggaccga tccagcctga ctctagccta gctctgaagt   1260
tggtggtgag gccctgggca ggttggtatc aaggttacaa gacaggttta aggagaccaa   1320
tagaaactgg gcatgtggag acagagaaga ctcttgggtt tctgataggc actgactctc   1380
tctgcctatt ggtctatttt cccaccctta ggctgctggt ctgagcctag gagatctctc   1440
gaggtcgacg gtatcgatgg gtaccggcgg ccgccctatt ctatagtgtc acctaaatgc   1500
tagagctcgc tgatcagcct cgactgtgcc ttctagttgc cagccatctg ttgtttgccc   1560
ctcccccgtg ccttccttga ccctggaagg tgccactccc actgtccttt cctaataaaa   1620
tgaggaaatt gcatcgcatt gtctgagtag gtgtcattct attctggggg gtggggtggg   1680
gcaggacagc aagggggagg attgggaaga caatagcagg catgctgggg atgcggtggg   1740
ctctatggct tctgaggcgg aaagaaccaa agcttaggct cgagcggccg ccacacaaaa   1800
aaccaacaca cagatgtaat gaaaataaag atattttatt tctagagaaa cgatatgggc   1860
tgaatacgga tccgtattca gcccatatcg tttcccagat ctctagcgga tctgacggtt   1920
cactaaacca gctctgctta tatagacctc ccaccgtaca cgcctaccgc ccatttgcgt   1980
caatggggcg gagttgttac gacattttgg aaagtcccgt tgattttggt gccaaaacaa   2040
actcccattg acgtcaatgg ggtggagact tggaaatccc cgtgagtcaa accgctatcc   2100
acgcccattg atgtactgcc aaaaccgcat caccatggta atagcgatga ctaatacgta   2160
gatgtactgc caagtaggaa agtcccataa ggtcatgtac tgggcataat gccaggcggg   2220
ccatttaccg tcattgacgt caataggggg cgtacttggc atatgataca cttgatgtac   2280
tgccaagtgg gcagtttacc gtaaatactc cacccattga cgtcaatgga aagtccctat   2340
tggcgttact atgggaacat acgtcattat tgacgtcaat gggcgggggt cgttgggcgg   2400
tcagccaggc gggccattta ccgtaagtta tgtaacgcgg aactccatat atgggctatg   2460
aactaatgac ccgtaattg attactatta cagtattacg cgctatgagt aacacaaaat   2520
tattcagatt tcacttcctc ttattcagtt ttcccgcgaa aatggccaaa tcttactcgg   2580
ttacgcccaa atttactaca acatccgcct aaaaccgcgc gaaaattgtc acttcctgtg   2640
```

```
tacaccggcg cacaccaaaa acgtcacttt tgccacatcc gtcgcttaca tgtgttccgc   2700
cacacttgca acatcacact tccgccacac tactacgtca cccgccccgt tcccacgccc   2760
cgcgccacgt cacaaactcc accccctcat tatcatattg gcttcaatcc aaaataaggt   2820
atattattga tgatgttaag cttgtcgact cgaagatctg ggcgtggtta agggtgggaa   2880
agaatatata aggtgggggt cttatgtagt tttgtatctg ttttgcagca gccgccgccg   2940
ccatgagcac caactcgttt gatggaagca ttgtgagctc atatttgaca acgcgcatgc   3000
ccccatgggc cggggtgcgt cagaatgtga tgggctccag cattgatggt cgccccgtcc   3060
tgcccgcaaa ctctactacc ttgacctacg agaccgtgtc tggaacgccg ttggagactg   3120
cagcctccgc cgccgcttca gccgctgcag ccaccgcccg cgggattgtg actgactttg   3180
ctttcctgag cccgcttgca agcagtgcag cttcccgttc atccgcccgc gatgacaagt   3240
tgacggctct tttggcacaa ttggattctt tgacccggga acttaatgtc gtttctcagc   3300
agctgttgga tctgcgccag caggtttctg ccctgaaggc ttcctcccct cccaatgcgg   3360
tttaaaacat aaataaaaaa ccagactctg tttggatttg gatcaagcaa gtgtcttgct   3420
gtctttattt aggggttttg cgcgcgcggt aggcccggga ccagcggtct cggtcgttga   3480
gggtcctgtg tatttttcc aggacgtggt aaaggtgact ctggatgttc agatacatgg   3540
gcataagccc gtctctgggg tggaggtagc accactgcag agcttcatgc tgcggggtgg   3600
tgttgtagat gatccagtcg tagcaggagc gctgggcgtg gtgcctaaaa atgtctttca   3660
gtagcaagct gattgccagg ggcaggccct tggtgtaagt gtttacaaag cggttaagct   3720
gggatgggtg catacgtggg gatatgagat gcatcttgga ctgtattttt aggttggcta   3780
tgttcccagc catatccctc cggggattca tgttgtgcag aaccaccagc acagtgtatc   3840
cggtgcactt gggaaatttg tcatgtagct tagaaggaaa tgcgtggaag aacttggaga   3900
cgcccttgtg acctccaaga ttttccatgc attcgtccat aatgatggca atgggcccac   3960
gggcggcggc ctgggcgaag atatttctgg gatcactaac gtcatagttg tgttccagga   4020
tgagatcgtc ataggccatt tttacaaagc gcgggcggag ggtgccagac tgcggtataa   4080
tggttccatc cggcccaggg gcgtagttac cctcacagat ttgcatttcc cacgctttga   4140
gttcagatgg ggggatcatg tctacctgcg gggcgatgaa gaaaacggtt tccggggtag   4200
gggagatcag ctgggaagaa agcaggttcc tgagcagctg cgacttaccg cagccggtgg   4260
gcccgtaaat cacacctatt accgggtgca actggtagtt aagagagctg cagctgccgt   4320
catccctgag caggggggcc acttcgttaa gcatgtccct gactcgcatg ttttccctga   4380
ccaaatccgc cagaaggcgc tcgccgccca gcgatagcag ttcttgcaag gaagcaaagt   4440
ttttcaacgg tttgagaccg tccgccgtag gcatgctttt gagcgtttga ccaagcagtt   4500
ccaggcggtc ccacagctcg gtcacctgct ctacggcatc tcgatccagc atatctcctc   4560
gtttcgcggg ttggggcggc tttcgctgta cggcagtagt cggtgctcgt ccagacgggc   4620
cagggtcatg tctttccacg ggcgcagggt cctcgtcagc gtagtctggg tcacggtgaa   4680
ggggtgcgct ccgggctgcg cgctggccag ggtgcgcttg aggctggtcc tgctggtgct   4740
gaagcgctgc cggtcttcgc cctgcgcgtc ggccaggtag catttgacca tggtgtcata   4800
gtccagcccc tccgcggcgt ggcccttggc gcgcagcttg cccttggagg aggcgccgca   4860
cgaggggcag tgcagacttt tgagggcgta gagcttgggc gcgagaaata ccgattccgg   4920
ggagtaggca tccgcgccgc aggccccgca gacggtctcg cattccacga gccaggtgag   4980
ctctggccgt tcggggtcaa aaaccaggtt tcccccatgc tttttgatgc gtttcttacc   5040
```

```
tctggtttcc atgagccggt gtccacgctc ggtgacgaaa aggctgtccg tgtccccgta   5100

tacagacttg agagggagtt taaacgaatt caatagcttg ttgcatgggc ggcgatataa   5160

aatgcaaggt gctgctcaaa aaatcaggca aagcctcgcg caaaaaagaa agcacatcgt   5220

agtcatgctc atgcagataa aggcaggtaa gctccggaac caccacagaa aaagacacca   5280

tttttctctc aaacatgtct gcgggtttct gcataaacac aaaataaaat aacaaaaaaa   5340

catttaaaca ttagaagcct gtcttacaac aggaaaaaca acccttataa gcataagacg   5400

gactacggcc atgccggcgt gaccgtaaaa aaactggtca ccgtgattaa aaagcaccac   5460

cgacagctcc tcggtcatgt ccggagtcat aatgtaagac tcggtaaaca catcaggttg   5520

attcatcggt cagtgctaaa aagcgaccga aatagcccgg gggaatacat acccgcaggc   5580

gtagagacaa cattacagcc cccataggag gtataacaaa attaatagga gagaaaaaca   5640

cataaacacc tgaaaaaccc tcctgcctag gcaaaatagc accctcccgc tccagaacaa   5700

catacagcgc ttcacagcgg cagcctaaca gtcagcctta ccagtaaaaa agaaaaccta   5760

ttaaaaaaac accactcgac acggcaccag ctcaatcagt cacagtgtaa aaaagggcca   5820

agtgcagagc gagtatatat aggactaaaa aatgacgtaa cggttaaagt ccacaaaaaa   5880

cacccagaaa accgcacgcg aacctacgcc cagaaacgaa agccaaaaaa cccacaactt   5940

cctcaaatcg tcacttccgt ttcccacgt tacgtaactt cccattttaa gaaaactaca   6000

attcccaaca catacaagtt actccgccct aaaacctacg tcacccgccc cgttcccacg   6060

ccccgcgcca cgtcacaaac tccacccccct cattatcata ttggcttcaa tccaaaataa   6120

ggtatattat tgatgatgtt aattaacatg catggatcca tatgcggtgt gaaataccgc   6180

acagatgcgt aaggagaaaa taccgcatca ggcgctcttc cgcttcctcg ctcactgact   6240

cgctgcgctc ggtcgttcgg ctgcggcgag cggtatcagc tcactcaaag gcggtaatac   6300

ggttatccac agaatcaggg gataacgcag gaaagaacat gtgagcaaaa ggccagcaaa   6360

aggccaggaa ccgtaaaaag gccgcgttgc tggcgttttt ccataggctc cgcccccctg   6420

acgagcatca caaaaatcga cgctcaagtc agaggtggcg aaacccgaca ggactataaa   6480

gataccaggc gtttccccct ggaagctccc tcgtgcgctc tcctgttccg accctgccgc   6540

ttaccggata cctgtccgcc tttctccctt cgggaagcgt ggcgctttct catagctcac   6600

gctgtaggta tctcagttcg gtgtaggtcg ttcgctccaa gctgggctgt gtgcacgaac   6660

cccccgttca gcccgaccgc tgcgccttat ccggtaacta tcgtcttgag tccaacccgg   6720

taagacacga cttatcgcca ctggcagcag ccactggtaa caggattagc agagcgaggt   6780

atgtaggcgg tgctacagag ttcttgaagt ggtggcctaa ctacggctac actagaagga   6840

cagtatttgg tatctgcgct ctgctgaagc cagttacctt cggaaaaaga gttggtagct   6900

cttgatccgg caaacaaacc accgctggta gcggtggttt ttttgtttgc aagcagcaga   6960

ttacgcgcag aaaaaaagga tctcaagaag atcctttgat cttttctacg gggtctgacg   7020

ctcagtggaa cgaaaactca cgttaaggga ttttggtcat gagattatca aaaaggatct   7080

tcacctagat ccttttaaat taaaaatgaa gttttaaatc aatctaaagt atatatgagt   7140

aaacttggtc tgacagttac caatgcttaa tcagtgaggc acctatctca gcgatctgtc   7200

tatttcgttc atccatagtt gcctgactcc ccgtcgtgta gataactacg atacgggagg   7260

gcttaccatc tggccccagt gctgcaatga taccgcgaga cccacgctca ccggctccag   7320

atttatcagc aataaaccag ccagccggaa gggccgagcg cagaagtggt cctgcaactt   7380

tatccgcctc catccagtct attaattgtt gccgggaagc tagagtaagt agttcgccag   7440
```

```
ttaatagttt gcgcaacgtt gttgccattg ctgcagccat gagattatca aaaaggatct   7500

tcacctagat ccttttcacg tagaaagcca gtccgcagaa acggtgctga ccccggatga   7560

atgtcagcta ctgggctatc tggacaaggg aaaacgcaag cgcaaagaga aagcaggtag   7620

cttgcagtgg gcttacatgg cgatagctag actgggcggt tttatggaca gcaagcgaac   7680

cggaattgcc agctggggcg ccctctggta aggttgggaa gccctgcaaa gtaaactgga   7740

tggctttctc gccgccaagg atctgatggc gcaggggatc aagctctgat caagagacag   7800

gatgaggatc gtttcgcatg attgaacaag atggattgca cgcaggttct ccggccgctt   7860

gggtggagag gctattcggc tatgactggg cacaacagac aatcggctgc tctgatgccg   7920

ccgtgttccg gctgtcagcg caggggcgcc cggttctttt tgtcaagacc gacctgtccg   7980

gtgccctgaa tgaactgcaa gacgaggcag cgcggctatc gtggctggcc acgacgggcg   8040

ttccttgcgc agctgtgctc gacgttgtca ctgaagcggg aagggactgg ctgctattgg   8100

gcgaagtgcc ggggcaggat ctcctgtcat ctcaccttgc tcctgccgag aaagtatcca   8160

tcatggctga tgcaatgcgg cggctgcata cgcttgatcc ggctacctgc ccattcgacc   8220

accaagcgaa acatcgcatc gagcgagcac gtactcggat ggaagccggt cttgtcgatc   8280

aggatgatct ggacgaagag catcaggggc tcgcgccagc cgaactgttc gccaggctca   8340

aggcgagcat gcccgacggc gaggatctcg tcgtgaccca tggcgatgcc tgcttgccga   8400

atatcatggt ggaaaatggc cgcttttctg gattcatcga ctgtggccgg ctgggtgtgg   8460

cggaccgcta tcaggacata gcgttggcta cccgtgatat tgctgaagag cttggcggcg   8520

aatgggctga ccgcttcctc gtgctttacg gtatcgccgc tcccgattcg cagcgcatcg   8580

ccttctatcg ccttcttgac gagttcttct gaattttgtt aaaatttttg ttaaatcagc   8640

tcatttttta accaataggc cgaaatcggc aacatccctt ataaatcaaa agaatagacc   8700

gcgatagggt tgagtgttgt tccagtttgg aacaagagtc cactattaaa gaacgtggac   8760

tccaacgtca aagggcgaaa aaccgtctat cagggcgatg gcccactacg tgaaccatca   8820

cccaaatcaa gtttttgcg gtcgaggtgc cgtaaagctc taaatcggaa ccctaaaggg   8880

agcccccgat ttagagcttg acggggaaag ccggcgaacg tggcgagaaa ggaagggaag   8940

aaagcgaaag gagcgggcgc tagggcgctg gcaagtgtag cggtcacgct gcgcgtaacc   9000

accacacccg cgcgcttaat gcgccgctac agggcgcgtc cattcgccat tcaggatcga   9060

attaattctt aat                                                      9073
```

<210> SEQ ID NO 16
<211> LENGTH: 50475
<212> TYPE: DNA
<213> ORGANISM: Artificial Sequence
<220> FEATURE:
<223> OTHER INFORMATION: chimeric adenoviral vector DS2bC-HA encoding TLR-3 agonist luc1, influenza hemagglutinin (HA) (A/Indo/5/2005; avian flu) and cytomegalovirus (CMV) promotor, pShuttle vector
<221> NAME/KEY: modified_base
<222> LOCATION: (1)...(50475)
<223> OTHER INFORMATION: n = g, a, c or t

<400> SEQUENCE: 16

```
taacatcatc aataatatac cttattttgg attgaagcca atatgataat gagggggtgg     60

agtttgtgac gtggcgcggg gcgtgggaac ggggcgggtg acgtagtagt gtggcggaag    120

tgtgatgttg caagtgtggc ggaacacatg taagcgacgg atgtggcaaa agtgacgttt    180

ttggtgtgcg ccggtgtaca caggaagtga caattttcgc gcggttttag gcggatgttg    240
```

```
tagtaaattt gggcgtaacc gagtaagatt tggccatttt cgcgggaaaa ctgaataaga    300
ggaagtgaaa tctgaataat tttgtgttac tcatagcgcg taatactgct agagatctgg    360
cgaaaggggg atgtgctgca aggcgattaa gttgggtaac gccagggttt tcccagtcac    420
gacgttgtaa aacgacggcc agtgaattgt aatacgactc actatagggc gaattgggta    480
ctggccacag agcttggccc attgcatacg ttgtatccat atcataatat gtacatttat    540
attggctcat gtccaacatt accgccatgt tgacattgat tattgactag ttattaatag    600
taatcaatta cggggtcatt agttcatagc ccatatatgg agttccgcgt tacataactt    660
acggtaaatg gcccgcctgg ctgaccgccc aacgaccccc gcccattgac gtcaataatg    720
acgtatgttc ccatagtaac gccaataggg actttccatt gacgtcaatg ggtggagtat    780
ttacggtaaa ctgcccactt ggcagtacat caagtgtatc atatgccaag tacgccccct    840
attgacgtca atgacggtaa atggcccgcc tggcattatg cccagtacat gaccttatgg    900
gactttccta cttggcagta catctacgta ttagtcatcg ctattaccat ggtgatgcgg    960
ttttggcagt acatcaatgg gcgtggatag cggtttgact cacggggatt tccaagtctc   1020
caccccattg acgtcaatgg gagtttgttt tggcaccaaa atcaacggga ctttccaaaa   1080
tgtcgtaaca actccgcccc attgacgcaa atgggcggta ggcgtgtacg gtgggaggtc   1140
tatataagca gagctcgttt agtgaaccgt cagatcgcct ggagacgcca tccacgctgt   1200
tttgacctcc atagaagaca ccgggaccga tccagcctga ctctagccta gctctgaagt   1260
tggtggtgag gccctgggca ggttggtatc aaggttacaa gacaggttta aggagaccaa   1320
tagaaactgg gcatgtggag acagagaaga ctcttgggtt tctgataggc actgactctc   1380
tctgcctatt ggtctatttt cccaccctta ggctgctggt ctgagcctag gagatctctc   1440
gaggtcgacg gtatcgatgc caccatggag aaaatcgtcc tgttgctcgc tattgtgtct   1500
ctagtgaaga gcgatcaaat ttgtatcggc taccatgcca ataactcaac agagcaggtc   1560
gatactatca tggagaaaaa cgtaacagtt actcatgccc aagacatctt ggaaaagacc   1620
cacaacggca aactttgcga cctggatgga gtgaagcccc tgatcctccg ggactgttca   1680
gtcgctggtt ggctgctcgg gaaccctatg tgtgatgagt ttatcaacgt gcctgaatgg   1740
tcttacattg tggagaaggc taaccctacc aatgacctct gctatcctgg gtcatttaac   1800
gattacgagg aactgaaaca cctgttgtct agaattaacc actttgaaaa gatacagatt   1860
atacccaagt ctagttggag tgatcacgaa gcctcctcag gcgttagctc agcgtgtccc   1920
tatctgggct ctccatcctt ctttagaaat gtggtctggt taatcaaaaa gaacagtacc   1980
tacccaacca tcaaaaagtc ttataacaat accaatcagg aggacctgct cgtgttgtgg   2040
ggtatccatc acccgaacga cgccgctgaa cagactaggc tgtatcagaa ccccactaca   2100
tacatcagta ttggcacgag tactctgaac cagcgattag tgccaaagat tgcaacacgg   2160
agcaaagtaa atgggcaatc tggcaggatg gagtttttct ggacaatctt aaaacccaac   2220
gatgcgataa atttcgagtc caatggcaat ttcatcgccc ctgaatacgc ctataagatc   2280
gtgaaaaagg gggactctgc aattatgaag tccgaattag agtatggcaa ttgcaacacg   2340
aagtgccaga caccaatggg agccattaat agctcaatgc ccttccataa tattcatcca   2400
ttgaccattg gggagtgccc aaagtacgtg aagtccaacc gcctggtcct cgcaaccggt   2460
ctaagaaata gcccgcagag agaatcgcgg aggaagaaac gtggcctgtt tggcgcgatt   2520
gccggattca tcgagggagg ctggcagggt atggtcgatg gttggtacgg ataccaccat   2580
agcaacgaac aggggtccgg ctatgcagca gataaggaga gcactcagaa agctattgac   2640
```

```
ggagttacaa acaaggttaa tagtattata gataaaatga acacgcaatt cgaggccgtt   2700
gggagggagt ttaacaatct ggaacgccgg atcgaaaatc tgaataagaa aatggaagac   2760
ggcttccttg acgtgtggac ttataatgca gagctgcttg tactcatgga gaacgagagg   2820
accctggatt tccacgatag caacgtgaag aacctttacg acaaggtgag acttcagctc   2880
cgagacaacg ccaaggagct ggggaatgga tgcttcgagt tttaccacaa atgtgacaat   2940
gagtgcatgg aaagtatacg caacgggacc tacaattacc ctcagtatag cgaagaggct   3000
cggctcaaac gcgaagagat aagcggggtg aaattggaat caatcggaac atatcaaatc   3060
ctgtccatct attccaccgt cgcctcttcg ctggccctcg ctatcatgat ggctggtctg   3120
tccctatgga tgtgttccaa tggaagcctt cagtgccgta tttgtatatg agcggccgcc   3180
ctattctata gtgtcaccta aatgctagag ctcgctgatc agcctcgact gtgccttcta   3240
gttgccagcc atctgttgtt tgcccctccc ccgtgccttc cttgaccctg gaaggtgcca   3300
ctcccactgt cctttcctaa taaaatgagg aaattgcatc gcattgtctg agtaggtgtc   3360
attctattct ggggggtggg gtggggcagg acagcaaggg ggaggattgg gaagacaata   3420
gcaggcatgc tggggatgcg gtgggctcta tggcttctga ggcggaaaga accaaagctt   3480
aacatcatca ataatatacc ttattttgga ttgaagccaa tatgataatg agggggtgga   3540
gtttgtgacg tggcgcgggg cgtgggaacg gggcgggtga cgtagtagtg tggcggaagt   3600
gtgatgttgc aagtgtggcg gaacacatgt aagcgacgga tgtggcaaaa gtgacgtttt   3660
tggtgtgcgc cggtgtacac aggaagtgac aattttcgcg cggttttagg cggatgttgt   3720
agtaaatttg ggcgtaaccg agtaagattt ggccattttc gcgggaaaac tgaataagag   3780
gaagtgaaat ctgaataatt ttgtgttact catagcgcgt aatactgtaa tagtaatcaa   3840
ttacggggtc attagttcat agcccatata tggagttccg cgttacataa cttacggtaa   3900
atggcccgcc tggctgaccg cccaacgacc cccgcccatt gacgtcaata atgacgtatg   3960
ttcccatagt aacgccaata gggactttcc attgacgtca atgggtggag tatttacggt   4020
aaactgccca cttggcagta catcaagtgt atcatatgcc aagtacgccc cctattgacg   4080
tcaatgacgg taaatggccc gcctggcatt atgcccagta catgacctta tgggactttc   4140
ctacttggca gtacatctac gtattagtca tcgctattac catggtgatg cggttttggc   4200
agtacatcaa tgggcgtgga tagcggtttg actcacgggg atttccaagt ctccacccca   4260
ttgacgtcaa tgggagtttg ttttggcacc aaaatcaacg ggactttcca aaatgtcgta   4320
acaactccgc cccattgacg caaatgggcg gtaggcgtgt acggtgggag gtctatataa   4380
gcagagctgg tttagtgaac cgtcagatcc gctagagatc tgggaaacga tatgggctga   4440
atacggatcc gtattcagcc catatcgttt ctctagaaat aaaatatctt tattttcatt   4500
acatctgtgt gttggttttt tgtgtggcgg ccgctcgagc ctaagcttct agataagata   4560
tccgatccac cggatctaga taactgatca taatcagcca taccacattt gtagaggttt   4620
tacttgcttt aaaaaacctc ccacacctcc ccctgaacct gaaacataaa atgaatgcaa   4680
ttgttgttgt taacttgttt attgcagctt ataatggtta caaataaagc aatagcatca   4740
caaatttcac aaataaagca tttttttcac tgcattctag ttgtggtttg tccaaactca   4800
tcaatgtatc ttaacgcgga tctgggcgtg gttaagggtg ggaaagaata tataaggtgg   4860
gggtcttatg tagttttgta tctgttttgc agcagccgcc gccgccatga gcaccaactc   4920
gtttgatgga agcattgtga gcttgtcgac tcgaagatct gggcgtggtt aagggtggga   4980
aagaatatat aaggtggggg tcttatgtag ttttgtatct gttttgcagc agccgccgcc   5040
```

```
gccatgagca ccaactcgtt tgatggaagc attgtgagct catatttgac aacgcgcatg   5100
cccccatggg ccggggtgcg tcagaatgtg atgggctcca gcattgatgg tcgccccgtc   5160
ctgcccgcaa actctactac cttgacctac gagaccgtgt ctggaacgcc gttggagact   5220
gcagcctccg ccgccgcttc agccgctgca gccaccgccc gcgggattgt gactgacttt   5280
gctttcctga gcccgcttgc aagcagtgca gcttcccgtt catccgcccg cgatgacaag   5340
ttgacggctc ttttggcaca attggattct ttgacccggg aacttaatgt cgtttctcag   5400
cagctgttgg atctgcgcca gcaggtttct gccctgaagg cttcctcccc tcccaatgcg   5460
gtttaaaaca taaataaaaa accagactct gtttggattt ggatcaagca agtgtcttgc   5520
tgtctttatt taggggtttt gcgcgcgcgg taggcccggg accagcggtc tcggtcgttg   5580
agggtcctgt gtatttttttc caggacgtgg taaaggtgac tctggatgtt cagatacatg   5640
ggcataagcc cgtctctggg gtggaggtag caccactgca gagcttcatg ctgcggggtg   5700
gtgttgtaga tgatccagtc gtagcaggag cgctgggcgt ggtgcctaaa aatgtctttc   5760
agtagcaagc tgattgccag gggcaggccc ttggtgtaag tgtttacaaa gcggttaagc   5820
tgggatgggt gcatacgtgg ggatatgaga tgcatcttgg actgtatttt taggttggct   5880
atgttcccag ccatatccct ccggggattc atgttgtgca gaaccaccag cacagtgtat   5940
ccggtgcact tgggaaattt gtcatgtagc ttagaaggaa atgcgtggaa gaacttggag   6000
acgcccttgt gacctccaag attttccatg cattcgtcca taatgatggc aatgggccca   6060
cgggcggcgg cctgggcgaa gatatttctg ggatcactaa cgtcatagtt gtgttccagg   6120
atgagatcgt cataggccat ttttacaaag cgcgggcgga gggtgccaga ctgcggtata   6180
atggttccat ccggcccagg ggcgtagtta ccctcacaga tttgcatttc ccacgctttg   6240
agttcagatg gggggatcat gtctacctgc ggggcgatga agaaaacggt ttccggggta   6300
ggggagatca gctgggaaga aagcaggttc ctgagcagct gcgacttacc gcagccggtg   6360
ggcccgtaaa tcacacctat taccgggtgc aactggtagt taagagagct gcagctgccg   6420
tcatccctga gcaggggggc cacttcgtta agcatgtccc tgactcgcat gttttccctg   6480
accaaatccg ccagaaggcg ctcgccgccc agcgatagca gttcttgcaa ggaagcaaag   6540
tttttcaacg gtttgagacc gtccgccgta ggcatgcttt tgagcgtttg accaagcagt   6600
tccaggcggt cccacagctc ggtcacctgc tctacggcat ctcgatccag catatctcct   6660
cgtttcgcgg gttggggcgg ctttcgctgt acggcagtag tcggtgctcg tccagacggg   6720
ccagggtcat gtctttccac gggcgcaggg tcctcgtcag cgtagtctgg gtcacggtga   6780
aggggtgcgc tccgggctgc gcgctggcca gggtgcgctt gaggctggtc ctgctggtgc   6840
tgaagcgctg ccggtcttcg ccctgcgcgt cggccaggta gcatttgacc atggtgtcat   6900
agtccagccc ctccgcggcg tggcccttgg cgcgcagctt gcccttggag gaggcgccgc   6960
acgaggggca gtgcagactt ttgagggcgt agagcttggg cgcgagaaat accgattccg   7020
gggagtaggc atccgcgccg caggccccgc agacggtctc gcattccacg agccaggtga   7080
gctctggccg ttcggggtca aaaaccaggt ttcccccatg ctttttgatg cgtttcttac   7140
ctctggtttc catgagccgg tgtccacgct cggtgacgaa aaggctgtcc gtgtccccgt   7200
atacagactt gagagggagt ttaaacgaat tcaatagctt gttgcatggg cggcgatata   7260
aaatgcaagg tgctgctcaa aaaatcaggc aaagcctcgc gcaaaaaaga aagcacatcg   7320
tagtcatgct catgcagata aaggcaggta agctccggaa ccaccacaga aaaagacacc   7380
atttttctct caaacatgtc tgcgggtttc tgcataaaca caaaataaaa taacaaaaaa   7440
```

```
acatttaaac attagaagcc tgtcttacaa caggaaaaac aacccttata agcataagac   7500
ggactacggc catgccggcg tgaccgtaaa aaaactggtc accgtgatta aaaagcacca   7560
ccgacagctc ctcggtcatg tccggagtca taatgtaaga ctcggtaaac acatcaggtt   7620
gattcatcgg tcagtgctaa aaagcgaccg aaatagcccg gggaataca tacccgcagg   7680
cgtagagaca acattacagc cccatagga ggtataacaa aattaatagg agagaaaaac   7740
acataaacac ctgaaaaacc ctcctgccta ggcaaaatag caccctcccg ctccagaaca   7800
acatacagcg cttcacagcg gcagcctaac agtcagcctt accagtaaaa aagaaaacct   7860
attaaaaaaa caccactcga cacggcacca gctcaatcag tcacagtgta aaaaagggcc   7920
aagtgcagag cgagtatata taggactaaa aaatgacgta acggttaaag tccacaaaaa   7980
acacccagaa aaccgcacgc gaacctacgc ccagaaacga aagccaaaaa acccacaact   8040
tcctcaaatc gtcacttccg ttttcccacg ttacgtaact tcccatttta agaaaactac   8100
aattcccaac acatacaagt tactccgccc taaaacctac gtcacccgcc ccgttcccac   8160
gccccgcgcc acgtcacaaa ctccaccccc tcattatcat attggcttca atccaaaata   8220
aggtatatta ttgatgatgt taattaacat gcatggatcc atatgcggtg tgaaataccg   8280
cacagatgcg taaggagaaa ataccgcatc aggcgctctt ccgcttcctc gctcactgac   8340
tcgctgcgct cggtcgttcg gctgcggcga gcggtatcag ctcactcaaa ggcggtaata   8400
cggttatcca cagaatcagg ggataacgca ggaaagaaca tgtgagcaaa aggccagcaa   8460
aaggccagga accgtaaaaa ggccgcgttg ctggcgtttt tccataggct ccgcccccct   8520
gacgagcatc acaaaaatcg acgctcaagt cagaggtggc gaaacccgac aggactataa   8580
agataccagg cgtttccccc tggaagctcc ctcgtgcgct ctcctgttcc gaccctgccg   8640
cttaccggat acctgtccgc ctttctccct tcgggaagcg tggcgctttc tcatagctca   8700
cgctgtaggt atctcagttc ggtgtaggtc gttcgctcca agctgggctg tgtgcacgaa   8760
ccccccgttc agcccgaccg ctgcgcctta tccggtaact atcgtcttga gtccaacccg   8820
gtaagacacg acttatcgcc actggcagca gccactggta acaggattag cagagcgagg   8880
tatgtaggcg gtgctacaga gttcttgaag tggtggccta actacggcta cactagaagg   8940
acagtatttg gtatctgcgc tctgctgaag ccagttacct tcggaaaaag agttggtagc   9000
tcttgatccg gcaaacaaac caccgctggt agcggtggtt tttttgtttg caagcagcag   9060
attacgcgca gaaaaaaagg atctcaagaa gatcctttga tcttttctac ggggtctgac   9120
gctcagtgga acgaaaactc acgttaaggg attttggtca tgagattatc aaaaaggatc   9180
ttcacctaga tccttttaaa ttaaaaatga agttttaaat caatctaaag tatatatgag   9240
taaacttggt ctgacagtta ccaatgctta atcagtgagg cacctatctc agcgatctgt   9300
ctatttcgtt catccatagt tgcctgactc cccgtcgtgt agataactac gatacgggag   9360
ggcttaccat ctggccccag tgctgcaatg ataccgcgag acccacgctc accggctcca   9420
gatttatcag caataaacca gccagccgga agggccgagc gcagaagtgg tcctgcaact   9480
ttatccgcct ccatccagtc tattaattgt tgccgggaag ctagagtaag tagttcgcca   9540
gttaatagtt tgcgcaacgt tgttgccatt gctgcagcca tgagattatc aaaaaggatc   9600
ttcacctaga tccttttcac gtagaaagcc agtccgcaga aacggtgctg accccggatg   9660
aatgtcagct actgggctat ctggacaagg gaaaacgcaa gcgcaaagag aaagcaggta   9720
gcttgcagtg ggcttacatg gcgatagcta gactgggcgg ttttatggac agcaagcgaa   9780
ccggaattgc cagctggggc gccctctggt aaggttggga agccctgcaa agtaaactgg   9840
```

```
atggctttct cgccgccaag gatctgatgg cgcaggggat caagctctga tcaagagaca   9900
ggatgaggat cgtttcgcat gattgaacaa gatggattgc acgcaggttc tccggccgct   9960
tgggtggaga ggctattcgg ctatgactgg gcacaacaga caatcggctg ctctgatgcc  10020
gccgtgttcc ggctgtcagc gcaggggcgc ccggttcttt ttgtcaagac cgacctgtcc  10080
ggtgccctga atgaactgca agacgaggca gcgcggctat cgtggctggc cacgacgggc  10140
gttccttgcg cagctgtgct cgacgttgtc actgaagcgg gaagggactg gctgctattg  10200
ggcgaagtgc cggggcagga tctcctgtca tctcaccttg ctcctgccga gaaagtatcc  10260
atcatggctg atgcaatgcg gcggctgcat acgcttgatc cggctacctg cccattcgac  10320
caccaagcga aacatcgcat cgagcgagca cgtactcgga tggaagccgg tcttgtcgat  10380
caggatgatc tggacgaaga gcatcagggg ctcgcgccag ccgaactgtt cgccaggctc  10440
aaggcgagca tgcccgacgg cgaggatctc gtcgtgaccc atggcgatgc ctgcttgccg  10500
aatatcatgg tggaaaatgg ccgcttttct ggattcatcg actgtggccg gctgggtgtg  10560
gcggaccgct atcaggacat agcgttggct acccgtgata ttgctgaaga gcttggcggc  10620
gaatgggctg accgcttcct cgtgctttac ggtatcgccg ctcccgattc gcagcgcatc  10680
gccttctatc gccttcttga cgagttcttc tgaattttgt taaaattttt gttaaatcag  10740
ctcatttttt aaccaatagg ccgaaatcgg caacatccct tataaatcaa aagaatagac  10800
cgcgataggg ttgagtgttg ttccagtttg gaacaagagt ccactattaa agaacgtgga  10860
ctccaacgtc aaagggcgaa aaaccgtcta tcagggcgat ggcccactac gtgaaccatc  10920
acccaaatca agttttttgc ggtcgaggtg ccgtaaagct ctaaatcgga accctaaagg  10980
gagcccccga tttagagctt gacggggaaa gccggcgaac gtggcgagaa aggaagggaa  11040
gaaagcgaaa ggagcgggcg ctagggcgct ggcaagtgta gcggtcacgc tgcgcgtaac  11100
caccacaccc gcgcgcttaa tgcgccgcta cagggcgcgt ccattcgcca ttcaggatcg  11160
aattaattct taattaagga tccnnncctg tcctcgaccg atgcccttga gagccttcaa  11220
cccagtcagc tccttccggt gggcgcgggg catgactatc gtcgccgcac ttatgactgt  11280
cttctttatc atgcaactcg taggacaggt gccggcagcg ctctgggtca ttttcggcga  11340
ggaccgcttt cgctggagcg cgacgatgat cggcctgtcg cttgcggtat tcggaatctt  11400
gcacgccctc gctcaagcct tcgtcactgg tcccgccacc aaacgtttcg gcgagaagca  11460
ggccattatc gccggcatgg cggccgacgc gctgggctac gtcttgctgg cgttcgcgac  11520
gcgaggctgg atggccttcc ccattatgat tcttctcgct tccggcggca tcgggatgcc  11580
cgcgttgcag gccatgctgt ccaggcaggt agatgacgac catcagggac agcttcaagg  11640
atcgctcgcg gctcttacca gcctaacttc gatcactgga ccgctgatcg tcacggcgat  11700
ttatgccgcc tcggcgagca catggaacgg gttggcatgg attgtaggcg ccgccctata  11760
ccttgtctgc ctccccgcgt tgcgtcgcgg tgcatggagc cgggccacct cgacctgaat  11820
ggaagccggc ggcacctcgc taacggattc accactccaa gaattggagc caatcaattc  11880
ttgcggagaa ctgtgaatgc gcaaaccaac ccttggcaga acatatccat cgcgtccgcc  11940
atctccagca gccgcacgcg gcgcatctcg ggcagcgttg ggtcctggcc acgggtgcgc  12000
atgatcgtgc tcctgtcgtt gaggacccgg ctaggctggc ggggttgcct tactggttag  12060
cagaatgaat caccgatacg cgagcgaacg tgaagcgact gctgctgcaa aacgtctgcg  12120
acctgagcaa caacatgaat ggtcttcggt ttccgtgttt cgtaaagtct ggaaacgcgg  12180
aagtcagcgc cctgcaccat tatgttccgg atctgcatcg caggatgctg ctggctaccc  12240
```

tgtggaacac ctacatctgt attaacgaag cgctggcatt gaccctgagt gatttttctc 12300
tggtcccgcc gcatccatac cgccagttgt ttaccctcac aacgttccag taaccgggca 12360
tgttcatcat cagtaacccg tatcgtgagc atcctctctc gtttcatcgg tatcattacc 12420
cccatgaaca gaaattcccc cttacacgga ggcatcaagt gaccaaacag gaaaaaaccg 12480
cccttaacat ggcccgcttt atcagaagcc agacattaac gcttctggag aaactcaacg 12540
agctggacgc ggatgaacag gcagacatct gtgaatcgct tcacgaccac gctgatgagc 12600
tttaccgcag ctgcctcgcg cgtttcggtg atgacggtga aaacctctga cacatgcagc 12660
tcccggagac ggtcacagct tgtctgtaag cggatgccgg gagcagacaa gcccgtcagg 12720
gcgcgtcagc gggtgttggc gggtgtcggg gcgcagccat gacccagtca cgtagcgata 12780
gcggagtgta tactggctta actatgcggc atcagagcag attgtactga gagtgcacca 12840
tatgcggtgt gaaataccgc acagatgcgt aaggagaaaa taccgcatca ggcgctcttc 12900
cgcttcctcg ctcactgact cgctgcgctc ggtcgttcgg ctgcggcgag cggtatcagc 12960
tcactcaaag gcggtaatac ggttatccac agaatcaggg gataacgcag gaaagaacat 13020
gtgagcaaaa ggccagcaaa aggccaggaa ccgtaaaaag gccgcgttgc tggcgttttt 13080
ccataggctc cgcccccctg acgagcatca caaaaatcga cgctcaagtc agaggtggcg 13140
aaacccgaca ggactataaa gataccaggc gtttccccct ggaagctccc tcgtgcgctc 13200
tcctgttccg accctgccgc ttaccggata cctgtccgcc tttctccctt cgggaagcgt 13260
ggcgctttct caatgctcac gctgtaggta tctcagttcg gtgtaggtcg ttcgctccaa 13320
gctgggctgt gtgcacgaac cccccgttca gcccgaccgc tgcgccttat ccggtaacta 13380
tcgtcttgag tccaacccgg taagacacga cttatcgcca ctggcagcag ccactggtaa 13440
caggattagc agagcgaggt atgtaggcgg tgctacagag ttcttgaagt ggtggcctaa 13500
ctacggctac actagaagga cagtatttgg tatctgcgct ctgctgaagc cagttacctt 13560
cggaaaaaga gttggtagct cttgatccgg caaacaaacc accgctggta gcggtggttt 13620
ttttgtttgc aagcagcaga ttacgcgcag aaaaaaagga tctcaagaag atcctttgat 13680
cttttctacg gggtctgacg ctcagtggaa cgaaaactca cgttaaggga ttttggtcat 13740
gagattatca aaaaggatct tcacctagat ccttttaaat taaaaatgaa gttttaaatc 13800
aatctaaagt atatatgagt aaacttggtc tgacagttac caatgcttaa tcagtgaggc 13860
acctatctca gcgatctgtc tatttcgttc atccatagtt gcctgactcc ccgtcgtgta 13920
gataactacg atacgggagg gcttaccatc tggccccagt gctgcaatga taccgcgaga 13980
cccacgctca ccggctccag atttatcagc aataaaccag ccagccggaa gggccgagcg 14040
cagaagtggt cctgcaactt tatccgcctc catccagtct attaattgtt gccgggaagc 14100
tagagtaagt agttcgccag ttaatagttt gcgcaacgtt gttgccattg ctgcagccat 14160
gagattatca aaaaggatct tcacctagat ccttttcacg tagaaagcca gtccgcagaa 14220
acggtgctga ccccggatga atgtcagcta ctgggctatc tggacaaggg aaaacgcaag 14280
cgcaaagaga aagcaggtag cttgcagtgg gcttacatgg cgatagctag actgggcggt 14340
tttatggaca gcaagcgaac cggaattgcc agctggggcg ccctctggta aggttgggaa 14400
gccctgcaaa gtaaactgga tggctttctc gccgccaagg atctgatggc gcaggggatc 14460
aagctctgat caagagacag gatgaggatc gtttcgcatg attgaacaag atggattgca 14520
cgcaggttct ccggccgctt gggtggagag gctattcggc tatgactggg cacaacagac 14580
aatcggctgc tctgatgccg ccgtgttccg gctgtcagcg caggggcgcc cggttctttt 14640

```
tgtcaagacc gacctgtccg gtgccctgaa tgaactgcaa gacgaggcag cgcggctatc  14700
gtggctggcc acgacgggcg ttccttgcgc agctgtgctc gacgttgtca ctgaagcggg  14760
aagggactgg ctgctattgg gcgaagtgcc ggggcaggat ctcctgtcat ctcaccttgc  14820
tcctgccgag aaagtatcca tcatggctga tgcaatgcgg cggctgcata cgcttgatcc  14880
ggctacctgc ccattcgacc accaagcgaa acatcgcatc gagcgagcac gtactcggat  14940
ggaagccggt cttgtcgatc aggatgatct ggacgaagag catcaggggc tcgcgccagc  15000
cgaactgttc gccaggctca aggcgagcat gcccgacggc gaggatctcg tcgtgaccca  15060
tggcgatgcc tgcttgccga atatcatggt ggaaaatggc cgcttttctg gattcatcga  15120
ctgtggccgg ctgggtgtgg cggaccgcta tcaggacata gcgttggcta cccgtgatat  15180
tgctgaagag cttggcggcg aatgggctga ccgcttcctc gtgctttacg gtatcgccgc  15240
tcccgattcg cagcgcatcg ccttctatcg ccttcttgac gagttcttct gaattttgtt  15300
aaaatttttg ttaaatcagc tcattttta accaataggc cgaaatcggc aacatccctt  15360
ataaatcaaa agaatagacc gcgatagggt tgagtgttgt tccagtttgg aacaagagtc  15420
cactattaaa gaacgtggac tccaacgtca aagggcgaaa aaccgtctat cagggcgatg  15480
gcccactacg tgaaccatca cccaaatcaa gttttttgcg gtcgaggtgc cgtaaagctc  15540
taaatcggaa ccctaaaggg agcccccgat ttagagcttg acggggaaag ccggcgaacg  15600
tggcgagaaa ggaagggaag aaagcgaaag gagcgggcgc tagggcgctg gcaagtgtag  15660
cggtcacgct gcgcgtaacc accacacccg cgcgcttaat gcgccgctac agggcgcgtc  15720
cattcgccat tcaggatcga attaattctt aattaacatc atcaataata taccttattt  15780
tggattgaag ccaatatgat aatgaggggg tggagtttgt gacgtggcgc ggggcgtggg  15840
aacggggcgg gtgacgtagt agtgtggcgg aagtgtgatg ttgcaagtgt ggcggaacac  15900
atgtaagcga cggatgtggc aaaagtgacg tttttggtgt gcgccggtgt acacaggaag  15960
tgacaatttt cgcgcggttt taggcggatg ttgtagtaaa tttgggcgta accgagtaag  16020
atttggccat tttcgcggga aaactgaata agaggaagtg aaatctgaat aattttgtgt  16080
tactcatagc gcgtaatact gctagagatc tggcgaaagg gggatgtgct gcaaggcgat  16140
taagttgggt aacgccaggg ttttcccagt cacgacgttg taaaacgacg gccagtgaat  16200
tgtaatacga ctcactatag ggcgaattgg gtactggcca cagagcttgg cccattgcat  16260
acgttgtatc catatcataa tatgtacatt tatattggct catgtccaac attaccgcca  16320
tgttgacatt gattattgac tagttattaa tagtaatcaa ttacggggtc attagttcat  16380
agcccatata tggagttccg cgttacataa cttacggtaa atggcccgcc tggctgaccg  16440
cccaacgacc cccgcccatt gacgtcaata atgacgtatg ttcccatagt aacgccaata  16500
gggactttcc attgacgtca atgggtggag tatttacggt aaactgccca cttggcagta  16560
catcaagtgt atcatatgcc aagtacgccc cctattgacg tcaatgacgg taaatggccc  16620
gcctggcatt atgcccagta catgacctta tgggactttc ctacttggca gtacatctac  16680
gtattagtca tcgctattac catggtgatg cggttttggc agtacatcaa tgggcgtgga  16740
tagcggtttg actcacgggg atttccaagt ctccacccca ttgacgtcaa tgggagtttg  16800
ttttggcacc aaaatcaacg ggactttcca aaatgtcgta acaactccgc cccattgacg  16860
caaatgggcg gtaggcgtgt acggtgggag gtctatataa gcagagctcg tttagtgaac  16920
cgtcagatcg cctggagacg ccatccacgc tgttttgacc tccatagaag acaccgggac  16980
cgatccagcc tgactctagc ctagctctga agttggtggt gaggccctgg gcaggttggt  17040
```

```
atcaaggtta caagacaggt ttaaggagac caatagaaac tgggcatgtg gagacagaga  17100
agactcttgg gtttctgata ggcactgact ctctctgcct attggtctat tttcccaccc  17160
ttaggctgct ggtctgagcc taggagatct ctcgaggtcg acggtatcga tgccaccatg  17220
gagaaaatcg tcctgttgct cgctattgtg tctctagtga agagcgatca aatttgtatc  17280
ggctaccatg ccaataactc aacagagcag gtcgatacta tcatggagaa aaacgtaaca  17340
gttactcatg cccaagacat cttggaaaag acccacaacg gcaaactttg cgacctggat  17400
ggagtgaagc ccctgatcct ccgggactgt tcagtcgctg gttggctgct cgggaaccct  17460
atgtgtgatg agtttatcaa cgtgcctgaa tggtcttaca ttgtggagaa ggctaaccct  17520
accaatgacc tctgctatcc tgggtcattt aacgattacg aggaactgaa acacctgttg  17580
tctagaatta accactttga aaagatacag attataccca agtctagttg gagtgatcac  17640
gaagcctcct caggcgttag ctcagcgtgt ccctatctgg gctctccatc cttctttaga  17700
aatgtggtct ggttaatcaa aaagaacagt acctacccaa ccatcaaaaa gtcttataac  17760
aataccaatc aggaggacct gctcgtgttg tggggtatcc atcacccgaa cgacgccgct  17820
gaacagacta ggctgtatca gaaccccact acatacatca gtattggcac gagtactctg  17880
aaccagcgat tagtgccaaa gattgcaaca cggagcaaag taaatgggca atctggcagg  17940
atggagtttt tctggacaat cttaaaaccc aacgatgcga taaatttcga gtccaatggc  18000
aatttcatcg cccctgaata cgcctataag atcgtgaaaa agggggactc tgcaattatg  18060
aagtccgaat tagagtatgg caattgcaac acgaagtgcc agacaccaat gggagccatt  18120
aatagctcaa tgcccttcca taatattcat ccattgacca ttggggagtg cccaaagtac  18180
gtgaagtcca accgcctggt cctcgcaacc ggtctaagaa atagcccgca gagagaatcg  18240
cggaggaaga aacgtggcct gtttggcgcg attgccggat tcatcgaggg aggctggcag  18300
ggtatggtcg atggttggta cggataccac catagcaacg aacaggggtc cggctatgca  18360
gcagataagg agagcactca gaaagctatt gacggagtta caaacaaggt taatagtatt  18420
atagataaaa tgaacacgca attcgaggcc gttgggaggg agtttaacaa tctggaacgc  18480
cggatcgaaa atctgaataa gaaaatggaa gacggcttcc ttgacgtgtg gacttataat  18540
gcagagctgc ttgtactcat ggagaacgag aggaccctgg atttccacga tagcaacgtg  18600
aagaaccttt acgacaaggt gagacttcag ctccgagaca acgccaagga gctggggaat  18660
ggatgcttcg agttttacca caaatgtgac aatgagtgca tggaaagtat acgcaacggg  18720
acctacaatt accctcagta tagcgaagag gctcggctca aacgcgaaga gataagcggg  18780
gtgaaattgg aatcaatcgg aacatatcaa atcctgtcca tctattccac cgtcgcctct  18840
tcgctggccc tcgctatcat gatggctggt ctgtccctat ggatgtgttc caatggaagc  18900
cttcagtgcc gtatttgtat atgagcggcc gccctattct atagtgtcac ctaaatgcta  18960
gagctcgctg atcagcctcg actgtgcctt ctagttgcca gccatctgtt gtttgcccct  19020
cccccgtgcc ttccttgacc ctggaaggtg ccactcccac tgtcctttcc taataaaatg  19080
aggaaattgc atcgcattgt ctgagtaggt gtcattctat tctggggggt ggggtggggc  19140
aggacagcaa gggggaggat tgggaagaca atagcaggca tgctggggat gcggtgggct  19200
ctatggcttc tgaggcggaa agaaccaaag cttaacatca tcaataatat accttatttt  19260
ggattgaagc caatatgata atgagggggt ggagtttgtg acgtggcgcg gggcgtggga  19320
acggggcggg tgacgtagta gtgtggcgga agtgtgatgt tgcaagtgtg gcggaacaca  19380
tgtaagcgac ggatgtggca aaagtgacgt tttggtgtg cgccggtgta cacaggaagt  19440
```

```
gacaatttc gcgcggtttt aggcggatgt tgtagtaaat ttgggcgtaa ccgagtaaga  19500
tttggccatt ttcgcgggaa aactgaataa gaggaagtga aatctgaata attttgtgtt  19560
actcatagcg cgtaatactg taatagtaat caattacggg gtcattagtt catagcccat  19620
atatggagtt ccgcgttaca taacttacgg taaatggccc gcctggctga ccgcccaacg  19680
acccccgccc attgacgtca ataatgacgt atgttcccat agtaacgcca atagggactt  19740
tccattgacg tcaatgggtg gagtatttac ggtaaactgc ccacttggca gtacatcaag  19800
tgtatcatat gccaagtacg ccccctattg acgtcaatga cggtaaatgg cccgcctggc  19860
attatgccca gtacatgacc ttatgggact ttcctacttg gcagtacatc tacgtattag  19920
tcatcgctat taccatggtg atgcggtttt ggcagtacat caatgggcgt ggatagcggt  19980
ttgactcacg gggatttcca agtctccacc ccattgacgt caatgggagt ttgttttggc  20040
accaaaatca acgggacttt ccaaaatgtc gtaacaactc cgccccattg acgcaaatgg  20100
gcggtaggcg tgtacggtgg gaggtctata taagcagagc tggtttagtg aaccgtcaga  20160
tccgctagag atctgggaaa cgatatgggc tgaatacgga tccgtattca gcccatatcg  20220
tttctctaga aataaaatat ctttattttc attacatctg tgtgttggtt ttttgtgtgg  20280
cggccgctcg agcctaagct tctagataag atatccgatc caccggatct agataactga  20340
tcataatcag ccataccaca tttgtagagg ttttacttgc tttaaaaaac ctcccacacc  20400
tcccctgaa cctgaaacat aaaatgaatg caattgttgt tgttaacttg tttattgcag  20460
cttataatgg ttacaaataa agcaatagca tcacaaattt cacaaataaa gcattttttt  20520
cactgcattc tagttgtggt ttgtccaaac tcatcaatgt atcttaacgc ggatctgggc  20580
gtggttaagg gtgggaaaga atatataagg tgggggtctt atgtagtttt gtatctgttt  20640
tgcagcagcc gccgccgcca tgagcaccaa ctcgtttgat ggaagcattg tgagcttgtc  20700
gactcgaaga tctgggcgtg gttaagggtg ggaaagaata tataaggtgg gggtcttatg  20760
tagttttgta tctgttttgc agcagccgcc gccgccatga gcaccaactc gtttgatgga  20820
agcattgtga gctcatattt gacaacgcgc atgcccccat gggccggggt gcgtcagaat  20880
gtgatgggct ccagcattga tggtcgcccc gtcctgcccg caaactctac taccttgacc  20940
tacgagaccg tgtctggaac gccgttggag actgcagcct ccgccgccgc ttcagccgct  21000
gcagccaccg cccgcgggat tgtgactgac tttgctttcc tgagcccgct tgcaagcagt  21060
gcagcttccc gttcatccgc ccgcgatgac aagttgacgg ctcttttggc acaattggat  21120
tctttgaccc gggaacttaa tgtcgtttct cagcagctgt tggatctgcg ccagcaggtt  21180
tctgccctga aggcttcctc ccctcccaat gcggtttaaa acataaataa aaaaccagac  21240
tctgtttgga tttggatcaa gcaagtgtct tgctgtcttt atttaggggt tttgcgcgcg  21300
cggtaggccc gggaccagcg gtctcggtcg ttgagggtcc tgtgtatttt ttccaggacg  21360
tggtaaaggt gactctggat gttcagatac atgggcataa gcccgtctct ggggtggagg  21420
tagcaccact gcagagcttc atgctgcggg gtggtgttgt agatgatcca gtcgtagcag  21480
gagcgctggg cgtggtgcct aaaaatgtct ttcagtagca agctgattgc caggggcagg  21540
cccttggtgt aagtgtttac aaagcggtta agctgggatg ggtgcatacg tggggatatg  21600
agatgcatct tggactgtat ttttaggttg gctatgttcc cagccatatc cctccgggga  21660
ttcatgttgt gcagaaccac cagcacagtg tatccggtgc acttgggaaa tttgtcatgt  21720
agcttagaag gaaatgcgtg gaagaacttg gagacgccct tgtgacctcc aagattttcc  21780
atgcattcgt ccataatgat ggcaatgggc ccacgggcgg cggcctgggc gaagatattt  21840
```

```
ctgggatcac taacgtcata gttgtgttcc aggatgagat cgtcataggc catttttaca  21900
aagcgcgggc ggagggtgcc agactgcggt ataatggttc catccggccc aggggcgtag  21960
ttaccctcac agatttgcat ttcccacgct ttgagttcag atggggggat catgtctacc  22020
tgcggggcga tgaagaaaac ggtttccggg gtaggggaga tcagctggga agaaagcagg  22080
ttcctgagca gctgcgactt accgcagccg gtgggcccgt aaatcacacc tattaccggg  22140
tgcaactggt agttaagaga gctgcagctg ccgtcatccc tgagcagggg ggccacttcg  22200
ttaagcatgt ccctgactcg catgttttcc ctgaccaaat ccgccagaag gcgctcgccg  22260
cccagcgata gcagttcttg caaggaagca aagtttttca acggtttgag accgtccgcc  22320
gtaggcatgc ttttgagcgt ttgaccaagc agttccaggc ggtcccacag ctcggtcacc  22380
tgctctacgg catctcgatc cagcatatct cctcgtttcg cgggttgggg cggctttcgc  22440
tgtacggcag tagtcggtgc tcgtccagac gggccagggt catgtctttc cacgggcgca  22500
gggtcctcgt cagcgtagtc tgggtcacgg tgaaggggtg cgctccgggc tgcgcgctgg  22560
ccagggtgcg cttgaggctg gtcctgctgg tgctgaagcg ctgccggtct tcgccctgcg  22620
cgtcggccag gtagcatttg accatggtgt catagtccag cccctccgcg gcgtggccct  22680
tggcgcgcag cttgcccttg gaggaggcgc cgcacgaggg gcagtgcaga cttttgaggg  22740
cgtagagctt gggcgcgaga aataccgatt ccggggagta ggcatccgcg ccgcaggccc  22800
cgcagacggt ctcgcattcc acgagccagg tgagctctgg ccgttcgggg tcaaaaacca  22860
ggtttccccc atgctttttg atgcgtttct tacctctggt ttccatgagc cggtgtccac  22920
gctcggtgac gaaaaggctg tccgtgtccc cgtatacaga cttgagaggc ctgtcctcga  22980
gcggtgttcc gcggtcctcc tcgtatagaa actcggacca ctctgagaca aaggctcgcg  23040
tccaggccag cacgaaggag gctaagtggg aggggtagcg gtcgttgtcc actagggggt  23100
ccactcgctc cagggtgtga agacacatgt cgccctcttc ggcatcaagg aaggtgattg  23160
gtttgtaggt gtaggccacg tgaccgggtg ttcctgaagg ggggctataa aagggggtgg  23220
gggcgcgttc gtcctcactc tcttccgcat cgctgtctgc gagggccagc tgttggggtg  23280
agtactccct ctgaaaagcg ggcatgactt ctgcgctaag attgtcagtt tccaaaaacg  23340
aggaggattt gatattcacc tggcccgcgg tgatgccttt gagggtggcc gcatccatct  23400
ggtcagaaaa gacaatcttt ttgttgtcaa gcttggtggc aaacgacccg tagagggcgt  23460
tggacagcaa cttggcgatg gagcgcaggg tttggttttt gtcgcgatcg gcgcgctcct  23520
tggccgcgat gtttagctgc acgtattcgc gcgcaacgca ccgccattcg ggaaagacgg  23580
tggtgcgctc gtcgggcacc aggtgcacgc gccaaccgcg gttgtgcagg gtgacaaggt  23640
caacgctggt ggctacctct ccgcgtaggc gctcgttggt ccagcagagg cggccgccct  23700
tgcgcgagca gaatggcggt agggggtcta gctgcgtctc gtccgggggg tctgcgtcca  23760
cggtaaagac cccgggcagc aggcgcgcgt cgaagtagtc tatcttgcat ccttgcaagt  23820
ctagcgcctg ctgccatgcg cgggcggcaa gcgcgcgctc gtatgggttg agtgggggac  23880
cccatggcat ggggtgggtg agcgcggagg cgtacatgcc gcaaatgtcg taaacgtaga  23940
ggggctctct gagtattcca agatatgtag ggtagcatct tccaccgcgg atgctggcgc  24000
gcacgtaatc gtatagttcg tgcgagggag cgaggaggtc gggaccgagg ttgctacggg  24060
cgggctgctc tgctcggaag actatctgcc tgaagatggc atgtgagttg gatgatatgg  24120
ttggacgctg gaagacgttg aagctggcgt ctgtgagacc taccgcgtca cgcacgaagg  24180
aggcgtagga gtcgcgcagc ttgttgacca gctcggcggt gacctgcacg tctagggcgc  24240
```

```
agtagtccag ggtttccttg atgatgtcat acttatcctg tccctttttt ttccacagct  24300
cgcggttgag gacaaactct tcgcggtctt tccagtactc ttggatcgga aacccgtcgg  24360
cctccgaacg gtaagagcct agcatgtaga actggttgac ggcctggtag gcgcagcatc  24420
ccttttctac gggtagcgcg tatgcctgcg cggccttccg gagcgaggtg tgggtgagcg  24480
caaaggtgtc cctgaccatg actttgaggt actggtattt gaagtcagtg tcgtcgcatc  24540
cgccctgctc ccagagcaaa aagtccgtgc gctttttgga acgcggattt ggcagggcga  24600
aggtgacatc gttgaagagt atctttcccg cgcgaggcat aaagttgcgt gtgatgcgga  24660
agggtcccgg cacctcggaa cggttgttaa ttacctgggc ggcgagcacg atctcgtcaa  24720
agccgttgat gttgtggccc acaatgtaaa gttccaagaa gcgcgggatg cccttgatgg  24780
aaggcaattt tttaagttcc tcgtaggtga gctcttcagg ggagctgagc ccgtgctctg  24840
aaagggccca gtctgcaaga tgagggttgg aagcgacgaa tgagctccac aggtcacggg  24900
ccattagcat ttgcaggtgg tcgcgaaagg tcctaaactg gcgacctatg gccatttttt  24960
ctggggtgat gcagtagaag gtaagcgggt cttgttccca gcggtcccat ccaaggttcg  25020
cggctaggtc tcgcgcggca gtcactagag gctcatctcc gccgaacttc atgaccagca  25080
tgaagggcac gagctgcttc ccaaaggccc ccatccaagt ataggtctct acatcgtagg  25140
tgacaaagag acgctcggtg cgaggatgcg agccgatcgg gaagaactgg atctcccgcc  25200
accaattgga ggagtggcta ttgatgtggt gaaagtagaa gtccctgcga cgggccgaac  25260
actcgtgctg gcttttgtaa aaacgtgcgc agtactggca gcggtgcacg ggctgtacat  25320
cctgcacgag gttgacctga cgaccgcgca caaggaagca gagtgggaat ttgagcccct  25380
cgcctggcgg gtttggctgg tggtcttcta cttcggctgc ttgtccttga ccgtctggct  25440
gctcgagggg agttacggtg gatcggacca ccacgccgcg cgagcccaaa gtccagatgt  25500
ccgcgcgcgg cggtcggagc ttgatgacaa catcgcgcag atgggagctg tccatggtct  25560
ggagctcccg cggcgtcagg tcaggcggga gctcctgcag gtttacctcg catagacggg  25620
tcagggcgcg ggctagatcc aggtgatacc taatttccag gggctggttg gtggcggcgt  25680
cgatggcttg caagaggccg catccccgcg gcgcgactac ggtaccgcgc ggcgggcggt  25740
gggccgcggg ggtgtccttg gatgatgcat ctaaaagcgg tgacgcgggc gagcccccgg  25800
aggtaggggg ggctccggac ccgccgggag agggggcagg ggcacgtcgg cgccgcgcgc  25860
gggcaggagc tggtgctgcg cgcgtaggtt gctggcgaac gcgacgacgc ggcggttgat  25920
ctcctgaatc tggcgcctct gcgtgaagac gacgggcccg gtgagcttga gcctgaaaga  25980
gagttcgaca gaatcaattt cggtgtcgtt gacggcggcc tggcgcaaaa tctcctgcac  26040
gtctcctgag ttgtcttgat aggcgatctc ggccatgaac tgctcgatct cttcctcctg  26100
gagatctccg cgtccggctc gctccacggt ggcggcgagg tcgttggaaa tgcgggccat  26160
gagctgcgag aaggcgttga ggcctccctc gttccagacg cggctgtaga ccacgccccc  26220
ttcggcatcg cgggcgcgca tgaccacctg cgcgagattg agctccacgt gccgggcgaa  26280
gacggcgtag tttcgcaggc gctgaaagag gtagttgagg gtggtggcgg tgtgttctgc  26340
cacgaagaag tacataaccc agcgtcgcaa cgtggattcg ttgatatccc ccaaggcctc  26400
aaggcgctcc atggcctcgt agaagtccac ggcgaagttg aaaaactggg agttgcgcgc  26460
cgacacggtt aactcctcct ccagaagacg gatgagctcg gcgacagtgt cgcgcacctc  26520
gcgctcaaag gctacagggg cctcttcttc ttcttcaatc tcctcttcca taagggcctc  26580
cccttcttct tcttctggcg gcggtggggg agggggggaca cggcggcgac gacggcgcac  26640
```

```
cgggaggcgg tcgacaaagc gctcgatcat ctccccgcgg cgacggcgca tggtctcggt  26700
gacggcgcgg ccgttctcgc gggggcgcag ttggaagacg ccgcccgtca tgtcccggtt  26760
atgggttggc ggggggctgc catgcggcag ggatacggcg ctaacgatgc atctcaacaa  26820
ttgttgtgta ggtactccgc cgccgaggga cctgagcgag tccgcatcga ccggatcgga  26880
aaacctctcg agaaaggcgt ctaaccagtc acagtcgcaa ggtaggctga gcaccgtggc  26940
gggcggcagc gggcggcggt cggggttgtt tctggcggag gtgctgctga tgatgtaatt  27000
aaagtaggcg gtcttgagac ggcggatggt cgacagaagc accatgtcct tgggtccggc  27060
ctgctgaatg cgcaggcggt cggccatgcc ccaggcttcg ttttgacatc ggcgcaggtc  27120
tttgtagtag tcttgcatga gcctttctac cggcacttct tcttctcctt cctcttgtcc  27180
tgcatctctt gcatctatcg ctgcggcggc ggcggagttt ggccgtaggt ggcgccctct  27240
tcctcccatg cgtgtgaccc cgaagcccct catcggctga agcagggcta ggtcggcgac  27300
aacgcgctcg gctaatatgg cctgctgcac ctgcgtgagg gtagactgga agtcatccat  27360
gtccacaaag cggtggtatg cgcccgtgtt gatggtgtaa gtgcagttgg ccataacgga  27420
ccagttaacg gtctggtgac ccggctgcga gagctcggtg tacctgagac gcgagtaagc  27480
cctcgagtca aatacgtagt cgttgcaagt ccgcaccagg tactggtatc ccaccaaaaa  27540
gtgcggcggc ggctggcggt agaggggcca gcgtagggtg gccggggctc cgggggcgag  27600
atcttccaac ataaggcgat gatatccgta gatgtacctg gacatccagg tgatgccggc  27660
ggcggtggtg gaggcgcgcg gaaagtcgcg gacgcggttc cagatgttgc gcagcggcaa  27720
aaagtgctcc atggtcggga cgctctggcc ggtcaggcgc gcgcaatcgt tgacgctcta  27780
ccgtgcaaaa ggagagcctg taagcgggca ctcttccgtg gtctggtgga taaattcgca  27840
agggtatcat ggcggacgac cggggttcga gccccgtatc cggccgtccg ccgtgatcca  27900
tgcggttacc gcccgcgtgt cgaacccagg tgtgcgacgt cagacaacgg gggagtgctc  27960
cttttggctt ccttccaggc gcggcggctg ctgcgctagc ttttttggcc actggccgcg  28020
cgcagcgtaa gcggttaggc tggaaagcga aagcattaag tggctcgctc cctgtagccg  28080
gagggttatt ttccaagggt tgagtcgcgg gacccccggt tcgagtctcg gaccggccgg  28140
actgcggcga acgggggttt gcctccccgt catgcaagac cccgcttgca aattcctccg  28200
gaaacaggga cgagcccctt ttttgctttt cccagatgca tccggtgctg cggcagatgc  28260
gcccccctcc tcagcagcgg caagagcaag agcagcggca gacatgcagg gcaccctccc  28320
ctcctcctac cgcgtcagga ggggcgacat ccgcggttga cgcggcagca gatggtgatt  28380
acgaaccccc gcggcgccgg gcccggcact acctggactt ggaggagggc gagggcctgg  28440
cgcggctagg agcgccctct cctgagcggt acccaagggt gcagctgaag cgtgatacgc  28500
gtgaggcgta cgtgccgcgg cagaacctgt ttcgcgaccg cgagggagag gagcccgagg  28560
agatgcggga tcgaaagttc cacgcagggc gcgagctgcg gcatggcctg aatcgcgagc  28620
ggttgctgcg cgaggaggac tttgagcccg acgcgcgaac cgggattagt cccgcgcgcg  28680
cacacgtggc ggccgccgac ctggtaaccg catacgagca gacggtgaac caggagatta  28740
actttcaaaa aagctttaac aaccacgtgc gtacgcttgt ggcgcgcgag gaggtggcta  28800
taggactgat gcatctgtgg gactttgtaa gcgcgctgga gcaaaaccca aatagcaagc  28860
cgctcatggc gcagctgttc cttatagtgc agcacagcag ggacaacgag gcattcaggg  28920
atgcgctgct aaacatagta gagcccgagg gccgctggct gctcgatttg ataaacatcc  28980
tgcagagcat agtggtgcag gagcgcagct tgagcctggc tgacaaggtg gccgccatca  29040
```

```
actattccat gcttagcctg ggcaagtttt acgcccgcaa gatataccat accccttacg  29100

ttcccataga caaggaggta aagatcgagg ggttctacat gcgcatggcg ctgaaggtgc  29160

ttaccttgag cgacgacctg ggcgtttatc gcaacgagcg catccacaag gccgtgagcg  29220

tgagccggcg gcgcgagctc agcgaccgcg agctgatgca cagcctgcaa agggccctgg  29280

ctggcacggg cagcggcgat agagaggccg agtcctactt tgacgcgggc gctgacctgc  29340

gctgggcccc aagccgacgc gccctggagg cagctggggc cggacctggg ctggcggtgg  29400

cacccgcgcg cgctggcaac gtcggcggcg tggaggaata tgacgaggac gatgagtacg  29460

agccagagga cggcgagtac taagcggtga tgtttctgat cagatgatgc aagacgcaac  29520

ggacccggcg gtgcgggcgg cgctgcagag ccagccgtcc ggccttaact ccacggacga  29580

ctggcgccag gtcatggacc gcatcatgtc gctgactgcg cgcaatcctg acgcgttccg  29640

gcagcagccg caggccaacc ggctctccgc aattctggaa gcggtggtcc cggcgcgcgc  29700

aaaccccacg cacgagaagg tgctggcgat cgtaaacgcg ctggccgaaa acagggccat  29760

ccggcccgac gaggccggcc tggtctacga cgcgctgctt cagcgcgtgg ctcgttacaa  29820

cagcggcaac gtgcagacca acctggaccg gctggtgggg gatgtgcgcg aggccgtggc  29880

gcagcgtgag cgcgcgcagc agcagggcaa cctgggctcc atggttgcac taaacgcctt  29940

cctgagtaca cagcccgcca acgtgccgcg gggacaggag gactacacca actttgtgag  30000

cgcactgcgg ctaatggtga ctgagacacc gcaaagtgag gtgtaccagt ctgggccaga  30060

ctattttttc cagaccagta gacaaggcct gcagaccgta aacctgagcc aggctttcaa  30120

aaacttgcag gggctgtggg gggtgcgggc tcccacaggc gaccgcgcga ccgtgtctag  30180

cttgctgacg cccaactcgc gcctgttgct gctgctaata gcgcccttca cggacagtgg  30240

cagcgtgtcc cgggacacat acctaggtca cttgctgaca ctgtaccgcg aggccatagg  30300

tcaggcgcat gtggacgagc atactttcca ggagattaca agtgtcagcc gcgcgctggg  30360

gcaggaggac acgggcagcc tggaggcaac cctaaactac ctgctgacca accggcggca  30420

gaagatcccc tcgttgcaca gtttaaacag cgaggaggag cgcattttgc gctacgtgca  30480

gcagagcgtg agccttaacc tgatgcgcga cggggtaacg cccagcgtgg cgctggacat  30540

gaccgcgcgc aacatggaac cgggcatgta tgcctcaaac cggccgttta tcaaccgcct  30600

aatggactac ttgcatcgcg cggccgccgt gaaccccgag tatttcacca atgccatctt  30660

gaacccgcac tggctaccgc cccctggttt ctacaccggg ggattcgagg tgcccgaggg  30720

taacgatgga ttcctctggg acgacataga cgacagcgtg ttttccccgc aaccgcagac  30780

cctgctagag ttgcaacagc gcgagcaggc agaggcggcg ctgcgaaagg aaagcttccg  30840

caggccaagc agcttgtccg atctaggcgc tgcggccccg cggtcagatg ctagtagccc  30900

atttccaagc ttgatagggt ctcttaccag cactcgcacc acccgcccgc gcctgctggg  30960

cgaggaggag tacctaaaca actcgctgct gcagccgcag cgcgaaaaaa acctgcctcc  31020

ggcatttccc aacaacggga tagagagcct agtggacaag atgagtagat ggaagacgta  31080

cgcgcaggag cacagggacg tgccaggccc gcgcccgccc acccgtcgtc aaaggcacga  31140

ccgtcagcgg ggtctggtgt gggaggacga tgactcggca gacgacagca gcgtcctgga  31200

tttgggaggg agtggcaacc cgtttgcgca ccttcgcccc aggctgggga gaatgtttta  31260

aaaaaaaaaa agcatgatgc aaaataaaaa actcaccaag gccatggcac cgagcgttgg  31320

ttttcttgta ttccccttag tatgcggcgc gcggcgatgt atgaggaagg tcctcctccc  31380

tcctacgaga gtgtggtgag cgcggcgcca gtggcggcgg cgctgggttc tcccttcgat  31440
```

gctcccctgg acccgccgtt tgtgcctccg cggtacctgc ggcctaccgg ggggagaaac 31500
agcatccgtt actctgagtt ggcaccccta ttcgacacca cccgtgtgta cctggtggac 31560
aacaagtcaa cggatgtggc atccctgaac taccagaacg accacagcaa ctttctgacc 31620
acggtcattc aaaacaatga ctacagcccg ggggaggcaa gcacacagac catcaatctt 31680
gacgaccggt cgcactgggg cggcgacctg aaaaccatcc tgcataccaa catgccaaat 31740
gtgaacgagt tcatgtttac caataagttt aaggcgcggg tgatggtgtc gcgcttgcct 31800
actaaggaca atcaggtgga gctgaaatac gagtgggtgg agttcacgct gcccgagggc 31860
aactactccg agaccatgac catagacctt atgaacaacg cgatcgtgga gcactacttg 31920
aaagtgggca gacagaacgg ggttctggaa agcgacatcg ggtaaagtt tgacacccgc 31980
aacttcagac tggggtttga ccccgtcact ggtcttgtca tgcctggggt atatacaaac 32040
gaagccttcc atccagacat cattttgctg ccaggatgcg gggtggactt cacccacagc 32100
cgcctgagca acttgttggg catccgcaag cggcaaccct tccaggaggg ctttaggatc 32160
acctacgatg atctggaggg tggtaacatt cccgcactgt tggatgtgga cgcctaccag 32220
gcgagcttga aagatgacac cgaacagggc gggggtggcg caggcggcag caacagcagt 32280
ggcagcggcg cggaagagaa ctccaacgcg gcagccgcgg caatgcagcc ggtggaggac 32340
atgaacgatc atgccattcg cggcgacacc tttgccacac gggctgagga gaagcgcgct 32400
gaggccgaag cagcggccga agctgccgcc cccgctgcgc aacccgaggt cgagaagcct 32460
cagaagaaac cggtgatcaa acccctgaca gaggacagca agaaacgcag ttacaaccta 32520
ataagcaatg acagcacctt cacccagtac cgcagctggt accttgcata caactacggc 32580
gaccctcaga ccggaatccg ctcatggacc ctgctttgca ctcctgacgt aacctgcggc 32640
tcggagcagg tctactggtc gttgccagac atgatgcaag accccgtgac cttccgctcc 32700
acgcgccaga tcagcaactt tccggtggtg ggcgccgagc tgttgcccgt gcactccaag 32760
agcttctaca acgaccaggc cgtctactcc caactcatcc gccagtttac ctctctgacc 32820
cacgtgttca atcgctttcc cgagaaccag attttggcgc gcccgccagc cccccaccatc 32880
accaccgtca gtgaaaacgt tcctgctctc acagatcacg ggacgctacc gctgcgcaac 32940
agcatcggag gagtccagcg agtgaccatt actgacgcca gacgccgcac ctgcccctac 33000
gtttacaagg ccctgggcat agtctcgccg cgcgtcctat cgagccgcac tttttgagca 33060
agcatgtcca tccttatatc gcccagcaat aacacaggct ggggcctgcg cttcccaagc 33120
aagatgtttg gcggggccaa gaagcgctcc gaccaacacc cagtgcgcgt gcgcgggcac 33180
taccgcgcgc cctggggcgc gcacaaacgc ggccgcactg ggcgcaccac cgtcgatgac 33240
gccatcgacg cggtggtgga ggaggcgcgc aactacacgc ccacgccgcc accagtgtcc 33300
acagtggacg cggccattca gaccgtggtg cgcggagccc ggcgctatgc taaaatgaag 33360
agacggcgga ggcgcgtagc acgtcgccac cgccgccgac ccggcactgc cgcccaacgc 33420
gcggcggcgg ccctgcttaa ccgcgcacgt cgcaccggcc gacgggcggc catgcgggcc 33480
gctcgaaggc tggccgcggg tattgtcact gtgcccccca ggtccaggcg acgagcggcc 33540
gccgcagcag ccgcggccat tagtgctatg actcagggtc gcaggggcaa cgtgtattgg 33600
gtgcgcgact cggttagcgg cctgcgcgtg cccgtgcgca cccgcccccc gcgcaactag 33660
attgcaagaa aaaactactt agactcgtac tgttgtatgt atccagcggc ggcggcgcgc 33720
aacgaagcta tgtccaagcg caaaatcaaa gaagagatgc tccaggtcat cgcgccggag 33780
atctatggcc ccccgaagaa ggaagagcag gattacaagc cccgaaagct aaagcgggtc 33840

```
aaaaagaaaa agaaagatga tgatgatgaa cttgacgacg aggtggaact gctgcacgct  33900
accgcgccca ggcgacgggt acagtggaaa ggtcgacgcg taaaacgtgt tttgcgaccc  33960
ggcaccaccg tagtctttac gcccggtgag cgctccaccc gcacctacaa gcgcgtgtat  34020
gatgaggtgt acggcgacga ggacctgctt gagcaggcca acgagcgcct cggggagttt  34080
gcctacggaa agcggcataa ggacatgctg gcgttgccgc tggacgaggg caacccaaca  34140
cctagcctaa agcccgtaac actgcagcag gtgctgcccg cgcttgcacc gtccgaagaa  34200
aagcgcggcc taaagcgcga gtctggtgac ttggcaccca ccgtgcagct gatggtaccc  34260
aagcgccagc gactggaaga tgtcttggaa aaaatgaccg tggaacctgg gctggagccc  34320
gaggtccgcg tgcggccaat caagcaggtg gcgccgggac tgggcgtgca gaccgtggac  34380
gttcagatac ccactaccag tagcaccagt attgccaccg ccacagaggg catggagaca  34440
caaacgtccc cggttgcctc agcggtggcg gatgccgcgg tgcaggcggt cgctgcggcc  34500
gcgtccaaga cctctacgga ggtgcaaacg gacccgtgga tgtttcgcgt ttcagccccc  34560
cggcgcccgc gcggttcgag gaagtacggc gccgccagcg cgctactgcc cgaatatgcc  34620
ctacatcctt ccattgcgcc tacccccggc tatcgtggct acacctaccg ccccagaaga  34680
cgagcaacta cccgacgccg aaccaccact ggaacccgcc gccgccgtcg ccgtcgccag  34740
cccgtgctgg ccccgatttc cgtgcgcagg gtggctcgcg aaggaggcag gaccctggtg  34800
ctgccaacag cgcgctacca ccccagcatc gtttaaaagc cggtctttgt ggttcttgca  34860
gatatggccc tcacctgccg cctccgtttc ccggtgccgg gattccgagg aagaatgcac  34920
cgtaggaggg gcatggccgg ccacggcctg acgggcggca tgcgtcgtgc gcaccaccgg  34980
cggcggcgcg cgtcgcaccg tcgcatgcgc ggcggtatcc tgcccctcct tattccactg  35040
atcgccgcgg cgattggcgc cgtgcccgga attgcatccg tggccttgca ggcgcagaga  35100
cactgattaa aaacaagttg catgtggaaa aatcaaaata aaaagtctgg actctcacgc  35160
tcgcttggtc ctgtaactat tttgtagaat ggaagacatc aactttgcgt ctctggcccc  35220
gcgacacggc tcgcgcccgt tcatgggaaa ctggcaagat atcggcacca gcaatatgag  35280
cggtggcgcc ttcagctggg gctcgctgtg gagcggcatt aaaaatttcg gttccaccgt  35340
taagaactat ggcagcaagg cctggaacag cagcacaggc cagatgctga gggataagtt  35400
gaaagagcaa aatttccaac aaaaggtggt agatggcctg gcctctggca ttagcggggt  35460
ggtggacctg gccaaccagg cagtgcaaaa taagattaac agtaagcttg atccccgccc  35520
tcccgtagag gagcctccac cggccgtgga gacagtgtct ccagaggggc gtggcgaaaa  35580
gcgtccgcgc cccgacaggg aagaaactct ggtgacgcaa atagacgagc ctccctcgta  35640
cgaggaggca ctaaagcaag gcctgcccac cacccgtccc atcgcgccca tggctaccgg  35700
agtgctgggc cagcacacac ccgtaacgct ggacctgcct ccccccgccg acacccagca  35760
gaaacctgtg ctgccaggcc cgaccgccgt tgttgtaacc cgtcctagcc gcgcgtccct  35820
gcgccgcgcc gccagcggtc cgcgatcgtt gcggcccgta gccagtggca actggcaaag  35880
cacactgaac agcatcgtgg gtctgggggt gcaatccctg aagcgccgac gatgcttctg  35940
aatagctaac gtgtcgtatg tgtgtcatgt atgcgtccat gtcgccgcca gaggagctgc  36000
tgagccgccg cgcgcccgct ttccaagatg gctacccctt cgatgatgcc gcagtggtct  36060
tacatgcaca tctcgggcca ggacgcctcg gagtacctga gccccgggct ggtgcagttt  36120
gcccgcgcca ccgagacgta cttcagcctg aataacaagt ttagaaaccc cacggtggcg  36180
cctacgcacg acgtgaccac agaccggtcc cagcgtttga cgctgcggtt catccctgtg  36240
```

```
gaccgtgagg atactgcgta ctcgtacaag gcgcggttca ccctagctgt gggtgataac  36300
cgtgtgctgg acatggcttc cacgtacttt gacatccgcg gcgtgctgga caggggccct  36360
acttttaagc cctactctgg cactgcctac aacgccctgg ctcccaaggg tgccccaaat  36420
ccttgcgaat gggatgaagc tgctactgct cttgaaataa acctagaaga agaggacgat  36480
gacaacgaag acgaagtaga cgagcaagct gagcagcaaa aaactcacgt atttgggcag  36540
gcgccttatt ctggtataaa tattacaaag gagggtattc aaataggtgt cgaaggtcaa  36600
acacctaaat atgccgataa aacatttcaa cctgaacctc aaataggaga atctcagtgg  36660
tacgaaactg aaattaatca tgcagctggg agagtcctta aaaagactac cccaatgaaa  36720
ccatgttacg gttcatatgc aaaacccaca aatgaaaatg gagggcaagg cattcttgta  36780
aagcaacaaa atggaaagct agaaagtcaa gtggaaatgc aatttttctc aactactgag  36840
gcgaccgcag gcaatggtga taacttgact cctaaagtgg tattgtacag tgaagatgta  36900
gatatagaaa ccccagacac tcatatttct tacatgccca ctattaagga aggtaactca  36960
cgagaactaa tgggccaaca atctatgccc aacaggccta attacattgc ttttagggac  37020
aattttattg gtctaatgta ttacaacagc acgggtaata tgggtgttct ggcgggccaa  37080
gcatcgcagt tgaatgctgt tgtagatttg caagacagaa acacagagct ttcataccag  37140
cttttgcttg attccattgg tgatagaacc aggtactttt ctatgtggaa tcaggctgtt  37200
gacagctatg atccagatgt tagaattatt gaaaatcatg gaactgaaga tgaacttcca  37260
aattactgct ttccactggg aggtgtgatt aatacagaga ctcttaccaa ggtaaaacct  37320
aaaacaggtc aggaaaatgg atgggaaaaa gatgctacag aattttcaga taaaaatgaa  37380
ataagagttg gaaataattt tgccatggaa atcaatctaa atgccaacct gtggagaaat  37440
ttcctgtact ccaacatagc gctgtatttg cccgacaagc taaagtacag tccttccaac  37500
gtaaaaattt ctgataaccc aaacacctac gactacatga acaagcgagt ggtggctccc  37560
gggttagtgg actgctacat taaccttgga gcacgctggt cccttgacta tatggacaac  37620
gtcaacccat ttaaccacca ccgcaatgct ggcctgcgct accgctcaat gttgctgggc  37680
aatggtcgct atgtgccctt ccacatccag gtgcctcaga agttctttgc cattaaaaac  37740
ctccttctcc tgccgggctc atacacctac gagtggaact tcaggaagga tgttaacatg  37800
gttctgcaga gctccctagg aaatgaccta agggttgacg gagccagcat taagtttgat  37860
agcatttgcc tttacgccac cttcttcccc atggcccaca acaccgcctc cacgcttgag  37920
gccatgctta gaaacgacac caacgaccag tcctttaacg actatctctc cgccgccaac  37980
atgctctacc ctatacccgc caacgctacc aacgtgccca tatccatccc ctcccgcaac  38040
tgggcggctt tccgcggctg ggccttcacg cgccttaaga ctaaggaaac cccatcactg  38100
ggctcgggct acgaccctta ttacacctac tctggctcta taccctacct agatggaacc  38160
ttttacctca accacacctt taagaaggtg gccattacct ttgactcttc tgtcagctgg  38220
cctggcaatg accgcctgct tacccccaac gagtttgaaa ttaagcgctc agttgacggg  38280
gagggttaca acgttgccca gtgtaacatg accaaagact ggttcctggt acaaatgcta  38340
gctaactaca acattggcta ccagggcttc tatatcccag agagctacaa ggaccgcatg  38400
tactccttct ttagaaactt ccagcccatg agccgtcagg tggtggatga tactaaatac  38460
aaggactacc aacaggtggg catcctacac caacacaaca actctggatt tgttggctac  38520
cttgccccca ccatgcgcga aggacaggcc taccctgcta acttccccta tccgcttata  38580
ggcaagaccg cagttgacag cattacccag aaaaagtttc tttgcgatcg caccctttgg  38640
```

```
cgcatcccat tctccagtaa ctttatgtcc atgggcgcac tcacagacct gggccaaaac  38700
cttctctacg ccaactccgc ccacgcgcta gacatgactt ttgaggtgga tcccatggac  38760
gagcccaccc ttctttatgt tttgtttgaa gtctttgacg tggtccgtgt gcaccggccg  38820
caccgcggcg tcatcgaaac cgtgtacctg cgcacgccct tctcggccgg caacgccaca  38880
acataaagaa gcaagcaaca tcaacaacag ctgccgccat gggctccagt gagcaggaac  38940
tgaaagccat tgtcaaagat cttggttgtg ggccatattt tttgggcacc tatgacaagc  39000
gctttccagg ctttgtttct ccacacaagc tcgcctgcgc catagtcaat acggccggtc  39060
gcgagactgg gggcgtacac tggatggcct ttgcctggaa cccgcactca aaaacatgct  39120
acctctttga gccctttggc ttttctgacc agcgactcaa gcaggtttac cagtttgagt  39180
acgagtcact cctgcgccgt agcgccattg cttcttcccc cgaccgctgt ataacgctgg  39240
aaaagtccac ccaaagcgta caggggccca actcggccgc ctgtggacta ttctgctgca  39300
tgtttctcca cgcctttgcc aactggcccc aaactcccat ggatcacaac cccaccatga  39360
accttattac cggggtaccc aactccatgc tcaacagtcc ccaggtacag cccaccctgc  39420
gtcgcaacca ggaacagctc tacagcttcc tggagcgcca ctcgccctac ttccgcagcc  39480
acagtgcgca gattaggagc gccacttctt tttgtcactt gaaaaacatg taaaaataat  39540
gtactagaga cactttcaat aaaggcaaat gcttttattt gtacactctc gggtgattat  39600
ttacccccac ccttgccgtc tgcgccgttt aaaaatcaaa ggggttctgc cgcgcatcgc  39660
tatgcgccac tggcagggac acgttgcgat actggtgttt agtgctccac ttaaactcag  39720
gcacaaccat ccgcggcagc tcggtgaagt tttcactcca caggctgcgc accatcacca  39780
acgcgtttag caggtcgggc gccgatatct tgaagtcgca gttggggcct ccgccctgcg  39840
cgcgcgagtt gcgatacaca gggttgcagc actggaacac tatcagcgcc gggtggtgca  39900
cgctggccag cacgctcttg tcggagatca gatccgcgtc caggtcctcc gcgttgctca  39960
gggcgaacgg agtcaacttt ggtagctgcc ttcccaaaaa gggcgcgtgc ccaggctttg  40020
agttgcactc gcaccgtagt ggcatcaaaa ggtgaccgtg cccggtctgg gcgttaggat  40080
acagcgcctg cataaaagcc ttgatctgct taaaagccac ctgagccttt gcgccttcag  40140
agaagaacat gccgcaagac ttgccggaaa actgattggc cggacaggcc gcgtcgtgca  40200
cgcagcacct tgcgtcggtg ttggagatct gcaccacatt tcggccccac cggttcttca  40260
cgatcttggc cttgctagac tgctccttca gcgcgcgctg cccgttttcg ctcgtcacat  40320
ccatttcaat cacgtgctcc ttatttatca taatgcttcc gtgtagacac ttaagctcgc  40380
cttcgatctc agcgcagcgg tgcagccaca acgcgcagcc cgtgggctcg tgatgcttgt  40440
aggtcacctc tgcaaacgac tgcaggtacg cctgcaggaa tcgccccatc atcgtcacaa  40500
aggtcttgtt gctggtgaag gtcagctgca acccgcggtg ctcctcgttc agccaggtct  40560
tgcatacggc cgccagagct tccacttggt caggcagtag tttgaagttc gcctttagat  40620
cgttatccac gtggtacttg tccatcagcg cgcgcgcagc ctccatgccc ttctcccacg  40680
cagacacgat cggcacactc agcgggttca tcaccgtaat ttcactttcc gcttcgctgg  40740
gctcttcctc ttcctcttgc gtccgcatac cacgcgccac tgggtcgtct tcattcagcc  40800
gccgcactgt gcgcttacct cctttgccat gcttgattag caccggtggg ttgctgaaac  40860
ccaccatttg tagcgccaca tcttctcttt cttcctcgct gtccacgatt acctctggtg  40920
atggcgggcg ctcgggcttg ggagaagggc gcttcttttt cttcttgggc gcaatggcca  40980
aatccgccgc cgaggtcgat ggccgcgggc tgggtgtgcg cggcaccagc gcgtcttgtg  41040
```

```
atgagtcttc ctcgtcctcg gactcgatac gccgcctcat ccgctttttt gggggcgccc  41100
ggggaggcgg cggcgacggg gacggggacg acacgtcctc catggttggg ggacgtcgcg  41160
ccgcaccgcg tccgcgctcg gggtggttt cgcgctgctc ctcttcccga ctggccattt  41220
ccttctccta taggcagaaa aagatcatgg agtcagtcga gaagaaggac agcctaaccg  41280
ccccctctga gttcgccacc accgcctcca ccgatgccgc caacgcgcct accaccttcc  41340
ccgtcgaggc accccgcctt gaggaggagg aagtgattat cgagcaggac ccaggttttg  41400
taagcgaaga cgacgaggac cgctcagtac caacagagga taaaaagcaa gaccaggaca  41460
acgcagaggc aaacgaggaa caagtcgggc ggggggacga aaggcatggc gactacctag  41520
atgtgggaga cgacgtgctg ttgaagcatc tgcagcgcca gtgcgccatt atctgcgacg  41580
cgttgcaaga gcgcagcgat gtgcccctcg ccatagcgga tgtcagcctt gcctacgaac  41640
gccacctatt ctcaccgcgc gtaccccca aacgccaaga aaacggcaca tgcgagccca  41700
acccgcgcct caacttctac cccgtatttg ccgtgccaga ggtgcttgcc acctatcaca  41760
tctttttcca aaactgcaag atacccctat cctgccgtgc caaccgcagc cgagcggaca  41820
agcagctggc cttgcggcag ggcgctgtca tacctgatat cgcctcgctc aacgaagtgc  41880
caaaaatctt tgagggtctt ggacgcgacg agaagcgcgc ggcaaacgct ctgcaacagg  41940
aaaacagcga aaatgaaagt cactctggag tgttggtgga actcgagggt gacaacgcgc  42000
gcctagccgt actaaaacgc agcatcgagg tcacccactt tgcctacccg gcacttaacc  42060
tacccccaa ggtcatgagc acagtcatga gtgagctgat cgtgcgccgt gcgcagcccc  42120
tggagaggga tgcaaatttg caagaacaaa cagaggaggg cctacccgca gttggcgacg  42180
agcagctagc gcgctggctt caaacgcgcg agcctgccga cttggaggag cgacgcaaac  42240
taatgatggc cgcagtgctc gttaccgtgg agcttgagtg catgcagcgg ttctttgctg  42300
acccggagat gcagcgcaag ctagaggaaa cattgcacta cacctttcga cagggctacg  42360
tacgccaggc ctgcaagatc tccaacgtgg agctctgcaa cctggtctcc taccttggaa  42420
ttttgcacga aaaccgcctt gggcaaaacg tgcttcattc cacgctcaag ggcgaggcgc  42480
gccgcgacta cgtccgcgac tgcgtttact tatttctatg ctacacctgg cagacggcca  42540
tgggcgtttg gcagcagtgc ttggaggagt gcaacctcaa ggagctgcag aaactgctaa  42600
agcaaaactt gaaggaccta tggacggcct tcaacgagcg ctccgtggcc gcgcacctgg  42660
cggacatcat tttccccgaa cgcctgctta aaaccctgca acagggtctg ccagacttca  42720
ccagtcaaag catgttgcag aactttagga actttatcct agagcgctca ggaatcttgc  42780
ccgccacctg ctgtgcactt cctagcgact ttgtgcccat taagtaccgc gaatgccctc  42840
cgccgctttg gggccactgc taccttctgc agctagccaa ctaccttgcc taccactctg  42900
acataatgga agacgtgagc ggtgacggtc tactggagtg tcactgtcgc tgcaacctat  42960
gcaccccgca ccgctccctg gtttgcaatt cgcagctgct taacgaaagt caaattatcg  43020
gtacctttga gctgcagggt ccctcgcctg acgaaaagtc cgcggctccg gggttgaaac  43080
tcactccggg gctgtggacg tcggcttacc ttcgcaaatt tgtacctgag gactaccacg  43140
cccacgagat taggttctac gaagaccaat cccgcccgcc aaatgcggag cttaccgcct  43200
gcgtcattac ccagggccac attcttggcc aattgcaagc catcaacaaa gcccgccaag  43260
agtttctgct acgaaaggga cgggggggttt acttggaccc ccagtccggc gaggagctca  43320
acccaatccc cccgccgccg cagccctatc agcagcagcc gcgggccctt gcttcccagg  43380
atggcaccca aaaagaagct gcagctgccg ccgccaccca cggacgagga ggaatactgg  43440
```

```
gacagtcagg cagaggaggt tttggacgag gaggaggagg acatgatgga agactgggag  43500
agcctagacg aggaagcttc cgaggtcgaa gaggtgtcag acgaaacacc gtcaccctcg  43560
gtcgcattcc cctcgccggc gccccagaaa tcggcaaccg gttccagcat ggctacaacc  43620
tccgctcctc aggcgccgcc ggcactgccc gttcgccgac ccaaccgtag atgggacacc  43680
actggaacca gggccggtaa gtccaagcag ccgccgccgt tagcccaaga gcaacaacag  43740
cgccaaggct accgctcatg gcgcgggcac aagaacgcca tagttgcttg cttgcaagac  43800
tgtgggggca acatctcctt cgcccgccgc tttcttctct accatcacgg cgtggccttc  43860
ccccgtaaca tcctgcatta ctaccgtcat ctctacagcc catactgcac cggcggcagc  43920
ggcagcggca gcaacagcag cggccacaca gaagcaaagg cgaccggata gcaagactct  43980
gacaaagccc aagaaatcca cagcggcggc agcagcagga ggaggagcgc tgcgtctggc  44040
gcccaacgaa cccgtatcga cccgcgagct tagaaacagg atttttccca ctctgtatgc  44100
tatatttcaa cagagcaggg gccaagaaca agagctgaaa ataaaaaaca ggtctctgcg  44160
atccctcacc cgcagctgcc tgtatcacaa aagcgaagat cagcttcggc gcacgctgga  44220
agacgcggag gctctcttca gtaaatactg cgcgctgact cttaaggact agtttcgcgc  44280
cctttctcaa atttaagcgc gaaaactacg tcatctccag cggccacacc cggcgccagc  44340
acctgtcgtc agcgccatta tgagcaagga aattcccacg ccctacatgt ggagttacca  44400
gccacaaatg ggacttgcgg ctggagctgc ccaagactac tcaacccgaa taaactacat  44460
gagcgcggga ccccacatga tatcccgggt caacggaatc cgcgcccacc gaaaccgaat  44520
tctcttggaa caggcggcta ttaccaccac acctcgtaat aaccttaatc cccgtagttg  44580
gcccgctgcc ctggtgtacc aggaaagtcc cgctcccacc actgtggtac ttcccagaga  44640
cgcccaggcc gaagttcaga tgactaactc aggggcgcag cttgcgggcg gctttcgtca  44700
cagggtgcgg tcgcccgggc agggtataac tcacctgaca atcagagggc gaggtattca  44760
gctcaacgac gagtcggtga gctcctcgct tggtctccgt ccggacggga catttcagat  44820
cggcggcgcc ggccgtcctt cattcacgcc tcgtcaggca atcctaactc tgcagacctc  44880
gtcctctgag ccgcgctctg gaggcattgg aactctgcaa tttattgagg agtttgtgcc  44940
atcggtctac tttaacccct tctcgggacc tcccggccac tatccggatc aatttattcc  45000
taactttgac gcggtaaagg actcggcgga cggctacgac tgaatgttaa gtggagaggc  45060
agagcaactg cgcctgaaac acctggtcca ctgtcgccgc cacaagtgct ttgcccgcga  45120
ctccggtgag ttttgctact ttgaattgcc cgaggatcat atcgagggcc cggcgcacgg  45180
cgtccggctt accgcccagg gagagcttgc ccgtagcctg attcgggagt ttacccagcg  45240
ccccctgcta gttgagcggg acaggggacc ctgtgttctc actgtgattt gcaactgtcc  45300
taaccttgga ttacatcaag atcctctagt tataactaga gtacccgggg atcttattcc  45360
ctttaactaa taaaaaaaaa taataaagca tcacttactt aaaatcagtt agcaaatttc  45420
tgtccagttt attcagcagc acctccttgc cctcctccca gctctggtat tgcagcttcc  45480
tcctggctgc aaactttctc cacaatctaa atggaatgtc agtttcctcc tgttcctgtc  45540
catccgcacc cactatcttc atgttgttgc agatgaagcg cgcaagaccg tctgaagata  45600
ccttcaaccc cgtgtatcca tatgacacgg aaaccggtcc tccaactgtg ccttttctta  45660
ctcctccctt tgtatccccc aatgggtttc aagagagtcc ccctggggta ctctctttgc  45720
gcctatccga acctctagtt acctccaatg gcatgcttgc gctcaaaatg ggcaacggcc  45780
tctctctgga cgaggccggc aaccttacct cccaaaatgt aaccactgtg agcccacctc  45840
```

```
tcaaaaaaac caagtcaaac ataaacctgg aaatatctgc acccctcaca gttacctcag  45900
aagccctaac tgtggctgcc gccgcacctc taatggtcgc gggcaacaca ctcaccatgc  45960
aatcacaggc cccgctaacc gtgcacgact ccaaacttag cattgccacc caaggacccc  46020
tcacagtgtc agaaggaaag ctagccctgc aaacatcagg cccccctcacc accaccgata  46080
gcagtaccct tactatcact gcctcacccc ctctaactac tgccactggt agcttgggca  46140
ttgacttgaa agagcccatt tatacacaaa atggaaaact aggactaaag tacggggctc  46200
ctttgcatgt aacagacgac ctaaacactt tgaccgtagc aactggtcca ggtgtgacta  46260
ttaataatac ttccttgcaa actaaagtta ctggagcctt gggttttgat tcacaaggca  46320
atatgcaact taatgtagca ggaggactaa ggattgattc tcaaaacaga cgccttatac  46380
ttgatgttag ttatccgttt gatgctcaaa accaactaaa tctaagacta ggacagggcc  46440
ctctttttat aaactcagcc cacaacttgg atattaacta caacaaaggc ctttacttgt  46500
ttacagcttc aaacaattcc aaaaagcttg aggttaacct aagcactgcc aaggggttga  46560
tgtttgacgc tacagccata gccattaatg caggagatgg gcttgaattt ggttcaccta  46620
atgcaccaaa cacaaatccc ctcaaaacaa aaattggcca tggcctagaa tttgattcaa  46680
acaaggctat ggttcctaaa ctaggaactg gccttagttt tgacagcaca ggtgccatta  46740
cagtaggaaa caaaaataat gataagctaa ctttgtggac cacaccagct ccatctccta  46800
actgtagact aaatgcagag aaagatgcta aactcacttt ggtcttaaca aaatgtggca  46860
gtcaaatact tgctacagtt tcagttttgg ctgttaaagg cagtttggct ccaatatctg  46920
gaacagttca aagtgctcat cttattataa gatttgacga aaatggagtg ctactaaaca  46980
attccttcct ggacccagaa tattggaact ttagaaatgg agatcttact gaaggcacag  47040
cctatacaaa cgctgttgga tttatgccta acctatcagc ttatccaaaa tctcacggta  47100
aaactgccaa aagtaacatt gtcagtcaag tttacttaaa cggagacaaa actaaacctg  47160
taacactaac cattacacta aacggtacac aggaaacagg agacacaact ccaagtgcat  47220
actctatgtc attttcatgg gactggtctg gccacaacta cattaatgaa atatttgcca  47280
catcctctta cactttttca tacattgccc aagaataaag aatcgtttgt gttatgtttc  47340
aacgtgttta tttttcaatt gcagaaaatt tcaagtcatt tttcattcag tagtatagcc  47400
ccaccaccac atagcttata cagatcaccg taccttaatc aaactcacag aaccctagta  47460
ttcaacctgc cacctccctc ccaacacaca gagtacacag tcctttctcc ccggctggcc  47520
ttaaaaagca tcatatcatg ggtaacagac atattcttag gtgttatatt ccacacggtt  47580
tcctgtcgag ccaaacgctc atcagtgata ttaataaact ccccgggcag ctcacttaag  47640
ttcatgtcgc tgtccagctg ctgagccaca ggctgctgtc caacttgcgg ttgcttaacg  47700
ggcggcgaag gagaagtcca cgcctacatg ggggtagagt cataatcgtg catcaggata  47760
gggcggtggt gctgcagcag cgcgcgaata aactgctgcc gccgccgctc cgtcctgcag  47820
gaatacaaca tggcagtggt ctcctcagcg atgattcgca ccgcccgcag cataaggcgc  47880
cttgtcctcc gggcacagca gcgcaccctg atctcactta aatcagcaca gtaactgcag  47940
cacagcacca caatattgtt caaaatccca cagtgcaagg cgctgtatcc aaagctcatg  48000
gcggggacca cagaacccac gtggccatca taccacaagc gcaggtagat taagtggcga  48060
cccctcataa acacgctgga cataaacatt acctcttttg gcatgttgta attcaccacc  48120
tcccggtacc atataaacct ctgattaaac atggcgccat ccaccaccat cctaaaccag  48180
ctggccaaaa cctgcccgcc ggctatacac tgcagggaac cgggactgga acaatgacag  48240
```

```
tggagagccc aggactcgta accatggatc atcatgctcg tcatgatatc aatgttggca  48300

caacacaggc acacgtgcat acacttcctc aggattacaa gctcctcccg cgttagaacc  48360

atatcccagg gaacaaccca ttcctgaatc agcgtaaatc ccacactgca gggaagacct  48420

cgcacgtaac tcacgttgtg cattgtcaaa gtgttacatt cgggcagcag cggatgatcc  48480

tccagtatgg tagcgcgggt ttctgtctca aaaggaggta gacgatccct actgtacgga  48540

gtgcgccgag acaaccgaga tcgtgttggt cgtagtgtca tgccaaatgg aacgccggac  48600

gtagtcatat ttcctgaagc aaaaccaggt gcgggcgtga caaacagatc tgcgtctccg  48660

gtctcgccgc ttagatcgct ctgtgtagta gttgtagtat atccactctc tcaaagcatc  48720

caggcgcccc ctggcttcgg gttctatgta aactccttca tgcgccgctg ccctgataac  48780

atccaccacc gcagaataag ccacacccag ccaacctaca cattcgttct gcgagtcaca  48840

cacgggagga gcgggaagag ctggaagaac catgtttttt tttttattcc aaaagattat  48900

ccaaaacctc aaaatgaaga tctattaagt gaacgcgctc ccctccggtg gcgtggtcaa  48960

actctacagc caaagaacag ataatggcat ttgtaagatg ttgcacaatg gcttccaaaa  49020

ggcaaacggc cctcacgtcc aagtggacgt aaaggctaaa cccttcaggg tgaatctcct  49080

ctataaacat tccagcacct tcaaccatgc ccaaataatt ctcatctcgc caccttctca  49140

atatatctct aagcaaatcc cgaatattaa gtccggccat tgtaaaaatc tgctccagag  49200

cgccctccac cttcagcctc aagcagcgaa tcatgattgc aaaaattcag gttcctcaca  49260

gacctgtata agattcaaaa gcggaacatt aacaaaaata ccgcgatccc gtaggtccct  49320

tcgcagggcc agctgaacat aatcgtgcag gtctgcacgg accagcgcgg ccacttcccc  49380

gccaggaacc ttgacaaaag aacccacact gattatgaca cgcatactcg gagctatgct  49440

aaccagcgta gccccgatgt aagctttgtt gcatgggcgg cgatataaaa tgcaaggtgc  49500

tgctcaaaaa atcaggcaaa gcctcgcgca aaaaagaaag cacatcgtag tcatgctcat  49560

gcagataaag gcaggtaagc tccggaacca ccacagaaaa agacaccatt tttctctcaa  49620

acatgtctgc gggtttctgc ataaacacaa aataaaataa caaaaaaaca tttaaacatt  49680

agaagcctgt cttacaacag gaaaaacaac ccttataagc ataagacgga ctacggccat  49740

gccggcgtga ccgtaaaaaa actggtcacc gtgattaaaa agcaccaccg acagctcctc  49800

ggtcatgtcc ggagtcataa tgtaagactc ggtaaacaca tcaggttgat tcatcggtca  49860

gtgctaaaaa gcgaccgaaa tagcccgggg gaatacatac ccgcaggcgt agagacaaca  49920

ttacagcccc cataggaggt ataacaaaat taataggaga gaaaaacaca taaacacctg  49980

aaaaaccctc ctgcctaggc aaaatagcac cctcccgctc cagaacaaca tacagcgctt  50040

cacagcggca gcctaacagt cagccttacc agtaaaaaag aaaacctatt aaaaaaacac  50100

cactcgacac ggcaccagct caatcagtca cagtgtaaaa aagggccaag tgcagagcga  50160

gtatatatag gactaaaaaa tgacgtaacg gttaaagtcc acaaaaaaca cccagaaaac  50220

cgcacgcgaa cctacgccca gaaacgaaag ccaaaaaacc cacaacttcc tcaaatcgtc  50280

acttccgttt tcccacgtta cgtaacttcc cattttaaga aaactacaat tcccaacaca  50340

tacaagttac tccgccctaa aacctacgtc acccgccccg ttcccacgcc ccgcgccacg  50400

tcacaaactc caccccctca ttatcatatt ggcttcaatc caaaataagg tatattattg  50460

atgatnnnnn ttaat                                                   50475
```

<210> SEQ ID NO 17
<211> LENGTH: 39301

<212> TYPE: DNA
<213> ORGANISM: Artificial Sequence
<220> FEATURE:
<223> OTHER INFORMATION: chimeric adenoviral vector ND1.1 214, pAd vector containing DS2C-luc
<221> NAME/KEY: modified_base
<222> LOCATION: (1)...(39301)
<223> OTHER INFORMATION: n = g, a, c or t

<400> SEQUENCE: 17

```
taaggatccn nncctgtcct cgaccgatgc ccttgagagc cttcaaccca gtcagctcct     60
tccggtgggc gcggggcatg actatcgtcg ccgcacttat gactgtcttc tttatcatgc    120
aactcgtagg acaggtgccg gcagcgctct gggtcatttt cggcgaggac cgctttcgct    180
ggagcgcgac gatgatcggc ctgtcgcttg cggtattcgg aatcttgcac gccctcgctc    240
aagccttcgt cactggtccc gccaccaaac gtttcggcga gaagcaggcc attatcgccg    300
gcatggcggc cgacgcgctg ggctacgtct tgctggcgtt cgcgacgcga ggctggatgg    360
ccttccccat tatgattctt ctcgcttccg gcggcatcgg gatgcccgcg ttgcaggcca    420
tgctgtccag gcaggtagat gacgaccatc agggacagct tcaaggatcg ctcgcggctc    480
ttaccagcct aacttcgatc actggaccgc tgatcgtcac ggcgatttat gccgcctcgg    540
cgagcacatg gaacgggttg gcatggattg taggcgccgc cctatacctt gtctgcctcc    600
ccgcgttgcg tcgcggtgca tggagccggg ccacctcgac ctgaatggaa gccggcggca    660
cctcgctaac ggattcacca ctccaagaat tggagccaat caattcttgc ggagaactgt    720
gaatgcgcaa accaaccctt ggcagaacat atccatcgcg tccgccatct ccagcagccg    780
cacgcggcgc atctcgggca gcgttgggtc ctggccacgg gtgcgcatga tcgtgctcct    840
gtcgttgagg acccggctag gctggcgggg ttgccttact ggttagcaga atgaatcacc    900
gatacgcgag cgaacgtgaa gcgactgctg ctgcaaaacg tctgcgacct gagcaacaac    960
atgaatggtc ttcggtttcc gtgtttcgta aagtctggaa acgcggaagt cagcgccctg   1020
caccattatg ttccggatct gcatcgcagg atgctgctgg ctaccctgtg gaacacctac   1080
atctgtatta acgaagcgct ggcattgacc ctgagtgatt tttctctggt cccgccgcat   1140
ccataccgcc agttgtttac cctcacaacg ttccagtaac cgggcatgtt catcatcagt   1200
aacccgtatc gtgagcatcc tctctcgttt catcggtatc attaccccca tgaacagaaa   1260
ttccccctta cacggaggca tcaagtgacc aaacaggaaa aaaccgccct taacatggcc   1320
cgctttatca gaagccagac attaacgctt ctggagaaac tcaacgagct ggacgcggat   1380
gaacaggcag acatctgtga atcgcttcac gaccacgctg atgagcttta ccgcagctgc   1440
ctcgcgcgtt tcggtgatga cggtgaaaac ctctgacaca tgcagctccc ggagacggtc   1500
acagcttgtc tgtaagcgga tgccgggagc agacaagccc gtcagggcgc gtcagcgggt   1560
gttggcgggt gtcggggcgc agccatgacc cagtcacgta gcgatagcgg agtgtatact   1620
ggcttaacta tgcggcatca gagcagattg tactgagagt gcaccatatg cggtgtgaaa   1680
taccgcacag atgcgtaagg agaaaatacc gcatcaggcg ctcttccgct tcctcgctca   1740
ctgactcgct gcgctcggtc gttcggctgc ggcgagcggt atcagctcac tcaaaggcgg   1800
taatacggtt atccacagaa tcaggggata acgcaggaaa gaacatgtga gcaaaaggcc   1860
agcaaaaggc caggaaccgt aaaaaggccg cgttgctggc gtttttccat aggctccgcc   1920
cccctgacga gcatcacaaa aatcgacgct caagtcagag gtggcgaaac ccgacaggac   1980
tataaagata ccaggcgttt ccccctggaa gctccctcgt gcgctctcct gttccgaccc   2040
tgccgcttac cggatacctg tccgcctttc tcccttcggg aagcgtggcg ctttctcaat   2100
```

```
gctcacgctg taggtatctc agttcggtgt aggtcgttcg ctccaagctg ggctgtgtgc   2160
acgaaccccc cgttcagccc gaccgctgcg ccttatccgg taactatcgt cttgagtcca   2220
acccggtaag acacgactta tcgccactgg cagcagccac tggtaacagg attagcagag   2280
cgaggtatgt aggcggtgct acagagttct tgaagtggtg gcctaactac ggctacacta   2340
gaaggacagt atttggtatc tgcgctctgc tgaagccagt taccttcgga aaaagagttg   2400
gtagctcttg atccggcaaa caaaccaccg ctggtagcgg tggttttttt gtttgcaagc   2460
agcagattac gcgcagaaaa aaaggatctc aagaagatcc tttgatcttt tctacggggt   2520
ctgacgctca gtggaacgaa aactcacgtt aagggatttt ggtcatgaga ttatcaaaaa   2580
ggatcttcac ctagatcctt ttaaattaaa aatgaagttt taaatcaatc taaagtatat   2640
atgagtaaac ttggtctgac agttaccaat gcttaatcag tgaggcacct atctcagcga   2700
tctgtctatt tcgttcatcc atagttgcct gactccccgt cgtgtagata actacgatac   2760
gggagggctt accatctggc cccagtgctg caatgatacc gcgagaccca cgctcaccgg   2820
ctccagattt atcagcaata aaccagccag ccggaagggc cgagcgcaga agtggtcctg   2880
caactttatc cgcctccatc cagtctatta attgttgccg ggaagctaga gtaagtagtt   2940
cgccagttaa tagtttgcgc aacgttgttg ccattgctgc agccatgaga ttatcaaaaa   3000
ggatcttcac ctagatcctt ttcacgtaga aagccagtcc gcagaaacgg tgctgacccc   3060
ggatgaatgt cagctactgg gctatctgga caagggaaaa cgcaagcgca aagagaaagc   3120
aggtagcttg cagtgggctt acatggcgat agctagactg ggcggtttta tggacagcaa   3180
gcgaaccgga attgccagct ggggcgccct ctggtaaggt tgggaagccc tgcaaagtaa   3240
actggatggc tttctcgccg ccaaggatct gatggcgcag gggatcaagc tctgatcaag   3300
agacaggatg aggatcgttt cgcatgattg aacaagatgg attgcacgca ggttctccgg   3360
ccgcttgggt ggagaggcta ttcggctatg actgggcaca acagacaatc ggctgctctg   3420
atgccgccgt gttccggctg tcagcgcagg ggcgcccggt tctttttgtc aagaccgacc   3480
tgtccggtgc cctgaatgaa ctgcaagacg aggcagcgcg gctatcgtgg ctggccacga   3540
cgggcgttcc ttgcgcagct gtgctcgacg ttgtcactga agcgggaagg gactggctgc   3600
tattgggcga agtgccgggg caggatctcc tgtcatctca ccttgctcct gccgagaaag   3660
tatccatcat ggctgatgca atgcggcggc tgcatacgct tgatccggct acctgcccat   3720
tcgaccacca agcgaaacat cgcatcgagc gagcacgtac tcggatggaa gccggtcttg   3780
tcgatcagga tgatctggac gaagagcatc aggggctcgc gccagccgaa ctgttcgcca   3840
ggctcaaggc gagcatgccc gacggcgagg atctcgtcgt gacccatggc gatgcctgct   3900
tgccgaatat catggtggaa aatggccgct tttctggatt catcgactgt ggccggctgg   3960
gtgtggcgga ccgctatcag gacatagcgt tggctacccg tgatattgct gaagagcttg   4020
gcggcgaatg ggctgaccgc ttcctcgtgc tttacggtat cgccgctccc gattcgcagc   4080
gcatcgcctt ctatcgcctt cttgacgagt tcttctgaat tttgttaaaa tttttgttaa   4140
atcagctcat tttttaacca ataggccgaa atcggcaaca tcccttataa atcaaaagaa   4200
tagaccgcga tagggttgag tgttgttcca gtttggaaca agagtccact attaaagaac   4260
gtggactcca acgtcaaagg gcgaaaaacc gtctatcagg gcgatggccc actacgtgaa   4320
ccatcaccca aatcaagttt tttgcggtcg aggtgccgta aagctctaaa tcggaaccct   4380
aaagggagcc cccgatttag agcttgacgg ggaaagccgg cgaacgtggc gagaaaggaa   4440
gggaagaaag cgaaaggagc gggcgctagg gcgctggcaa gtgtagcggt cacgctgcgc   4500
```

```
gtaaccacca cacccgcgcg cttaatgcgc cgctacaggg cgcgtccatt cgccattcag   4560
gatcgaatta attcttaatt aacatcatca ataatatacc ttattttgga ttgaagccaa   4620
tatgataatg agggggtgga gtttgtgacg tggcgcgggg cgtgggaacg gggcgggtga   4680
cgtagtagtg tggcggaagt gtgatgttgc aagtgtggcg gaacacatgt aagcgacgga   4740
tgtggcaaaa gtgacgtttt tggtgtgcgc cggtgtacac aggaagtgac aattttcgcg   4800
cggttttagg cggatgttgt agtaaatttg ggcgtaaccg agtaagattt ggccattttc   4860
gcgggaaaac tgaataagag gaagtgaaat ctgaataatt ttgtgttact catagcgcgt   4920
aatactgcta gagatctggc gaaaggggga tgtgctgcaa ggcgattaag ttgggtaacg   4980
ccagggtttt cccagtcacg acgttgtaaa acgacggcca gtgaattgta atacgactca   5040
ctatagggcg aattgggtac tggccacaga gcttggccca ttgcatacgt tgtatccata   5100
tcataatatg tacatttata ttggctcatg tccaacatta ccgccatgtt gacattgatt   5160
attgactagt tattaatagt aatcaattac ggggtcatta gttcatagcc catatatgga   5220
gttccgcgtt acataactta cggtaaatgg cccgcctggc tgaccgccca acgacccccg   5280
cccattgacg tcaataatga cgtatgttcc catagtaacg ccaataggga ctttccattg   5340
acgtcaatgg gtggagtatt tacggtaaac tgcccacttg gcagtacatc aagtgtatca   5400
tatgccaagt acgcccccta ttgacgtcaa tgacggtaaa tggcccgcct ggcattatgc   5460
ccagtacatg accttatggg actttcctac ttggcagtac atctacgtat tagtcatcgc   5520
tattaccatg gtgatgcggt tttggcagta catcaatggg cgtggatagc ggtttgactc   5580
acggggattt ccaagtctcc accccattga cgtcaatggg agtttgtttt ggcaccaaaa   5640
tcaacgggac tttccaaaat gtcgtaacaa ctccgcccca ttgacgcaaa tgggcggtag   5700
gcgtgtacgg tgggaggtct atataagcag agctcgttta gtgaaccgtc agatcgcctg   5760
gagacgccat ccacgctgtt ttgacctcca tagaagacac cgggaccgat ccagcctgac   5820
tctagcctag ctctgaagtt ggtggtgagg ccctgggcag gttggtatca aggttacaag   5880
acaggtttaa ggagaccaat agaaactggg catgtggaga cagagaagac tcttgggttt   5940
ctgataggca ctgactctct ctgcctattg gtctattttc ccacccttag gctgctggtc   6000
tgagcctagg agatctctcg aggtcgacgg tatcgatgcc accatggaga aaatcgtcct   6060
gttgctcgct attgtgtctc tagtgaagag cgatcaaatt tgtatcggct accatgccaa   6120
taactcaaca gagcaggtcg atactatcat ggagaaaaac gtaacagtta ctcatgccca   6180
agacatcttg gaaaagaccc acaacggcaa actttgcgac ctggatggag tgaagcccct   6240
gatcctccgg gactgttcag tcgctggttg gctgctcggg aaccctatgt gtgatgagtt   6300
tatcaacgtg cctgaatggt cttacattgt ggagaaggct aaccctacca atgacctctg   6360
ctatcctggg tcatttaacg attacgagga actgaaacac ctgttgtcta gaattaacca   6420
ctttgaaaag atacagatta tacccaagtc tagttggagt gatcacgaag cctcctcagg   6480
cgttagctca gcgtgtccct atctgggctc tccatccttc tttagaaatg tggtctggtt   6540
aatcaaaaag aacagtacct acccaaccat caaaaagtct tataacaata ccaatcagga   6600
ggacctgctc gtgttgtggg gtatccatca cccgaacgac gccgctgaac agactaggct   6660
gtatcagaac cccactacat acatcagtat tggcacgagt actctgaacc agcgattagt   6720
gccaaagatt gcaacacgga gcaaagtaaa tgggcaatct ggcaggatgg agtttttctg   6780
gacaatctta aaacccaacg atgcgataaa tttcgagtcc aatggcaatt tcatcgcccc   6840
tgaatacgcc tataagatcg tgaaaaaggg ggactctgca attatgaagt ccgaattaga   6900
```

```
gtatggcaat tgcaacacga agtgccagac accaatggga gccattaata gctcaatgcc   6960
cttccataat attcatccat tgaccattgg ggagtgccca aagtacgtga agtccaaccg   7020
cctggtcctc gcaaccggtc taagaaatag cccgcagaga gaatcgcgga ggaagaaacg   7080
tggcctgttt ggcgcgattg ccggattcat cgagggaggc tggcagggta tggtcgatgg   7140
ttggtacgga taccaccata gcaacgaaca ggggtccggc tatgcagcag ataaggagag   7200
cactcagaaa gctattgacg gagttacaaa caaggttaat agtattatag ataaaatgaa   7260
cacgcaattc gaggccgttg ggagggagtt taacaatctg gaacgccgga tcgaaaatct   7320
gaataagaaa atggaagacg gcttccttga cgtgtggact tataatgcag agctgcttgt   7380
actcatggag aacgagagga ccctggattt ccacgatagc aacgtgaaga acctttacga   7440
caaggtgaga cttcagctcc gagacaacgc caaggagctg gggaatggat gcttcgagtt   7500
ttaccacaaa tgtgacaatg agtgcatgga aagtatacgc aacgggacct acaattaccc   7560
tcagtatagc gaagaggctc ggctcaaacg cgaagagata agcggggtga aattggaatc   7620
aatcggaaca tatcaaatcc tgtccatcta ttccaccgtc gcctcttcgc tggccctcgc   7680
tatcatgatg gctggtctgt ccctatggat gtgttccaat ggaagccttc agtgccgtat   7740
ttgtatatga gcggccgccc tattctatag tgtcacctaa atgctagagc tcgctgatca   7800
gcctcgactg tgccttctag ttgccagcca tctgttgttt gcccctcccc cgtgccttcc   7860
ttgaccctgg aaggtgccac tcccactgtc ctttcctaat aaaatgagga aattgcatcg   7920
cattgtctga gtaggtgtca ttctattctg gggggtgggg tggggcagga cagcaagggg   7980
gaggattggg aagacaatag caggcatgct ggggatgcgg tgggctctat ggcttctgag   8040
gcggaaagaa ccaaagctta acatcatcaa taatatacct tattttggat tgaagccaat   8100
atgataatga gggggtggag tttgtgacgt ggcgcggggc gtgggaacgg ggcgggtgac   8160
gtagtagtgt ggcggaagtg tgatgttgca agtgtggcgg aacacatgta agcgacggat   8220
gtggcaaaag tgacgttttt ggtgtgcgcc ggtgtacaca ggaagtgaca attttcgcgc   8280
ggttttaggc ggatgttgta gtaaatttgg gcgtaaccga gtaagatttg gccattttcg   8340
cgggaaaact gaataagagg aagtgaaatc tgaataattt tgtgttactc atagcgcgta   8400
atactgtaat agtaatcaat tacggggtca ttagttcata gcccatatat ggagttccgc   8460
gttacataac ttacggtaaa tggcccgcct ggctgaccgc ccaacgaccc ccgcccattg   8520
acgtcaataa tgacgtatgt tcccatagta acgccaatag ggactttcca ttgacgtcaa   8580
tgggtggagt atttacggta aactgcccac ttggcagtac atcaagtgta tcatatgcca   8640
agtacgcccc ctattgacgt caatgacggt aaatggcccg cctggcatta tgcccagtac   8700
atgaccttat gggactttcc tacttggcag tacatctacg tattagtcat cgctattacc   8760
atggtgatgc ggttttggca gtacatcaat gggcgtggat agcggtttga ctcacgggga   8820
tttccaagtc tccaccccat tgacgtcaat gggagtttgt tttggcacca aaatcaacgg   8880
gactttccaa aatgtcgtaa caactccgcc ccattgacgc aaatgggcgg taggcgtgta   8940
cggtgggagg tctatataag cagagctggt ttagtgaacc gtcagatccg ctagagatct   9000
gggaaacgat atgggctgaa tacggatccg tattcagccc atatcgtttc tctagaaata   9060
aaatatcttt attttcatta catctgtgtg ttggtttttt gtgtggcggc cgctcgagcc   9120
taagcttcta gataagatat ccgatccacc ggatctagat aactgatcat aatcagccat   9180
accacatttg tagaggtttt acttgcttta aaaaacctcc cacacctccc cctgaacctg   9240
aaacataaaa tgaatgcaat tgttgttgtt aacttgttta ttgcagctta taatggttac   9300
```

```
aaataaagca atagcatcac aaatttcaca aataaagcat ttttttcact gcattctagt   9360
tgtggtttgt ccaaactcat caatgtatct taacgcggat ctgggcgtgg ttaagggtgg   9420
gaaagaatat ataaggtggg ggtcttatgt agttttgtat ctgttttgca gcagccgccg   9480
ccgccatgag caccaactcg tttgatggaa gcattgtgag cttgtcgact cgaagatctg   9540
ggcgtggtta agggtgggaa agaatatata aggtgggggt cttatgtagt tttgtatctg   9600
ttttgcagca gccgccgccg ccatgagcac caactcgttt gatggaagca ttgtgagctc   9660
atatttgaca acgcgcatgc ccccatgggc cggggtgcgt cagaatgtga tgggctccag   9720
cattgatggt cgccccgtcc tgcccgcaaa ctctactacc ttgacctacg agaccgtgtc   9780
tggaacgccg ttggagactg cagcctccgc cgccgcttca gccgctgcag ccaccgcccg   9840
cgggattgtg actgactttg ctttcctgag cccgcttgca agcagtgcag cttcccgttc   9900
atccgcccgc gatgacaagt tgacggctct tttggcacaa ttggattctt tgacccggga   9960
acttaatgtc gtttctcagc agctgttgga tctgcgccag caggtttctg ccctgaaggc  10020
ttcctcccct cccaatgcgg tttaaaacat aaataaaaaa ccagactctg tttggatttg  10080
gatcaagcaa gtgtcttgct gtctttattt aggggttttg cgcgcgcggt aggcccggga  10140
ccagcggtct cggtcgttga gggtcctgtg tatttttttcc aggacgtggt aaaggtgact  10200
ctggatgttc agatacatgg gcataagccc gtctctgggg tggaggtagc accactgcag  10260
agcttcatgc tgcggggtgg tgttgtagat gatccagtcg tagcaggagc gctgggcgtg  10320
gtgcctaaaa atgtctttca gtagcaagct gattgccagg ggcaggccct tggtgtaagt  10380
gtttacaaag cggttaagct gggatgggtg catacgtggg gatatgagat gcatcttgga  10440
ctgtattttt aggttggcta tgttcccagc catatccctc cggggattca tgttgtgcag  10500
aaccaccagc acagtgtatc cggtgcactt gggaaatttg tcatgtagct tagaaggaaa  10560
tgcgtggaag aacttggaga cgcccttgtg acctccaaga ttttccatgc attcgtccat  10620
aatgatggca atgggcccac gggcggcggc ctgggcgaag atatttctgg gatcactaac  10680
gtcatagttg tgttccagga tgagatcgtc ataggccatt tttacaaagc gcgggcggag  10740
ggtgccagac tgcggtataa tggttccatc cggcccaggg gcgtagttac cctcacagat  10800
ttgcatttcc cacgctttga gttcagatgg ggggatcatg tctacctgcg gggcgatgaa  10860
gaaaacggtt tccggggtag gggagatcag ctgggaagaa agcaggttcc tgagcagctg  10920
cgacttaccg cagccggtgg gcccgtaaat cacacctatt accgggtgca actggtagtt  10980
aagagagctg cagctgccgt catccctgag caggggggcc acttcgttaa gcatgtccct  11040
gactcgcatg ttttccctga ccaaatccgc cagaaggcgc tcgccgccca gcgatagcag  11100
ttcttgcaag gaagcaaagt ttttcaacgg tttgagaccg tccgccgtag gcatgctttt  11160
gagcgtttga ccaagcagtt ccaggcggtc ccacagctcg gtcacctgct ctacggcatc  11220
tcgatccagc atatctcctc gtttcgcggg ttggggcggc tttcgctgta cggcagtagt  11280
cggtgctcgt ccagacgggc cagggtcatg tctttccacg ggcgcagggt cctcgtcagc  11340
gtagtctggg tcacggtgaa ggggtgcgct ccgggctgcg cgctggccag ggtgcgcttg  11400
aggctggtcc tgctggtgct gaagcgctgc cggtcttcgc cctgcgcgtc ggccaggtag  11460
catttgacca tggtgtcata gtccagcccc tccgcggcgt ggcccttggc gcgcagcttg  11520
cccttggagg aggcgccgca cgaggggcag tgcagacttt tgagggcgta gagcttgggc  11580
gcgagaaata ccgattccgg ggagtaggca tccgcgccgc aggccccgca gacggtctcg  11640
cattccacga gccaggtgag ctctggccgt tcggggtcaa aaaccaggtt tcccccatgc  11700
```

tttttgatgc gtttcttacc tctggtttcc atgagccggt gtccacgctc ggtgacgaaa 11760
aggctgtccg tgtccccgta tacagacttg agaggcctgt cctcgagcgg tgttccgcgg 11820
tcctcctcgt atagaaactc ggaccactct gagacaaagg ctcgcgtcca ggccagcacg 11880
aaggaggcta agtgggaggg gtagcggtcg ttgtccacta gggggtccac tcgctccagg 11940
gtgtgaagac acatgtcgcc ctcttcggca tcaaggaagg tgattggttt gtaggtgtag 12000
gccacgtgac cgggtgttcc tgaagggggg ctataaaagg gggtgggggc gcgttcgtcc 12060
tcactctctt ccgcatcgct gtctgcgagg gccagctgtt ggggtgagta ctccctctga 12120
aaagcgggca tgacttctgc gctaagattg tcagtttcca aaaacgagga ggatttgata 12180
ttcacctggc ccgcggtgat gcctttgagg gtggccgcat ccatctggtc agaaaagaca 12240
atctttttgt tgtcaagctt ggtggcaaac gacccgtaga gggcgttgga cagcaacttg 12300
gcgatggagc gcagggtttg gtttttgtcg cgatcggcgc gctccttggc cgcgatgttt 12360
agctgcacgt attcgcgcgc aacgcaccgc cattcgggaa agacggtggt gcgctcgtcg 12420
ggcaccaggt gcacgcgcca accgcggttg tgcagggtga caaggtcaac gctggtggct 12480
acctctccgc gtaggcgctc gttggtccag cagaggcggc cgcccttgcg cgagcagaat 12540
ggcggtaggg ggtctagctg cgtctcgtcc ggggggtctg cgtccacggt aaagaccccg 12600
ggcagcaggc gcgcgtcgaa gtagtctatc ttgcatcctt gcaagtctag cgcctgctgc 12660
catgcgcggg cggcaagcgc gcgctcgtat gggttgagtg ggggacccca tggcatgggg 12720
tgggtgagcg cggaggcgta catgccgcaa atgtcgtaaa cgtagagggg ctctctgagt 12780
attccaagat atgtagggta gcatcttcca ccgcggatgc tggcgcgcac gtaatcgtat 12840
agttcgtgcg agggagcgag gaggtcggga ccgaggttgc tacgggcggg ctgctctgct 12900
cggaagacta tctgcctgaa gatggcatgt gagttggatg atatggttgg acgctggaag 12960
acgttgaagc tggcgtctgt gagacctacc gcgtcacgca cgaaggaggc gtaggagtcg 13020
cgcagcttgt tgaccagctc ggcggtgacc tgcacgtcta gggcgcagta gtccagggtt 13080
tccttgatga tgtcatactt atcctgtccc ttttttttcc acagctcgcg gttgaggaca 13140
aactcttcgc ggtctttcca gtactcttgg atcggaaacc cgtcggcctc cgaacggtaa 13200
gagcctagca tgtagaactg gttgacggcc tggtaggcgc agcatccctt ttctacgggt 13260
agcgcgtatg cctgcgcggc cttccggagc gaggtgtggg tgagcgcaaa ggtgtccctg 13320
accatgactt tgaggtactg gtatttgaag tcagtgtcgt cgcatccgcc ctgctcccag 13380
agcaaaaagt ccgtgcgctt tttggaacgc ggatttggca gggcgaaggt gacatcgttg 13440
aagagtatct ttcccgcgcg aggcataaag ttgcgtgtga tgcggaaggg tcccggcacc 13500
tcggaacggt tgttaattac ctgggcggcg agcacgatct cgtcaaagcc gttgatgttg 13560
tggcccacaa tgtaaagttc caagaagcgc gggatgccct tgatggaagg caattttta 13620 agttcctcgt aggtgagctc ttcaggggag ctgagcccgt gctctgaaag ggcccagtct 13680
gcaagatgag ggttggaagc gacgaatgag ctccacaggt cacgggccat tagcatttgc 13740
aggtggtcgc gaaaggtcct aaactggcga cctatggcca ttttttctgg ggtgatgcag 13800
tagaaggtaa gcgggtcttg ttcccagcgg tcccatccaa ggttcgcggc taggtctcgc 13860
gcggcagtca ctagaggctc atctccgccg aacttcatga ccagcatgaa gggcacgagc 13920
tgcttcccaa aggcccccat ccaagtatag gtctctacat cgtaggtgac aaagagacgc 13980
tcggtgcgag gatgcgagcc gatcgggaag aactggatct cccgccacca attggaggag 14040
tggctattga tgtggtgaaa gtagaagtcc ctgcgacggg ccgaacactc gtgctggctt 14100

```
ttgtaaaaac gtgcgcagta ctggcagcgg tgcacgggct gtacatcctg cacgaggttg  14160
acctgacgac cgcgcacaag gaagcagagt gggaatttga gcccctcgcc tggcgggttt  14220
ggctggtggt cttctacttc ggctgcttgt ccttgaccgt ctggctgctc gaggggagtt  14280
acggtggatc ggaccaccac gccgcgcgag cccaaagtcc agatgtccgc gcgcggcggt  14340
cggagcttga tgacaacatc gcgcagatgg gagctgtcca tggtctggag ctcccgcggc  14400
gtcaggtcag gcgggagctc ctgcaggttt acctcgcata gacgggtcag ggcgcgggct  14460
agatccaggt gatacctaat ttccaggggc tggttggtgg cggcgtcgat ggcttgcaag  14520
aggccgcatc cccgcggcgc gactacggta ccgcgcggcg ggcggtgggc cgcgggggtg  14580
tccttggatg atgcatctaa aagcggtgac gcgggcgagc cccggaggt agggggggct  14640
ccggacccgc cgggagaggg ggcaggggca cgtcggcgcc gcgcgcgggc aggagctggt  14700
gctgcgcgcg taggttgctg gcgaacgcga cgacgcggcg gttgatctcc tgaatctggc  14760
gcctctgcgt gaagacgacg ggcccggtga gcttgagcct gaaagagagt tcgacagaat  14820
caatttcggt gtcgttgacg gcggcctggc gcaaaatctc ctgcacgtct cctgagttgt  14880
cttgataggc gatctcggcc atgaactgct cgatctcttc ctcctggaga tctccgcgtc  14940
cggctcgctc cacggtggcg gcgaggtcgt tggaaatgcg ggccatgagc tgcgagaagg  15000
cgttgaggcc tccctcgttc cagacgcggc tgtagaccac gcccccttcg gcatcgcggg  15060
cgcgcatgac cacctgcgcg agattgagct ccacgtgccg ggcgaagacg gcgtagtttc  15120
gcaggcgctg aaagaggtag ttgagggtgg tggcggtgtg ttctgccacg aagaagtaca  15180
taacccagcg tcgcaacgtg gattcgttga tatcccccaa ggcctcaagg cgctccatgg  15240
cctcgtagaa gtccacggcg aagttgaaaa actgggagtt gcgcgccgac acggttaact  15300
cctcctccag aagacggatg agctcggcga cagtgtcgcg cacctcgcgc tcaaaggcta  15360
caggggcctc ttcttcttct tcaatctcct cttccataag ggcctcccct tcttcttctt  15420
ctggcggcgg tgggggaggg gggacacggc ggcgacgacg gcgcaccggg aggcggtcga  15480
caaagcgctc gatcatctcc ccgcggcgac ggcgcatggt ctcggtgacg gcgcggccgt  15540
tctcgcgggg gcgcagttgg aagacgccgc ccgtcatgtc ccggttatgg gttggcgggg  15600
ggctgccatg cggcagggat acggcgctaa cgatgcatct caacaattgt tgtgtaggta  15660
ctccgccgcc gagggacctg agcgagtccg catcgaccgg atcggaaaac ctctcgagaa  15720
aggcgtctaa ccagtcacag tcgcaaggta ggctgagcac cgtggcgggc ggcagcgggc  15780
ggcggtcggg gttgtttctg gcggaggtgc tgctgatgat gtaattaaag taggcggtct  15840
tgagacggcg gatggtcgac agaagcacca tgtccttggg tccggcctgc tgaatgcgca  15900
ggcggtcggc catgccccag gcttcgtttt gacatcggcg caggtctttg tagtagtctt  15960
gcatgagcct ttctaccggc acttcttctt ctccttcctc ttgtcctgca tctcttgcat  16020
ctatcgctgc ggcggcggcg gagtttggcc gtaggtggcg ccctcttcct cccatgcgtg  16080
tgaccccgaa gcccctcatc ggctgaagca gggctaggtc ggcgacaacg cgctcggcta  16140
atatggcctg ctgcacctgc gtgagggtag actggaagtc atccatgtcc acaaagcggt  16200
ggtatgcgcc cgtgttgatg gtgtaagtgc agttggccat aacggaccag ttaacggtct  16260
ggtgacccgg ctgcgagagc tcggtgtacc tgagacgcga gtaagccctc gagtcaaata  16320
cgtagtcgtt gcaagtccgc accaggtact ggtatcccac caaaaagtgc ggcggcggct  16380
ggcggtagag gggccagcgt agggtggccg gggctccggg ggcgagatct tccaacataa  16440
ggcgatgata tccgtagatg tacctggaca tccaggtgat gccggcggcg gtggtggagg  16500
```

```
cgcgcggaaa gtcgcggacg cggttccaga tgttgcgcag cggcaaaaag tgctccatgg  16560
tcgggacgct ctggccggtc aggcgcgcgc aatcgttgac gctctaccgt gcaaaaggag  16620
agcctgtaag cgggcactct tccgtggtct ggtggataaa ttcgcaaggg tatcatggcg  16680
gacgaccggg gttcgagccc cgtatccggc cgtccgccgt gatccatgcg gttaccgccc  16740
gcgtgtcgaa cccaggtgtg cgacgtcaga caacgggga gtgctccttt tggcttcctt  16800
ccaggcgcgg cggctgctgc gctagctttt ttggccactg gccgcgcgca gcgtaagcgg  16860
ttaggctgga aagcgaaagc attaagtggc tcgctccctg tagccggagg gttattttcc  16920
aagggttgag tcgcgggacc cccggttcga gtctcggacc ggccggactg cggcgaacgg  16980
gggtttgcct ccccgtcatg caagaccccg cttgcaaatt cctccggaaa cagggacgag  17040
ccccttttt gcttttccca gatgcatccg gtgctgcggc agatgcgccc ccctcctcag  17100
cagcggcaag agcaagagca gcggcagaca tgcagggcac cctcccctcc tcctaccgcg  17160
tcaggagggg cgacatccgc ggttgacgcg gcagcagatg gtgattacga acccccgcgg  17220
cgccgggccc ggcactacct ggacttggag gagggcgagg gcctggcgcg gctaggagcg  17280
ccctctcctg agcggtaccc aagggtgcag ctgaagcgtg atacgcgtga ggcgtacgtg  17340
ccgcggcaga acctgtttcg cgaccgcgag ggagaggagc ccgaggagat gcgggatcga  17400
aagttccacg cagggcgcga gctgcggcat ggcctgaatc gcgagcggtt gctgcgcgag  17460
gaggactttg agcccgacgc gcgaaccggg attagtcccg cgcgcgcaca cgtggcggcc  17520
gccgacctgg taaccgcata cgagcagacg gtgaaccagg agattaactt tcaaaaaagc  17580
tttaacaacc acgtgcgtac gcttgtggcg cgcgaggagg tggctatagg actgatgcat  17640
ctgtgggact ttgtaagcgc gctggagcaa aacccaaata gcaagccgct catggcgcag  17700
ctgttcctta tagtgcagca cagcagggac aacgaggcat tcagggatgc gctgctaaac  17760
atagtagagc ccgagggccg ctggctgctc gatttgataa acatcctgca gagcatagtg  17820
gtgcaggagc gcagcttgag cctggctgac aaggtggccg ccatcaacta ttccatgctt  17880
agcctgggca agttttacgc ccgcaagata taccataccc cttacgttcc catagacaag  17940
gaggtaaaga tcgaggggtt ctacatgcgc atggcgctga aggtgcttac cttgagcgac  18000
gacctgggcg tttatcgcaa cgagcgcatc cacaaggccg tgagcgtgag ccggcggcgc  18060
gagctcagcg accgcgagct gatgcacagc ctgcaaaggg ccctggctgg cacgggcagc  18120
ggcgatagag aggccgagtc ctactttgac gcgggcgctg acctgcgctg ggccccaagc  18180
cgacgcgccc tggaggcagc tggggccgga cctgggctgg cggtggcacc cgcgcgcgct  18240
ggcaacgtcg gcggcgtgga ggaatatgac gaggacgatg agtacgagcc agaggacggc  18300
gagtactaag cggtgatgtt tctgatcaga tgatgcaaga cgcaacggac ccggcggtgc  18360
gggcggcgct gcagagccag ccgtccggcc ttaactccac ggacgactgg cgccaggtca  18420
tggaccgcat catgtcgctg actgcgcgca atcctgacgc gttccggcag cagccgcagg  18480
ccaaccggct ctccgcaatt ctggaagcgg tggtcccggc gcgcgcaaac cccacgcacg  18540
agaaggtgct ggcgatcgta aacgcgctgg ccgaaaacag ggccatccgg cccgacgagg  18600
ccggcctggt ctacgacgcg ctgcttcagc gcgtggctcg ttacaacagc ggcaacgtgc  18660
agaccaacct ggaccggctg gtgggggatg tgcgcgaggc cgtggcgcag cgtgagcgcg  18720
cgcagcagca gggcaacctg ggctccatgg ttgcactaaa cgccttcctg agtacacagc  18780
ccgccaacgt gccgcgggga caggaggact acaccaactt tgtgagcgca ctgcggctaa  18840
tggtgactga gacaccgcaa agtgaggtgt accagtctgg gccagactat tttttccaga  18900
```

```
ccagtagaca aggcctgcag accgtaaacc tgagccaggc tttcaaaaac ttgcaggggc  18960
tgtgggggt gcgggctccc acaggcgacc gcgcgaccgt gtctagcttg ctgacgccca  19020
actcgcgcct gttgctgctg ctaatagcgc ccttcacgga cagtggcagc gtgtcccggg  19080
acacatacct aggtcacttg ctgacactgt accgcgaggc cataggtcag gcgcatgtgg  19140
acgagcatac tttccaggag attacaagtg tcagccgcgc gctggggcag gaggacacgg  19200
gcagcctgga ggcaacccta aactacctgc tgaccaaccg gcggcagaag atcccctcgt  19260
tgcacagttt aaacagcgag gaggagcgca ttttgcgcta cgtgcagcag agcgtgagcc  19320
ttaacctgat gcgcgacggg gtaacgccca gcgtggcgct ggacatgacc gcgcgcaaca  19380
tggaaccggg catgtatgcc tcaaaccggc cgtttatcaa ccgcctaatg gactacttgc  19440
atcgcgcggc cgccgtgaac cccgagtatt tcaccaatgc catcttgaac ccgcactggc  19500
taccgccccc tggtttctac accgggggat tcgaggtgcc cgagggtaac gatggattcc  19560
tctgggacga catagacgac agcgtgtttt ccccgcaacc gcagaccctg ctagagttgc  19620
aacagcgcga gcaggcagag gcggcgctgc gaaaggaaag cttccgcagg ccaagcagct  19680
tgtccgatct aggcgctgcg gccccgcggt cagatgctag tagcccattt ccaagcttga  19740
tagggtctct taccagcact cgcaccaccc gcccgcgcct gctgggcgag gaggagtacc  19800
taaacaactc gctgctgcag ccgcagcgcg aaaaaaacct gcctccggca tttcccaaca  19860
acgggataga gagcctagtg gacaagatga gtagatggaa gacgtacgcg caggagcaca  19920
gggacgtgcc aggcccgcgc ccgcccaccc gtcgtcaaag gcacgaccgt cagcggggtc  19980
tggtgtggga ggacgatgac tcggcagacg acagcagcgt cctggatttg ggagggagtg  20040
gcaacccgtt tgcgcacctt cgccccaggc tggggagaat gttttaaaaa aaaaaaagca  20100
tgatgcaaaa taaaaaactc accaaggcca tggcaccgag cgttggtttt cttgtattcc  20160
ccttagtatg cggcgcgcgg cgatgtatga ggaaggtcct cctccctcct acgagagtgt  20220
ggtgagcgcg gcgccagtgg cggcggcgct gggttctccc ttcgatgctc ccctggaccc  20280
gccgtttgtg cctccgcggt acctgcggcc taccgggggg agaaacagca tccgttactc  20340
tgagttggca cccctattcg acaccacccg tgtgtacctg gtggacaaca agtcaacgga  20400
tgtggcatcc ctgaactacc agaacgacca cagcaacttt ctgaccacgg tcattcaaaa  20460
caatgactac agcccggggg aggcaagcac acagaccatc aatcttgacg accggtcgca  20520
ctggggcggc gacctgaaaa ccatcctgca taccaacatg ccaaatgtga acgagttcat  20580
gtttaccaat aagtttaagg cgcgggtgat ggtgtcgcgc ttgcctacta aggacaatca  20640
ggtggagctg aaatacgagt gggtggagtt cacgctgccc gagggcaact actccgagac  20700
catgaccata gaccttatga acaacgcgat cgtggagcac tacttgaaag tgggcagaca  20760
gaacggggtt ctggaaagcg acatcggggt aaagtttgac acccgcaact tcagactggg  20820
gtttgacccc gtcactggtc ttgtcatgcc tggggtatat acaaacgaag ccttccatcc  20880
agacatcatt ttgctgccag gatgcggggt ggacttcacc cacagccgcc tgagcaactt  20940
gttgggcatc cgcaagcggc aacccttcca ggagggcttt aggatcacct acgatgatct  21000
ggagggtggt aacattcccg cactgttgga tgtggacgcc taccaggcga gcttgaaaga  21060
tgacaccgaa cagggcgggg gtggcgcagg cggcagcaac agcagtggca gcggcgcgga  21120
agagaactcc aacgcggcag ccgcggcaat gcagccggtg gaggacatga acgatcatgc  21180
cattcgcggc gacacctttg ccacacgggc tgaggagaag cgcgctgagg ccgaagcagc  21240
ggccgaagct gccgcccccg ctgcgcaacc cgaggtcgag aagcctcaga agaaaccggt  21300
```

```
gatcaaaccc ctgacagagg acagcaagaa acgcagttac aacctaataa gcaatgacag  21360
caccttcacc cagtaccgca gctggtacct tgcatacaac tacggcgacc ctcagaccgg  21420
aatccgctca tggaccctgc tttgcactcc tgacgtaacc tgcggctcgg agcaggtcta  21480
ctggtcgttg ccagacatga tgcaagaccc cgtgaccttc cgctccacgc gccagatcag  21540
caactttccg gtggtgggcg ccgagctgtt gcccgtgcac tccaagagct tctacaacga  21600
ccaggccgtc tactcccaac tcatccgcca gtttacctct ctgacccacg tgttcaatcg  21660
ctttcccgag aaccagattt tggcgcgccc gccagccccc accatcacca ccgtcagtga  21720
aaacgttcct gctctcacag atcacgggac gctaccgctg cgcaacagca tcggaggagt  21780
ccagcgagtg accattactg acgccagacg ccgcacctgc ccctacgttt acaaggccct  21840
gggcatagtc tcgccgcgcg tcctatcgag ccgcactttt tgagcaagca tgtccatcct  21900
tatatcgccc agcaataaca caggctgggg cctgcgcttc ccaagcaaga tgtttggcgg  21960
ggccaagaag cgctccgacc aacacccagt gcgcgtgcgc gggcactacc gcgcgccctg  22020
gggcgcgcac aaacgcggcc gcactgggcg caccaccgtc gatgacgcca tcgacgcggt  22080
ggtggaggag gcgcgcaact acacgcccac gccgccacca gtgtccacag tggacgcggc  22140
cattcagacc gtggtgcgcg gagcccggcg ctatgctaaa atgaagagac ggcggaggcg  22200
cgtagcacgt cgccaccgcc gccgacccgg cactgccgcc caacgcgcgg cggcggccct  22260
gcttaaccgc gcacgtcgca ccggccgacg ggcggccatg cgggccgctc gaaggctggc  22320
cgcgggtatt gtcactgtgc cccccaggtc caggcgacga gcggccgccg cagcagccgc  22380
ggccattagt gctatgactc agggtcgcag gggcaacgtg tattgggtgc gcgactcggt  22440
tagcggcctg cgcgtgcccg tgcgcacccg ccccccgcgc aactagattg caagaaaaaa  22500
ctacttagac tcgtactgtt gtatgtatcc agcggcggcg gcgcgcaacg aagctatgtc  22560
caagcgcaaa atcaaagaag agatgctcca ggtcatcgcg ccggagatct atggcccccc  22620
gaagaaggaa gagcaggatt acaagccccg aaagctaaag cgggtcaaaa agaaaaagaa  22680
agatgatgat gatgaacttg acgacgaggt ggaactgctg cacgctaccg cgcccaggcg  22740
acgggtacag tggaaaggtc gacgcgtaaa acgtgttttg cgacccggca ccaccgtagt  22800
ctttacgccc ggtgagcgct ccacccgcac ctacaagcgc gtgtatgatg aggtgtacgg  22860
cgacgaggac ctgcttgagc aggccaacga gcgcctcggg gagtttgcct acggaaagcg  22920
gcataaggac atgctggcgt tgccgctgga cgagggcaac ccaacaccta gcctaaagcc  22980
cgtaacactg cagcaggtgc tgcccgcgct tgcaccgtcc gaagaaaagc gcggcctaaa  23040
gcgcgagtct ggtgacttgg cacccaccgt gcagctgatg gtacccaagc gccagcgact  23100
ggaagatgtc ttggaaaaaa tgaccgtgga acctgggctg gagcccgagg tccgcgtgcg  23160
gccaatcaag caggtggcgc cgggactggg cgtgcagacc gtggacgttc agatacccac  23220
taccagtagc accagtattg ccaccgccac agagggcatg gagacacaaa cgtccccggt  23280
tgcctcagcg gtggcggatg ccgcggtgca ggcggtcgct gcggccgcgt ccaagacctc  23340
tacggaggtg caaacggacc cgtggatgtt tcgcgtttca gccccccggc gcccgcgcgg  23400
ttcgaggaag tacggcgccg ccagcgcgct actgcccgaa tatgccctac atccttccat  23460
tgcgcctacc cccggctatc gtggctacac ctaccgcccc agaagacgag caactacccg  23520
acgccgaacc accactggaa cccgccgccg ccgtcgccgt cgccagcccg tgctggcccc  23580
gatttccgtg cgcagggtgg ctcgcgaagg aggcaggacc ctggtgctgc caacagcgcg  23640
ctaccacccc agcatcgttt aaaagccggt ctttgtggtt cttgcagata tggccctcac  23700
```

```
ctgccgcctc cgtttcccgg tgccgggatt ccgaggaaga atgcaccgta ggaggggcat  23760
ggccggccac ggcctgacgg gcggcatgcg tcgtgcgcac caccggcggc ggcgcgcgtc  23820
gcaccgtcgc atgcgcggcg gtatcctgcc cctccttatt ccactgatcg ccgcggcgat  23880
tggcgccgtg cccggaattg catccgtggc cttgcaggcg cagagacact gattaaaaac  23940
aagttgcatg tggaaaaatc aaaataaaaa gtctggactc tcacgctcgc ttggtcctgt  24000
aactattttg tagaatggaa gacatcaact ttgcgtctct ggccccgcga cacggctcgc  24060
gcccgttcat gggaaactgg caagatatcg gcaccagcaa tatgagcggt ggcgccttca  24120
gctggggctc gctgtggagc ggcattaaaa atttcggttc caccgttaag aactatggca  24180
gcaaggcctg gaacagcagc acaggccaga tgctgaggga taagttgaaa gagcaaaatt  24240
tccaacaaaa ggtggtagat ggcctggcct ctggcattag cggggtggtg gacctggcca  24300
accaggcagt gcaaaataag attaacagta agcttgatcc ccgccctccc gtagaggagc  24360
ctccaccggc cgtggagaca gtgtctccag aggggcgtgg cgaaaagcgt ccgcgccccg  24420
acagggaaga aactctggtg acgcaaatag acgagcctcc ctcgtacgag gaggcactaa  24480
agcaaggcct gcccaccacc cgtcccatcg cgcccatggc taccggagtg ctgggccagc  24540
acacacccgt aacgctggac ctgcctcccc ccgccgacac ccagcagaaa cctgtgctgc  24600
caggcccgac cgccgttgtt gtaacccgtc ctagccgcgc gtccctgcgc cgcgccgcca  24660
gcggtccgcg atcgttgcgg cccgtagcca gtggcaactg gcaaagcaca ctgaacagca  24720
tcgtgggtct gggggtgcaa tccctgaagc gccgacgatg cttctgaata gctaacgtgt  24780
cgtatgtgtg tcatgtatgc gtccatgtcg ccgccagagg agctgctgag ccgccgcgcg  24840
cccgctttcc aagatggcta ccccttcgat gatgccgcag tggtcttaca tgcacatctc  24900
gggccaggac gcctcggagt acctgagccc cgggctggtg cagtttgccc gcgccaccga  24960
gacgtacttc agcctgaata acaagtttag aaaccccacg gtggcgccta cgcacgacgt  25020
gaccacagac cggtcccagc gtttgacgct gcggttcatc cctgtggacc gtgaggatac  25080
tgcgtactcg tacaaggcgc ggttcaccct agctgtgggt gataaccgtg tgctggacat  25140
ggcttccacg tactttgaca tccgcggcgt gctggacagg ggccctactt ttaagcccta  25200
ctctggcact gcctacaacg ccctggctcc caagggtgcc ccaaatcctt gcgaatggga  25260
tgaagctgct actgctcttg aaataaacct agaagaagag gacgatgaca acgaagacga  25320
agtagacgag caagctgagc agcaaaaaac tcacgtattt gggcaggcgc cttattctgg  25380
tataaatatt acaaaggagg gtattcaaat aggtgtcgaa ggtcaaacac ctaaatatgc  25440
cgataaaaca tttcaacctg aacctcaaat aggagaatct cagtggtacg aaactgaaat  25500
taatcatgca gctgggagag tccttaaaaa gactacccca atgaaaccat gttacggttc  25560
atatgcaaaa cccacaaatg aaaatggagg gcaaggcatt cttgtaaagc aacaaaatgg  25620
aaagctagaa agtcaagtgg aaatgcaatt tttctcaact actgaggcga ccgcaggcaa  25680
tggtgataac ttgactccta aagtggtatt gtacagtgaa gatgtagata tagaaacccc  25740
agacactcat atttcttaca tgcccactat taaggaaggt aactcacgag aactaatggg  25800
ccaacaatct atgcccaaca ggcctaatta cattgctttt agggacaatt ttattggtct  25860
aatgtattac aacagcacgg gtaatatggg tgttctggcg ggccaagcat cgcagttgaa  25920
tgctgttgta gatttgcaag acagaaacac agagctttca taccagcttt tgcttgattc  25980
cattggtgat agaaccaggt acttttctat gtggaatcag gctgttgaca gctatgatcc  26040
agatgttaga attattgaaa atcatggaac tgaagatgaa cttccaaatt actgctttcc  26100
```

```
actgggaggt gtgattaata cagagactct taccaaggta aaacctaaaa caggtcagga  26160
aaatggatgg gaaaaagatg ctacagaatt ttcagataaa aatgaaataa gagttggaaa  26220
taattttgcc atggaaatca atctaaatgc caacctgtgg agaaatttcc tgtactccaa  26280
catagcgctg tatttgcccg acaagctaaa gtacagtcct tccaacgtaa aaatttctga  26340
taacccaaac acctacgact acatgaacaa gcgagtggtg gctcccgggt tagtggactg  26400
ctacattaac cttggagcac gctggtccct tgactatatg gacaacgtca acccatttaa  26460
ccaccaccgc aatgctggcc tgcgctaccg ctcaatgttg ctgggcaatg gtcgctatgt  26520
gcccttccac atccaggtgc ctcagaagtt ctttgccatt aaaaacctcc ttctcctgcc  26580
gggctcatac acctacgagt ggaacttcag gaaggatgtt aacatggttc tgcagagctc  26640
cctaggaaat gacctaaggg ttgacggagc cagcattaag tttgatagca tttgccttta  26700
cgccaccttc ttccccatgg cccacaacac cgcctccacg cttgaggcca tgcttagaaa  26760
cgacaccaac gaccagtcct ttaacgacta tctctccgcc gccaacatgc tctaccctat  26820
acccgccaac gctaccaacg tgcccatatc catcccctcc cgcaactggg cggctttccg  26880
cggctgggcc ttcacgcgcc ttaagactaa ggaaacccca tcactgggct cgggctacga  26940
cccttattac acctactctg gctctatacc ctacctagat ggaacctttt acctcaacca  27000
cacctttaag aaggtggcca ttacctttga ctcttctgtc agctggcctg gcaatgaccg  27060
cctgcttacc cccaacgagt ttgaaattaa gcgctcagtt gacggggagg gttacaacgt  27120
tgcccagtgt aacatgacca aagactggtt cctggtacaa atgctagcta actacaacat  27180
tggctaccag ggcttctata tcccagagag ctacaaggac cgcatgtact ccttctttag  27240
aaacttccag cccatgagcc gtcaggtggt ggatgatact aaatacaagg actaccaaca  27300
ggtgggcatc ctacaccaac acaacaactc tggatttgtt ggctaccttg cccccaccat  27360
gcgcgaagga caggcctacc ctgctaactt cccctatccg cttataggca agaccgcagt  27420
tgacagcatt acccagaaaa agtttctttg cgatcgcacc ctttggcgca tcccattctc  27480
cagtaacttt atgtccatgg gcgcactcac agacctgggc caaaaccttc tctacgccaa  27540
ctccgcccac gcgctagaca tgacttttga ggtggatccc atggacgagc ccacccttct  27600
ttatgttttg tttgaagtct ttgacgtggt ccgtgtgcac cggccgcacc gcggcgtcat  27660
cgaaaccgtg tacctgcgca cgcccttctc ggccggcaac gccacaacat aaagaagcaa  27720
gcaacatcaa caacagctgc cgccatgggc tccagtgagc aggaactgaa agccattgtc  27780
aaagatcttg gttgtgggcc atatttttg ggcacctatg acaagcgctt tccaggcttt  27840
gtttctccac acaagctcgc ctgcgccata gtcaatacgg ccggtcgcga gactgggggc  27900
gtacactgga tggcctttgc ctggaacccg cactcaaaaa catgctacct ctttgagccc  27960
tttggctttt ctgaccagcg actcaagcag gtttaccagt ttgagtacga gtcactcctg  28020
cgccgtagcg ccattgcttc ttcccccgac cgctgtataa cgctggaaaa gtccacccaa  28080
agcgtacagg ggcccaactc ggccgcctgt ggactattct gctgcatgtt tctccacgcc  28140
tttgccaact ggccccaaac tcccatggat cacaacccca ccatgaacct tattaccggg  28200
gtacccaact ccatgctcaa cagtccccag gtacagccca ccctgcgtcg caaccaggaa  28260
cagctctaca gcttcctgga gcgccactcg ccctacttcc gcagccacag tgcgcagatt  28320
aggagcgcca cttctttttg tcacttgaaa aacatgtaaa aataatgtac tagagacact  28380
ttcaataaag gcaaatgctt ttatttgtac actctcgggt gattatttac ccccaccctt  28440
gccgtctgcg ccgtttaaaa atcaaagggg ttctgccgcg catcgctatg cgccactggc  28500
```

```
agggacacgt tgcgatactg gtgtttagtg ctccacttaa actcaggcac aaccatccgc  28560
ggcagctcgg tgaagttttc actccacagg ctgcgcacca tcaccaacgc gtttagcagg  28620
tcgggcgccg atatcttgaa gtcgcagttg ggcctccgc cctgcgcgcg cgagttgcga  28680
tacacagggt tgcagcactg gaacactatc agcgccgggt ggtgcacgct ggccagcacg  28740
ctcttgtcgg agatcagatc cgcgtccagg tcctccgcgt tgctcagggc gaacggagtc  28800
aactttggta gctgccttcc caaaaagggc gcgtgcccag gctttgagtt gcactcgcac  28860
cgtagtggca tcaaaaggtg accgtgcccg gtctgggcgt taggatacag cgcctgcata  28920
aaagccttga tctgcttaaa agccacctga gcctttgcgc cttcagagaa gaacatgccg  28980
caagacttgc cggaaaactg attggccgga caggccgcgt cgtgcacgca gcaccttgcg  29040
tcggtgttgg agatctgcac cacatttcgg ccccaccggt tcttcacgat cttggccttg  29100
ctagactgct ccttcagcgc gcgctgcccg ttttcgctcg tcacatccat ttcaatcacg  29160
tgctccttat ttatcataat gcttccgtgt agacacttaa gctcgccttc gatctcagcg  29220
cagcggtgca gccacaacgc gcagcccgtg ggctcgtgat gcttgtaggt cacctctgca  29280
aacgactgca ggtacgcctg caggaatcgc cccatcatcg tcacaaaggt cttgttgctg  29340
gtgaaggtca gctgcaaccc gcggtgctcc tcgttcagcc aggtcttgca tacggccgcc  29400
agagcttcca cttggtcagg cagtagtttg aagttcgcct ttagatcgtt atccacgtgg  29460
tacttgtcca tcagcgcgcg cgcagcctcc atgcccttct cccacgcaga cacgatcggc  29520
acactcagcg ggttcatcac cgtaatttca ctttccgctt cgctgggctc ttcctcttcc  29580
tcttgcgtcc gcataccacg cgccactggg tcgtcttcat tcagccgccg cactgtgcgc  29640
ttacctcctt tgccatgctt gattagcacc ggtgggttgc tgaaacccac catttgtagc  29700
gccacatctt ctctttcttc ctcgctgtcc acgattacct ctggtgatgg cgggcgctcg  29760
ggcttgggag aagggcgctt ctttttcttc ttgggcgcaa tggccaaatc cgccgccgag  29820
gtcgatggcc gcgggctggg tgtgcgcggc accagcgcgt cttgtgatga gtcttcctcg  29880
tcctcggact cgatacgccg cctcatccgc ttttttgggg gcgcccgggg aggcggcggc  29940
gacggggacg gggacgacac gtcctccatg gttgggggac gtcgcgccgc accgcgtccg  30000
cgctcggggg tggtttcgcg ctgctcctct tcccgactgg ccatttcctt ctcctatagg  30060
cagaaaaaga tcatggagtc agtcgagaag aaggacagcc taaccgcccc ctctgagttc  30120
gccaccaccg cctccaccga tgccgccaac gcgcctacca ccttccccgt cgaggcaccc  30180
ccgcttgagg aggaggaagt gattatcgag caggacccag gttttgtaag cgaagacgac  30240
gaggaccgct cagtaccaac agaggataaa aagcaagacc aggacaacgc agaggcaaac  30300
gaggaacaag tcgggcgggg ggacgaaagg catggcgact acctagatgt gggagacgac  30360
gtgctgttga agcatctgca gcgccagtgc gccattatct gcgacgcgtt gcaagagcgc  30420
agcgatgtgc ccctcgccat agcggatgtc agccttgcct acgaacgcca cctattctca  30480
ccgcgcgtac cccccaaacg ccaagaaaac ggcacatgcg agcccaaccc gcgcctcaac  30540
ttctaccccg tatttgccgt gccagaggtg cttgccacct atcacatctt tttccaaaac  30600
tgcaagatac ccctatcctg ccgtgccaac cgcagccgag cggacaagca gctggccttg  30660
cggcagggcg ctgtcatacc tgatatcgcc tcgctcaacg aagtgccaaa aatctttgag  30720
ggtcttggac gcgacgagaa gcgcgcggca aacgctctgc aacaggaaaa cagcgaaaat  30780
gaaagtcact ctggagtgtt ggtggaactc gagggtgaca acgcgcgcct agccgtacta  30840
aaacgcagca tcgaggtcac ccactttgcc tacccggcac ttaacctacc ccccaaggtc  30900
```

```
atgagcacag tcatgagtga gctgatcgtg cgccgtgcgc agcccctgga gagggatgca  30960
aatttgcaag aacaaacaga ggagggccta cccgcagttg gcgacgagca gctagcgcgc  31020
tggcttcaaa cgcgcgagcc tgccgacttg gaggagcgac gcaaactaat gatggccgca  31080
gtgctcgtta ccgtggagct tgagtgcatg cagcggttct ttgctgaccc ggagatgcag  31140
cgcaagctag aggaaacatt gcactacacc tttcgacagg gctacgtacg ccaggcctgc  31200
aagatctcca acgtggagct ctgcaacctg gtctcctacc ttggaatttt gcacgaaaac  31260
cgccttgggc aaaacgtgct tcattccacg ctcaagggcg aggcgcgccg cgactacgtc  31320
cgcgactgcg tttacttatt tctatgctac acctggcaga cggccatggg cgtttggcag  31380
cagtgcttgg aggagtgcaa cctcaaggag ctgcagaaac tgctaaagca aaacttgaag  31440
gacctatgga cggccttcaa cgagcgctcc gtggccgcgc acctggcgga catcattttc  31500
cccgaacgcc tgcttaaaac cctgcaacag ggtctgccag acttcaccag tcaaagcatg  31560
ttgcagaact ttaggaactt tatcctagag cgctcaggaa tcttgcccgc cacctgctgt  31620
gcacttccta gcgactttgt gcccattaag taccgcgaat gccctccgcc gctttggggc  31680
cactgctacc ttctgcagct agccaactac cttgcctacc actctgacat aatggaagac  31740
gtgagcggtg acggtctact ggagtgtcac tgtcgctgca acctatgcac cccgcaccgc  31800
tccctggttt gcaattcgca gctgcttaac gaaagtcaaa ttatcggtac ctttgagctg  31860
cagggtccct cgcctgacga aaagtccgcg gctccggggt tgaaactcac tccggggctg  31920
tggacgtcgg cttaccttcg caaatttgta cctgaggact accacgccca cgagattagg  31980
ttctacgaag accaatcccg cccgccaaat gcggagctta ccgcctgcgt cattacccag  32040
ggccacattc ttggccaatt gcaagccatc aacaaagccc gccaagagtt tctgctacga  32100
aagggacggg gggtttactt ggacccccag tccggcgagg agctcaaccc aatccccccg  32160
ccgccgcagc cctatcagca gcagccgcgg gcccttgctt cccaggatgg cacccaaaaa  32220
gaagctgcag ctgccgccgc cacccacgga cgaggaggaa tactgggaca gtcaggcaga  32280
ggaggttttg gacgaggagg aggaggacat gatggaagac tgggagagcc tagacgagga  32340
agcttccgag gtcgaagagg tgtcagacga aacaccgtca ccctcggtcg cattcccctc  32400
gccggcgccc cagaaatcgg caaccggttc cagcatggct acaacctccg ctcctcaggc  32460
gccgccggca ctgcccgttc gccgacccaa ccgtagatgg gacaccactg gaaccagggc  32520
cggtaagtcc aagcagccgc cgccgttagc ccaagagcaa caacagcgcc aaggctaccg  32580
ctcatggcgc gggcacaaga acgccatagt tgcttgcttg caagactgtg ggggcaacat  32640
ctccttcgcc cgccgctttc ttctctacca tcacggcgtg gccttccccc gtaacatcct  32700
gcattactac cgtcatctct acagcccata ctgcaccggc ggcagcggca gcggcagcaa  32760
cagcagcggc cacacagaag caaaggcgac cggatagcaa gactctgaca aagcccaaga  32820
aatccacagc ggcggcagca gcaggaggag gagcgctgcg tctggcgccc aacgaacccg  32880
tatcgacccg cgagcttaga aacaggattt ttcccactct gtatgctata tttcaacaga  32940
gcaggggcca agaacaagag ctgaaaataa aaaacaggtc tctgcgatcc ctcacccgca  33000
gctgcctgta tcacaaaagc gaagatcagc ttcggcgcac gctggaagac gcggaggctc  33060
tcttcagtaa atactgcgcg ctgactctta aggactagtt tcgcgccctt tctcaaattt  33120
aagcgcgaaa actacgtcat ctccagcggc cacacccggc gccagcacct gtcgtcagcg  33180
ccattatgag caaggaaatt cccacgccct acatgtggag ttaccagcca caaatgggac  33240
ttgcggctgg agctgcccaa gactactcaa cccgaataaa ctacatgagc gcgggacccc  33300
```

```
acatgatatc ccgggtcaac ggaatccgcg cccaccgaaa ccgaattctc ttggaacagg  33360
cggctattac caccacacct cgtaataacc ttaatccccg tagttggccc gctgccctgg  33420
tgtaccagga aagtcccgct cccaccactg tggtacttcc cagagacgcc caggccgaag  33480
ttcagatgac taactcaggg gcgcagcttg cgggcggctt tcgtcacagg gtgcggtcgc  33540
ccgggcaggg tataactcac ctgacaatca gagggcgagg tattcagctc aacgacgagt  33600
cggtgagctc ctcgcttggt ctccgtccgg acgggacatt tcagatcggc ggcgccggcc  33660
gtccttcatt cacgcctcgt caggcaatcc taactctgca gacctcgtcc tctgagccgc  33720
gctctggagg cattggaact ctgcaattta ttgaggagtt tgtgccatcg gtctacttta  33780
accccttctc gggacctccc ggccactatc cggatcaatt tattcctaac tttgacgcgg  33840
taaaggactc ggcggacggc tacgactgaa tgttaagtgg agaggcagag caactgcgcc  33900
tgaaacacct ggtccactgt cgccgccaca agtgctttgc ccgcgactcc ggtgagtttt  33960
gctactttga attgcccgag gatcatatcg agggcccggc gcacggcgtc cggcttaccg  34020
cccagggaga gcttgcccgt agcctgattc gggagtttac ccagcgcccc ctgctagttg  34080
agcgggacag gggaccctgt gttctcactg tgatttgcaa ctgtcctaac cttggattac  34140
atcaagatcc tctagttata actagagtac ccggggatct tattcccttt aactaataaa  34200
aaaaaataat aaagcatcac ttacttaaaa tcagttagca aatttctgtc cagtttattc  34260
agcagcacct ccttgccctc ctcccagctc tggtattgca gcttcctcct ggctgcaaac  34320
tttctccaca atctaaatgg aatgtcagtt tcctcctgtt cctgtccatc cgcacccact  34380
atcttcatgt tgttgcagat gaagcgcgca agaccgtctg aagatacctt caaccccgtg  34440
tatccatatg acacggaaac cggtcctcca actgtgcctt ttcttactcc tccctttgta  34500
tcccccaatg ggtttcaaga gagtccccct ggggtactct ctttgcgcct atccgaacct  34560
ctagttacct ccaatggcat gcttgcgctc aaaatgggca acggcctctc tctggacgag  34620
gccggcaacc ttacctccca aaatgtaacc actgtgagcc cacctctcaa aaaaaccaag  34680
tcaaacataa acctggaaat atctgcaccc ctcacagtta cctcagaagc cctaactgtg  34740
gctgccgccg cacctctaat ggtcgcgggc aacacactca ccatgcaatc acaggccccg  34800
ctaaccgtgc acgactccaa acttagcatt gccacccaag gacccctcac agtgtcagaa  34860
ggaaagctag ccctgcaaac atcaggcccc ctcaccacca ccgatagcag tacccttact  34920
atcactgcct caccccctct aactactgcc actggtagct tgggcattga cttgaaagag  34980
cccatttata cacaaaatgg aaaactagga ctaaagtacg gggctccttt gcatgtaaca  35040
gacgacctaa acactttgac cgtagcaact ggtccaggtg tgactattaa taatacttcc  35100
ttgcaaacta aagttactgg agccttgggt tttgattcac aaggcaatat gcaacttaat  35160
gtagcaggag gactaaggat tgattctcaa aacagacgcc ttatacttga tgttagttat  35220
ccgtttgatg ctcaaaacca actaaatcta agactaggac agggccctct ttttataaac  35280
tcagcccaca acttggatat taactacaac aaaggccttt acttgtttac agcttcaaac  35340
aattccaaaa agcttgaggt taacctaagc actgccaagg ggttgatgtt tgacgctaca  35400
gccatagcca ttaatgcagg agatgggctt gaatttggtt cacctaatgc accaaacaca  35460
aatcccctca aaacaaaaat tggccatggc ctagaatttg attcaaacaa ggctatggtt  35520
cctaaactag gaactggcct tagttttgac agcacaggtg ccattacagt aggaaacaaa  35580
aataatgata agctaacttt gtggaccaca ccagctccat ctcctaactg tagactaaat  35640
gcagagaaag atgctaaact cactttggtc ttaacaaaat gtggcagtca aatacttgct  35700
```

```
acagtttcag ttttggctgt taaaggcagt ttggctccaa tatctggaac agttcaaagt  35760
gctcatctta ttataagatt tgacgaaaat ggagtgctac taaacaattc cttcctggac  35820
ccagaatatt ggaactttag aaatggagat cttactgaag gcacagccta tacaaacgct  35880
gttggattta tgcctaacct atcagcttat ccaaaatctc acggtaaaac tgccaaaagt  35940
aacattgtca gtcaagttta cttaaacgga gacaaaacta aacctgtaac actaaccatt  36000
acactaaacg gtacacagga aacaggagac acaactccaa gtgcatactc tatgtcattt  36060
tcatgggact ggtctggcca caactacatt aatgaaatat ttgccacatc ctcttacact  36120
ttttcataca ttgcccaaga ataaagaatc gtttgtgtta tgtttcaacg tgtttatttt  36180
tcaattgcag aaaatttcaa gtcatttttc attcagtagt atagccccac caccacatag  36240
cttatacaga tcaccgtacc ttaatcaaac tcacagaacc ctagtattca acctgccacc  36300
tccctcccaa cacacagagt acacagtcct ttctccccgg ctggccttaa aaagcatcat  36360
atcatgggta acagacatat tcttaggtgt tatattccac acggtttcct gtcgagccaa  36420
acgctcatca gtgatattaa taaactcccc gggcagctca cttaagttca tgtcgctgtc  36480
cagctgctga gccacaggct gctgtccaac ttgcggttgc ttaacgggcg gcgaaggaga  36540
agtccacgcc tacatggggg tagagtcata atcgtgcatc aggatagggc ggtggtgctg  36600
cagcagcgcg cgaataaact gctgccgccg ccgctccgtc ctgcaggaat acaacatggc  36660
agtggtctcc tcagcgatga ttcgcaccgc ccgcagcata aggcgccttg tcctccgggc  36720
acagcagcgc accctgatct cacttaaatc agcacagtaa ctgcagcaca gcaccacaat  36780
attgttcaaa atcccacagt gcaaggcgct gtatccaaag ctcatggcgg ggaccacaga  36840
acccacgtgg ccatcatacc acaagcgcag gtagattaag tggcgacccc tcataaacac  36900
gctggacata aacattacct cttttggcat gttgtaattc accacctccc ggtaccatat  36960
aaacctctga ttaaacatgg cgccatccac caccatccta aaccagctgg ccaaaacctg  37020
cccgccggct atacactgca gggaaccggg actggaacaa tgacagtgga gagcccagga  37080
ctcgtaacca tggatcatca tgctcgtcat gatatcaatg ttggcacaac acaggcacac  37140
gtgcatacac ttcctcagga ttacaagctc ctcccgcgtt agaaccatat cccagggaac  37200
aacccattcc tgaatcagcg taaatcccac actgcaggga agacctcgca cgtaactcac  37260
gttgtgcatt gtcaaagtgt tacattcggg cagcagcgga tgatcctcca gtatggtagc  37320
gcgggtttct gtctcaaaag gaggtagacg atccctactg tacggagtgc gccgagacaa  37380
ccgagatcgt gttggtcgta gtgtcatgcc aaatggaacg ccggacgtag tcatatttcc  37440
tgaagcaaaa ccaggtgcgg gcgtgacaaa cagatctgcg tctccggtct cgccgcttag  37500
atcgctctgt gtagtagttg tagtatatcc actctctcaa agcatccagg cgccccctgg  37560
cttcgggttc tatgtaaact ccttcatgcg ccgctgccct gataacatcc accaccgcag  37620
aataagccac acccagccaa cctacacatt cgttctgcga gtcacacacg ggaggagcgg  37680
gaagagctgg aagaaccatg ttttttttt tattccaaaa gattatccaa aacctcaaaa  37740
tgaagatcta ttaagtgaac gcgctcccct ccggtggcgt ggtcaaactc tacagccaaa  37800
gaacagataa tggcatttgt aagatgttgc acaatggctt ccaaaaggca aacggccctc  37860
acgtccaagt ggacgtaaag gctaaaccct tcagggtgaa tctcctctat aaacattcca  37920
gcaccttcaa ccatgcccaa ataattctca tctcgccacc ttctcaatat atctctaagc  37980
aaatcccgaa tattaagtcc ggccattgta aaaatctgct ccagagcgcc ctccaccttc  38040
agcctcaagc agcgaatcat gattgcaaaa attcaggttc ctcacagacc tgtataagat  38100
```

-continued

```
tcaaaagcgg aacattaaca aaaataccgc gatcccgtag gtcccttcgc agggccagct  38160

gaacataatc gtgcaggtct gcacggacca gcgcggccac ttccccgcca ggaaccttga  38220

caaaagaacc cacactgatt atgacacgca tactcggagc tatgctaacc agcgtagccc  38280

cgatgtaagc tttgttgcat gggcggcgat ataaaatgca aggtgctgct caaaaaatca  38340

ggcaaagcct cgcgcaaaaa agaaagcaca tcgtagtcat gctcatgcag ataaaggcag  38400

gtaagctccg gaaccaccac agaaaaagac accatttttc tctcaaacat gtctgcgggt  38460

ttctgcataa acacaaaata aaataacaaa aaaacattta aacattagaa gcctgtctta  38520

caacaggaaa aacaaccctt ataagcataa gacggactac ggccatgccg gcgtgaccgt  38580

aaaaaaactg gtcaccgtga ttaaaaagca ccaccgacag ctcctcggtc atgtccggag  38640

tcataatgta agactcggta aacacatcag gttgattcat cggtcagtgc taaaaagcga  38700

ccgaaatagc ccgggggaat acatacccgc aggcgtagag acaacattac agcccccata  38760

ggaggtataa caaaattaat aggagagaaa aacacataaa cacctgaaaa accctcctgc  38820

ctaggcaaaa tagcaccctc ccgctccaga acaacataca gcgcttcaca gcggcagcct  38880

aacagtcagc cttaccagta aaaaagaaaa cctattaaaa aaacaccact cgacacggca  38940

ccagctcaat cagtcacagt gtaaaaaagg gccaagtgca gagcgagtat atataggact  39000

aaaaaatgac gtaacggtta aagtccacaa aaaacaccca gaaaaccgca cgcgaaccta  39060

cgcccagaaa cgaaagccaa aaaacccaca acttcctcaa atcgtcactt ccgttttccc  39120

acgttacgta acttcccatt ttaagaaaac tacaattccc aacacataca agttactccg  39180

ccctaaaacc tacgtcaccc gccccgttcc cacgccccgc gccacgtcac aaactccacc  39240

ccctcattat catattggct tcaatccaaa ataaggtata ttattgatga tnnnnnttaa  39300

t                                                                  39301
```

CHIMERIC ADENOVIRAL VECTORS

CROSS-REFERENCES TO RELATED APPLICATIONS

The present application is a divisional of U.S. patent application Ser. No. 11/712,794, filed Feb. 28, 2007, now U.S. Pat. No. 7,879,602, which claims priority to U.S. Provisional Patent Application No. 60/778,026, filed Feb. 28, 2006, U.S. Provisional Patent Application No. 60/801,645, filed May 19, 2006, U.S. Provisional Patent Application No. 60/802,992, filed May 22, 2006, U.S. Provisional Patent Application No. 60/821,492, filed Aug. 4, 2006, U.S. Provisional Patent Application No. 60/846,658, filed Sep. 22, 2006, and U.S. Provisional Patent Application No. 60/848,195, filed Sep. 28, 2006), the disclosures of which are hereby incorporated by reference in their entirety for all purposes.

BACKGROUND OF THE INVENTION

Vaccines are an important means for preventing and/or treating a number of diseases and disorders (e.g., viral infection, bacterial infection, and cancer). Nucleic acid-based vaccines have several advantages over protein or attenuated-live vaccines. Introduction of a nucleic acid that expresses an antigen into a target cell allows for rapid development of vaccine that generates and immune response against an antigen of interest. For protein vaccines, an effective and efficient method of protein purification needs to be developed each time a new vaccine is created. For live vaccines, a method of attenuation needs to be identified that doesn't completely stop the growth of the pathogen, yet proven to be completely safe in humans. Development of protein purification and attenuation methodologies are extremely time-consuming processes. In contrast, most nucleic acid-based vaccines can be manufactured very quickly using the same manufacturing techniques each time with just a quick change in the nucleic acid encoding the antigen of interest. Replication incompetent adenovirus is one nucleic acid-based vaccine system which is rapidly, predictably, and inexpensively made at high titer [Polo, J. M. and Dubensky, T. W., Jr., *Drug Discov Today,* 7(13), 719-727 (2002)]. However, the efficiency of the antigen-specific response following administration of adenoviral vectors known in the art is low. Thus, there is a need in the art for new adenoviral vectors that can be used to efficiently elicit an immune response against an antigen of interest. The present invention satisfies these and other needs.

SUMMARY OF THE INVENTION

The present invention provides chimeric adenoviral vectors comprising nucleic acids encoding a heterologous polypeptide and methods for eliciting an immune response against the heterologous polypeptide.

One embodiment of the invention provides chimeric adenoviral expression vectors comprising an expression cassette comprising: (a) first promoter operably linked to a nucleic acid encoding a toll-like receptor (TLR)-3 agonist; and (b) a second promoter operably linked to a nucleic acid encoding a heterologous polypeptide. In some embodiments, the TLR-3 agonist is dsRNA. In some embodiments, the nucleic acid encoding the TLR agonist comprises a sequence selected from SEQ ID NOS: 3, 7, 8, 9, 10, 11, and 12. In some embodiments, the heterologous polypeptide is selected from an HIV envelope polypeptide (e.g., gp41, gp120 or gp160) and influenza HA polypeptide. In some embodiments, the first and second promoters are the same. In some embodiments, the first and second embodiments are different. In some embodiments, the promoters are selected from the beta actin promoter and the CMV promoter. The invention also provides immunogenic compositions comprising the expression vector.

A further embodiment of the invention provides methods of eliciting an immune response against the heterologous polypeptide by administering an immunogenically effective amount of the compositions to a mammalian subject (e.g., a rodent such as a mouse, a rat, or a guinea pig or a primate such as a chimpanzee, a rhesus macaque, or a human). In some embodiments, the vector is administered via any non-parenteral route (e.g., orally, intranasally, or mucosally). In some embodiments, the heterologous polypeptide is expressed in a cell selected from a dendritic cell, a microfold cell, and an intestinal epithelial cell.

A further embodiment of the invention provides immunogenic compositions comprising: (a) a chimeric adenoviral expression vector comprising a promoter operably linked to a nucleic acid encoding a heterologous polypeptide; and (b) a TLR-3 agonist (e.g., a dsRNA). In some embodiments, the TLR-3 agonist is encoded by a nucleic acid. The invention also provides methods of eliciting an immune response by administering the compositions to a mammalian subject (e.g., a rodent such as a mouse, a rat, or a guinea pig or a primate such as a chimpanzee, a rhesus macaque, or a human) via any non-parenteral route (e.g., oral, intranasal, or mucosal).

Another embodiment of the invention provides an isolated nucleic acid comprising the sequence set forth in SEQ ID NOS:1, 2, 6, 7, 13, 14, 15, 16, or 17.

BRIEF DESCRIPTION OF THE DRAWINGS

FIG. 1 illustrates data demonstrating that a chimeric adnenoviral vector of the invention (i.e., DS1) in combination with a TLR-3 agonist is more effective than a standard adenoviral vector (i.e., rAd5) at inducing an antigen specific immune response following oral vector delivery.

FIG. 2 illustrates data demonstrating that a chimeric adenoviral vector of the invention (i.e., DS1b or DS1c) in combination with a TLR-3 agonist is more effective at inducing an antigen specific immune response than a standard adenoviral vector (i.e., rAd5).

FIG. 3 illustrates data demonstrating that the chimeric adenoviral vectors of the invention are superior for eliciting immune responses when administered non-parenterally.

FIG. 4 illustrates data demonstrating that the expressed TLR-3 ligand agonists can induce activation of antigen presenting cells.

FIG. 6 illustrates data depicting anti-gp120 antibody titer 3 weeks following oral administration of a chimeric adenoviral comprising a nucleic acid sequence encoding the dsRNA TLR-3 agonist luc1.

FIG. 8 illustrates data demonstrating that chimeric adenoviral vectors of the invention are effective at inducing an antigen-specific immune response following oral delivery.

BRIEF DESCRIPTION OF THE SEQUENCES

Figure 1A:
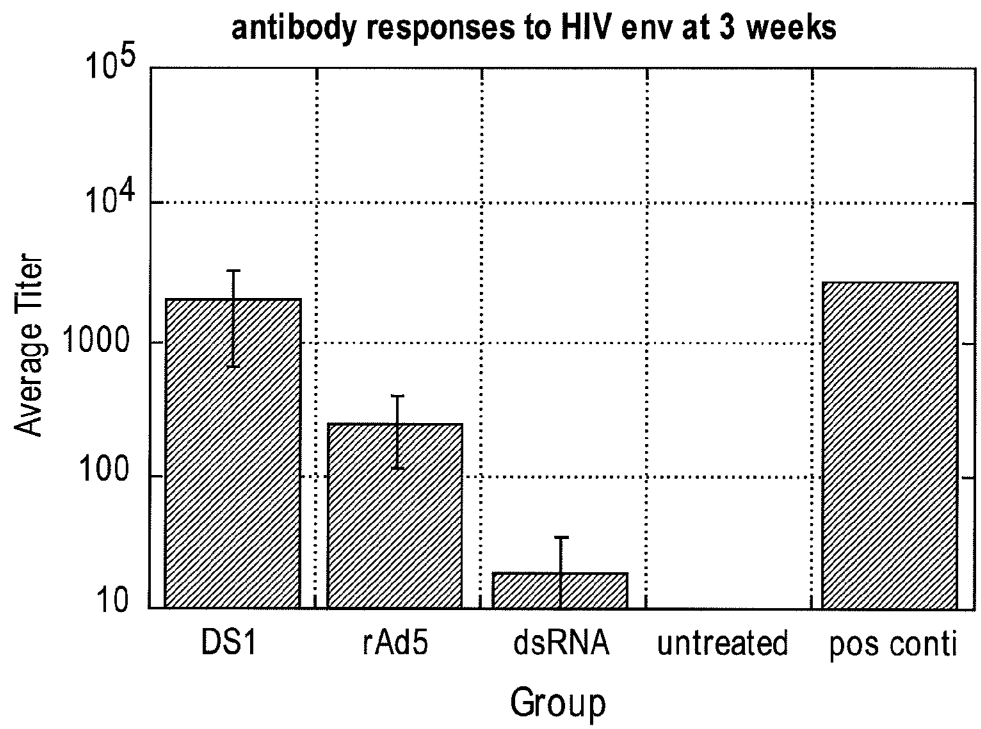
FIG. 1A illustrates data depicting the antibody titer to HIV envelope protein (i.e., gp120) at 3 weeks following oral delivery of the adenoviral vectors.

SEQ ID NO:1 sets forth the nucleotide sequence for the chimeric adenoviral vector DS1.

SEQ ID NO:2 sets forth the nucleotide sequence for the chimeric adenoviral vector DS2.

SEQ ID NO:3 sets forth a nucleotide sequence encoding a TLR-3 agonist.

SEQ ID NO:4 sets forth a nucleotide sequence encoding a TLR-3 agonist.

SEQ ID NO:5 sets forth a nucleotide sequence encoding a TLR-3 agonist.

SEQ ID NO:6 sets forth a nucleotide sequence for a chimeric adenoviral vector comprising a nucleic acid encoding influenza HA and a nucleic acid encoding a TLR-3 agonist (luc), wherein the influenza HA and the TLR-3 agonist are in the same orientation.

SEQ ID NO: 7 sets forth a nucleotide sequence for a chimeric adenoviral vector comprising a nucleic acid encoding influenza HA and a nucleic acid encoding a TLR-3 agonist (luc), wherein the influenza HA and the TLR-3 agonist are in the opposite orientation.

SEQ ID NO: 8 sets forth a nucleotide sequence encoding a short hairpin RNA TLR-3 agonist. Complementary portions of the sequence are shown in capital letters and the linker sequence is shown in lower case letters.

SEQ ID NO: 9 sets forth a nucleotide sequence encoding a short hairpin RNA TLR-3 agonist (g1). Complementary portions of the sequence are shown in capital letters and the linker sequence is shown in lower case letters.

SEQ ID NO: 10 sets forth a nucleotide sequence encoding a short hairpin RNA TLR-3 agonist (luc). Complementary portions of the sequence are shown in capital letters and the linker sequence is shown in lower case letters.

SEQ ID NO: 11 sets forth a nucleotide sequence encoding a short hairpin RNA TLR-3 agonist (m1). Complementary portions of the sequence are shown in capital letters and the linker sequence is shown in lower case letters.

SEQ ID NO: 12 sets forth a nucleotide sequence encoding a short hairpin RNA TLR-3 agonist. Complementary portions of the sequence are shown in capital letters and the linker sequence is shown in lower case letters.

SEQ ID NO: 13 sets forth the nucleotide sequence for the chimeric adenoviral vector DS1c. The sequence comprises a nucleotide encoding HA(PR8/34).

SEQ ID NO: 14 sets forth the nucleotide sequence for the chimeric adenoviral vector DS2beta-luc. The vector comprises a sequence encoding the TLR-3 agonist luc under the control of the beta actin promoter. The vector also comprises open cloning sites for insertion of nucleic acid sequence(s) encoding an antigen of interest.

SEQ ID NO: 15 sets forth the nucleotide sequence for the chimeric adenoviral vector DS2C-luc The vector comprises a sequence encoding the TLR-3 agonist luc under the control of the CMV promoter. The vector also comprises open cloning sites for insertion of nucleic acid sequence(s) encoding an antigen of interest.

SEQ ID NO: 16 sets forth the nucleotide sequence for the pShuttle vector comprising a nucleic acid sequence encoding the TLR-3 agonist luc under the control of the CMV promoter and a nucleic acid sequence encoding HA (avian flu) under the control of a separate CMV promoter.

SEQ ID NO: 17 sets forth the nucleotide sequence for the chimeric adenoviral vector ND1.1 214. The nucleic acid encoding the heterologous antigen is in bold text and is flanked by a Cla I recognition site on the 5' end and a Not 1 recognition site on the 3' end. The nucleic acid sequence encoding the TLR-3 agonists is in italic, with the linker sequence in bold.

DETAILED DESCRIPTION OF THE INVENTION

I. Introduction

The present invention provides novel chimeric adenoviral vectors that can be administered non-parenterally to elicit an immune response against an antigen of interest. The chimeric adenoviral vectors of the invention comprise a nucleic acid encoding a heterologous polypeptide and a nucleic acid encoding a TLR-3 agonist. The chimeric adenoviral vectors elicit strong and effective immune responses specific for the heterologous polypeptide, particularly when administered via a non-parenteral route (e.g., orally, intranasally, or mucosally).

The invention is based on the suprising discovery that administration of dsRNA TLR-3 agonists are effective adjuvants when administered in conjunction with viral vectors. In fact, the use of dsRNA as an adjuvant for viral vectors would be counterintuitive considering that the major proposed utility of the dsRNA mimetic poly I:C was as an antiviral agent [Nemes, et al., *Proc Soc Exp Biol Med*. (1969) 132:776; Schafer, et al, *Nature*. (1970) 226:449; Fenje, et al, *Nature* (1970) 226:171.].

II. Definitions

The term “chimeric” or “recombinant” as used herein with reference, e.g., to a nucleic acid, protein, or vector, indicates that the nucleic acid, protein or vector, has been modified by the introduction of a heterologous nucleic acid or protein or the alteration of a native nucleic acid or protein. Thus, for example, chimeric and recombinant vectors include nucleic acid sequences that are not found within the native (non-chimeric or non-recombinant) form of the vector. A chimeric adenoviral expression vector refers to an adenoviral expression vector comprising a nucleic acid sequence encoding a heterologous polypeptide.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "promoter" and "expression control sequence" are used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Promoters include constitutive and inducible promoters. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The terms "TLR agonist" or "Toll-like receptor agonist" as used herein refers to a compound that binds and stimulates a Toll-like receptor including, e.g., TLR-2, TLR-3, TLR-6, TLR-7, or TLR-8. TLR agonists are reviewed in MacKichan, *IAVI Report.* 9:1-5 (2005) and Abreu et al., *J Immunol,* 174 (8), 4453-4460 (2005). Agonists induce signa transduction following binding to their receptor.

The terms "TLR-3 agonist" or "Toll-like receptor 3 agonist" as used herein refers to a compound that binds and stimulates the TLR-3. TLR-3 agonists have been identified including double-stranded RNA, virally derived dsRNA, several chemically synthesized analogs to double-stranded RNA including polyinosine-polycytidylic acid (poly I:C)-polyadenylic-polyuridylic acid (poly A:U) and poly I:poly C, and antibodies (or cross-linking of antibodies) to TLR-3 that lead to IFN-beta production [Matsumoto, M, et al, *Biochem Biophys Res Commun* 24:1364 (2002), de Bouteiller, et al, *J Biol Chem* 18:38133-45 (2005)]. TLR-3 agonists also include expressed dsRNA (e.g., dsRNA encoded by a nucleic acid comprising a sequence set forth in SEQ ID NOS: 3, 7, 8, 9, 10, 11, or 12).

The terms "TLR-7/8 agonist" or "Toll-like receptor 7/8 agonist" as used herein refers to a compound that binds and stimulates either the TLR-7 or TLR-8 receptors; these receptors recognize several of same ligands. Several TLR-7/8 agonists have been identified such as viral single-stranded RNA, imiquimod, loxoribine, polyuridylic acid, or resiquimod.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

Antigen—refers to a protein or part of a polypeptide chain that can be recognized by T cell receptors and/or antibodies. Typically, antigens are derived from bacterial, viral, or fungal proteins.

An "immunogenically effective dose or amount" of the of the compositions of the present invention is an amount that elicits or modulates an immune response specific for the heterologous polypeptide. Immune responses include humoral immune responses and cell-mediated immune responses. An immunogenic composition can be used therapeutically or prophylactically to treat or prevent disease at any stage.

"Humoral immune responses" are mediated by cell free components of the blood, i.e., plasma or serum; transfer of the serum or plasma from one individual to another transfers immunity.

"Cell mediated immune responses" are mediated by antigen specific lymphocytes; transfer of the antigen specific lymphocytes from one individual to another transfers immunity.

A "therapeutic dose" or "therapeutically effective amount" or "effective amount" of a chimeric adenoviral vector or a composition comprising a chimeric adenoviral vector is an amount of the vector or composition comprising the vector which prevents, alleviates, abates, or reduces the severity of symptoms of diseases and disorders associated with the source of the heterologous polypeptide (e.g., a virus, bacteria, a parasite, or a cancer).

Antibody—refers to a polypeptide encoded by an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

T cells—refer to a particular class of lymphocytes that express a specific receptor (T cell receptor) encoded by a family of genes. The recognized T cell receptor genes include alpha, beta, delta, and gamma loci, and the T cell receptors typically (but not universally) recognize a combination of MHC plus a short peptide.

Adaptive immune response—refers to T cell and/or antibody recognition of antigen.

Antigen presenting cells (APCs)—as used herein refers to cells that are able to present immunogenic peptides or fragments thereof to T cells to activate or enhance an immune response. APCs include dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may be isolated from any of a variety of biological fluids and organs including bone marrow, peripheral blood, tumor and peritumoral tissues, and may be autologous, allogeneic, syngeneic or xenogeneic cells. APCs typically utilize a receptor from the major histocompatability (MHC) locus to present short polypeptides to T cells.

Adjuvant—is a non-specific immune response enhancer. Suitable adjuvants include, for example, cholera toxin, monophosphoryl lipid A (MPL), Freund's Complete Adjuvant, Freund's Incomplete Adjuvant, Quil A, and Al(OH). Adjuvants can also be those substances that cause APC activation and enhanced presentation of T cells through secondary signaling molecules like Toll-like receptors. Examples of Toll-like receptors include the receptors that recognize double-stranded RNA, bacterial flagella, LPS, CpG DNA, and bacterial lipopeptide (Reviewed recently in [Abreu et al., *J Immunol,* 174(8), 4453-4460 (2005)]).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an γ carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine I, Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point I for the specific sequence at a defined ionic strength Ph. The $T_m$ is the temperature (under defined ionic strength, Ph, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at Ph 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to fusion proteins can be selected to obtain only those polyclonal antibodies that are specifically immunoreactive with fusion protein and not with individual components of the fusion proteins. This selection may be achieved by subtracting out antibodies that cross-react with the individual antigens. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

Polynucleotides may comprise a native sequence (i.e., an endogenous sequence that encodes an individual polypeptide or dsRNA or a portion thereof) or may comprise a variant of such a sequence. Polynucleotide variants may contain one or more substitutions, additions, deletions and/or insertions such that the biological activity of the encoded polypeptide is not diminished, relative to a polypeptide comprising native antigens. Polynucleotide variants may contain one or more substitutions, additions, deletions and/or insertions such that the TLR-3 agonist activity of the encoded dsRNA is not diminished, relative to a dsRNA that does not contain the substitutions, additions, deletions and/or insertions. Variants preferably exhibit at least about 50%, 55%, 60%, 65%, 70%, 75%, 80%, 85%, 90%, 91%, 92%, 93%, 94%, 95%, 96%, 97%, 98%, 99%, to a polynucleotide sequence that encodes a native polypeptide or a portion thereof or to a polynucleotide sequence that encodes a dsRNA with TLR-3 agonist activity.

The terms "identical" or percent "identity," in the context of two or more nucleic acids (e.g., a dsRNA that is a TLR-3 agonist) or polypeptide sequences, refer to two or more sequences or subsequences that are the same or have a specified percentage of amino acid residues or nucleotides that are the same (i.e., 50%, 55%, 60%, 65%, 70%, 75%, 80%, 85%, 90%, 91%, 92%, 93%, 94%, 95%, 96%, 97%, 98%, 99%, or more identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 10 to about 100, about 20 to about 75, about 30 to about 50 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions from about 10 to about 500, about 25 to about 200, 50 to about 150, in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

III. Compositions of the Present Invention

The invention provides compositions comprising chimerical adenoviral vectors. In some embodiments, the chimeric adenoviral vectors of the invention comprise a first promoter operably linked to a nucleic acid encoding a heterologous polypeptide and a second promoter operably linked to a nucleic acid encoding a TLR3 agonist. The first and second promoters may be the same or different. In some embodiments, the first and second promoters are independently selected from: the beta actin promoter and the CMV promoter.

In some embodiments, the chimeric adenoviral vector comprises the adenoviral genome (minus the E1 and E3 genes) and a nucleic acid encoding a gene that activates IRF-3 and other signaling molecules downstream of TLR-3. The chimeric vector can be administered to a cell that expresses Ad's E1 gene such that recombinant adenovirus (rAd) is produced by the cell. This rAd can be harvested and is capable of a single round of infection that will deliver the transgenic compostion to another cell within a mammal in order to elicit immune responses to the heterologous polypeptide.

A. Suitable Adenoviral Vectors

In some embodiments, the adenoviral vector is adenovirus 5, including, for example, Ad5 with deletions of the E1/E3 regions and Ad5 with a deletion of the E4 region. Other suitable adenoviral vectors include strains 2, orally tested strains 4 and 7, enteric adenoviruses 40 and 41, and other strains (e.g. Ad34) that are sufficient for delivering an antigen and eliciting an adaptive immune response to the transgene antigen [Lubeck et al., *Proc Natl Acad Sci USA,* 86(17), 6763-6767 (1989); Shen et al., *J Virol,* 75(9), 4297-4307 (2001); Bailey et al., *Virology,* 202(2), 695-706 (1994)]. In some embodiments, the adenoviral vector is a live, replication incompetent adenoviral vector (such as E1 and E3 deleted rAd5), live and attenuated adenoviral vector (such as the E1B55K deletion viruses), or a live adenoviral vector with wild-type replication.

The transcriptional and translational control sequences in expression vectors to be used in transforming vertebrate cells in vivo may be provided by viral sources. For example, commonly used promoters and enhancers are derived, e.g., from beta actin, adenovirus, simian virus (SV40), and human cytomegalovirus (CMV). For example, vectors allowing expression of proteins under the direction of the CMV promoter, SV40 early promoter, SV40 later promoter, metallothionein promoter, murine mammary tumor virus promoter, Rous sarcoma virus promoter, transducer promoter, or other promoters shown effective for expression in mammalian cells are suitable. Further viral genomic promoter, control and/or signal sequences may be used, provided such control sequences are compatible with the host cell chosen.

B. Heterologous Polypeptides

Nucleic acids encoding suitable heterologous polypeptides may be derived from antigens, such as, for example, viral antigens, bacterial antigens, cancer antigens, fungal antigens, or parasite antigens.

Viral antigens may be derived from, for example, human immunodeficiency virus (e.g., gag (p55 and p160), pol, env (gp120 and gp41) as set forth in Shiver et al. *Nature* 415 (6869):331 (2002); the HIV genomic sequences set forth in Genbank Accession Nos. EF363127; EF363126; EF363125; EF363124; EF363123; EF363122; EF192592; and EF192591; the HIV gag sequences set forth in Genbank Accession Nos. EF396891; EF396890; EF396889; EF396888; EF396887; EF396886; EF396885; EF396884; EF396883; EF396882; EF396881; EF396880; EF396879; EF396878; EF396877; EF396876; EF39687; EF396874; EF396873; and EF396872; the HIV pol sequences set forth in Genbank Accession Nos. EF396810; EF396809; EF396808; EF396807; EF396806; EF396805; EF396804; EF396803; EF396802; EF396801; EF396800; EF396799; EF396798; EF396797; EF396796; EF396795; EF396794; EF396793; EF396792; and EF396791; and the HIV env sequences set forth in Genbank Accession Nos. 9: EF367234; EF367233; EF367232; EF367231; EF367230; EF367229; EF367228; EF367227; EF367226; EF367225; EF367224; and EF367223, human papilloma virus (e.g., capsid protein L1 as described in, e.g., Donnelly et al. J Infect Dis. 173:314 (1996) and the sequences set forth in Genbank Accession Nos. EF362755; EF362754; NC_001694; NC_001693; NC_001691; NC_001690; NC_005134; NC_001458; NC_001457; NC_001354; NC_001352; NC_001526; and X94164), Epstein Barr virus, herpes simplex virus, human herpes virus, rhinoviruses, cocksackieviruses, enteroviruses, hepatitis A, B, C, and E (e.g., hepatitis B surface antigen as described in e.g., Lubeck et al, *PNAS USA* 86:6763 (1989) and the sequences set forth in GenBank Accession Nos. AB236481; AB236471; AB206501; AB206489; AB206487; AB221788; AB221777; AB221773; AR933671; AR933670; AB236514; AB236513; AB236512; AB236511; AB236510; AB236509; AB236508; AB236507); hepatitis C NS5 (see, e.g., Genbank Accession Nos. X59609; DQ911563; S71627; S70787; S70786; S70341; S62220; S70790; S70789; S70788; and AB204642)), mumps virus, rubella virus, measles virus, poliovirus, smallpox virus, rabies virus, and Variella-zoster virus. Influenza antigens include, e.g., hemagglutinin (HA), matrix protein 1 (M1), and nucleoprotein (NP) (see, e.g., Donnelly, et al, *Vaccine* 15:865 (1997) and the influenza HA sequences set forth in Genbank Accession Nos. AB294219; AB294217; AB294215; AB294213; EF102944; EF102943; EF102942; EF102941; EF102940; EF102939; EF102938; EF102937; EF102936; EF102935; EF102934; EF102933; DQ643982; DQ464354; CY019432; CY019424; CY019416; CY019408; CY019400; CY019392; CY019384; CY019376; CY019368; CY019360; CY019352; EF124794; EF110519; EF110518; EF165066; EF165065; EF165064; and EF165063; the influenza M1 sequences set forth in Genbank Accession Nos. AB292791; CY019980; CY019972; CY019964; CY019956; CY019948; CY019940; CY019628; CY019652; CY019644; CY019932; CY019924; CY019916; CY019908; CY019900; CY019892; CY019884; CY019876; CY019868; CY019860; and the influenza NP sequences set forth in Genbank Accession Nos. AB292790; CY019461; CY019974; CY019966; CY019958; CY019950; CY019942; CY019630; CY019654; CY019646; CY019934; CY019926; CY019918 CY019910; CY019902; CY019894; CY019886; CY019878; CY019870; and CY019862.

Suitable viral antigens also include, e.g., viral nonstructural proteins. The term "Viral nonstructural protein" as used herein refers to proteins encoded by viral nucleic acid that do not encode for structural polypeptides, such as those that make capsid or the protein surrounding a virus. Non-structural proteins include those proteins that promote viral nucleic acid replication and viral gene expression such as, for example, Nonstructural proteins 1, 2, 3, and 4 (NS1, NS2, NS3, and NS4, respectively) from Venezuelan Equine encephalitis (VEE), EEE, or Semliki Forest virus [Dubensky et al., *J Virol,* 70(1), 508-519 (1996); Petrakova et al *J Virol* 2005 79(12): 7597-608; U.S. Pat. Nos. 5,185,440; 5,739,026; 6,566,093; and 5,814,482. Several representative examples of suitable alphaviruses include Aura (ATCC VR-368), Bebaru virus (ATCC VR-600, ATCC VR-1240), Cabassou (Genbank Accession Nos. AF398387, ATCC VR-922), Chikungunya virus (ATCC VR-64, ATCC VR-1241), Eastern equine encephalomyelitis virus (Genbank Accession Nos. AY705241, AY705240, ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (Genbank Accession Nos. AJ251359, ATCC VR-67, ATCC VR-1247), Sindbis virus (Genbank Accession Nos. J02363, ATCC VR-68, ATCC VR-1248), Tonate (ATCC VR-925), Triniti (ATCC VR-469), Una (ATCC VR-374), Venezuelan equine encephalomyelitis (ATCC VR-69), Venezuelan equine encephalomyelitis virus (Genbank Accession Nos. AY986475, AY973944, NC 001449, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

Bacterial antigens may be derived from, for example, *Staphylococcus aureus, Staphylococcus epidermis, Helicobacter pylori, Streptococcus bovis, Streptococcus pyogenes, Streptococcus pneumoniae, Listeria monocytogenes, Mycobacterium tuberculosis, Mycobacterium leprae, Corynebacterium diphtheriae, Borrelia burgdorferi, Bacillus anthracis, Bacillus cereus, Clostridium botulinum, Clostridium difficile, Salmonella typhi, Vibrio chloerae, Haemophilus influenzae, Bordetella pertussis, Yersinia pestis, Neisseria gonorrhoeae, Treponema pallidum, Mycoplasm* sp., *Neisseria ransducer s, Legionella pneumophila, Rickettsia typhi, Chlamydia trachomatis*, and *Shigella dysenteriae, Vibrio cholera* (e.g., Cholera toxin subunit B as set forth in Genbank Accession Nos. U25679; A09803; EF158842; X76391; AF390572; cholera toxin-coregulated pilus (TCP) as described in Wu et al., *Infection and Immunity* Vol. 69(12):7695 (2001) and as set forth in Genbank Accession Nos. NC_002505 and AE004169); *Helicobacter pylorii* (VacA as set forth in Genbank Accession Nos. AY848858; AF042737; AF042736; AF042735; AF042734; NC_000921; CagA as set forth in Genbank Accession Nos. AF043490; AF043489; AF043488; AF043487; NAP as set forth in Genbank Accession Nos. AF284121; AF284120; AF284119; AF284118; AF284117; AF284116; AB045143; AB045142; AF227081; AF227080; AF227079; AF227078; AF227077; AF227076; AF227075; AF227074; Hsp or catalase as set forth in Genbank Accession No. NC_000921; urease as set forth in Genbank Accession Nos. AM417610; AM417609; AM417608; AM417607; AM417606; AM417605; AM417604; AM417603; AM417602; AM417601; and AM417600; *E. coli* antigens as set forth in Genbank Accession Nos. NC_000913; U00096;

NC_002655; BA000007; AE014075; including *E. coli* fimbrial antigens as set forth in Genbank Accession Nos. AB214865; AB214864; AB214863; AB214862; *E. coli* heat-labile enterotoxin as set forth in Genbank Accession Nos. X83966; V00275; X83966; J01646; V00275; M35581; M17873; M17874; K01995; M61015; M17894; M17101; K00433.

Parasite antigens may be derived from, for example, *Giardia lamblia, Leishmania* sp., *Trypanosoma* sp., *Trichomonas* sp., *Plasmodium* sp. (e.g., *P. faciparum* surface protein antigens such as pfs25 sequences as set forth in Genbank Accession Nos. XM_001347551; X07802; AF193769; AF179423; AF154117; and AF030628, pfs28 sequences as set forth in Genbank Accession No. L25843, pfs45 sequences as set forth in Genbank Accession Nos. EF158081; EF158079; EF158078; EF158076; EF158075; and EF158085, pfs84, pfs 48/45 sequences as set forth in Genbank Accession Nos. AF356146; AF356145; AF356144; AF356143; AF356142; AF356141; AF356140; AF356139; AF356138; AF356137; AF356136; AF356135; AF356134; AF356133; AF356132; AF356131; AF356130; AF356129; AF356128; AF356127, pfs 230 sequences as set forth in Genbank Accession Nos. NC_000910; XM_001349564; AE001393; L22219; L08135; and AF269242, *P. vivax* antigens such as Pvs25 sequences as set forth in Genbank Accession Nos. DQ641509; DQ641508; DQ641507; AY639972; AY639971; AY639970; AY639969; AY639968; AY639967; AY639966; and AY639965; and Pvs28 sequences as set forth in Genbank Accession Nos. AB033364; AB033363; AB033362; AB033361; AB033360; AB033359; AB033358; AB033357; AB033356; B033355; AB033354; AB033353; AB033352; AB033351; AB033350; AB033349; AB033348; AB033347; AB033346; and AB033345), *Schistosoma* sp., *Mycobacterium tuberculosis* (e.g., Ag85 sequences as set forth in Genbank Accession Nos. AX253506; AX253504; AX253502; and AX211309; MPT64, ESAT-6, CFP10, R8307, MTB-32 MTB-39, CSP, LSA-1, LSA-3, EXP1, SSP-2, SALSA, STARP, GLURP, MSP-1, MSP-2, MSP-3, MSP-4, MSP-5, MSP-8, MSP-9, AMA-1, Type 1 integral membrane protein, RESA, EBA-175, and DBA sequences as set forth in Genbank Accession Nos. BX842572; BX842573; BX842574; BX842575; BX842576; BX842577; BX842578; BX842579; BX842580; BX842581; BX842582; BX842583; BX842584 and NC_000962, HSP65 sequences as set forth in Genbank Accession Nos. AY299175; AY299174; AY299144; AF547886; and AF547885).

Cancer antigens include, for example, antigens expressed, for example, in colon cancer, stomach cancer, pancreatic cancer, lung cancer, ovarian cancer, prostate cancer, breast cancer, skin cancer (e.g., melanoma), leukemia, lymphoma, or myeloma, exemplary cancer antigens include, for example, HPV L1, HPV L2, HPV E1, HPV E2, placental alkaline phosphatase, AFP, BRCA1, Her2/neu, CA 15-3, CA 19-9, CA-125, CEA, Hcg, urokinase-type plasminogen activator (Upa), plasminogen activator inhibitor.

Fungal antigens may be derived from, for example, *Tinea pedis, Tinea corporus, Tinea cruris, Tinea unguium, Cladosporium carionii, Coccidioides immitis, Candida* sp., *Aspergillus fumigatus*, and *Pneumocystis carinii.*

The nucleic acids encoding immunogenic polypeptides, are typically produced by recombinant DNA methods (see, e.g., Ausubel, et al. ed. (2001) *Current Protocols in Molecular Biology*). For example, the DNA sequences encoding the immunogenic polypeptide can be assembled from cDNA fragments and short oligonucleotide linkers, or from a series of oligonucleotides, or amplified from cDNA using appropriate primers to provide a synthetic gene which is capable of being inserted in a recombinant expression vector (i.e., a plasmid vector or a viral vector) and expressed in a recombinant transcriptional unit. Once the nucleic acid encoding an immunogenic polypeptide is produced, it may be inserted into a recombinant expression vector that is suitable for in vivo or ex-vivo expression.

Recombinant expression vectors contain a DNA sequence encoding an immunogenic polypeptide operably linked to suitable transcriptional or translational regulatory elements derived from mammalian or viral genes. Such regulatory elements include a transcriptional promoter, an optional operator sequence to control transcription, a sequence encoding suitable mRNA ribosomal binding sites, and sequences which control the termination of transcription and translation. An origin of replication and a selectable marker to facilitate recognition of transformants may additionally be incorporated. The genes utilized in the recombinant expression vectors may be divided between more than one virus such that the gene products are on two different vectors, and the vectors are used for co-transduction to provide all the gene products in trans. There may be reasons to divide up the gene products such as size limitations for insertions, or toxicity of the combined gene products to the virus produce cell-lines.

C. TLR Agonists

According to the methods of the invention, TLR agonists are used to enhance the immune response to the heterologous polypeptide. In some embodiments, TLR-3 agonists are used. In other embodiments, TLR 7/8 agonists are used. The TLR agonists described herein can be delivered simultaneously with the expression vector encoding an antigen of interest or delivered separately (i.e., temporally or spatially) from the expression vector encoding an antigen of interest. For example, the expression vector may be administered via a non-parenteral route (e.g., orally, intranasally, or mucosally), while the TLR-agonist is delivered by a parenteral route (e.g., intramuscularly, intraperitoneally, or subcutaneously).

1. TLR-3 Agonists

In a preferred embodiment of the present invention, a TLR-3 agonist is used to stimulate immune recognition of an antigen of interest. TLR-3 agonists include, for example, short hairpin RNA, virally derived RNA, short segments of RNA that can form double-strands or short hairpin RNA, and short interfering RNA (siRNA). In one embodiment of the invention, the TLR-3 agonist is virally derived dsRNA, such as for example, a dsRNA derived from a Sindbis virus or dsRNA viral intermediates [Alexopoulou et al, *Nature* 413: 732-8 (2001)]. In some embodiments, the TLR-3 agonists is a short hairpin RNA. Short hairpin RNA sequences typically comprise two complementary sequences joined by a linker sequence. The particular linker sequence is not a critical aspect of the invention. Any appropriate linker sequence can be used so long as it does not interfere with the binding of the two complementary sequences to form a dsRNA.

In some embodiments, the short hairpin RNA comprises a sequence set forth in SEQ ID NOS: 3, 4, 5, 8, 9, 10, 11, or 12, a sequence with substantial identity to a sequence set forth in SEQ ID NOS: 3, 4, 5, 8, 9, 10, 11, or 12, or a variant of a sequence set forth in SEQ ID NOS: 3, 4, 5, 8, 9, 10, 11, or 12. In certain embodiments, dsRNA that is a TLR-3 agonist does not encode a particular polypeptide, but produces a pro-inflammatory cytokine (e.g. IL-6, IL-8, TNF-alpha, IFN-alpha, IFN-beta) when contacted with a responder cell (e.g., a dendritic cell, a peripheral blood mononuclear cell, or a macrophage) in vitro or in-vivo. In some cases, the nucleic acid encoding the TLR-3 agonist (e.g., an expressed dsRNA) and the chimeric adenoviral vector comprising a nucleic acid encoding a heterologous antigen are administered in the same formulation. In other cases the nucleic acid encoding the TLR-3 agonist and the chimeric adenoviral vector comprising a nucleic acid encoding a heterologous polypeptide are administered in different formulations. When the nucleic acid encoding the TLR-3 agonist and the adenoviral vector comprising a nucleic acid encoding a heterologous antigen are administered in different formulations, their administration may be simultaneous or sequential. For example, the nucleic acid encoding the TLR-3 agonist may be administered first, followed by the chimeric adenoviral vector (e.g., 1, 2, 4, 8, 12, 16, 20, or 24 hours, 2, 4, 6, 8, or 10 days later). Alternatively, the adenoviral vector may be administered first, followed by the nucleic acid encoding the TLR-3 agonist (e.g., 1, 2, 4, 8, 12, 16, 20, or 24 hours, 2, 4, 6, 8, or 10 days later). In some embodiment, the nucleic acid encoding the TLR-3 agonist and the nucleic acid encoding the heterologous antigen are under the control of the same promoter. In other embodiments, the nucleic acid encoding the TLR-3 agonist and the nucleic acid encoding the heterologous antigen are under the control of different promoters.

Several chemically synthesized analogs to double-stranded RNA are commercially available. These include polyinosine-polycytidylic acid (poly I:C), polyadenylic: polyuridylic acid (poly A:U), and poly I:poly C. Antibodies (or cross-linking of antibodies) to TLR-3 can also lead to IFN-beta or pro-inflammatory cytokine production [Matsumoto et al, *Biochem. Biophys. Res. Commun.* 24:1364 (2002), de Bouteiller et al, *J Biol. Chem.* 18:38133-45 (2005)]. Commercially available siRNA segments of any sequence can also be obtained through sources such as Invitrogen.

2. TLR7/8 Agonists

In some embodiments, the TLR agonists are TLR7/8 agonists. TLR7/8 ligands are typically single-stranded, virally derived RNA. Because the receptors are expressed in intracellular compartments such as the endosome, not all short segments of RNA will trigger the TLR7/8 signaling cascade because they need to reach the correct compartment. Some ligands that have been shown to trigger this through exogenous addition are polyuridylic acid, resiquimod, and imiquimod [Westwood, et al, Vaccine 24:1736-1745 (2006)].

IV. Pharmaceutical Compositions

Pharmaceutical compositions comprising the vectors described herein may also contain other compounds, which may be biologically active or inactive. Polypeptides may, but need not, be conjugated to other macromolecules as described, for example, in U.S. Pat. Nos. 4,372,945 and 4,474,757. Pharmaceutical compositions may generally be used for prophylactic and therapeutic purposes. Pharmaceutical compositions may be composed of methods to protect against stomach degradation such that the administered chimeric adenoviral vector may reach the desired locations. For the oral environment, several of these are available including the Eudragit and the TimeClock release systems as well as other methods specifically designed for adenovirus [Lubeck et al., *Proc Natl Acad Sci USA,* 86(17), 6763-6767 (1989); Chourasia and Jain, *J Pharm Pharm Sci,* 6(1), 33-66 (2003)]. There are also several methods already described for microencapsulation of DNA and drugs for oral delivery (see, e.g., U.S. Patent Publication No. 2004043952). In some embodiments, the Eudragit system will be used to deliver the chimeric adenoviral vecto to the lower small intestine. However, delivery to other locations of the small intestine should also work.

As noted above, the chimeric adenoviral vectors on the invention may be delivered using any delivery systems known to those of ordinary skill in the art. Numerous gene delivery techniques are well known in the art, such as those described by Rolland (1998) *Crit. Rev. Therap. Drug Carrier Systems* 15:143-198, and references cited therein.

It will be apparent that an immunogenic compostions may contain pharmaceutically acceptable salts of the polynucleotides encoding the heterologous polypeptides (e.g., immunogenic polypeptides). Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts). Some particular examples of salts include phosphate buffered saline and saline for injection.

Any suitable carrier known to those of ordinary skill in the art may be employed in the pharmaceutical compositions of this invention. Suitable carriers include, for example, water, saline, alcohol, a fat, a wax, a buffer, a solid carrier, such as mannitol, lactose, starch, magnesium stearate, sodium saccharine, talcum, cellulose, glucose, sucrose, and magnesium carbonate, or biodegradable microspheres (e.g., polylactate polyglycolate). Suitable biodegradable microspheres are disclosed, for example, in U.S. Pat. Nos. 4,897,268; 5,075,109; 5,928,647; 5,811,128; 5,820,883. The immunogenic polypeptide and/or carrier virus may be encapsulated within the biodegradable microsphere or associated with the surface of the microsphere.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

In some embodiments of the present invention, the compositions further comprise an adjuvant. Suitable adjuvants include, for example, the lipids and non-lipid compounds, cholera toxin (CT), CT subunit B, CT derivative CTK63, *E. coli* heat labile enterotoxin (LT), LT derivative LTK63, $Al(OH)_3$, and polyionic organic acids as described in e.g., WO 04/020592, Anderson and Crowle, *Infect. Immun.* 31(1): 413-418 (1981), Roterman et al., *J. Physiol. Pharmacol.,* 44(3):213-32 (1993), Arora and Crowle, *J. Reticuloendothel.* 24(3):271-86 (1978), and Crowle and May, *Infect. Immun.* 38(3):932-7 (1982)). Suitable polyionic organic acids include for example, 6,6'-[3,3'-demithyl[1,1'-biphenyl]-4,4'-diyl]bis (azo)bis[4-amino-5-hydroxy-1,3-naphthalene-disulfonic acid] (Evans Blue) and 3,3'-[1,1' biphenyl]-4,4'-diylbis(azo) bis[4-amino-1-naphthalenesulfonic acid] (Congo Red). It will be appreciated by those of skill in the art that the polyionic organic acids may be used for any genetic vaccination method in conjunction with any type of administration.

Other suitable adjuvants include topical immunomodulators such as, members of the imidazoquinoline family such as, for example, imiquimod and resiquimod (see, e.g., Hengge et al., *Lancet Infect. Dis.* 1(3):189-98 (2001). Expressed TLR-3 agonists (e.g., dsRNA) and TLR-7 agonists (e.g., ssRNA) could also be used with the invention Additional suitable adjuvants are commercially available as, for example, additional alum-based adjuvants (e.g., Alhydrogel, Rehydragel, aluminum phosphate, Algammulin); oil based adjuvants (Freund's Incomplete Adjuvant and Complete Adjuvant (Difco Laboratories, Detroit, Mich.), Specol, RIBI, TiterMax, Montanide ISA50 or Seppic MONTANIDE ISA 720); nonionic block copolymer-based adjuvants, cytokines (e.g., GM-CSF or Flat3-ligand); Merck Adjuvant 65 (Merck and Company, Inc., Rahway, N.J.); AS-2 (SmithKline Beecham, Philadelphia, Pa.); salts of calcium, iron or zinc; an insoluble suspension of acylated tyrosine; acylated sugars; cationically or anionically derivatized polysaccharides; polyphosphazenes; biodegradable microspheres; monophosphoryl lipid A and Quil A. Cytokines, such as GM-CSF or interleukin-2, -7, or -12, are also suitable adjuvants. Hemocyanins (e.g., keyhole limpet hemocyanin) and hemoerythrins may also be used in the invention. Polysaccharide adjuvants such as, for example, chitin, chitosan, and deacetylated chitin are also suitable as adjuvants. Other suitable adjuvants include muramyl dipeptide (MDP, N acetylmuramyl L alanyl D isoglutamine) bacterial peptidoglycans and their derivatives (e.g., threonyl-MDP, and MTPPE). BCG and BCG cell wall skeleton (CWS) may also be used as adjuvants in the invention, with or without trehalose dimycolate. Trehalose dimycolate may be used itself (see, e.g., U.S. Pat. No. 4,579,945). Detoxified endotoxins are also useful as adjuvants alone or in combination with other adjuvants (see, e.g., U.S. Pat. Nos. 4,866,034; 4,435,386; 4,505,899; 4,436,727; 4,436,728; 4,505,900; and 4,520,019. The saponins QS21, QS17, QS7 are also useful as adjuvants (see, e.g., U.S. Pat. No. 5,057, 540; EP 0362 279; WO 96/33739; and WO 96/11711). Other suitable adjuvants include Montanide ISA 720 (Seppic, France), SAF (Chiron, Calif., United States), ISCOMS (CSL), MF-59 (Chiron), the SBAS series of adjuvants (e.g., SBAS-2, SBAS-4 or SBAS-6 or variants thereof, available from SmithKline Beecham, Rixensart, Belgium), Detox (Corixa, Hamilton, Mont.), and RC-529 (Corixa, Hamilton, Mont.).

Superantigens are also contemplated for use as adjuvants in the present invention. Superantigens include *Staphylococcus* exoproteins, such as the α, β, γ and Δ enterotoxins from *S. aureus* and *S. epidermidis*, and the α, β, γ and Δ *E. coli* exotoxins. Common *Staphylococcus* enterotoxins are known as staphylococcal enterotoxin A (SEA) and staphylococcal enterotoxin B (SEB), with enterotoxins through E (SEE) being described (Rott et al., 1992). *Streptococcus pyogenes* B (SEB), *Clostridium perfringens* enterotoxin (Bowness et al., 1992), cytoplasmic membrane-associated protein (CAP) from *S. pyogenes* (Sato et al., 1994) and toxic shock syndrome toxin 1 (TSST 1) from *S. aureus* (Schwab et al., 1993) are further useful superantigens.

Within the pharmaceutical compositions provided herein, the adjuvant composition can be designed to induce, e.g., an immune response predominantly of the Th1 or Th2 type. High levels of Th1-type cytokines (e.g., IFN-gamma, TNF-alpha, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following oral delivery of a composition comprising an immunogenic polypeptide as provided herein, an immune response that includes Th1- and Th2-type responses will typically be elicited.

The compositions described herein may be administered as part of a sustained release formulation (i.e., a formulation such as a capsule or sponge that effects a slow release of compound following administration). Such formulations may generally be prepared using well known technology (see, e.g., Coombes et al. (1996) *Vaccine* 14:1429-1438). Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-co-glycolide), as well as polyacrylate, latex, starch, cellulose and dextran. Other delayed-release carriers include supramolecular biovectors, which comprise a non-liquid hydrophilic core (e.g., a cross-linked polysaccharide or oligosaccharide) and, optionally, an external layer comprising an amphiphilic compound (see, e.g., WO 94/20078; WO 94/23701; and WO 96/06638). The amount of active compound contained within a sustained release formulation depends upon the site of implantation, the rate and expected duration of release and the nature of the condition to be treated or prevented.

The pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

V. Therapeutic Uses of the Invention

One aspect of the present invention involves using the immunogenic compositions described herein to elicit an antigen specific immune response from a subject or patient with a disease such as, for example, a viral infection, bacterial infection, a parasitic infection, a fungal infection, or cancer. As used herein, a “subject” or a “patient” refers to any warm-blooded animal, such as, for example, a rodent, a feline, a canine, or a primate, preferably a human. The immunogenic compositions may be used to treat at any stage of the disease, i.e., at the pre-cancer, cancer, or metastatic stages, or to prevent disease. For example, the compositions described herein may be used to treat a viral disease such as HIV or hepatitis or for prevention or treatment of cancer. Within such methods, pharmaceutical compositions are typically administered to a patient. The patient may or may not be afflicted with the disease or disorder (e.g., a viral infection, a bacterial infection, or cancer). Accordingly, the above pharmaceutical compositions may be used to prevent the development of a disease or disorder (e.g., a viral infection, a bacterial infection, or cancer) or to treat a patient afflicted with the disease or disorder (e.g., a viral infection, a bacterial infection, or cancer). The disease or disorder may be diagnosed using criteria generally accepted in the art. For example, viral infection may be diagnosed by the measurement of viral titer in a sample from the patient, bacterial infection may be diagnosed by detecting the bacteria in a sample from the patient, and cancer may be diagnosed by detecting the presence of a malignant tumor. Pharmaceutical compositions may be administered either prior to or following surgical removal of primary tumors and/or treatment such as administration of radiotherapy or conventional chemotherapeutic drugs.

Immunotherapy is typically active immunotherapy, in which treatment relies on the in vivo stimulation of the endogenous host immune system to react against, e.g., tumors or bacterially or virally infected cells, with the administration of immune response-modifying agents (compositions comprising nucleic acids encoding immunogenic polypeptides as provided herein).

Frequency of administration of the prophylactic or therapeutic compositions described herein, as well as dosage, will vary from individual to individual, and may be readily established using standard techniques. Often between 1 and 10 doses may be administered over a 52 week period. Typically 3 doses are administered, at intervals of 1 month, more typically, 2-3 doses are administered every 2-3 months. It is possible that the intervals will be more like once a year for certain therapies. Booster vaccinations may be given periodically thereafter. Alternate protocols may be appropriate for individual patients and particular diseases and disorders. A suitable dose is an amount of a compound that, when administered as described above, is capable of promoting, e.g., an anti-tumor, an anti-viral, or an antibacterial, immune response, and is at least 10-50% above the basal (i.e., untreated) level. Such response can be monitored by measuring the anti-tumor antibodies in a patient or by vaccine-dependent generation of cytolytic T cells capable of killing, e.g., the patient's tumor cells, the patient's virally infected cells, or the patient's bacterially infected cells in vitro. Such vaccines should also be capable of causing an immune response that leads to an improved clinical outcome (e.g., more frequent remissions, complete or partial or longer disease-free survival) in vaccinated patients as compared to non-vaccinated patients. Typically, the amount of the viral titers will be between 1.0×104 pfu/animal and 1.0×1015 pfu/animal. Suitable dose sizes will vary with the size of the patient, but will typically range from about 0.01 ml to about 10 ml, more typically from about 0.025 to about 7.5 ml, most typically from about 0.05 to about 5 ml. Those of skill in the art will appreciate that the dose size may be adjusted based on the particular patient or the particular disease or disorder being treated. For oral administration, the chimeric adenoviral vector can conveniently be formulated in a pill.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Such immune responses may generally be evaluated using standard proliferation, cytotoxicity or cytokine assays described above, which may be performed using samples obtained from a patient before and after treatment.

For example, detection of immunocomplexes formed between immunogenic polypeptides and antibodies in body fluid which are specific for immunogenic polypeptides may be used to monitor the effectiveness of therapy, which involves a particular immunogenic polypeptide, for a disease or disorder in which the immunogenic polypeptide is associated. Samples of body fluid taken from an individual prior to and subsequent to initiation of therapy may be analyzed for the immunocomplexes by the methodologies described above. Briefly, the number of immunocomplexes detected in both samples are compared. A substantial change in the number of immunocomplexes in the second sample (post-therapy initiation) relative to the first sample (pre-therapy) reflects successful therapy.

A. Administration of the Compositions of the Present Invention

According to the methods of the present invention, a composition comprising the chimeric adenoviral vector is administered by any non-parenteral route (e.g., orally, intranasally, or mucosally via, for example, the vagina, lungs, salivary glands, nasal cavities, small intestine, colon, rectum, tonsils, or Peyer's patches). The composition may be administered alone or with an adjuvant as described above. In some embodiments, the adjuvants are encoded by a nucleic acid sequence (e.g., a nucleic acid encoding IL-2, GM-CSF, IL-12, or bacterial flagellin). In some embodiments of the present invention, the adjuvant is administered at the same time as the composition. In other embodiments of the present invention, the adjuvant is administered after the composition, e.g., 6, 12, 18, 24, 36, 48, 60, or 72 hours after administration of the composition.

B. Detection of an Immune Response to Atigens of Interest

An immune response to the heterologous polypeptide can be detected using any means know in the art including, for example detecting specific activation of $CD4^+$ or $CD8^+$ T cells or by detecting the presence of antibodies that specifically bind to the polypeptide.

Specific activation of $CD4^+$ or $CD8^+$ T cells associated with a mucosal, humoral, or cell-mediated immune response may be detected in a variety of ways. Methods for detecting specific T cell activation include, but are not limited to, detecting the proliferation of T cells, the production of cytokines (e.g., lymphokines), or the generation of cytolytic activity (i.e., generation of cytotoxic T cells specific for the immunogenic polypeptide). For $CD4^+$ T cells, a preferred method for detecting specific T cell activation is the detection of the proliferation of T cells. For $CD8^+$ T cells, a preferred method for detecting specific T cell activation is the detection of the generation of cytolytic activity using $^{51}Cr$ release assays (see, e.g., Brossart and Bevan, *Blood* 90(4): 1594-1599 (1997) and Lenz et al., *J. Exp. Med.* 192(8):1135-1142 (2000)).

Detection of the proliferation of T cells may be accomplished by a variety of known techniques. For example, T cell proliferation can be detected by measuring the rate of DNA synthesis. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, Ca2+ flux, or dye uptake, such as 3-(4,5-dimethylthiazol-2-yl)-2,5-diphenyltetrazolium. Alternatively, synthesis of lymphokines (e.g., interferon-gamma) can be measured or the relative number of T cells that can respond to the immunogenic polypeptide may be quantified.

Antibody immune responses (aka Humoral immune responses or B cell responses), including mucosal antibody responses can be detected using immunoassays known in the art [Tucker et al., *Mol Therapy,* 8, 392-399 (2003); Tucker et al., *Vaccine,* 22, 2500-2504 (2004)]. Suitable immunoassays include the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh (1970)); the "western blot" method of Gordon et al. (U.S. Pat. No. 4,452,901); immunoprecipitation of labeled ligand (Brown et al. (1980) *J. Biol. Chem.* 255:4980-4983); enzyme-linked immunosorbent assays (ELISA) as described, for example, by Raines et al. (1982) *J. Biol. Chem.* 257:5154-5160; immunocytochemical techniques, including the use of fluorochromes (Brooks et al. (1980) *Clin. Exp. Immunol.* 39:477); and neutralization of activity (Bowen-Pope et al. (1984) *Proc. Natl. Acad. Sci. USA* 81:2396-2400). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876.

EXAMPLES

The following examples are intended to illustrate, but not to limit the present invention.

Example 1

Construction of a Chimeric Adenoviral Vector (DS1)

To demonstrate that TLR-3 agonists can improve adaptive immune responses to expressed antigens of interest, several different chimeric adenoviral vectors were constructed that comprise nucleic acid sequences encoding several different antigens of interest. In this example, the nucleic acid encoding gp120 (from the NIH AIDS Reagent and Reference Reagent Program) was placed under control of a CMV promoter with a small intron just upstream of the start codon in the shuttle vector (pShuttle, Qbiogene). A poly A tail from bGH was placed downstream of the nucleic acid encoding gp120. The vector sequence is set forth in SEQ ID NO: 1. Homologous recombination with the vector pAd (Qbiogene) was performed to generate a vector capable of producing recombinant Ad (E1/E3 deleted) that contained the nucleic acid encoding gp120. DS1 was generated by transfecting the new pAd-CMV-gp120 expression construct into 293 cells. Titers were measured by standard methods.

Example 2

Figure 1B:
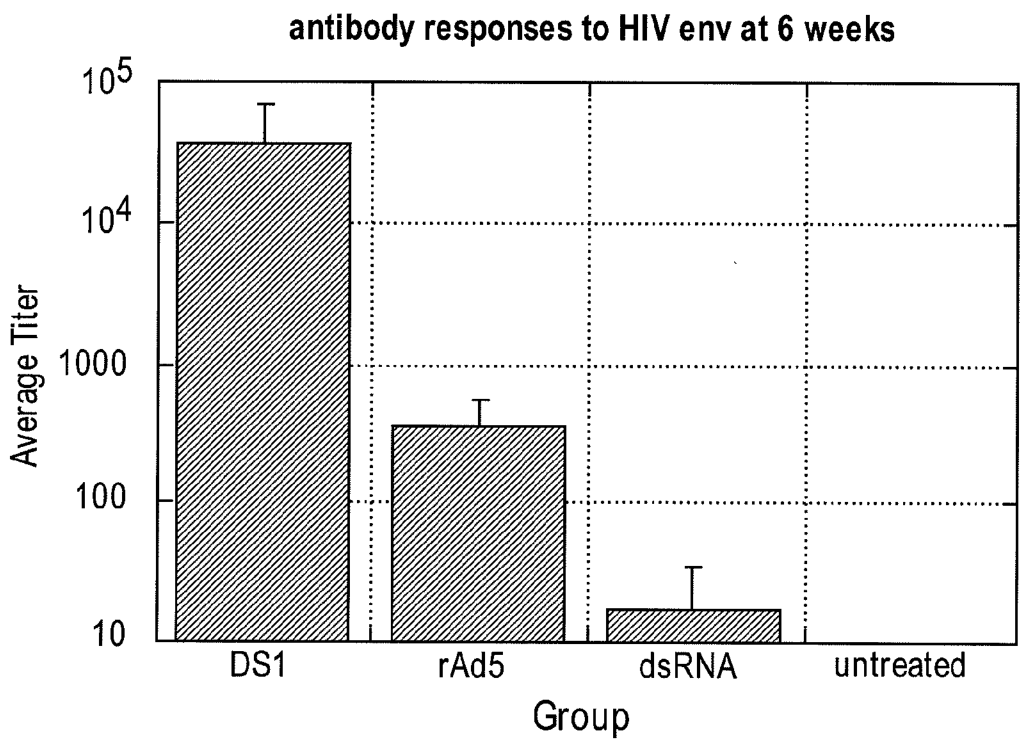
FIG. 1B illustrates data depicting the antibody titer to HIV envelope protein (i.e., gp120) at 6 weeks following oral delivery of the adenoviral vectors.

DS1 (Vector Plus TLR-3 Agonist) is Superior to Standard rAd5 for Inducing an Antigen Specific Immune Response To determine whether the addition of TLR-3 agonist could improve adaptive immune responses, $10\times10^7$ PFU of either rAd-CMV-gp120 plus 5 ug/ml poly I:C (DS1) or rAd-CMV-gp120 alone (rAd5) were administered to animals by oral gavage on weeks 0 and 3. Both vectors express HIV gp120 under control of the CMV promoter and use recombinant E1/E3 deleted adenovirus type 5. Antibody titers to gp120 were measured in the plasma 3 and 6 weeks after the initial administration by anti-gp120 IgG ELISA as described in Tucker, et al., *Mol Ther* 8:392 (2004)). As shown in FIG. 1, DS1 performed significantly better than rAd5 in eliciting antibody responses to the protein gp120 both at 3 and 6 weeks post initial oral administration. In particular, the average antibody titer to gp120 was 100 fold better with the DS1 group than with the rAd5 group at week 6. It also appears that the DS1 group was boosted by readministration at week 4 in that the average titer increased greater than 20 fold between weeks 3 and 6 whereas the rAd5 group showed only a slight increase in mean antibody titer. The results demonstrate that the addition of a TLR-3 agonist can greatly improve Ad5 mediated antibody responses to antigens of interest following oral administration of a chimeric adenoviral vector comprising a nucleic acid encoding the antigen of interest. As a positive control for the assay, sera from an animal injected subcutaneously with gp120 plus Complete Freund's Adjuvant was also measured in the anti-gp120 ELISA at week 3. Untreated animals and animals administered the dsRNA analog alone (dsRNA) served as negative and background controls respectively for the ELISA. Each group contained 6 animals.

Example 3

Construction of a Second Chimeric Adenoviral Vector (DS1b) and a Third Chimeric Adenoviral Vector (DS1c)

A nucleic acid encoding green fluorescent protein (GFP) was inserted into pShuttle-CMV (Qbiogene) using standard restriction enzyme digests. The plasmid pShuttleCMV-GFP was combined by homologous recombination with the vector pAd (Qbiogene) as described before in order to generate a vector capable of producing recombinant Ad (E1/E3 deleted) comprising a nucleic acid sequence encoding GFP. A nucleic acid encoding hemagluttinin (HA) from influenza A/PR/8/34 was cloned and placed in the pShuttle-CMV vector (Qbiogene) (SEQ ID NO: 13). The plasmid pShuttleCMV-HA (PR/8) was combined by homologous recombination with the vector pAd (Qbiogene) as described before in order to generate a vector capable of producing recombinant Ad (E1/E3 deleted) comprising a nucleic acid sequence encoding HA. Recombinant Ad was generated by transfecting the new pAd-CMV-GFP and pAd-CMV-HA expression construct into 293 cells. Titers were measured by standard methods.

Example 4

Figure 2A:
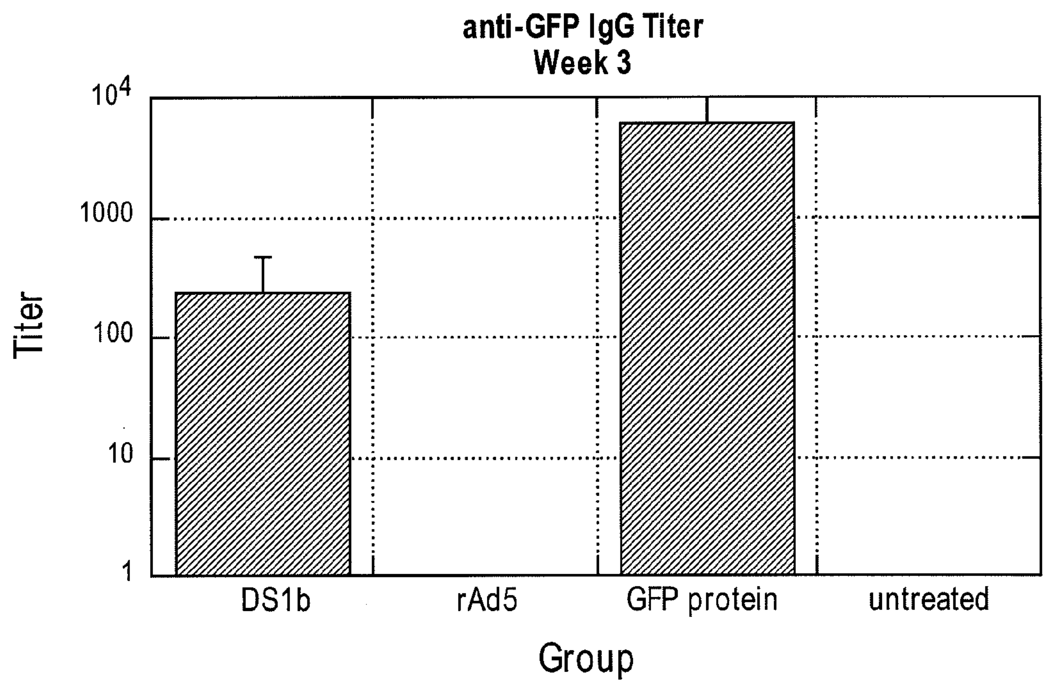
FIG. 2A illustrates data depicting the anti-GFP IgG titer at 3 weeks following oral administration of the vectors.

DS1b (Ad-CMV-GFP Plus TLR-3 Agonist) and DS1c (Ad-CMV-HA Plus TLR-3 Agonist) is Superior to Standard rAd5 for Inducing an Antigen Specific Immune Response $1.0\times10^7$ PFU of either Ad-CMV-GFP plus 5 ug/ml poly I:C (DS1b) or Ad-CMV-GFP (rAd5) were administered to animals by oral gavage on week 0. Both viruses express the GFP under control of the CMV promoter and use recombinant E1/E3 deleted adenovirus type 5. Antibody titers to GFP were measured in the plasma 3 weeks after the initial virus administration by anti-GFP IgG ELISA. As shown in FIG. 2, the DS1b group performed significantly better than rAd5 in eliciting antibody responses to the protein GFP at 3 weeks post initial oral administration.

Figure 2B:
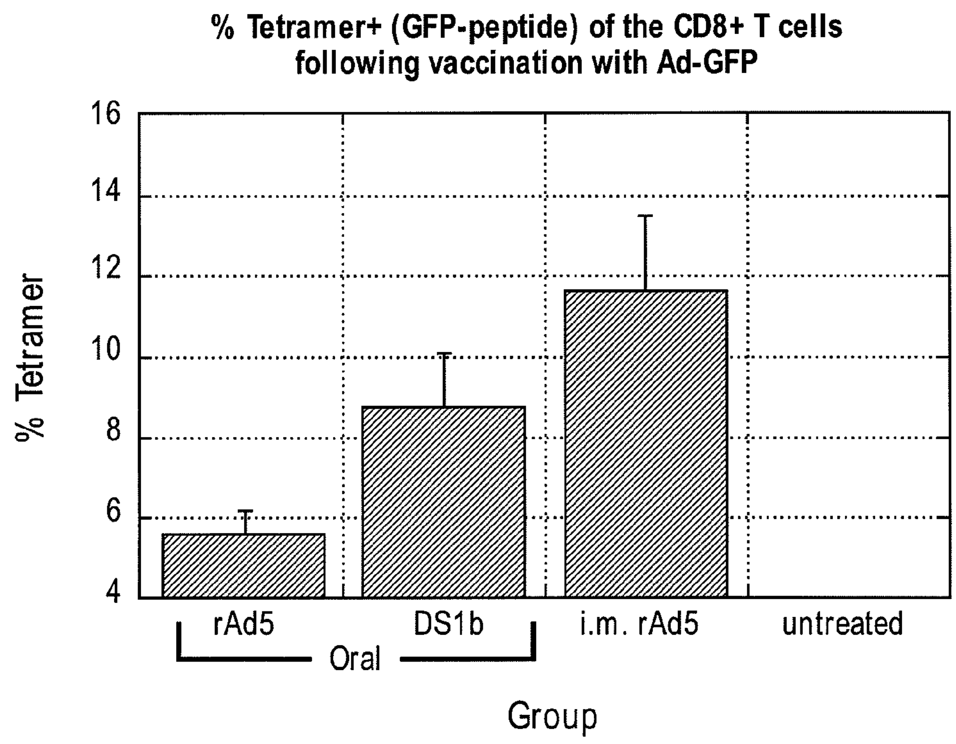
FIG. 2B illustrates data depicting the CD8+ T cell response to GFP at 10 weeks following administration of the vector at 0, 4, and 8 weeks.

The $CD8^+$ T cell responses to GFP were measured by tetramer staining of splenocytes. Animals were vaccinated on weeks 0, 4, 8 and spleens were harvested on week 10. The splenocytes were stained with CD8-FITC and the tetramer which recognizes the immunodominant epitope to GFP in Balb/c mice. Results show that oral administration of the DS1b vector was statistically better than rAd alone in inducing tetramer positive CD8 cells (FIG. 2*b*).

Figure 2C:
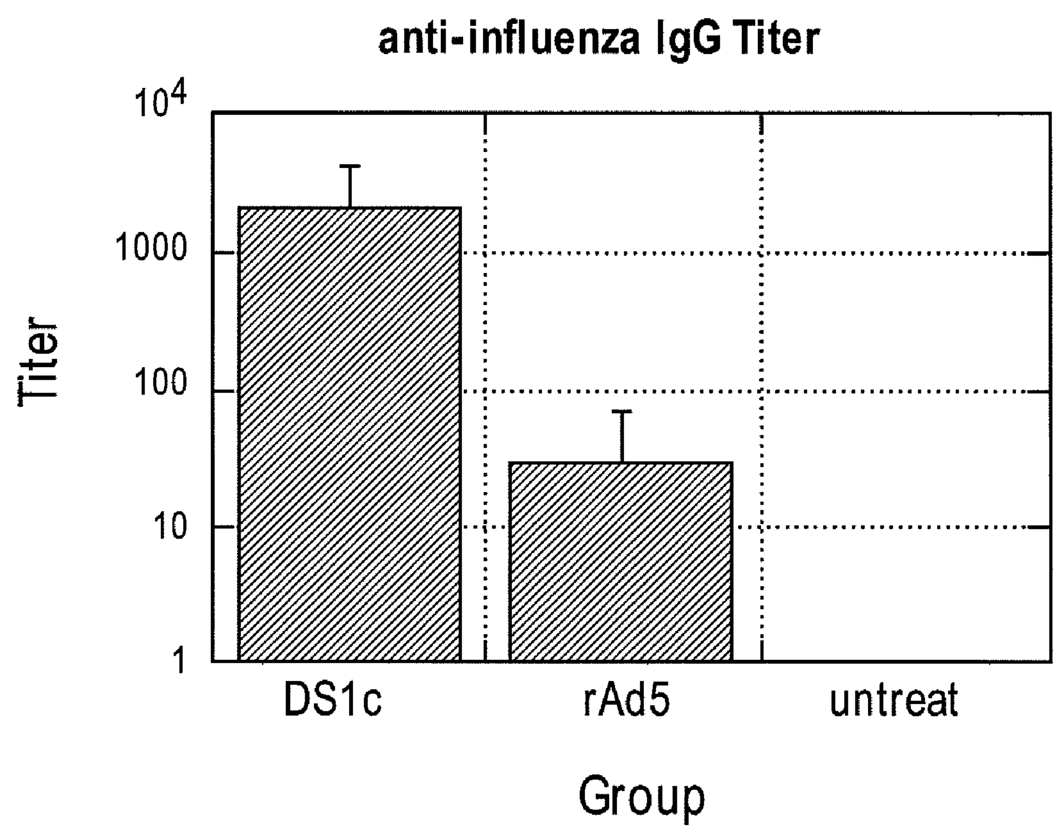
FIG. 2C illustrates data depicting the anti-HA antibody titer at 3 weeks following oral administration of the vectors.

$1.0\times10^7$ PFU of either Ad-CMV-HA plus 5 ug/ml poly I:C (DS1c) or Ad-CMV-HA (rAd5) were administered to animals by oral gavage on week 0. Both viruses express HA under control of the CMV promoter and use recombinant E1/E3 deleted adenovirus type 5. Antibody titers to HA were measured in the plasma 3 weeks after the initial virus administration by anti-PR8/34 IgG ELISA. The procedure for measuring antibody responses is similar to that described before with the exception that the ELISA plates were coated with 5 ug/ml of whole A/PR8/34 lysate (Advanced Biotechnology Incorporated, Gaithersburg, Md.). As shown in FIG. 2C, the DS1c group performed significantly better (approximate 100 fold better) than rAd5 in eliciting antibody responses to influenza at 3 weeks post initial oral administration. The results of these studies also demonstrate that the approach of using TLR-3 agonist along with a chimeric recombinant adenoviral vector can be generally applied to multiple different heterologous antigens, with a 100 fold improvement in antibody titer.

Example 5

Non-Parenteral Routes of Delivery are Superior to Parenteral Routes

Figure 3A:
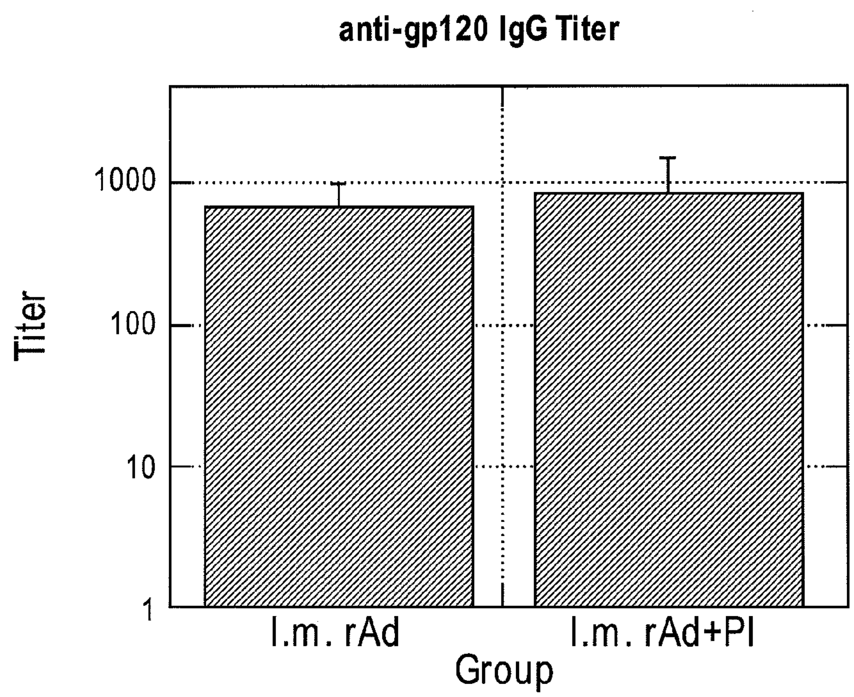
FIG. 3A illustrates data depicting the anti-gp120 antibody titer 3 weeks following intramuscular administration of DS1.
Figure 3B:
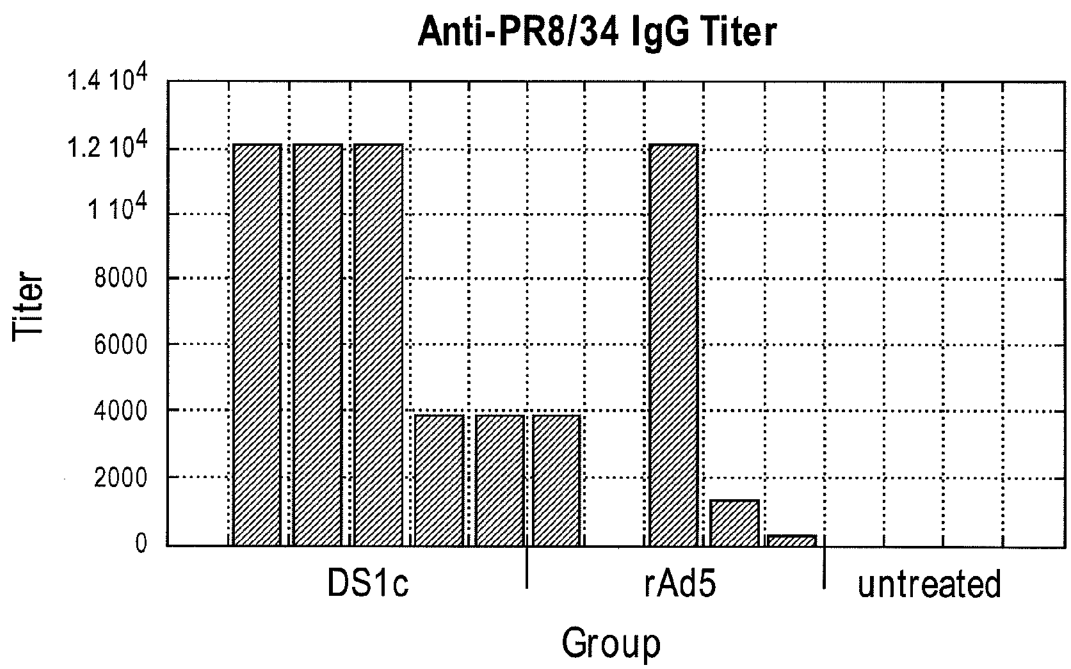
FIG. 3B illustrates data depicting the anti-HA antibody titer three weeks following intransal administration of DS1c.

Intramuscular delivery was tested by directly injecting 1.0×107 pfu of pAd-CMV-gp120 (DS10+/−poly I:C at 5 ug/ml into the quadriceps of animals. Plasma serum IgG titers to GFP were measured as described before. Each group contained 6 animals. As shown in FIG. 3A, significant antibody titers to gp120 were observed at 3 weeks post administration in the group with TLR-3 agonist (i.m. rAd+PI). (FIG. 3*a*).

Intranasal administration was tested by administering 20 ul of $1.1\times10^6$ pfu of DS1c+/−5 ug/ml of poly I:C into the nasal cavity of mice. The mice were lightly anesthetized with isoflurane before administering the virus formulated in sterile saline. The results show that the rAd-CMV-HA plus poly I:C (DS1c) had slightly higher antibody titers compared to animals given the standard rAd-CMV-HA. Results are plotted as individual animals for the DS1c (N=6) and the rAd (N=5) groups. Untreated animals (N=4) are used for negative controls.

Example 6

Construction of an Expressed TLR3 Agonist

A short 45 bp segment of DNA was synthesized by ordering of DNA oligos that when annealed together formed a 45 bp segment designed to make a hairpin of double-stranded RNA (GAAACGATATGGGCTGAATACGGATCCG-TATTCAGCCCATATCGTTTC) (SEQ ID NO:10). This short segment (called luc1) was cloned into the plasmid pSK- containing the human beta actin promoter and a BGH poly A tail. This plasmid is called pSk-luc1.

Example 7

Figure 4A:
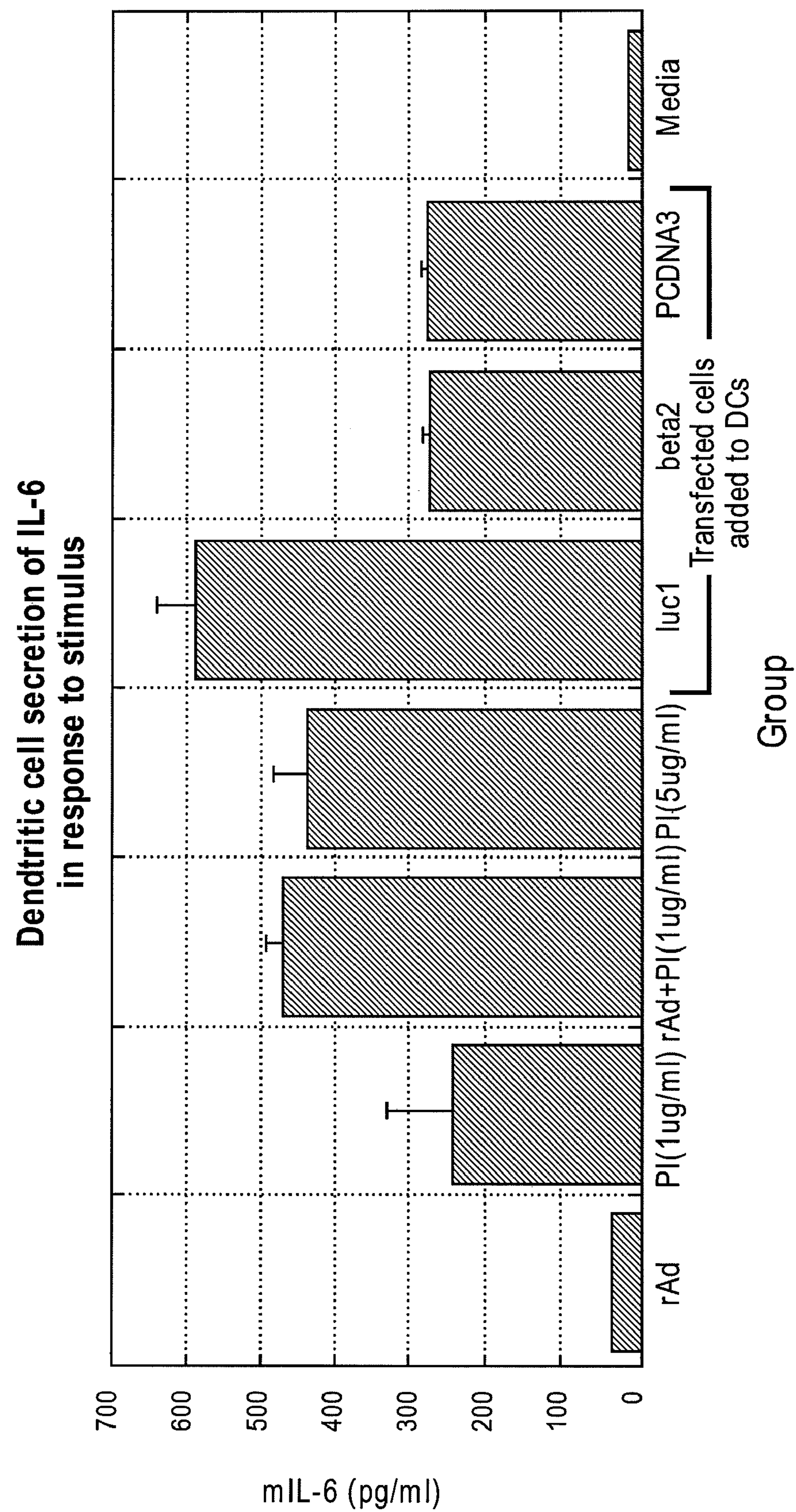
FIG. 4A illustrates data depicting dendritic cell activation by the expressed dsRNA TLR-3 agonist luc1.

The pSK-luc1 Functions in Dendritic Cell Cultures like Poly I:C, the Effects of Poly I:C and rAd are Additive To determine whether the expressed TLR-3 agonist of Example 6 above could function as an inducer of pro-inflammatory cytokines and dendritic cell maturation like the TLR-3 ligand poly I:C, an expressed dsRNA TLR-3 agonist was tested in dendritic cell cultures. Bone marrow from the femurs of Balb/c mice were cultured with flt-3 ligand (200 ng/ml), 5% serum, in DMEM media in order to make primary dendritic cell cultures. Five days after primary bone marrow cultures were set-up, 293 cells were transfected with either pSk-luc1, pSK-beta2 (a long segment of beta galactosidase that forms a 200 bp hairpin), or pcDNA3 (empty expression vector). On day 6, the transfected cells were treated by UV irradiation (20 seconds at 40 kJ/cm2) to cause apoptosis and these cells were given to the dendritic cells. Either poly I:C (1 ug/ml), rAd (1 pfu/cell), rAd+poly I:C, pSK-luc1 transfected cells, pSK-beta2 transfected cells, or pcDNA3 transfected cells were given to the dendritic cells and cultured overnight. As shown in FIG. 4A, pSK-luc1 transfected cells can significantly improve dendritic cell activation as measured by the mouse IL-6 ELISA. The results of this experiment also show that the combination of rAd plus TLR3 ligand (poly I:C) together can greatly improve dendritic cell activity.

Figure 4B:
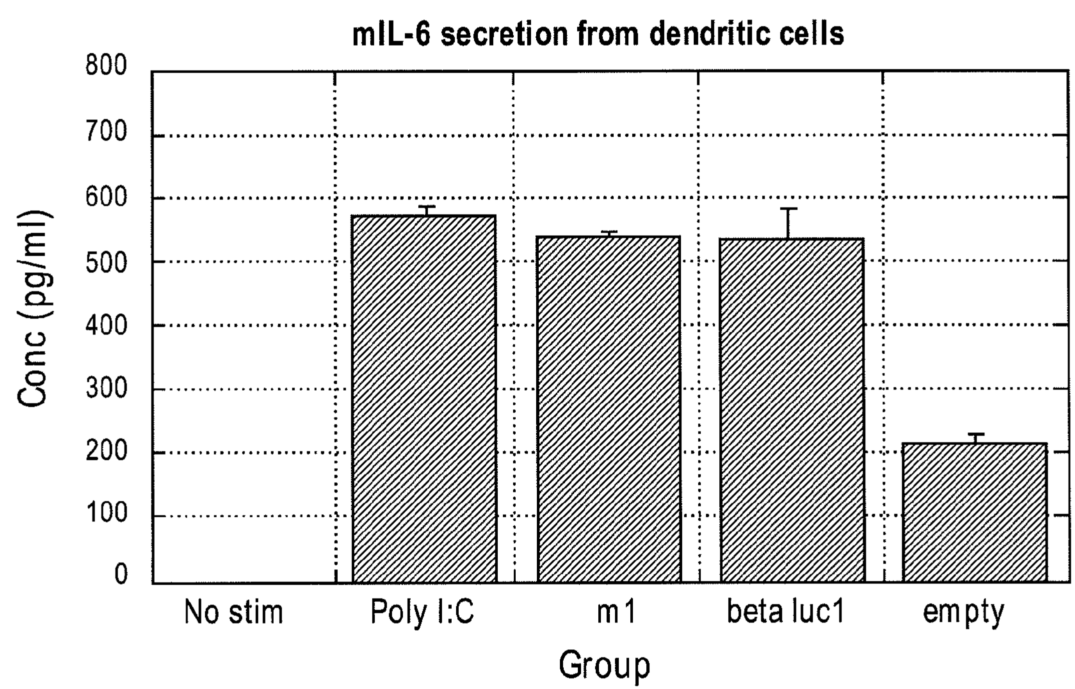
FIG. 4B illustrates data depicting dendritic cell activation by the expressed dsRNA TLR-3 agonists luc1 and m1.

Additional ligands were also tested. The TLR-3 agonist set forth in SEQ ID NO: 11 (m1) also forms a dsRNA hairpin of approximately the same size as luc1. These were made by overlapping oligonucleotides and annealing them together before cloning into the pSK-vector under control of the human beta actin promoter. The vectors were transfected into 293 cells and given to primary dendritic cells as described before. As shown in FIG. 4B, these additional ligands can activate dendritic cells similar to that of the ligand luc1 (FIG. 4B).

Example 8

Construction of a Fourth Chimeric Adenoviral Vector (DS2) and Rapid Cloning Vectors (DS2beta-luc and DS2C-luc)

Figure 5:
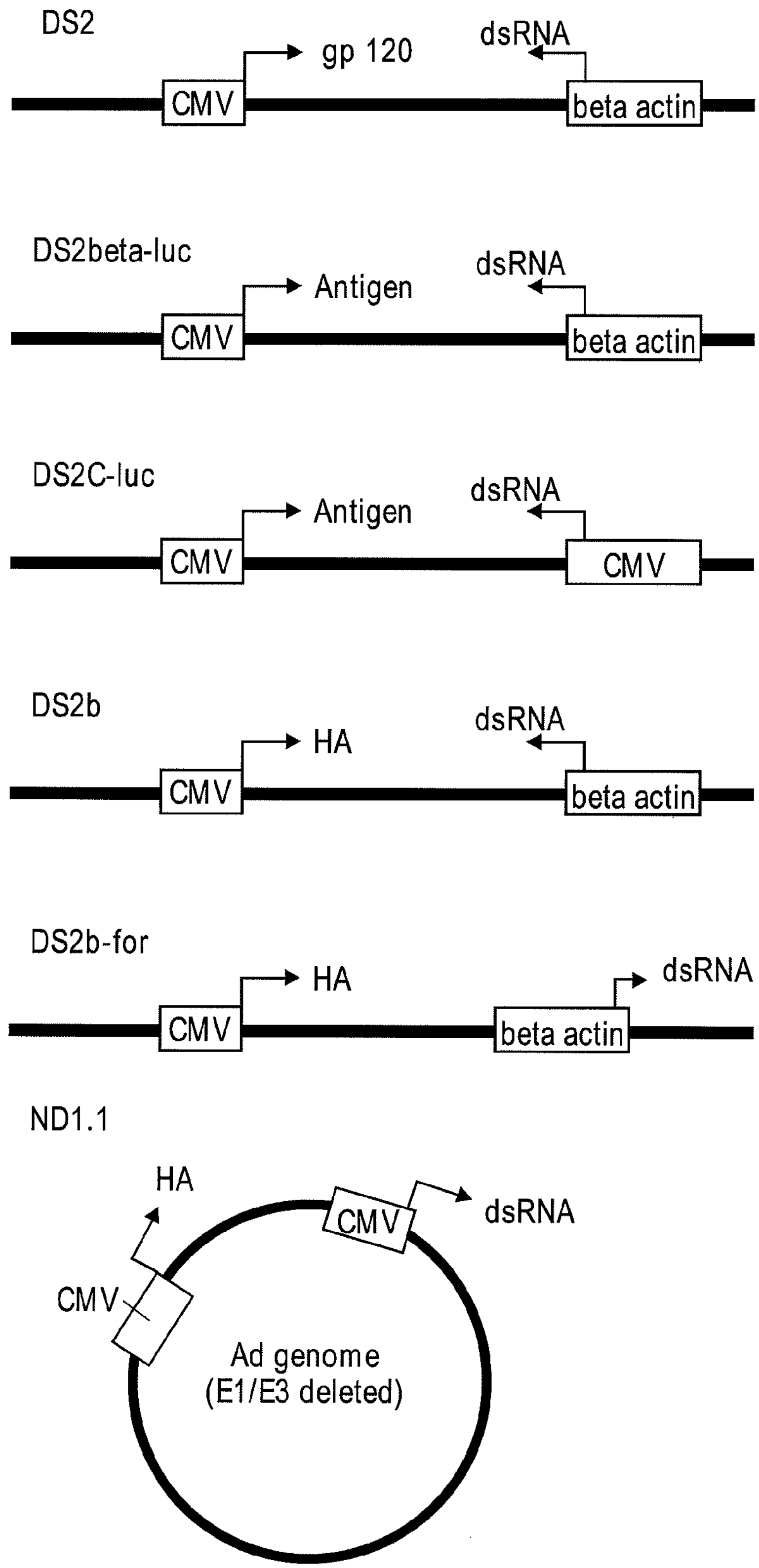
FIG. 5 is a graphic illustration of the chimeric adenoviral vectors of the invention, i.e., chimeric adenoviral vectors comprising nucleic acids encoding expressed ds RNA TLR-3 agonists.

A nucleic acid encoding gp120 (from the NIH AIDS Research and Reference Reagent Program)) was placed under control of a CMV promoter with a small intron just upstream of the start codon in the shuttle vector (pShuttleCMV, Qbiogene). A poly A tail from bGH was placed downstream of the nucleic acid encoding gp120. The dsRNA TLR-3 agonist luc1 under the control of the human beta actin promoter and poly A (described in example 5 above) was inserted into the gp120 pShuttle vector such that both the nucleic acid encoding gp120 and the nucleic acid encoding TLR-3 agonist were contained in a single vector under the control of two separate promoters. The orientation of the expression of the nucleic acid encoding the antigen of interest and the expression of the TLR-3 agonist is illustrated in FIG. 5.

Two generic shuttle vectors called DS2beta-luc (SEQ ID NO: 14) and DS2C-luc (SEQ ID NO: 15) were also constructed such that a nucleic acid encoding any antigen of interest could be inserted under the CMV promoter and either the human beta actin promoter or the CMV promoter is used to drive expression of a dsRNA TLR-3 agonist. In particular, the vector DS2C-luc has a unique Kpn 1 site that a nucleic acid encoding an antigen of interest can easily be cloned into. The purpose of these vectors is to make subsequent vector construction much easier because a nucleic acid encoding any antigen of interest could be inserted into the cloning site to rapidly manufacture a vector capable of eliciting antibody and T cells responses against the antigen of interest. Homologous recombination of DS2 with the vector pAd (Qbiogene) was performed as before in order to generate a vector capable of producing recombinant Ad (E1/E3 deleted) that contained a nucleic acid encoding GFP and a nucleic acid encoding the dsRNA TLR-3 agonist luc1. Recombinant Ad was generated by transfecting the new pAd-betaactin-luc1-CMV-gp120 expression construct into 293 cells. Titers were measured by standard methods.

Example 9

Induction of an Antigen Specific Immune Response Following Oral Delivery of DS2

Figure 6:
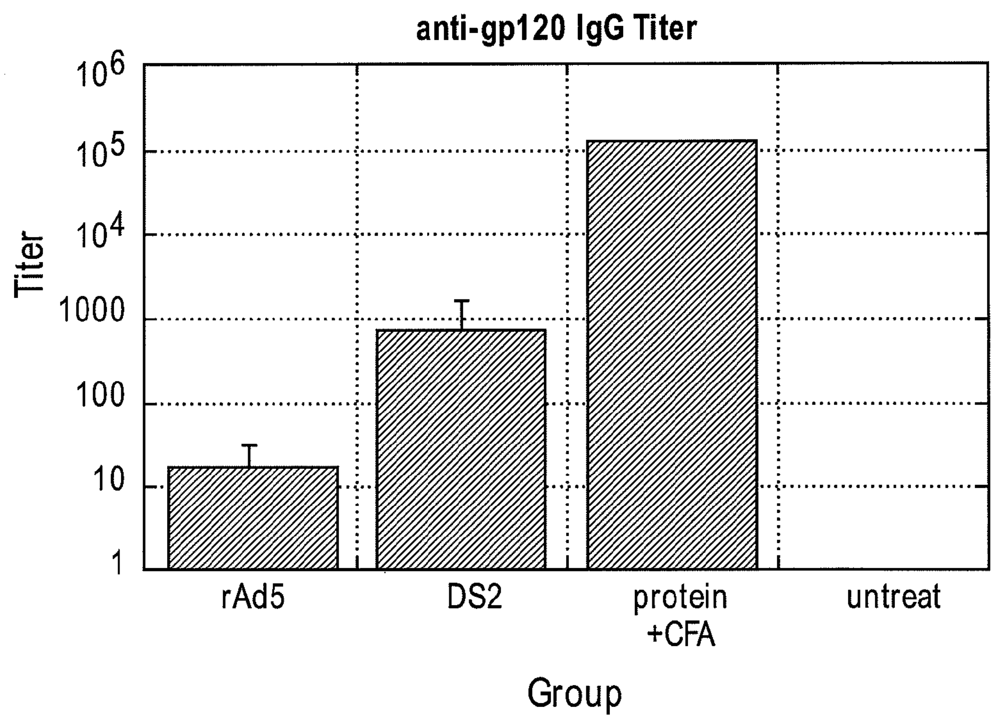
FIG. 6 illustrates data demonstrating that the chimeric adenoviral vectors of the invention are effective at inducing an antigen-specific immune response following oral delivery.

$1.0\times10^7$ PFU of either pAd-CMV-gp120 plus the TLR-3 agonist luc1 (DS2) or pAd-CMV-gp120 (rAd5) were administered to animals by oral gavage on week. Both viruses express the gp120 under control of the CMV promoter and use recombinant E1/E3 deleted adenovirus type 5. Antibody titers to gp120 were measured in the plasma 3 weeks after virus administration by anti-gp120 IgG ELISA. The ELISA protocol has been described before (Tucker, et al, Mol Therapy 8:392 (2004)). Results demonstrate that DS2 can induce approximately a 2 log improvement in antibody titer to gp120, the heterologous antigen used in the experiment. The DS2 vector comprises a nucleic acid sequence encoding expressing gp120 and a nucleic acid sequence expressing a dsRNA TLR-3 agonist. As a positive control for the assay, sera from two animals injected subcutaneously with 10 micrograms gp120 protein plus Complete Freund's Adjuvant was also measured in the anti-gp120 ELISA. Untreated animals served as negative controls for the ELISA. Each group contained 6 animals. The results are illustrated in FIG. 6.

Example 10

Induction of an Antigen Specific Immune Response Following Oral Delivery of DS3

Figure 7:
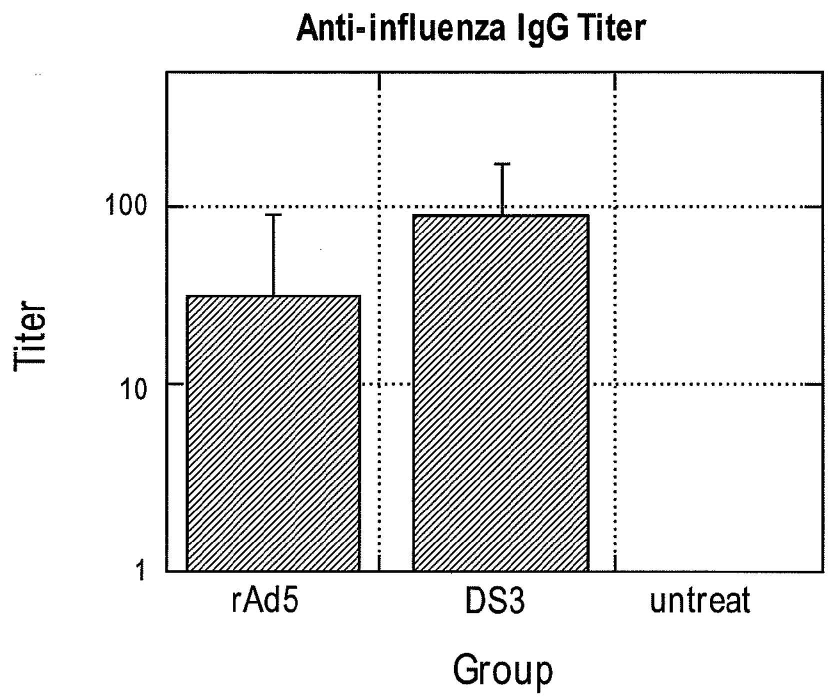
FIG. 7 illustrates data demonstrating that TLR-7/8 agonists have poor effectiveness in inducing an antigen-specific immune response.

$1.0\times10^{7}$ PFU of either pAd-CMV-influenza HA (from A/PR/8/34) plus the TLR7/8 ligand polyuridylic acid (DS3) or pAd-CMV-HA (rAd5) were administered to animals by oral gavage on week 0. Both viruses express influenza HA under control of the CMV promoter and use recombinant E1/E3 deleted adenovirus type 5. Antibody titers to HA were measured in the plasma 3 weeks after virus administration by anti-influenza HA IgG ELISA. Each group contained 6 animals. The results are illustrated in FIG. 7.

Example 11

Construction of a Fifth, Sixth, and Seventh Chimeric Adenoviral Vector (DS2b, DS2b-for, and ND1.1 214)

The gene influenza HA (A/Indo/5/2005) was synthesized by CelTek (Nashville, Tenn.) and placed into the vector pShuttleCMV (Qbiogene) which has a CMV promoter with a small intron just upstream of the start codon in the shuttle vector. The luc1 DNA with human beta actin promoter and poly A (described in example 5) were placed into the vector downstream of the antigen, in the orientation shown in FIG. 5 for DS2b. The sequence of luc1 is (GAAACGATATGGGCTGAATACGGATCCGTATTCAGCCCATATCGTTTC) (SEQ ID NO:10) and the completed pShuttle vector is set forth in SEQ ID NO: 6. An alternative orientation of luc1 with promoter in a shuttle vector is described as SEQ ID NO: 7 and is designated DS2b-for. We have also constructed another pShuttle vector (called DS2bC-HA) (SEQ ID NO: 16) that comprises two separate CMV promoters driving expression of the TLR-3 agonist luc1 and influenza HA described above. Homologous recombination with the vector pAd (Qbiogene) was performed as before in order to generate vectors capable of producing recombinant Ad (E1/E3 deleted) that contained the nucleic acid encoding HA and the TLR-3 agonist luc1 under separate promoters. Recombinant Ad was generated by transfecting the new pAd-constructs into 293 cells. Titers were measured by standard methods. The completed pAd vector containing DS2C-luc was named ND1.1 214 and deposited in the ATCC patent depository on Feb. 22, 2007 (Manassus, Va.). The nucleic acid sequence of this chimeric adenoviral vector is set forth in SEQ ID NO: 17. The nucleic acid encoding the heterologous antigen is in bold text and is flanked by a Cla I recognition site on the 5' end and a Not 1 recognition site on the 3' end. The nucleic acid sequence encoding the TLR-3 agonists is in italic, with the linker sequence in bold. A nucleic acid sequence encoding any antigen of interest and a nucleic acid sequence encoding any suitable expressed TLR-3 agonist can be inserted into the chimeric adenoviral vector.

Example 12

Figure 8A:
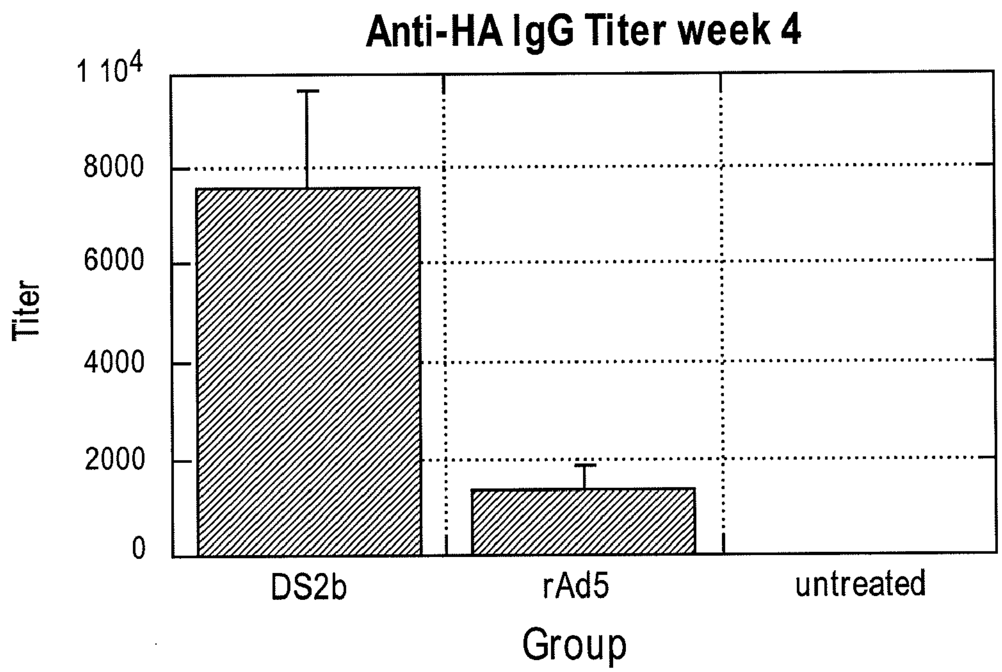
FIG. 8A illustrates data depicting the anti-HA antibody titer 4 weeks following oral administration of a chimeric adenoviral comprising a nucleic acid sequence encoding the dsRNA TLR-3 agonist luc1.

Induction of an Antigen Specific Immune Response Following Oral Delivery of DS2b $1.0\times10^{7}$ PFU of either pAd-CMV-HA plus the TLR-3 agonists luc1 in the reverse orientation (DS2b) or forward orientation (DS2b-for), or pAd-CMV-HA (rAd5) were administered to animals by oral gavage on week 0. These viruses express the antigen influenza HA under control of the CMV promoter and use recombinant E1/E3 deleted adenovirus type 5. Antibody titers to HA were measured in the plasma 3 weeks after virus administration by anti-HA IgG ELISA. Results demonstrate that the DS2b vector elicits an antibody responses to the protein HA greater than the standard rAd vector (rAd5). The DS2b vector contains rAd5 expressing HA as well as expresses a toll-like receptor 3 (TLR3) agonist, a hairpin of double-stranded RNA, demonstrating that the use of the encoded dsRNA ligand can improve adaptive immune responses to antigens of interest. As shown in FIG. 8A and FIG. 6, expressed dsRNA can improve adaptive immune responses to multiple different heterologous antigens. Untreated animals served as negative control for the ELISA. Each group contained 6 animals.

Figure 8B:
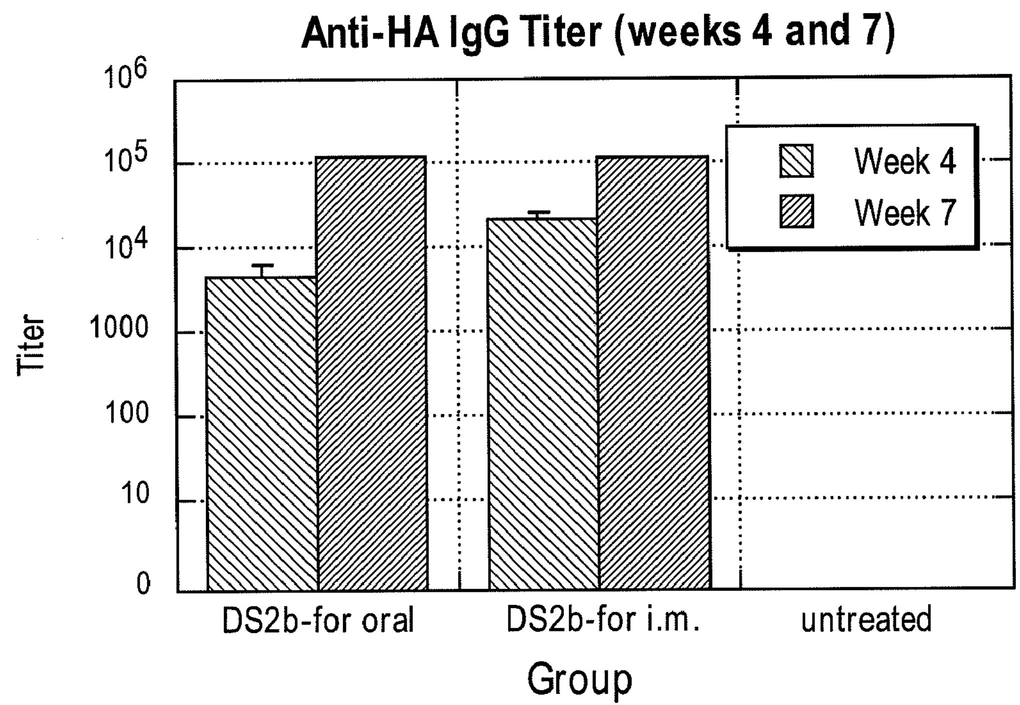
FIG. 8B illustrates data depicting the anti-HA antibody titer 4 weeks or 7 weeks following administration of a chimeric adenoviral comprising a nucleic acid sequence encoding the dsRNA TLR-3 agonist luc1.

Vectors in the opposite orientation (DS2for) were examined for antibody responses following either oral or intramuscular administration of $1.0\times10^{7}$ pfu virus per animal at 0 and 5 weeks. Antibody responses to HA were measured at 4 and 7 weeks post initial administration. As shown in FIG. 8B, the opposite orientation vector can also induce substantial antibody responses to heterologous antigens. The DS1b and DS1bfor vectors induced similar responses to HA at the 4 week time point. Significantly, the effect of boosting of the antibody response was demonstrated with the DS1bfor vector and showed that multiple doses could be used to increase antibody responses to the heterologous antigen.

Figure 8C:
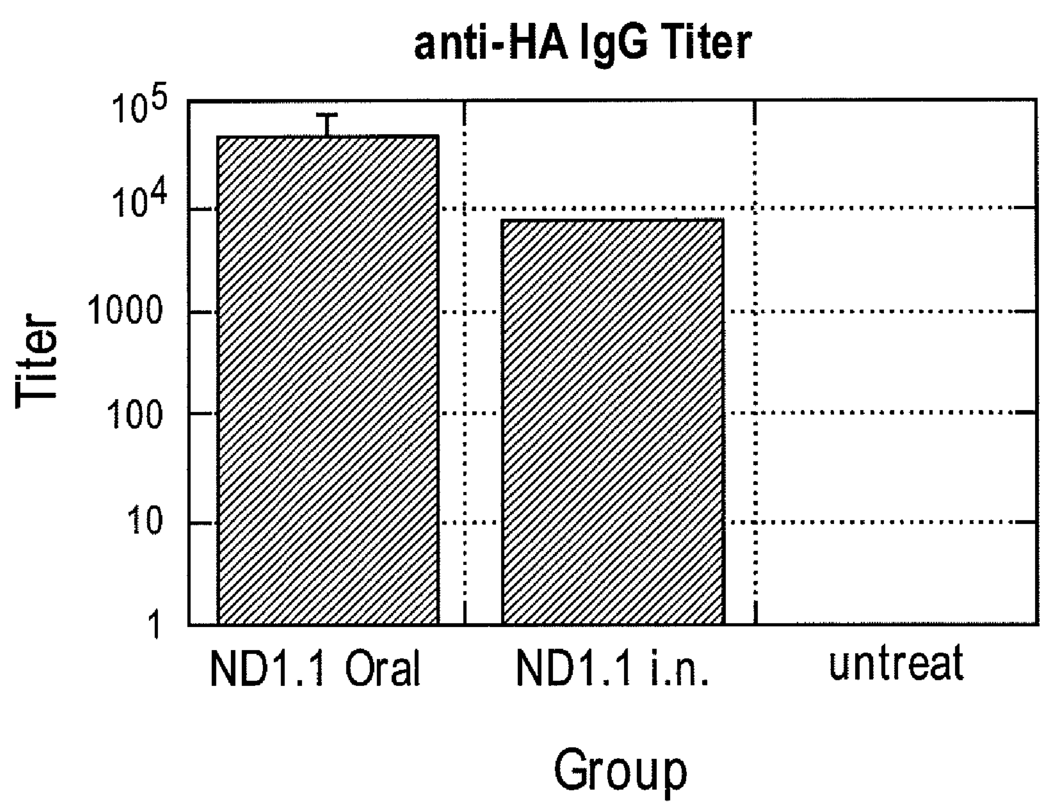
FIG. 8C illustrates data depicting the anti-HA antibody titer 3 weeks following oral or intranasal administration of a chimeric adenoviral comprising a nucleic acid sequence encoding the dsRNA TLR-3 agonist luc1.

Another example of potential of the chimeric adenoviral vector approach was demonstrated as well. The vector ND1.1 214 was given to animals by oral ($1.0\times10^{7}$ pfu) or intranasal administration ($3\times10^{6}$ pfu) and the antibody responses to the heterologous antigen were measured at week 3. As shown in FIG. 8C, substantial antibody responses to HA were measured following oral administration, well beyond the typical values from a single oral administration of rAd vector.

All publications, patent publications, patents, and Genback Accession Nos. applications cited in this specification are herein incorporated by reference in their entirety for all purposes as if each individual publication, patent publication, or patent were specifically and individually indicated to be incorporated by reference.

What is claimed is:

1. A method for eliciting an immune response, said method comprising administering an immunogenic composition to a mammalian subject, said immunogenic composition comprising:

(a) a chimeric viral vector comprising a first promoter operably linked to a nucleic acid encoding a heterologous polypeptide;

(b) a non-specific immune response enhancer selected from dsRNA and a dsRNA mimetic; and (c) a pharmaceutically acceptable carrier, wherein the immune response is directed against the heterologous polypeptide, and wherein the route of administration is selected from the group consisting of: oral, intranasal, and mucosal.

2. The method of claim 1, wherein the immune response enhancer is encoded on the chimeric viral vector under the control of a second promoter.

3. The method of claim 2, wherein the first promoter and second promoter are the same.

4. The method of claim 2, wherein the first promoter and second promoter are different.

5. The method of claim 1, wherein the heterologous polypeptide is a viral antigen.

6. The method of claim 5, wherein the viral antigen is from a virus selected from influenza, HIV, HPV, Epstein Barr virus, Herpes simplex virus, hepatitis A, hepatitis B, hepatitis C, hepatitis E, mumps virus, rubella virus, measles virus, poliovirus, smallpox virus, rabies virus, and Variella-zoster virus.

7. The method of claim 1, wherein the heterologous polypeptide is a bacterial antigen.

8. The method of claim 1, wherein the heterologous polypeptide is a fungal antigen.

9. A method for eliciting an immune response, said method comprising administering an immunogenic composition to a mammalian subject, said immunogenic composition comprising a chimeric adenoviral expression vector comprising:

(a) a first promoter operably linked to a nucleic acid encoding a toll-like receptor-3 (TLR-3) agonist, wherein the TLR-3 agonist is a double stranded RNA (dsRNA); and (b) a second promoter operably linked to a nucleic acid encoding a heterologous polypeptide; and (c) a pharmaceutically acceptable carrier, wherein the immune response is directed against the heterologous polypeptide, and wherein the route of administration is oral.

* * * * *